US011802275B2

(12) United States Patent
Kralj et al.

(10) Patent No.: US 11,802,275 B2
(45) Date of Patent: Oct. 31, 2023

(54) ALPHA-GLUCOSE-1-PHOSPHATE SYNTHESIS FROM SUCROSE AND GLUCAN SYNTHESIS USING GLUCAN PHOSPHORYLASES

(71) Applicant: DANISCO US INC, Palo Alto, CA (US)

(72) Inventors: Slavko Kralj, Copenhagen K (DK); Zheyong Yu, Shanghai (CN); Zhenghong Zhang, Shanghai (CN)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 17/261,937

(22) PCT Filed: Jul. 18, 2019

(86) PCT No.: PCT/US2019/042385

§ 371 (c)(1),
(2) Date: Jan. 21, 2021

(87) PCT Pub. No.: WO2020/023278

PCT Pub. Date: Jan. 30, 2020

(65) Prior Publication Data

US 2021/0163902 A1 Jun. 3, 2021

(30) Foreign Application Priority Data

Jul. 23, 2018 (WO) ................ PCT/CN2018/096588

(51) Int. Cl.
*C12P 19/04* (2006.01)
*C12N 9/10* (2006.01)

(52) U.S. Cl.
CPC ............ *C12N 9/1051* (2013.01); *C12P 19/04* (2013.01); *C12Y 204/01001* (2013.01); *C12Y 204/01007* (2013.01)

(58) Field of Classification Search
CPC ...................................................... C12P 19/04
See application file for complete search history.

(56) References Cited

U.S. PATENT DOCUMENTS

2004/0115778 A1* 6/2004 Fujii ....................... C08B 30/20 536/123.12

* cited by examiner

*Primary Examiner* — Tekchand Saidha

(57) ABSTRACT

Reactions are disclosed herein comprising water, alpha-glucose-1-phosphate (alpha-G1P), an acceptor molecule, and an alpha-1,4-glucan phosphorylase. Novel alpha-1,4-glucan phosphorylase enzymes are also disclosed. Additional disclosures herein regard sucrose phosphorylase enzymes and methods of use thereof to produce alpha-G1P.

14 Claims, No Drawings

Specification includes a Sequence Listing.

ALPHA-GLUCOSE-1-PHOSPHATE SYNTHESIS FROM SUCROSE AND GLUCAN SYNTHESIS USING GLUCAN PHOSPHORYLASES

This application is the National Stage application of International Application No. PCT/US2019/042385 (filed Jul. 18, 2019), which claims the benefit of International Application No. PCT/CN2018/096588 (filed Jul. 23, 2018), both of which prior applications are incorporated herein by reference in theft entirety.

FIELD

The present disclosure is in the field of enzymatic reactions. For example, the disclosure pertains to reactions and methods using alpha-1,4-glucan phosphorylase and/or sucrose phosphorylase.

REFERENCE TO SEQUENCE LISTING SUBMITTED ELECTRONICALLY

The official copy of the sequence listing is submitted electronically via EFS-Web as an ASCII formatted sequence listing with a file named 20190715_NB41262WOPCT2_SequenceListing created on Jul. 15, 2019, and having a size of about 286 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,4-glucan, a glucan polymer characterized by having alpha-1,4-glycosidic linkages. A particularly useful alpha-1,4-glucan, amylose, has been applied in developing various film and food innovations, for example. While amylose production typically has been through isolation from plant starch, enzymatic processes have also been developed for producing amylose from the renewable feed, sucrose. Some enzymatic approaches for amylose production have employed reactions with amylosucrase or glucan phosphorylase enzymes (e.g., Potocki-Veronese et al., 2005, *Biomacromolecules* 6:1000-1011; Qi et al., 2014, *ACS Catal.* 4:1311-1317).

Further ways of enzymatically producing glucan containing alpha-1,4 glycosidic linkages, such as amylose, are presently disclosed. Also disclosed are other means for enzymatically producing alpha-glucose-1-phosphate (alpha-G1P), which can be used as a precursor for glucan synthesis.

SUMMARY

In one embodiment, the present disclosure concerns a method for producing alpha-1,4-glucan, the method comprising: (a) contacting at least water, alpha-G1P, an acceptor molecule, and an alpha-1,4-glucan phosphorylase comprising an amino acid sequence that is at least 90% identical to SEQ ID NO:32, SEQ ID NO:30, SEQ ID NO:26, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52, wherein alpha-1,4-glucan is produced; and (b) optionally, isolating the alpha-1,4-glucan produced in step (a).

In another embodiment, the present disclosure concerns a reaction composition comprising at least water, alpha-G1P, an acceptor molecule, and an alpha-1,4-glucan phosphorylase comprising an amino acid sequence that is at least 90% identical to SEQ ID NO:32, SEQ ID NO:30, SEQ ID NO:26, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52, wherein the alpha-1,4-glucan phosphorylase synthesizes alpha-1,4-glucan.

In another embodiment, the present disclosure concerns a composition comprising an isolated alpha-1,4-glucan phosphorylase that comprises an amino acid sequence that is at least 90% identical to SEQ ID NO:32, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52.

In another embodiment, the present disclosure concerns a composition comprising a polynucleotide that comprises a nucleotide sequence encoding an isolated alpha-1,4-glucan phosphorylase that comprises an amino acid sequence that is at least 90% identical to SEQ ID NO:32, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52, optionally wherein one or more regulatory sequences are operably linked to the nucleotide sequence, and preferably wherein the one or more regulatory sequences include a promoter sequence.

In another embodiment, the present disclosure concerns a method for producing alpha-G1P, the method comprising: (a) contacting at least water, inorganic phosphate, sucrose, and a sucrose phosphorylase comprising an amino acid sequence that is at least 90% identical to SEQ ID NO:10, SEQ ID NO:12, SEQ ID NO:14, SEQ ID NO:20, or SEQ ID NO:22, wherein alpha-G1P is produced; and (b) optionally, isolating the alpha-G1P produced in step (a).

In another embodiment, the present disclosure concerns a reaction composition comprising at least water, inorganic phosphate, sucrose, and a sucrose phosphorylase comprising an amino acid sequence that is at least 90% identical to SEQ ID NO:10, SEQ ID NO:12, SEQ ID NO:14, SEQ ID NO:20, or SEQ ID NO:22, wherein the sucrose phosphorylase produces alpha-G1P.

In another embodiment, the present disclosure concerns a composition comprising an isolated sucrose phosphorylase that comprises an amino acid sequence that is at least 90% identical to SEQ ID NO:10, SEQ ID NO:12, SEQ ID NO:14, or SEQ ID NO:22.

In another embodiment, the present disclosure concerns a polynucleotide comprising a nucleotide sequence encoding an isolated sucrose phosphorylase that comprises an amino acid sequence that is at least 90% identical to SEQ ID NO:10, SEQ ID NO:12, SEQ ID NO:14, or SEQ ID NO:22, optionally wherein one or more regulatory sequences are operably linked to the nucleotide sequence, and preferably wherein the one or more regulatory sequences include a promoter sequence.

BRIEF DESCRIPTION OF THE SEQUENCES

TABLE 1

| Summary of Nucleic Acid and Protein SEQ ID Numbers | | |
|---|---|---|
| Description | Nucleic acid SEQ ID NO. | Protein SEQ ID NO. |
| "Sp14", *Leuconostoc mesenteroides* sucrose phosphorylase (LEI02180). | 1 | 2 (490 aa) |
| "Sp14", *L. mesenteroides* sucrose phosphorylase (LEI02180). Nucleotide sequence codon-optimized for expression of SEQ ID NO: 2 (but with an Ala inserted after the start Met) in *Bacillus subtilis*. | 55 | |
| "Sp15", *Bifidobacterium adolescentis* sucrose phosphorylase (LEI02181). | 3 | 4 (504 aa) |
| "Sp15", *B. adolescentis* sucrose phosphorylase (LEI02181). Nucleotide sequence codon-optimized for expression of SEQ ID NO: 4 (but with an Ala inserted after the start Met) in *B. subtilis*. | 56 | |
| "Sp16", *Bifidobacterium longum* sucrose phosphorylase (LEI02182). | 5 | 6 (508 aa) |
| "Sp16", *B. longum* sucrose phosphorylase (LEI02182). Nucleotide sequence codon-optimized for expression of SEQ ID NO: 6 (but with an Ala inserted after the start Met) in *B. subtilis*. | 57 | |
| "Sp17", *Lactobacillus amylovorus* GRL1118 sucrose phosphorylase (LEI02183). | 7 | 8 (480 aa) |
| "Sp17", *L. amylovorus* GRL1118 sucrose phosphorylase (LEI02183). Nucleotide sequence codon-optimized for expression of SEQ ID NO: 8 (but with an Ala inserted after the start Met) in *B. subtilis*. | 58 | |
| "Sp157", *Streptomyces* sp. K96/N1.7S sucrose phosphorylase. | 9 | 10 (499 aa) |
| "Sp157", *Streptomyces* sp. K96/N1.7S sucrose phosphorylase. Nucleotide sequence codon-optimized for expression of SEQ ID NO: 10 in *B. subtilis*. | 59 | |
| "Sp159", *Alkalimonas* sp. SWT317 sucrose phosphorylase. | 11 | 12 (496 aa) |
| "Sp159", *Alkalimonas* sp. SWT317 sucrose phosphorylase. Nucleotide sequence codon-optimized for expression of SEQ ID NO: 12 in *B. subtilis*. | 60 | |
| "Sp236", *Bacillus* sp. SWT141 sucrose phosphorylase. | 13 | 14 (486 aa) |
| "Sp236", *Bacillus* sp. SWT141 sucrose phosphorylase. Nucleotide sequence codon-optimized for expression of SEQ ID NO: 14 in *B. subtilis*. | 61 | |
| "Sp254", *Aerococcus* sp. RPC0096 sucrose phosphorylase. | 15 | 16 (481 aa) |
| "Sp254", *Aerococcus* sp. RPC0096 sucrose phosphorylase. Nucleotide sequence codon-optimized for expression of SEQ ID NO: 16 in *B. subtilis*. | 62 | |
| "Sp277", sucrose phosphorylase, metagenomic sample "GK14-2 Sorokin", DNA from soil, Sorokin, Russia. | 17 | 18 (479 aa) |
| "Sp277", sucrose phosphorylase, metagenomic sample "GK14-2 Sorokin". Nucleotide sequence codon-optimized for expression of SEQ ID NO: 18 in *B. subtilis*. | 63 | |
| "Sp75", *Herbinix* sp. L100 sucrose phosphorylase. | 19 | 20 (573 aa) |
| "Sp75", *Herbinix* sp. L100 sucrose phosphorylase. Nucleotide sequence codon-optimized for expression of SEQ ID NO: 20 in *B. subtilis*. | 64 | |
| "Sp156", *Cellulomonas* sp. SWT255 sucrose phosphorylase. | 21 | 22 (501 aa) |
| "Sp156", *Cellulomonas* sp. SWT255 sucrose phosphorylase. Nucleotide sequence codon-optimized for expression of SEQ ID NO: 22 in *B. subtilis*. | 65 | |
| "Sp158", *Paenibacillus daejeonensis* sucrose phosphorylase. | 23 | 24 (499 aa) |
| "Sp158", *P. daejeonensis* sucrose phosphorylase. Nucleotide sequence codon-optimized for expression of SEQ ID NO: 24 in *B. subtilis*. | 66 | |

TABLE 1-continued

| Summary of Nucleic Acid and Protein SEQ ID Numbers | | |
|---|---|---|
| Description | Nucleic acid SEQ ID NO. | Protein SEQ ID NO. |
| "GP-3", *Aquifex aeolicus* alpha-1,4-glucan phosphorylase. | 25 | 26 (692 aa) |
| "GP-3", *A. aeolicus* alpha-1,4-glucan phosphorylase. Nucleotide sequence codon-optimized for expression of SEQ ID NO: 26 (but with an Ala inserted after the start Met) in *B. subtilis*. | 67 | |
| "GP-4", *Thermus caldophilus* GK24 alpha-1,4-glucan phosphorylase. | 27 | 28 (819 aa) |
| "GP-4", *T. caldophilus* GK24 alpha-1,4-glucan phosphorylase. Nucleotide sequence codon-optimized for expression of SEQ ID NO: 28 (but with an Ala inserted after the start Met) in *B. subtilis*. | 68 | |
| "GP-5", *Caldanaerobacter subterraneus* alpha-1,4-glucan phosphorylase. | 29 | 30 (540 aa) |
| "GP-5", *C. subterraneus* alpha-1,4-glucan phosphorylase. Nucleotide sequence codon-optimized for expression of SEQ ID NO: 30 (but with an Ala inserted after the start Met) in *B. subtilis*. | 69 | |
| "GP-006", alpha-1,4-glucan phosphorylase, metagenomic sample "GK14-2 Sorokin", DNA from soil, Sorokin, Russia. | 31 | 32 (868 aa) |
| "GP-006", alpha-1,4-glucan phosphorylase, metagenomic sample "GK14-2 Sorokin". Nucleotide sequence codon-optimized for expression of SEQ ID NO: 32 in *B. subtilis*. | 70 | |
| "GP-011", *Paenibacillus* sp. DSM-34 alpha-1,4-glucan phosphorylase. | 33 | 34 (856 aa) |
| "GP-011", *Paenibacillus* sp. DSM-34 alpha-1,4-glucan phosphorylase. Nucleotide sequence codon-optimized for expression of SEQ ID NO: 34 in *B. subtilis*. | 71 | |
| "GP-017", alpha-1,4-glucan phosphorylase, metagenomic sample "354 Sorokin", DNA from soil, Sorokin, Russia. | 35 | 36 (852 aa) |
| "GP-017", alpha-1,4-glucan phosphorylase, metagenomic sample "354 Sorokin". Nucleotide sequence codon-optimized for expression of SEQ ID NO: 36 in *B. subtilis*. | 72 | |
| "GP-022", alpha-1,4-glucan phosphorylase, metagenomic sample "346 Sorokin", DNA from soil, Sorokin, Russia. | 37 | 38 (848 aa) |
| "GP-022", alpha-1,4-glucan phosphorylase, metagenomic sample "346 Sorokin". Nucleotide sequence codon-optimized for expression of SEQ ID NO: 38 in *B. subtilis*. | 73 | |
| "GP-005", *Mycobacterium* sp. alpha-1,4-glucan phosphorylase. | 39 | 40 (869 aa) |
| "GP-005", *Mycobacterium* sp. alpha-1,4-glucan phosphorylase. Nucleotide sequence codon-optimized for expression of SEQ ID NO: 40 in *B. subtilis*. | 74 | |
| "GP-007", *Paenibacillus filicis* DSM-23916 alpha-1,4-glucan phosphorylase. | 41 | 42 (865 aa) |
| "GP-007", *P. filicis* DSM-23916 alpha-1,4-glucan phosphorylase. Nucleotide sequence codon-optimized for expression of SEQ ID NO: 42 in *B. subtilis*. | 75 | |
| "GP-009", *Microbacterium* sp. alpha-1,4-glucan phosphorylase. | 43 | 44 (863 aa) |
| "GP-009", *Microbacterium* sp. alpha-1,4-glucan phosphorylase. Nucleotide sequence codon-optimized for expression of SEQ ID NO: 44 in *B. subtilis*. | 76 | |
| "GP-013", alpha-1,4-glucan phosphorylase, metagenomic sample "330 Sorokin", DNA from soil, Sorokin, Russia. | 45 | 46 (853 aa) |
| "GP-013", alpha-1,4-glucan phosphorylase, metagenomic sample "330 Sorokin". Nucleotide sequence codon-optimized for expression of SEQ ID NO: 46 in *B. subtilis*. | 77 | |

TABLE 1-continued

Summary of Nucleic Acid and Protein SEQ ID Numbers

| Description | Nucleic acid SEQ ID NO. | Protein SEQ ID NO. |
|---|---|---|
| "GP-043", alpha-1,4-glucan phosphorylase, metagenomic sample "354 Sorokin", DNA from soil, Sorokin, Russia. | 47 | 48 (708 aa) |
| "GP-043", alpha-1,4-glucan phosphorylase, metagenomic sample "354 Sorokin". Nucleotide sequence codon-optimized for expression of SEQ ID NO: 48 in *B. subtilis*. | 78 | |
| "GP-044", alpha-1,4-glucan phosphorylase, metagenomic. | 49 | 50 (705 aa) |
| "GP-044", alpha-1,4-glucan phosphorylase, metagenomic. Nucleotide sequence codon-optimized for expression of SEQ ID NO: 50 in *B. subtilis*. | 79 | |
| "GP-046", *Streptomyces* sp. K96/N1.7S alpha-1,4-glucan phosphorylase. | 51 | 52 (702 aa) |
| "GP-046", *Streptomyces* sp. K96/N1.7S alpha-1,4-glucan phosphorylase. Nucleotide sequence codon-optimized for expression of SEQ ID NO: 52 in *B. subtilis*. | 80 | |
| "GP-048", alpha-1,4-glucan phosphorylase, metagenomic sample "BG-15 Sorokin", DNA from soil, Sorokin, Russia. | 53 | 54 (690 aa) |
| "GP-048", alpha-1,4-glucan phosphorylase, metagenomic sample "BG-15 Sorokin". Nucleotide sequence codon-optimized for expression of SEQ ID NO: 54 in *B. subtilis*. | 81 | |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The term "saccharide" and other like terms herein refer to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 3 to 15 monosaccharides, for example, joined by glycosidic linkages. An oligosaccharide can also be referred to as an "oligomer". Monosaccharides (e.g., glucose and/or fructose) comprised within disaccharides/oligosaccharides can be referred to as "monomeric units", "monosaccharide units", or other like terms.

The terms "alpha-glucan", "alpha-glucan polymer" and the like are used interchangeably herein. An alpha-glucan is a polymer comprising glucose monomeric units linked together by alpha-glycosidic linkages. Alpha-glucan herein can be in the form of an oligosaccharide or polysaccharide. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,4-glucan. Glucose as comprised within a saccharide, alpha-glucan, or other carbohydrate herein can be referred to as glucose monomeric unit(s), glucose monomer(s), glucose units, or other like terms.

The terms "poly alpha-1,4-glucan", "alpha-1,4-glucan", "alpha-1,4-glucan polymer" and the like are used interchangeably herein. Alpha-1,4-glucan is a polymer of at least DP3 and comprises glucose monomeric units linked together by glycosidic linkages, wherein at least about 90% of the glycosidic linkages are alpha-1,4. Alpha-1,4-glucan in certain embodiments has about 100% alpha-1,4 glycosidic linkages, or comprises at least about 90% or 95% alpha-1,4 glycosidic linkages. Most or all of other linkages (if present) in alpha-1,4-glucan herein typically are alpha-1,6 (typically forming a branch), but can also be alpha-1,2 and/or alpha-1,3. An example of alpha-1,4-glucan herein is amylose.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,4-glycosidic linkage" as used herein refers to the type of covalent bond that joins alpha-D-glucose molecules to each other through carbons 1 and 4 on adjacent alpha-D-glucose rings. The glycosidic linkages of a glucan polymer herein can also be referred to as "glucosidic linkages". Herein, "alpha-D-glucose" is referred to as "glucose", unless otherwise noted.

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^{1}$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as DPw (weight average degree of polymerization) or DPn (number average degree of polymerization). The molecular weight of smaller alpha-glucan polymers such as oligosaccharides typically can be provided as "DP" (degree of polymerization), which simply refers to the number of glucose monomeric units comprised within the alpha-glucan. Various means are known in the art for calculating these various molecular weight measurements such as with high-pressure liquid chromatography (H PLC), size exclusion chromatography (SEC), or gel permeation chromatography (GPC).

Unless otherwise disclosed, the terms "phosphorylase", "phosphorylase enzyme" and the like as used herein refer to a particular class of enzymes that can reversibly catalyze synthesis (such reversibility is typically only under isolated/in vitro conditions) of a certain type of disaccharide, oligosaccharide, or polysaccharide (e.g., alpha-glucan) and free phosphate (reaction products) from alpha-glucose-1-phosphate (alpha-G1P) and a suitable acceptor (reaction substrates). An "alpha-1,4-glucan phosphorylase" (or "phosphorylase enzyme that synthesizes alpha-1,4-glucan", "1,4-alpha-D-glucan phosphorylase", and like terms) herein catalyzes synthesis of alpha-1,4 glycosidic linkage-containing oligosaccharides or polysaccharides and free phosphate from alpha-G1P and a suitable acceptor. An alpha-1,4-glucan phosphorylase is of the Enzyme Commission (EC) entry 2.4.1.1, and in certain aspects catalyzes the following reversible reaction: alpha-G1P+(1,4-alpha-D-glucosyl)$_{n-1}$$\leftrightarrow$(1,4-alpha-glucosyl)$_n$+phosphate; while "(1,4-alpha-D-glucosyl)$_{n-1}$" is shown as an acceptor in this reaction, an alpha-1,4-glucan phosphorylase can use other acceptor types such as those disclosed herein. An alpha-1,4-glucan phosphorylase in certain aspects comprises an amino acid sequence that is at least 90% identical to SEQ ID NO:26, 28, 30, 32, 34, 36, 38, 40, 42, 44, 46, 48, 50, 52, or 54. Depending on the acceptor used in an alpha-1,4-glucan phosphorylase reaction herein, an alpha-1,4 glycosidic linkage-containing oligosaccharide or polysaccharide product can (i) be comprised entirely of glucose monomeric units (when acceptor itself is comprised only of one or more glucose units in certain aspects), or (ii) comprise non-glucose monosaccharide units and/or non-saccharide moieties in addition to glucose units (when acceptor itself comprises such other monosaccharide units and/or moieties). Either of these product types (i or ii), for example, can optionally be characterized with respect to the alpha-1,4 glycosidic linkage-containing oligosaccharide or polysaccharide that was synthesized from the acceptor (i.e., the product linkage profile does not include the linkages of the acceptor).

The terms "acceptor", "acceptor molecule", "acceptor compound" and the like are used interchangeably herein. A suitable acceptor herein is contemplated to be an organic molecule comprising at least one hydroxyl moiety (—OH), which hydroxyl moiety is capable of being involved in formation of a glycosidic linkage (involving the oxygen atom of the hydroxyl moiety) with the 1-position of glucose of alpha-G1P (phosphate group is replaced during linkage formation) via catalytic activity of an alpha-1,4-glucan phosphorylase herein. A suitable acceptor can be a carbohydrate or non-carbohydrate. Examples of non-carbohydrate acceptors include alcohols, polyols, phenolic compounds, and amino acids. Examples of carbohydrate acceptors include disaccharides, oligosaccharides and polysaccharides; all or some of the monomeric units of a carbohydrate acceptor in some embodiments can be glucose units. The non-reducing end of a carbohydrate acceptor is typically involved in glycosidic linkage formation. The term "initial acceptor" can optionally be used herein to characterize an acceptor as used when preparing an alpha-1,4-glucan phosphorylase reaction. An initial acceptor has not yet had a glucose linked to it by alpha-1,4-glucan phosphorylase. During an alpha-1,4-glucan phosphorylase reaction, an acceptor typically serves iteratively as an acceptor for subsequent glucose addition by the phosphorylase.

"Glucose-1-phosphate" (G1P) as used herein refers to a glucose molecule with a phosphate group on the 1-carbon. G1P herein typically is alpha-D-glucose-1-phosphate (alpha-G1P), which is D-glucopyranose with alpha configuration at the anomeric center. Unless as otherwise disclosed, G1P herein is not beta-D-glucose-1-phosphate (beta-G1P).

"Inorganic phosphate", which can be denoted as "$P_i$", refers to a free phosphate ion in solution, and is distinguished from phosphate as bound in a phosphate ester such as G1P.

The terms "alpha-1,4-glucan phosphorylase reaction", "alpha-1,4-glucan phosphorylase reaction composition" and like terms are used interchangeably herein and, except as otherwise noted, refer to a reaction that is performed by an alpha-1,4-glucan phosphorylase enzyme. An alpha-1,4-glucan phosphorylase reaction generally refers to an aqueous solution/preparation comprising at least alpha-G1P, an acceptor, and an active alpha-1,4-glucan phosphorylase enzyme. It is in such a reaction where the step of contacting water, alpha-G1P, acceptor and alpha-1,4-glucan phosphorylase enzyme is performed. The term "under suitable alpha-1,4-glucan phosphorylase reaction conditions" and like terms refer to reaction conditions that support conversion of substrates (alpha-G1P and acceptor) to alpha-1,4-glucan (as extended from the acceptor) and free phosphate products via alpha-1,4-glucan phosphorylase activity. It would be understood that, in certain embodiments, as an alpha-1,4-glucan phosphorylase reaction produces insoluble alpha-1,4-glucan product, such product is present out of solution (the reaction becomes a mixture).

"Sucrose phosphorylase" as used herein is of the EC entry 2.4.1.7 and can reversibly catalyze conversion of sucrose and phosphate to fructose and alpha-G1P. Such a reaction can also be written as: sucrose+phosphate↔fructose+alpha-G1P.

The terms "sucrose phosphorylase reaction", "sucrose phosphorylase reaction composition" and like terms are used interchangeably herein and, except as otherwise noted, refer to a reaction that is performed by a sucrose phosphorylase enzyme. A sucrose phosphorylase reaction generally refers to an aqueous solution/preparation comprising at least sucrose, phosphate, and an active sucrose phosphorylase enzyme. It is in such a reaction where the step of contacting water, phosphate, and sucrose phosphorylase enzyme is performed. The term "under suitable sucrose phosphorylase reaction conditions" and like terms refer to reaction conditions that support conversion of substrates (sucrose and phosphate) to fructose and alpha-G1P products via sucrose phosphorylase activity.

An "alpha-G1P-producing enzyme" herein refers to an enzyme that can catalyze synthesis of products including at least alpha-G1P. Examples of alpha-G1P-producing enzymes include starch phosphorylase, sucrose phosphorylase, and cellodextrin phosphorylase.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

A "second reaction" as used herein refers to a reaction that is in addition to an alpha-1,4-glucan phosphorylase reaction ("first reaction"), and which provides alpha-G1P substrate for the first reaction. A second reaction herein can optionally be characterized as an "alpha-G1P-producing reaction". The combination of at least first and second reactions herein is a form of a "coupled reaction". A second reaction herein typically provides alpha-G1P by using a phosphorylase and free phosphate to phosphorolyze a disaccharide, oligosaccharide, or polysaccharide, which phosphorolysis produces at least alpha-G1P.

The terms "percent by volume", "volume percent", "vol %", "v/v %" and the like are used interchangeably herein. The percent by volume of a solute in a solution can be determined using the formula:

$$[(\text{volume of solute})/(\text{volume of solution})]\times 100\%.$$

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises at least about 10 wt % water, for example. Examples of aqueous compositions include mixtures, solutions, dispersions (e.g., colloidal dispersions), suspensions and emulsions, for example.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise insoluble alpha-glucan of the present disclosure. The terms "dispersant" and "dispersion agent" are used interchangeably herein to refer to a material that promotes the formation and/or stabilization of a dispersion.

A glucan that is "insoluble", "aqueous-insoluble", "water-insoluble" (and like terms) (e.g., insoluble alpha-1,4-glucan) does not dissolve (or does not appreciably dissolve) in water or other aqueous conditions, optionally where the aqueous conditions are further characterized to have a pH of 4-9 (e.g., pH 6-8) (i.e., non-caustic) and/or a temperature of about 1 to 85° C. (e.g., 20-25° C.). In contrast, glucans herein that are "soluble", "aqueous-soluble", "water-soluble" and the like (e.g., soluble alpha-1,4-glucan) appreciably dissolve under these conditions.

The terms "sequence identity", "identity" and the like as used herein with respect to polynucleotide or polypeptide sequences refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: N.Y. (1988); 2) *Biocomputing: Informatics and Genome Projects* (Smith, D. W., Ed.) Academic: N.Y. (1993); 3) *Computer Analysis of Sequence Data, Part I* (Griffin, A. M., and Griffin, H. G., Eds.) Humana: N.J. (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: N.Y. (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.,* 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191 (1992); Thompson, J. D. et al., *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The term "isolated" as used herein characterizes a substance (or process) in a form or environment that does not occur in nature. A non-limiting example of an isolated substance includes any non-naturally occurring substance such as alpha-1,4-glucan or any other polymer as synthesized herein (as well as any of the presently disclosed alpha-1,4-glucan phosphorylases and reactions/processes using these enzymes). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

Reactions and methods for producing glucan containing alpha-1,4 glycosidic linkages with isolated glucan phosphorylases are presently disclosed. Also disclosed are reactions and methods using isolated sucrose phosphorylases to produce alpha-glucose-1-phosphate (alpha-G1P), which can be used as a precursor for glucan synthesis.

Certain embodiments of the present disclosure concern a method for producing alpha-1,4-glucan. Such a method comprises:

(a) contacting at least water, alpha-G1P, an acceptor molecule, and an alpha-1,4-glucan phosphorylase comprising an amino acid sequence that is at least 90% identical to SEQ ID NO:32, SEQ ID NO:30, SEQ ID NO:26, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52 (or any other alpha-1,4-glucan phosphorylase listed in Table 1), wherein alpha-1,4-glucan is produced; and (b) optionally, isolating the alpha-1,4-glucan produced in step (a).

The contacting step in a method herein of producing alpha-1,4-glucan can optionally be characterized as providing an alpha-1,4-glucan phosphorylase reaction as presently disclosed, which comprises at least water, alpha-G1P, an acceptor molecule, and an alpha-1,4-glucan phosphorylase enzyme. Thus, any feature of an alpha-1,4-glucan production method herein likewise characterizes an alpha-1,4-glucan phosphorylase reaction composition as presently disclosed.

An alpha-1,4-glucan phosphorylase suitable for use in an enzymatic reaction as presently disclosed can comprise, or consist of, an amino acid sequence that is 100% identical to, or at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:26, 30, 32, 34, 38, 40, 42, 44, 46, 48, 50, or 52 (or any other alpha-1,4-glucan phosphorylase listed in Table 1), for example. In some aspects, an alpha-1,4-glucan phosphorylase enzyme with between 80-99.5% amino acid identity with SEQ ID NO:26, 30, 32, 34, 38, 40, 42, 44, 46, 48, 50, or 52 can have some of (e.g., at least 30%, 40%, 50%, 60%, 70%, 80%, or 90% of), or all of, the enzymatic activity of an alpha-1,4-glucan phosphorylase of SEQ ID NO:26, 30, 32, 34, 38, 40, 42, 44, 46, 48, 50, or 52, respectively. In some aspects, an alpha-1,4-glucan phosphorylase herein can be one that is encoded by a polynucleotide sequence comprising a sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:25, 29, 31, 33, 37, 39, 41, 43, 45, 47, 49, 51, 67, 68, 69, 70, 71, 72, 73, 74, 75, 76, 77, 78, 79, 80, or 81 (or any other alpha-1,4-glucan phosphorylase-encoding sequence listed in Table 1).

Given that certain amino acids share similar structural and/or charge features with each other (i.e., conserved), one or more amino acids of an alpha-1,4-glucan phosphorylase sequence herein (and/or other types of polypeptides herein) can optionally be substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

In some aspects, an alpha-1,4-glucan phosphorylase enzyme herein can be obtained (or is obtainable) from a microbial source, such as a bacteria or fungus (e.g., yeast). Examples of bacteria herein include Aquifex species (e.g., *A. aeolicus*), *Thermoanaerobacter* species (e.g., *T. tengcongensis, T. yonseiensis, T. subterraneus*), *Caldanaerobacter* species (e.g., *C. subterraneus, C. uzonensis*), *Paenibacillus* species, *Mycobacterium* species, *Microbacterium* species, and *Streptomyces* species. In some aspects, an alpha-1,4-glucan phosphorylase enzyme herein is metagenomic in origin (e.g., the enzyme represents a metagenomic composite and/or is obtained/obtainable from a metagenomic source).

Examples of enzymes with alpha-1,4-glucan phosphorylase activity herein can be any of the disclosed alpha-1,4-glucan phosphorylase amino acid sequences and that further include 1-300 (or any integer there between [e.g., 10, 20, 30, 40, 50, 75, 100, 150, 200, 250]) residues on the N-terminus and/or C-terminus. Such additional residues may include a heterologous sequence such as an epitope tag (at either N- or C-terminus) or a heterologous signal peptide (at N-terminus), for example. In those embodiments in which a heterologous amino acid sequence is incorporated at the N-terminus, such a heterologous sequence can be adjacent to the original start-methionine of the alpha-1,4-glucan phosphorylase, or can replace the original start methionine, for example. In the latter embodiment, a new start-methionine can be at the N-terminus of the heterologous sequence. In some aspects, an alpha-1,4-glucan phosphorylase amino acid can further comprise six or more consecutive histidine residues at its N- or C-terminus (optionally, a Leu-Glu link can be between the phosphorylase sequence and the consecutive histidine sequence).

An enzyme with alpha-1,4-glucan phosphorylase activity as presently disclosed typically lacks an N-terminal signal peptide. However, an expression system for producing an alpha-1,4-glucan phosphorylase enzyme can optionally employ an enzyme-encoding polynucleotide that further comprises sequence encoding an N-terminal signal peptide to direct extra-cellular secretion. The signal peptide in such embodiments is cleaved from the enzyme during the secretion process. Since it is believed that alpha-1,4-glucan phosphorylase enzymes disclosed herein (e.g., SEQ ID NO:26, 30, 32, 34, 38, 40, 42, 44, 46, 48, 50 and 52) are not associated with a signal peptide, any added signal peptide can be considered as heterologous to the enzyme. An example of a signal peptide herein is one from a bacterial species (e.g., a *Bacillus* species such as *B. subtilis*) or fungal species.

An alpha-1,4-glucan phosphorylase herein can be prepared by fermentation of an appropriately engineered microbial strain, for example. Recombinant enzyme production by fermentation is well known in the art using microbial species such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*), *Trichoderma* (e.g., *T. reesei*) and *Myceliophthora* (e.g., *M. thermophila*) (e.g., see Adrio and Demain, *Biomolecules* 4:117-139, 2014, which is incorporated herein by reference). A nucleotide sequence encoding an alpha-1,4-glucan phosphorylase amino acid sequence is typically linked to a heterologous promoter sequence to create an expression cassette for the enzyme, and/or is codon-optimized accordingly. Such an expression cassette may be incorporated in a suitable plasmid or integrated into the microbial host chromosome, using methods well known in the art. The expression cassette may include a transcriptional terminator nucleotide sequence following the amino acid coding sequence. The expression cassette may also include, between the promoter sequence and phosphorylase amino acid coding sequence, a nucleotide sequence encoding a signal peptide (e.g., heterologous signal peptide) that is designed for direct secretion of the alpha-1,4-glucan phosphorylase. At the end of fermentation, cells may be ruptured accordingly (typically when a signal peptide for secretion is not employed) and the phosphorylase can be isolated using methods such as precipitation, filtration, and/or concentration. Alternatively, a lysate or extract comprising a phosphorylase can be used without further isolation. If the alpha-1,4-glucan phosphorylase was secreted (i.e., it is present in the fermentation broth), it can optionally be used as isolated from, or as comprised in, the fermentation broth. The activity of an alpha-1,4-glucan phosphorylase enzyme can be confirmed by biochemical assay, if desired, such as by measuring phosphorus release when placing the enzyme in a reaction herein containing alpha-G1P and a suitable acceptor (e.g., under conditions as described in Example 5 below).

An alpha-1,4-glucan phosphorylase reaction herein produces alpha-1,4-glucan. In some aspects, about, or at least about, 90%, 91%, 92%, 93%, 94%, 95%, 96%, 97%, 98%, 99%, 99.5%, or 100% of the constituent glycosidic linkages of alpha-1,4-glucan herein are contemplated to be alpha-1,4-linkages. In some aspects, accordingly, alpha-1,4-glucan has about, or less than about, 10%, 9%, 8%, 7%, 6%, 5%, 4%, 3%, 2%, 1%, 0.5%, or 0% glycosidic linkages that are not alpha-1,4. It should be understood that the higher the percentage of alpha-1,4 linkages present in alpha-1,4-glucan, the greater the probability that the alpha-1,4-glucan is linear, since there are lower occurrences of certain linkages forming branch points in the polymer. Thus, alpha-1,4-glucan with 100% alpha-1,4 linkages is completely linear. In certain embodiments, alpha-1,4-glucan has no branch points or less than about 5%, 4%, 3%, 2%, or 1%) branch points (typically beta-1,6) as a percent of the glycosidic linkages in the polymer. In some aspects, a given linkage profile characterizes that of the alpha-1,4-glucan as synthesized from an acceptor (i.e., the linkage profile does not include the linkage profile of the acceptor). In aspects in which an alpha-1,4-glucan itself (e.g., alpha-1,4-glucan oligosaccharide) is used as the initial acceptor molecule, any of the foregoing linkage percentages can optionally characterize the entire product.

Alpha-1,4-glucan herein (typically insoluble) is contemplated to have a molecular weight in DPw or DPn of about, or at least about, 40, 50, 60, 70, 80, 90, 100, 150, 200, 250, 300, 350, 400, 450, 500, 600, 700, 800, 900, or 1000, or a range between any two of these values such as 200-600, 200-500, 200-450, 250-600, 250-500, 250-450, 300-600, 300-500, 300-450, 350-600, 350-500, or 350-450, for example. In some aspects, a given molecular weight characterizes that of the alpha-1,4-glucan as synthesized from an acceptor (i.e., the molecular weight does not include the molecular weight of the acceptor). In aspects in which an alpha-1,4-glucan itself (e.g., alpha-1,4-glucan oligosaccharide) is used as the initial acceptor molecule, any of the foregoing molecular weight disclosures can optionally characterize the entire product.

Alpha-1,4-glucan in some aspects is insoluble in aqueous conditions. Such insolubility is in non-caustic aqueous conditions, such as those conditions of an alpha-1,4-glucan phosphorylase reaction herein (see below). In some aspects, linear alpha-1,4-glucan is soluble in non-caustic aqueous conditions. Non-caustic aqueous conditions (or aqueous conditions herein) can include, for example, water or an aqueous solution with a solvent having about, or at least about, 10, 20, 30, 40, 50, 60, 70, 80, 90, 95, or 100 wt % water, and a pH of 4-9 (e.g., pH 4-8 or 6-8).

Alpha-1,4-glucan herein is typically enzymatically derived in an inert vessel (typically under cell-free conditions) (in vitro), and is not derived from a plant, animal, fungus, protist (e.g., algae), or bacteria. Some embodiments are drawn to alpha-1,4-glucan as produced by, or that are producible (obtainable) by, any of the enzymatic reaction processes/conditions disclosed herein.

A suitable acceptor molecule is used in an alpha-1,4-glucan phosphorylase reaction herein, and can optionally be characterized as an "initial acceptor" since it typically is added when first preparing a reaction. An acceptor herein typically is aqueous-soluble, or at least a portion (more than 10 wt %) thereof is soluble.

In some aspects, an acceptor molecule comprises a monosaccharide, disaccharide, or oligosaccharide. Yet in some aspects, an acceptor consists of a monosaccharide, disaccharide, or oligosaccharide (e.g., the saccharide acceptor is not chemically derivatized/substituted). A disaccharide or oligosaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units. A disaccharide or oligosaccharide can optionally comprise, typically in addition to one or more glucose monomeric units, one or more non-glucose monomeric units. In some aspects, a disaccharide or oligosaccharide comprises only non-glucose monomeric units. A non-glucose monomeric unit of a disaccharide or oligosaccharide (or a non-glucose monosaccharide acceptor) can be fructose, arabinose, xylose, or galactose in some aspects. In some aspects, an acceptor is not (does not consist of) glucose, fructose, mannose, or glucosamine. An acceptor can be linear (no branches) or branched, for example.

A disaccharide or oligosaccharide acceptor molecule herein can comprise alpha-glycosidic linkages and/or beta-glycosidic linkages. The linkages of an acceptor can be 100% alpha-glycosidic linkages, or at least about 50%, 60%, 70%, 80%, 90%, or 95% alpha-glycosidic linkages, for example. Alpha- or beta-glycosidic linkages between glucose monomers of a disaccharide or oligosaccharide acceptor can comprise one type of, or more than one type of, the following linkages: 1,1; 1,2; 1,3; 1,4; and/or 1,6. Just to illustrate, the linkages can be all alpha-1,4 glucosidic linkages or all alpha-1,6 glucosidic linkages, or a mix of alpha-1,4 and alpha-1,6 glucosidic linkages.

An oligosaccharide acceptor herein can have, have at least, or have up to, 3, 4, 5, 6, 7, 8, 9, 10, 11, 12, 13, 14, or 15 monomeric units, for example. Particular examples of such an oligosaccharide acceptor molecule can comprise only glucose monomeric units linked by alpha-1,4 linkages.

In some aspects, an acceptor molecule comprises a polysaccharide. Yet in some aspects, an acceptor consists of a polysaccharide (e.g., the polysaccharide acceptor is not chemically derivatized/substituted). A polysaccharide acceptor molecule typically comprises one or more glucose monomeric units (e.g., at least about 10%, 20%, 30%, 40%, 50%, 60%, 70%, 80%, 90%, or 95% of the monomeric units are glucose), or comprises only glucose monomeric units (i.e., glucan). A polysaccharide can optionally comprise, typically in addition to one or more glucose monomeric units, one or more non-glucose monomeric units. A non-glucose monomeric unit of a polysaccharide can be fructose, arabinose, xylose, or galactose in some aspects.

A polysaccharide acceptor molecule herein can comprise alpha-glycosidic linkages and/or beta-glycosidic linkages. The linkages of a polysaccharide acceptor can be 100% alpha-glycosidic linkages (e.g., alpha-glucan), or at least about 50%, 60%, 70%, 80%, 90%, or 95% alpha-glycosidic linkages, for example. Alpha- or beta-glycosidic linkages between glucose monomers of a polysaccharide acceptor can comprise one type of, or more than one type of, the following linkages: 1,1; 1,2; 1,3; 1,4; and/or 1,6. Just to illustrate, the linkages can be all alpha-1,4 glucosidic linkages, or a mix of alpha-1,4 and alpha-1,6 glucosidic linkages (e.g., alpha-1,4-glucan with pendant alpha-1,6-linked glucose groups, or spans of alpha-1,4-glucan iteratively linked together through alpha-1,6 linkage [i.e., branch-on-branch]). A polysaccharide in some embodiments can be starch, amylopectin, or glycogen. A polysaccharide acceptor herein typically is aqueous-soluble.

A polysaccharide acceptor herein can have a DP or DPw of about, or at least about, 16, 17, 18, 19, 20, 21, 22, 23, 24, 25, 26, 27, 28, 29, 30, 35, 40, 45, 50, 75, 100, 150, 200, 250, 300, 400, or 500, for example. This DP/DPw can optionally be expressed as a range between any two of these values.

In some embodiments, an acceptor can have 2-40, 3-40, 4-40, 5-40, 10-40, 2-35, 3-35, 4-35, 5-35, 10-35, 2-30, 3-30, 4-30, 5-30, 10-30, 14-30, 2-25, 3-25, 4-25, 5-25, 10-25, 2-20, 3-20, 4-20, 5-20, or 10-20, monomeric units (e.g., only glucose units), and optionally be linked only by alpha-1,4 linkages.

The temperature of an alpha-1,4-glucan phosphorylase reaction herein can be controlled, if desired. In some aspects, the temperature is between about 5° C. to about 70° C. The temperature in some aspects is between about 20° C. to about 42° C. In still some aspects, the temperature is about 20, 25, 30, 35, 40, 45, 50, 55, 60, 65, 70, 28-32, 48-52, 20-60, 20-55, 20-50, 20-45, 20-40, 20-35, 20-30, 25-60, 25-55, 25-50, 25-45, 25-40, 25-35, 25-30, 30-60, 30-55, 30-50, 30-45, 30-40, 30-35, 35-60, 35-55, 35-50, 35-45, 35-40, 40-60, 40-55, 40-50, 40-45, 45-60, 45-55, 45-50, 50-60, 50-55, 55-70, 55-67, 55-65, 55-60, 60-70, 60-67, 60-65, 63-70, 63-67, 63-65, 65-70, or 65-67° C.

The pH of an alpha-1,4-glucan phosphorylase reaction composition in some aspects can be about 4.0-9.0, 4.0-8.5, 4.0-8.0, 5.0-8.0, 6.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate (e.g., sodium phosphate buffer), tris (tris [hydroxymethyl] aminomethane; e.g., Tris-HCl), citrate, or a combination thereof. Buffer concentration in the enzymatic reaction can be from 0 mM to about 100 or 150 mM, or about 10, 25, 50, 75, or 100 mM, for example. In some aspects, a buffer comprises, or consists of, tris; in this and some other aspects, a buffer optionally does not comprise phosphate.

The initial concentration of alpha-G1P in an alpha-1,4-glucan phosphorylase reaction herein can be about, or at least about, 1 to 100 mM, for example. Also for example, the alpha-G1P initial concentration can be about, or at least about, 1, 5, 10, 20, 30, 40, 50, 60, 70, 80, 90, or 100 mM, or about 10-50 mM. The initial concentration of an acceptor in an alpha-1,4-glucan phosphorylase reaction herein can be about 1 to 50 mM, for example. In some aspects, the initial concentration of an acceptor can be about, or at least about, 1, 5, 10, 15, 20, 25, 30, 35, 40, 45, or 50 mM, or about 1-10 or 5-10 mM. Still, in some aspects, the initial concentration of an acceptor can be about, or at least about, 0.05, 0.1, 0.5, 1.0, 2.5, 5, 7.5, or 10 g/L. "Initial concentration" of a substrate such as alpha-G1P or acceptor refers to the substrate concentration in an enzymatic reaction just after all the reaction components have been added (at least water, alpha-G1P, acceptor, alpha-1,4-glucan phosphorylase).

The amount of an alpha-1,4-glucan phosphorylase enzyme (active enzyme) comprised in an enzymatic reaction in some aspects can be about 0.01-60 mg/mL. For example, about, or at least about, 0.01, 0.05, 0.1, 0.5, 1, 5, 8, 10, 20, 30, 40, 50, or 60 mg/mL of enzyme can be employed in a reaction. A reaction herein can comprise one, two, or more alpha-1,4-glucan phosphorylase enzymes, for example. In some aspects, only one or two alpha-1,4-glucan phosphorylase enzymes is/are comprised in a reaction. A reaction composition herein can be, and typically is, cell-free (e.g., no whole cells present).

A reaction composition can be contained within any vessel (e.g., an inert vessel/container) suitable for applying one or more reaction conditions disclosed herein. An inert vessel in some aspects can be of stainless steel, plastic, or glass (or comprise two or more of these components) and be of a size suitable to contain a particular reaction. An inert vessel can optionally be equipped with a stirring device. A reaction composition in some aspects can be comprised within a product/application; production of alpha-1,4-glucan in such aspects can optionally be characterized as in situ production. In situ produced alpha-1,4-glucan typically is not subject to any downstream isolation process, but can be if desired. Any of the foregoing features, for example, can be used to characterize an isolated reaction herein.

Completion of a reaction in some aspects can be determined visually (e.g., no more accumulation of insoluble product), and/or by measuring the remaining amount of substrate(s) (alpha-G1P and/or acceptor) in the reaction (e.g., no more decrease in substrate levels over time). A reaction herein can be conducted for about, or at least about, 0.5, 1, 2, 4, 6, 8, 10, 12, 14, 16, 18, 20, 22, 24, 36, 48, 60, 72, 84, 96, 108, 120, 132, 144, 156, 168, 180, 192, 204, or 215 hours, for example.

The contacting step in a method herein of producing alpha-1,4-glucan can be performed in any number of ways. For example, a desired amount of alpha-G1P and/or acceptor can first be dissolved in water (optionally, other components may also be added at this stage of preparation, such as buffer components), followed by addition of one or more alpha-1, 4-glucan phosphorylase enzymes. The reaction may be kept still, or agitated (e.g., via stirring or orbital shaking), for example.

In some aspects, isolating alpha-1,4-glucan can include at least conducting a step of centrifugation, filtration, fractionation, chromatographic separation, dialysis, evaporation, and/or dilution. Isolation of insoluble alpha-1,4-glucan can include at least conducting a centrifugation or filtration step, for example, and can optionally further comprise washing the centrifuged and/or filtered alpha-1,4-glucan one, two, or more times with water or other aqueous liquid. A wash volume can optionally be at least about 10-100% of the volume of the reaction composition used to produce the alpha-1,4-glucan. Washing can be done by various modes, as desired, such as by displacement or re-slurry washing. Isolation herein can optionally further comprise drying alpha-1,4-glucan, and/or preparing an aqueous composition comprising insoluble alpha-1,4-glucan (e.g., dispersion).

An isolated alpha-1,4-glucan product herein, as provided in a dry form, can comprise no more than 2.0, 1.5, 1.0, 0.5, 0.25, 0.10, 0.05, or 0.01 wt % water, for example. In some aspects, an alpha-1,4-glucan product is provided in an amount of at least 1 gram (e.g., at least 2.5, 5, 10, 25, 50, 100, 250, 500, 750, or 1000 g); such an amount can be a dry amount, for example.

In some aspects, alpha-1,4-glucan that has been isolated (optionally characterized as "purified") can be present in a composition at a wt % (dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%. Such isolated alpha-1,4-glucan can be used as an ingredient/component in a product/application, for example.

Alpha-G1P for performing an alpha-1,4-glucan production method herein can be provided directly via addition of isolated alpha-G1P (e.g., alpha-G1P obtained from a commercial source), for example. Alternatively, alpha-G1P can be supplied by providing at least a second reaction, wherein the products of the second reaction comprise alpha-G1P (i.e., the second reaction produces alpha-G1P as a product).

A second reaction in some aspects can be provided in the same vessel in which an alpha-1,4-glucan phosphorylase enzymatic reaction (first reaction) is performed, and in which case can optionally be characterized as a "coupled reaction" (such aspects include in situ reaction compositions as disclosed above, for example). Alternatively, a second reaction can be performed outside of (separate from) the vessel in which a first reaction is performed. A second reaction can be performed before and/or continuously with a first reaction, for example. The conditions (e.g., time, temperature, pH) of a second reaction herein can be as disclosed for a first reaction, for example.

A second reaction for providing alpha-G1P in some aspects produces alpha-G1P by contacting (i) water, (ii) inorganic phosphate, (iii) a disaccharide, oligosaccharide, or polysaccharide (all of which comprise one or more glucose monomeric units), and (iv) a phosphorylase that phosphorolyzes the disaccharide, oligosaccharide, or polysaccharide. A phosphorylase in this aspect is an example of an alpha-G1P-producing enzyme herein. The monomeric units of a disaccharide, oligosaccharide, or polysaccharide substrate in a second reaction can be all glucose, or at least 30%, 40%, 50%, 60%, 70%, 80%, or 90% glucose, for example. The glycosidic linkages between the monomeric units can be alpha- and/or beta-linkages, and can be one type of, or more than one type of, the following linkages: 1,1; 1,2; 1,3; 1,4; and/or 1,6. A disaccharide or trisaccharide is typically employed in a second reaction herein.

Examples of a suitable phosphorylase as an alpha-G1P-producing enzyme herein include starch phosphorylase, sucrose phosphorylase and cellodextrin phosphorylase. In the presence of at least water and inorganic phosphate, these enzymes, respectively, convert starch (optionally debranched with a starch debranching enzyme such as pullulanase and/or isoamylase), sucrose, and cellodextrin (optionally prepared by treating cellulose with one or more beta-1,4-endoglucanases such as cellulase and/or endo-beta-1,4-glucanase, and optionally further with a lytic polysaccharide monooxygenase and/or cellobiohydrolase) to products including alpha-G1P. Any of these enzymes can have a plant, microbial (e.g., bacterial), or fungal (e.g., yeast) origin, for example. Examples of starch phosphorylase are disclosed in Patent Appl. Publ. No. 2002/0133849 and Tiwari and Kumar (2012, *Biotechnol. Mol. Biol. Rev.* 7:69-83), which are incorporated herein by reference. Examples of cellodextrin phosphorylases are disclosed in U.S. Pat. No. 8,889,379, and U.S. Patent Appl. Publ. Nos. 2014/0087435, 2014/0057323, 2013/0059340 and 2017/0327857, which are incorporated herein by reference. Examples of sucrose phosphorylase are disclosed in U.S. Pat. Nos. 5,716,837, 7,229,801 and 7,968,309, which are incorporated herein by reference. Further examples of sucrose phosphorylase comprise, or consist of, an amino acid sequence that is 100% identical to, or at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24; additional information regarding these sucrose phosphorylase enzymes is provided below.

Some embodiments of the present disclosure concern a composition comprising an isolated alpha-1,4-glucan phosphorylase that comprises an amino acid sequence that is at least 90% identical to SEQ ID NO:32, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52 (or any other alpha-1,4-glucan phosphorylase listed in Table 1). Such an alpha-1,4-glucan phosphorylase can have any of the features as disclosed herein for an alpha-1,4-glucan phosphorylase as used in an alpha-1,4-glucan synthesis method, for example. Some examples of a composition comprising an isolated alpha-1,4-glucan phosphorylase include (i) an isolated alpha-1,4-glucan phosphorylase reaction composition as disclosed herein, and (ii) a recombinant cell (or lysate thereof) that heterologously expresses the alpha-1,4-glucan phosphorylase. In some aspects, an isolated (optionally "purified") alpha-1,4-glucan phosphorylase can be present in a composition at a wt % (dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%.

Some embodiments of the present disclosure concern a composition comprising a polynucleotide that comprises a nucleotide sequence encoding an isolated alpha-1,4-glucan phosphorylase comprising an amino acid sequence that is at least 90% identical to SEQ ID NO:32, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52 (or any other alpha-1,4-glucan phosphorylase listed in Table 1). Such an alpha-1,4-glucan phosphorylase can have any of the features as disclosed herein for an alpha-1,4-glucan phosphorylase as used in an alpha-1,4-glucan synthesis method, for example. Optionally, one or more regulatory sequences are operably linked to the nucleotide sequence; an example of a regulatory sequence is a promoter sequence. In some aspects, a polynucleotide herein encoding an alpha-1,4-glucan phosphorylase comprises a sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:31, 33, 37, 39, 41, 43, 45, 47, 49, 51, 67, 68, 69, 70, 71, 72, 73, 74, 75, 76, 77, 78, 79, 80, or 81 (or any other alpha-1,4-glucan phosphorylase-encoding sequence listed in Table 1).

A polynucleotide comprising a nucleotide sequence encoding an alpha-1,4-glucan phosphorylase herein can be a vector or construct useful for transferring a nucleotide sequence into a cell, for example. Examples of a suitable vector/construct can be selected from a plasmid, yeast artificial chromosome (YAC), cosmid, phagemid, bacterial artificial chromosome (BAC), virus, or linear DNA (e.g., linear PCR product). A polynucleotide sequence in some aspects can be capable of existing transiently (i.e., not integrated into the genome) or stably (i.e., integrated into the genome) in a cell. A polynucleotide sequence in some aspects can comprise, or lack, one or more suitable marker sequences (e.g., selection or phenotype marker).

A polynucleotide sequence in certain embodiments can comprise one or more regulatory sequences operably linked to the nucleotide sequence encoding an alpha-1,4-glucan phosphorylase herein. For example, a nucleotide sequence encoding an alpha-1,4-glucan phosphorylase can be in operable linkage with a promoter sequence (e.g., a heterologous promoter). A promoter sequence can be suitable for expression in a cell (e.g., bacterial cell such as *E. coli* or *Bacillus*; eukaryotic cell such as a fungus, yeast, insect, or mammalian cell) or in an in vitro protein expression system, for example. Examples of other suitable regulatory sequences are disclosed herein (e.g., transcription terminator sequences).

Some aspects herein are drawn to a cell (host cell) comprising a polynucleotide sequence as presently disclosed. Such a cell can be any type disclosed herein (e.g., bacterial cell such as *E. coli* or *Bacillus* [e.g., *B. subtilis*]; eukaryotic cell such as a fungus, yeast, insect, or mammalian cell). Optionally, a cell can express the alpha-1,4-glucan phosphorylase encoded by the polynucleotide sequence; in such embodiments, the nucleotide encoding the alpha-1,4-glucan phosphorylase is typically operably linked to a promoter that is functional in the cell. In some aspects, the polynucleotide sequence exists transiently (i.e., not integrated into the genome) or stably (i.e., integrated into the genome) in the cell. A polynucleotide sequence herein as comprised in a cell typically is not derived (derivable) from that cell.

Some embodiments of the present disclosure concern a method for producing alpha-G1P. Such a method comprises:

(a) contacting at least water, inorganic phosphate, sucrose, and a sucrose phosphorylase comprising an amino acid sequence that is at least 90% identical to SEQ ID NO:10, SEQ ID NO:12, SEQ ID NO:14, SEQ ID NO:20, or SEQ ID NO:22 (or any other sucrose phosphorylase listed in Table 1), wherein alpha-G1P is produced; and (b) optionally, isolating the alpha-G1P produced in step (a).

The contacting step in a method herein of producing alpha-G1P can optionally be characterized as providing a sucrose phosphorylase reaction as presently disclosed, which comprises at least water, inorganic phosphate, sucrose, and a sucrose phosphorylase enzyme. Thus, any feature of an alpha-G1P production method herein likewise characterizes a sucrose phosphorylase reaction composition as presently disclosed.

A sucrose phosphorylase suitable for use in an enzymatic reaction as presently disclosed can comprise, or consist of, an amino acid sequence that is 100% identical to, or at least 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:10, SEQ ID NO:12, SEQ ID NO:14, SEQ ID NO:20, or SEQ ID NO:22 (or any other sucrose phosphorylase listed in Table 1), for example. In some aspects, a sucrose phosphorylase enzyme with between 80-99.5% amino acid identity with SEQ ID NO:10, 12, 14, 20, or 22 can have some of (e.g., at least 30%, 40%, 50%, 60%, 70%, 80%, or 90% of), or all of, the enzymatic activity of a sucrose phosphorylase of SEQ ID NO:10, 12, 14, 20, or 22, respectively. In some aspects, a sucrose phosphorylase herein can be one that is encoded by a polynucleotide sequence comprising a sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:9, 11, 13, 19, 21, 55, 56, 57, 58, 59, 60, 61, 62, 63, 64, 65, or 66 (or any other sucrose phosphorylase-encoding sequence listed in Table 1).

In some aspects, a sucrose phosphorylase enzyme herein can be obtained (or is obtainable) from a microbial source, such as a bacteria or fungus (e.g., yeast). Examples of bacteria herein include *Leuconostoc* species (e.g., *L. mesenteroides*), *Bifidobacterium* species (e.g., *B. adolescentis, B. longum*), *Lactobacillus* species (e.g., *L. amylovorus*), *Streptomyces* species, *Alkalimonas* species, *Bacillus* species, *Aerococcus* species, *Clostridiaceae* species, *Herbinix* species, *Cellulomonas* species, *Actinotalea* species, and *Paenibacillus* species. In some aspects, a sucrose phosphorylase enzyme herein is metagenomic in origin (e.g., the enzyme represents a metagenomic composite and/or is obtained/obtainable from a metagenomic source).

Examples of enzymes with sucrose phosphorylase activity herein can be any of the disclosed sucrose phosphorylase amino acid sequences and that further include 1-300 (or any integer there between [e.g., 10, 20, 30, 40, 50, 75, 100, 150, 200, 250]) residues on the N-terminus and/or C-terminus. Such additional residues may include a heterologous sequence such as an epitope tag (at either N- or C-terminus) or a heterologous signal peptide (at N-terminus), for example. In those embodiments in which a heterologous amino acid sequence is incorporated at the N-terminus, such a heterologous sequence can be adjacent to the original start-methionine of the sucrose phosphorylase, or can replace the original start methionine, for example. In the latter embodiment, a new start-methionine can be at the N-terminus of the heterologous sequence. In some aspects, a sucrose phosphorylase amino acid can further comprise six or more consecutive histidine residues at its N- or C-terminus (optionally, a Leu-Glu link can be between the phosphorylase sequence and the consecutive histidine sequence).

An enzyme with sucrose phosphorylase activity as presently disclosed typically lacks an N-terminal signal peptide. However, an expression system for producing a sucrose phosphorylase enzyme can optionally employ an enzyme-encoding polynucleotide that further comprises sequence encoding an N-terminal signal peptide to direct extra-cellular secretion. The signal peptide in such embodiments is cleaved from the enzyme during the secretion process. Since it is believed that sucrose phosphorylase enzymes disclosed herein are not associated with a signal peptide, any added signal peptide can be considered as heterologous to the enzyme. An example of a signal peptide herein is one from a bacterial species (e.g., a *Bacillus* species such as *B. subtilis*) or fungal species.

A sucrose phosphorylase herein can be prepared by fermentation of an appropriately engineered microbial strain, for example, as described above for preparing an alpha-1,4-glucan phosphorylase. The activity of a sucrose phosphorylase enzyme can be confirmed by biochemical assay, if desired, by measuring phosphorus release when placing the enzyme in a reaction herein containing alpha-G1P and fructose (e.g., under any of the conditions as described in Example 4 below).

Features of a sucrose phosphorylase reaction herein (e.g., temperature, pH, amount of enzyme, reaction vessel) can be the same as, or similar to, those as disclosed herein for alpha-1,4-glucan phosphorylase reactions. The initial concentration of inorganic phosphate in a sucrose phosphorylase reaction herein can be about, or at least about, 1 to 150 mM, for example. Also for example, the inorganic phosphate initial concentration can be about, or at least about, 10, 20, 30, 40, 50, 75, 100 125, or 150 mM. In some aspects, one or more features of a sucrose phosphorylase reaction herein can be any of those as disclosed in U.S. Pat. Appl. Publ. Nos. 2013/0029384 and 2008/0206822, which are incorporated herein by reference.

Some embodiments of the present disclosure concern a composition comprising an isolated sucrose phosphorylase that comprises an amino acid sequence that is at least 90% identical to SEQ ID NO:10, SEQ ID NO:12, SEQ ID NO:14, or SEQ ID NO:22 (or any other sucrose phosphorylase listed in Table 1). Such a sucrose phosphorylase can have any of the features as disclosed herein for a sucrose phosphorylase as used in an alpha-G1P synthesis method, for example. Some examples of a composition comprising an isolated sucrose phosphorylase include (i) an isolated sucrose phosphorylase reaction composition as disclosed herein, and (ii) a recombinant cell (or lysate thereof) that heterologously expresses the sucrose phosphorylase. In some aspects, an isolated (optionally "purified") sucrose phosphorylase can be present in a composition at a wt % (dry weight basis) of at least about 50%, 60%, 70%, 80%, 85%, 90%, 91%, 92%, 93%, 94%, 95%, 96%, 97%, 98%, 98.5%, 99% 99.5% 99.8% or 99.9%.

Some embodiments of the present disclosure concern a composition comprising a polynucleotide that comprises a nucleotide sequence encoding an isolated sucrose phosphorylase comprising an amino acid sequence that is at least 90% identical to SEQ ID NO:10, SEQ ID NO:12, SEQ ID NO:14, or SEQ ID NO:22 (or any other sucrose phosphorylase listed in Table 1). Such a sucrose phosphorylase can have any of the features as disclosed herein for a sucrose phosphorylase as used in an alpha-G1P method, for example. Optionally, one or more regulatory sequences are operably linked to the nucleotide sequence; an example of a regulatory sequence is a promoter sequence. Features of a polynucleotide comprising a sequence encoding a sucrose phosphorylase herein can be any of those as described above for sequences encoding an alpha-1,4-glucan phosphorylase, for example. In some aspects, a polynucleotide herein encoding a sucrose phosphorylase comprises a sequence that is 100% identical to, or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to, SEQ ID NO:9, 11, 13, 14, 21, 55, 56, 57, 58, 59, 60, 61, 62, 63, 64, 65, or 66 (or any other sucrose phosphorylase-encoding sequence listed in Table 1).

Non-limiting examples of compositions and methods disclosed herein include:

1. A method for producing alpha-1,4-glucan, the method comprising: (a) contacting at least water, alpha-G1P, an acceptor molecule, and an alpha-1,4-glucan phosphorylase comprising an amino acid sequence that is at least 90% identical to SEQ ID NO:32, SEQ ID NO:30, SEQ ID NO:26, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52, wherein alpha-1,4-glucan is produced; and (b) optionally, isolating the alpha-1,4-glucan produced in step (a).

2. The method of embodiment 1, wherein the acceptor molecule comprises a monosaccharide, disaccharide, or oligosaccharide.

3. The method of embodiment 1 or 2, wherein the acceptor molecule comprises alpha-1,4 glycosidic linkages and has a DP of 2 to 35.

4. The method of embodiment 1, wherein the acceptor molecule comprises a polysaccharide.

5. The method of embodiment 1, 2, 3, or 4, wherein the alpha-1,4-glucan has at least about 90% alpha-1,4 glycosidic linkages.

6. The method of embodiment 5, wherein the alpha-1,4-glucan has at least about 99% alpha-1,4 glycosidic linkages.

7. The method of embodiment 1, 2, 3, 4, 5, or 6, wherein the DP of the alpha-1,4-glucan is at least 3.

8. The method of embodiment 1, 2, 3, 4, 5, 6, or 7, wherein the alpha-G1P is provided in step (a) by providing a second reaction, wherein the products of the second reaction comprise alpha-G1P.

9. The method of embodiment 8, wherein the second reaction is provided in the same vessel in which step (a) is performed, and wherein the second reaction is performed before and/or continuously with step (a).

10. The method of embodiment 8 or 9, wherein the second reaction produces alpha-G1P by contacting (i) water, (ii) inorganic phosphate, (iii) a glucose-comprising disaccharide, oligosaccharide, or polysaccharide, and (iv) a phosphorylase that phosphorolyzes the disaccharide, oligosaccharide, or polysaccharide.

11. The method of embodiment 10, wherein the second reaction comprises: (I) water, inorganic phosphate, sucrose, and a sucrose phosphorylase; (II) water, inorganic phosphate, starch, and a starch phosphorylase; or (III) water, inorganic phosphate, cellodextrin, and a cellodextrin phosphorylase.

12. The method of embodiment 10, wherein the second reaction comprises water, inorganic phosphate, sucrose, and a sucrose phosphorylase comprising an amino acid sequence that is at least 90% identical to SEQ ID NO:8, SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, or SEQ ID NO:24.

13. A reaction composition comprising at least water, alpha-G1P (e.g., provided by a second reaction according to any of embodiments 8-12), an acceptor molecule (e.g., according to any of embodiments 2-4), and an alpha-1,4-glucan phosphorylase comprising an amino acid sequence that is at least 90% identical to SEQ ID NO:32, SEQ ID NO:30, SEQ ID NO:26, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52, wherein the alpha-1,4-glucan phosphorylase synthesizes alpha-1,4-glucan (e.g., according to any of embodiments 5-7).

14. A composition comprising an isolated alpha-1,4-glucan phosphorylase that comprises an amino acid sequence that is at least 90% identical to SEQ ID NO:32, SEQ ID NO:34, SEQ ID NO:38, SEQ ID NO:40, SEQ ID NO:42, SEQ ID NO:44, SEQ ID NO:46, SEQ ID NO:48, SEQ ID NO:50, or SEQ ID NO:52.

15. A composition comprising a polynucleotide that comprises a nucleotide sequence encoding an isolated alpha-1,4-glucan phosphorylase according to embodiment 14, optionally wherein one or more regulatory sequences are operably linked to the nucleotide sequence, and preferably wherein the one or more regulatory sequences include a promoter sequence.

16. A method for producing alpha-G1P, the method comprising: (a) contacting at least water, inorganic phosphate, sucrose, and a sucrose phosphorylase comprising an amino acid sequence that is at least 90% identical to SEQ ID NO:10, SEQ ID NO:12, SEQ ID NO:14, SEQ ID NO:20, or SEQ ID NO:22, wherein alpha-G1P is produced; and (b) optionally, isolating the alpha-G1P produced in step (a).

17. A reaction composition comprising at least water, inorganic phosphate, sucrose, and a sucrose phosphorylase comprising an amino acid sequence that is at least 90% identical to SEQ ID NO:10, SEQ ID NO:12, SEQ ID NO:14, SEQ ID NO:20, or SEQ ID NO:22, wherein the sucrose phosphorylase produces alpha-G1P.

18. A composition comprising an isolated sucrose phosphorylase that comprises an amino acid sequence that is at least 90% identical to SEQ ID NO:10, SEQ ID NO:12, SEQ ID NO:14, or SEQ ID NO:22.

19. A composition comprising a polynucleotide that comprises a nucleotide sequence encoding an isolated sucrose phosphorylase according to embodiment 18, optionally wherein one or more regulatory sequences are operably linked to the nucleotide sequence, and preferably wherein the one or more regulatory sequences include a promoter sequence.

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Identification of Putative Sucrose Phosphorylases

This Example describes identification of various putative sucrose phosphorylase enzymes. Specifically, the amino acid sequences of twelve putative sucrose phosphorylases were identified. These enzymes were denoted as Sp14 (SEQ ID NO:2), Sp15 (SEQ ID NO:4), Sp16 (SEQ ID NO:6), Sp17 (SEQ ID NO:8), Sp157 (SEQ ID NO:10), Sp159 (SEQ ID NO:12), Sp236 (SEQ ID NO:14), Sp254 (SEQ ID NO:16), Sp277 (SEQ ID NO:18), Sp75 (SEQ ID NO:20), Sp156 (SEQ ID NO:22) and Sp158 (SEQ ID NO:24). The respective SEQ ID numbers for genetic coding sequences (codon-optimized) of these enzymes are listed in Table 1. An alignment of the amino acid sequence of each of these enzymes was made against the GENBANK database via a BLAST search on the National Center for Biotechnology Information (NCBI) website. Table 2 lists database sequences provided by each alignment with the highest amino acid identity to the respective query sequence.

TABLE 2

Sequences Provided by BLAST Alignment of Putative Sucrose Phosphorylase Amino Acid Sequences Against the GENBANK Database

| Enzyme Name | SEQ ID NO.[c] | Origin | Aligning Database Sequence(s)[a] (% Identity)[b] |
|---|---|---|---|
| Sp14 | 2 | *Leuconostoc mesenteroides* | Q59495.1 (100%) |
| SP15 | 4 | *Bifidobacterium adolescentis* | WP_011742626.1 (100%) |
| Sp16 | 6 | *Bifidobacterium longum* | WP_022527209.1 (100%) |
| Sp17 | 8 | *Lactobacillus amylovorus* GRL1118 | WP_013642252.1 (100%) |
| Sp157 | 10 | *Streptomyces* sp. K96/N1.7S | WP_052666921.1 (69%) |
| Sp159 | 12 | *Alkalimonas* sp. SWT317 | WP_091340150.1 (88%) |
| Sp236 | 14 | *Bacillus* sp. SWT141 | WP_093047252.1 (85%) |
| Sp254 | 16 | *Aerococcus* sp. RPC0096 | WP_094517945.1 (99%) |
| Sp277 | 18 | metagenomic sample "GK14-2 Sorokin" | WP_086942797.1 (100%) |
| Sp75 | 20 | *Herbinix* sp. L100 | WP_103201760.1 (99%) |
| Sp156 | 22 | *Cellulomonas* sp. SWT255 | WP_035058588.1 (81%) |
| Sp158 | 24 | *P. daejeonensis* | WP_020617781.1 (100%) |

[a]GENBANK database Accession Number is provided for each aligning sequence.
[b]Percent identity of aligning sequence to entire query sequence or at least a 94% portion thereof.
[c]Query sequence used in alignment against GENBANK database sequences.

Example 2

Identification of Putative Alpha-1,4-Glucan Phosphorylases

This Example describes identification of various putative alpha-1,4-glucan phosphorylase enzymes. Specifically, the amino acid sequences of fifteen putative alpha-1,4-glucan phosphorylases were identified. These enzymes were denoted as GP-3 (SEQ ID NO:26), GP-4 (SEQ ID NO:28), GP-5 (SEQ ID NO:30), GP-006 (SEQ ID NO:32), GP-011 (SEQ ID NO:34), GP-017 (SEQ ID NO:36), GP-022 (SEQ ID NO:38), GP-005 (SEQ ID NO:40), GP-007 (SEQ ID NO:42), GP-009 (SEQ ID NO:44), GP-013 (SEQ ID NO:46), GP-043 (SEQ ID NO:48), GP-044 (SEQ ID NO:50), GP-046 (SEQ ID NO:52) and GP-048 (SEQ ID NO:54). An alignment of the amino acid sequence of each of these enzymes was made against the GENBANK database via a BLAST search on the NCBI website. Table 3 lists database sequences provided by each alignment with the highest amino acid identity to the respective query sequence.

TABLE 3

Sequences Provided by BLAST Alignment of Putative Alpha-1,4-Glucan Phosphorylase Amino Acid Sequences Against the GENBANK Database

| Enzyme Name | SEQ ID NO.[c] | Origin | Aligning Database Sequence(s)[a] (% Identity)[b] |
|---|---|---|---|
| GP-3 | 26 | *Aquifex aeolicus* | WP_010880430.1 (100%) |
| GP-4 | 28 | *Thermus caldophilus* GK24 | AAV68178.1 (100%) |
| GP-5 | 30 | *Caldanaerobacter subterraneus* | WP_011025994.1 (100%) |

TABLE 3-continued

Sequences Provided by BLAST Alignment of Putative Alpha-1,4-Glucan Phosphorylase Amino Acid Sequences Against the GENBANK Database

| Enzyme Name | SEQ ID NO.[c] | Origin | Aligning Database Sequence(s)[a] (% Identity)[b] |
|---|---|---|---|
| GP-006 | 32 | metagenomic sample "GK14-2 Sorokin" | WP_011430941.1 (86%)<br>WP_099834812.1 (86%)<br>WP_011434232.1 (86%) |
| GP-011 | 34 | *Paenibacillus* sp. DSM-34 | WP_079409940.1 (77%)<br>WP_068668363.1 (77%) |
| GP-017 | 36 | metagenomic sample "354 Sorokin" | GBD05908.1 (98%) |
| GP-022 | 38 | metagenomic sample "346 Sorokin" | ODV04609.1 (78%)<br>WP_018508004.1 (78%)<br>WP_066919075.1 (78%) |
| GP-005 | 40 | *Mycobacterium* sp. | WP_059157026.1 (88%)<br>WP_011856323.1 (88%)<br>WP_011561239.1 (88%) |
| GP-007 | 42 | *Paenibacillus filicis* DSM-23916 | WP_072334811.1 (77%) |
| GP-009 | 44 | *Microbacterium* sp. | WP_055963981.1 (76%)<br>WP_018170528.1 (76%)<br>WP_045299026.1 (76%)<br>WP_109209232.1 (76%)<br>WP_106813675.1 (76%)<br>WP_019181571.1 (76%) |
| GP-013 | 46 | metagenomic sample "330 Sorokin" | PWB39980.1 (69%)<br>PKO70515.1 (69%) |
| GP-043 | 48 | metagenomic sample "354 Sorokin" | WP_072151093.1 (85%)<br>WP_072263590.1 (85%)<br>CUU10065.1 (85%)<br>WP_072149868.1 (85%)<br>WP_072211730.1 (85%) |
| GP-044 | 50 | metagenomic | KPK29981.1 (60%) |
| GP-046 | 52 | *Streptomyces* sp. K96/N1.7S | WP_052664491.1 (65%) |
| GP-048 | 54 | metagenomic sample "BG-15 Sorokin" | GBD01646.1 (100%) |

[a]GENBANK database Accession Number is provided for each aligning sequence.
[b]Percent identity of aligning sequence to entire query sequence or at least a 98% portion thereof.
[c]Query sequence used in alignment against GENBANK database sequences.

Example 3

Cloning and Expression of Putative Sucrose Phosphorylases and Alpha-1,4-Glucan Phosphorylases This Example describes cloning and expression of the putative sucrose phosphorylase and alpha-1,4-glucan phosphorylase enzymes identified in Examples 1 and 2.

Nucleic acid sequences encoding the putative sucrose phosphorylases listed in Table 2 and the putative alpha-1,4-glucan phosphorylases listed in Table 3 were codon-optimized for expression in *Bacillus subtilis*. These sequences, which are listed in Table 1 as SEQ ID NOs:55-81, were individually inserted into replicating shuttle vector pHYT. The pHYT vector was derived from vector pHY300PLK (Takara), which is described in International Pat. Appl. Publ. No. WO2017/062687 and U.S. Pat. Appl. Publ. No. 2018/0265852 (both incorporated herein by reference). Each coding sequence as inserted into the pHYT vector further encoded a Leu-Glu-6×His-tag at the C-terminus. It is noted that each of SEQ ID NOs:55, 56, 57, 58, 67, 68 and 69 encode an extra Ala (inserted as position-2) as compared to the amino acid sequences of SEQ ID NOs:2, 4, 6, 8, 26, 28 and 30, respectively.

Each expression plasmid was individually transformed into *Bacillus subtilis* and the transformation mixes were spread onto Luria agar plates supplemented with 25 ppm tetracycline. Colonies carrying correct expression plasmids, as confirmed by polymerase chain reaction (PCR) and sequencing analyses, were inoculated into appropriate fermentation cultures to express each phosphorylase into the culture supernatant.

Each phosphorylase expression product present in the fermentation culture supernatant was purified using Ni-NTA affinity chromatography (HisPure™ ThermoScientific). Briefly, after incubating Ni-NTA resin with culture supernatant, the resin was washed two times with MILLI-Q water and once with wash buffer (10 mM imidazole, 50 mM Tris buffer pH 7.5, 500 mM NaCl, 10% glycerol) with intermediate centrifugation steps of 100×g. Each phosphorylase was eluted from the resin in elution buffer (250 mM imidazole, 50 mM Tris buffer pH 7.5, 500 mM NaCl, 10% glycerol) with centrifugation at 100×g. Each eluted phosphorylase was dialyzed against 5 mM Tris buffer pH 6.0 buffer using a 96-well DISPODIALYZER (10000-Dalton MWCO; Harvard Apparatus, Holliston, Mass.). After dialysis, phosphorylase enzyme concentration was determined by Bradford assay using bovine serum albumin (BSA) as a protein standard. Normalization of each purified phosphorylase to 20 ppm was achieved by appropriate dilution with 5 mM Tris pH 6.0 buffer.

Example 4

Analysis of Sucrose Phosphorylase Activity

This Example describes various assays that were used to measure the activity of the putative sucrose phosphorylases expressed and purified in Example 3.

PABAH assays were conducted to measure production of the reducing sugar, fructose, by the action of sucrose phosphorylase on sucrose (phosphorolytic direction). Sucrose phosphorylase enzyme activity was measured as follows: Individual reactions (100 μL volume) containing 50 mM sucrose, 50 mM sodium phosphate buffer pH 7.0, and 2 ppm sucrose phosphorylase were incubated for 30 minutes, 60 minutes, or overnight at 37° C. The fructose released in each reaction was analyzed using a PAHBAH assay mostly as described by Lever (1972, *Anal. Biochem.* 47:273-279), but with the following modifications: PAHBAH reagent A: 10 g p-hydroxy benzoic acid hydrazide (PAHBAH, Sigma H9882) was added to 60 mL of water and slurried. 10 mL of concentrated (4 M) HCl was then added and the volume was adjusted to 200 mL. PAHBAH Reagent B: 40 g NaOH and 160 g sodium potassium tartrate was added to 600 mL MILLI-Q water and dissolved, and then the volume was adjusted to 800 mL. PAHBAH working solution: 1 part of Reagent A was added to 4 parts of Reagent B. Ten (10) microliters of the incubated sucrose phosphorylase reaction were added to 90 μL of the PABAH working solution and incubated at 95° C. for 3 minutes. An absorbance measurement at 410 nm was then taken in a spectrophotometer for each PABAH preparation following the incubation. Each of the putative sucrose phosphorylases as prepared in Example 3 was shown to have sucrose phosphorylase activity in the phosphorolytic direction, although Sp75 and Sp156 were not as active as the other sucrose phosphorylases.

Enzyme activity in the synthetic direction (production of sucrose from fructose and alpha-G1P substrates) was determined using a colorimetric assay, as follows. Purified sucrose phosphorylases were individually incubated overnight with 50 mM fructose, 50 mM alpha-G1P and 50 mM Tris pH 7.0 at 37° C. After incubation, samples were taken and appropriately diluted; free phosphate concentrations were measured using a colorimetric kit (MAK030-1 KT, Sigma-Aldrich, St. Louis, Mo.) according to the instructions of the manufacturer. Each of the putative sucrose phosphorylases as prepared in Example 3, except for Sp75 and Sp156, was shown to have sucrose phosphorylase activity. Activity in the synthetic direction for Sp75 and Sp156 was not detectable; this low activity (probable, as opposed to no activity) is consistent with the above observation of low activity of both these enzymes in the phosphorolytic direction.

In another assay, the activity of purified Sp17 was determined by quantifying the formation of alpha-G1P as follows. A 100-μL reaction was prepared containing 80 mM sucrose, 20 mM Britton-Robinson buffer pH 4.5 (phosphate source), and 2.5 ppm of Sp17. The reaction was incubated at 37° C. for 15 minutes and terminated by incubation for 5 minutes at 95° C. The concentration of alpha-G1P product was determined by coupling the reduction of NADP in the presence of phosphoglucomutase (PMG) and glucose-6-phosphate dehydrogenase (G6PDH). A standard assay mix containing PGM (3.0 U/mL), G6PDH (3.0 U/mL), 1 mM EDTA, 15 mM $MgCl_2$, 10 μM glucose-1,6-diphosphate, 2.5 mM NADH+, and 100 mM phosphate buffer pH 6.8 was prepared. 25 μL of the terminated Sp17 enzymatic reaction was then mixed with 125 μL of the standard assay mix. The formation of NADH over time was monitored spectrophotometrically (340 nm absorbance) at 35° C. for approximately 10 minutes (until a stable signal was obtained). For the quantification of alpha-G1P in solution, a calibration curve from 0 to 5 mM was used. One unit of Sp17 activity was defined as the amount of enzyme that formed 1 μmol of alpha-G1P per minute under the test conditions. This assay is suitable for testing the activity of the other sucrose phosphorylases prepared above.

Example 5

Analysis of Alpha-1,4-Glucan Phosphorylase Activity

This Example describes an assay for measuring the activity of putative alpha-1,4-glucan phosphorylases.

Alpha-1,4-glucan phosphorylase enzyme activity in the phosphorolytic direction (i.e., phosphate used to break down alpha-1,4-glucan to alpha-G1P) was measured as follows. A mixture containing 18.75 mg maltotetraose (Sigma-Aldrich), 250 μL of 0.5 M phosphate pH 7.0, and 225 μL of water was prepared. Each of alpha-1,4-glucan phosphorylases GP-3, GP-4 and GP-5 (25 μL supernatant as prepared in Example 3) was then individually added to 100 μL of the mixture and incubated overnight at 65° C. Thin-layer chromatography (TLC) was used to monitor activity (described below).

Alpha-1,4-glucan phosphorylase enzyme activity in the synthetic direction (i.e., alpha-G1P and acceptor used as substrates to produce alpha-1,4-glucan and phosphate) was measured as follows. A mixture containing 18.75 mg alpha-G1P, 2 mg maltotetraose, 100 μL 0.5 M Tris pH 7.0, and 375 μL water was prepared. Each of alpha-1,4-glucan phosphorylases GP-3, GP-4 and GP-5 (25 μL supernatant as prepared in Example 3) was then individually added to 100 μL of the mixture and incubated overnight at 65° C. TLC was used to monitor activity (described below).

To characterize saccharide products of the above reactions (both synthetic and phosphorolytic directions), a 2-μL sample of each reaction was subjected to TLC analysis using SILICA GEL 60 F254 plates (Merck, Germany). After drying, each plate was run overnight using 1-butanol:ethanol:water (5:5:3) as the mobile phase. The plates were then air-dried, sprayed with developing solution (45:45:10 methanol:water:$H_2SO_4$) and developed at 110° C. for approximately 15 minutes. Alpha-G1P formation or alpha-1,4-glucan formation was then visualized.

Each of the putative alpha-1,4-glucan phosphorylases tested in this Example was shown to have alpha-1,4-glucan phosphorylase activity in both the phosphorolytic direction (i.e., alpha-G1P was produced) and synthetic direction (i.e., products with a DP greater than that of maltotetraose [DP4] were produced) following the above respective assays. It is contemplated that the other putative alpha-1,4-glucan phosphorylases disclosed herein can be tested following the above assays, but using incubation temperatures as noted in Example 6 below, for example.

Example 6

Alpha-1,4-Glucan Production in Coupled Reactions Comprising Sucrose Phosphorylase and Alpha-1,4-Glucan Phosphorylase This Example describes coupled reactions in which a sucrose phosphorylase is used to provide alpha-G1P substrate for alpha-1,4-glucan phosphorylase. Specifically, reactions were prepared to initially have (i) sucrose phosphorylase and its substrates (sucrose and free phosphate), and (ii) alpha-1,4-glucan phosphorylase and a suitable acceptor substrate (maltodextrin). In each reaction, alpha-G1P produced by the sucrose phosphorylase was in turn used by the alpha-1,4-glucan phosphorylase to extend the acceptor to produce alpha-1,4-glucan.

Coupled reactions were prepared comprising 100 mM sodium phosphate buffer pH 7.0 (i.e., free phosphate), 500 mM sucrose, 44 g/L maltodextrin (dextrose equivalent 4.0-7.0, Sigma-Aldrich; i.e., DP of about 14 to 30), 10 ppm of Sp17, 12.7 ppm of an alpha-1,4-glucan phosphorylase (GP-3, GP-4, or GP-5), and 0.02% sodium azide. Each of the enzymes was provided in a supernatant as prepared in Example 3. The reactions were incubated for 66 hours at either 30° C. or 50° C., after which they were spun down for 10 minutes at 5580×g at room temperature. Insoluble product (contemplated to comprise 100% alpha-1,4 linkages) formation served as an activity indicator. Insoluble polymer was produced in the reactions with GP-3 (50° C.) and GP-4 (30 and 50° C.); GP-5 did not produce insoluble product at either of the tested temperatures. It is expected that a coupled reaction using a sucrose phosphorylase active at 65° C. and GP-5 (or GP-3 or GP-4 for that matter) would produce insoluble product (refer to Example 5). Alpha-1,4-glucan product from each successful reaction was washed three times with distilled water using 10 minutes of centrifugation for each wash.

Other coupled reactions were conducted to test each of the alpha-1,4-glucan phosphorylases listed in Table 3. Briefly, the same conditions of the above reaction format were followed, but the reactions were allowed to commence for 12 days. While some of the reactions showed accumulation of insoluble product after 7 days (e.g., GP-006, 30 and 50° C.; GP-011, 30° C.; GP-017, 50° C.; GP-022, 50° C.), all of the reactions showed some production after 12 days (e.g., GP-006, 30 and 50° C.; GP-011, 30° C.; GP-017, 50° C.; GP-022, 50° C.); reactions with some enzymes had somewhat lower activity (GP-005, 30° C.; GP-007, 30° C.; GP-009, 30° C.; GP-013, 50° C.; GP-043, 50° C.; GP-044, 30° C.; GP-046, 30° C.; GP-048, 50° C.). It is contemplated that each insoluble product was alpha-glucan with 100% alpha-1,4 linkages.

It is contemplated that the above (and/or similar) coupled reactions can be performed using the other sucrose phosphorylases disclosed above.

What is claimed is:

1. An isolated composition comprising:

(i) an isolated sucrose phosphorylase that comprises an amino acid sequence that is at least 90% identical to SEQ ID NO:10, SEQ ID NO:12, SEQ ID NO:14, or SEQ ID NO:22, and (ii) an isolated alpha-1,4-glucan phosphorylase that comprises an amino acid sequence that is at least 90% identical to SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, or SEQ ID NO:54.

2. The composition of claim 1, wherein the sucrose phosphorylase comprises an amino acid sequence that is at least 95% identical to SEQ ID NO:10, SEQ ID NO:12, SEQ ID NO:14, or SEQ ID NO:22.

3. The composition of claim 2, wherein the sucrose phosphorylase comprises an amino acid sequence that is at least 97% identical to SEQ ID NO:10, SEQ ID NO:12, SEQ ID NO:14, or SEQ ID NO:22.

4. The composition of claim 3, wherein the sucrose phosphorylase comprises an amino acid sequence that is at least 98% identical to SEQ ID NO:10, SEQ ID NO:12, SEQ ID NO:14, or SEQ ID NO:22.

5. The composition of claim 1, wherein the composition further comprises at least water, inorganic phosphate, sucrose, and an acceptor molecule, wherein the sucrose phosphorylase produces alpha-glucose-1-phosphate in the composition, and wherein the alpha-1,4-glucan phosphorylase produces alpha-1,4-glucan in the composition.

6. The composition of claim 5, wherein the sucrose phosphorylase comprises an amino acid sequence that is at least 95% identical to SEQ ID NO:10, SEQ ID NO:12, SEQ ID NO:14, or SEQ ID NO:22.

7. The composition of claim 6, wherein the sucrose phosphorylase comprises an amino acid sequence that is at least 97% identical to SEQ ID NO:10, SEQ ID NO:12, SEQ ID NO:14, or SEQ ID NO:22.

8. The composition of claim 7, wherein the sucrose phosphorylase comprises an amino acid sequence that is at least 98% identical to SEQ ID NO:10, SEQ ID NO:12, SEQ ID NO:14, or SEQ ID NO:22.

9. The composition of claim 5, wherein the acceptor molecule comprises a monosaccharide, disaccharide, or oligosaccharide.

10. The composition of claim 5, wherein the acceptor molecule comprises alpha-1,4 glycosidic linkages and has a degree of polymerization (DP) of 2 to 35.

11. The composition of claim 5, wherein the acceptor molecule comprises a polysaccharide.

12. The composition of claim 5, wherein the alpha-1,4-glucan has at least about 90% alpha-1,4 glycosidic linkages.

13. The composition of claim 12, wherein the alpha-1,4-glucan has at least about 99% alpha-1,4 glycosidic linkages.

14. The composition of claim 5, wherein the alpha-1,4-glucan phosphorylase comprises an amino acid sequence that is at least 90% identical to SEQ ID NO:26, SEQ ID NO:30, SEQ ID NO:32, SEQ ID NO:34, SEQ ID NO:38, SEQ ID NO:40, SEQ ID NO:42, SEQ ID NO:44, SEQ ID NO:46, SEQ ID NO:48, or SEQ ID NO:50.

* * * * *

SEQUENCE LISTING

```
<160> NUMBER OF SEQ ID NOS: 81

<210> SEQ ID NO 1
<211> LENGTH: 1473
<212> TYPE: DNA
<213> ORGANISM: Leuconostoc mesenteroides

<400> SEQUENCE: 1

atggaaattc aaaacaaagc aatgttgatc acttatgctg attcgttggg caaaaactta     60

aaagatgttc atcaagtctt gaaagaagat attggagatg cgattggtgg ggttcatttg    120

ttgcctttct tcccttcaac aggtgatcgc ggttttgcgc cagccgatta tactcgtgtt    180

gatgccgcat ttggtgattg ggcagatgtc gaagcattgg gtgaagaata ctatttgatg    240

tttgacttca tgattaacca tatttctcgt gaatcagtga tgtatcaaga ttttaagaag    300

aatcatgacg attcaaagta taaagatttc tttattcgtt gggaaaagtt ctgggcaaag    360

gccggcgaaa accgtccaac acaagccgat gttgacttaa tttacaagcg taaagataag    420

gcaccaacgc aagaaatcac ttttgatgat ggcacaacag aaaacttgtg gaatactttt    480

ggtgaagaac aaattgacat tgatgttaat tcagccattg ccaaggaatt tattaagaca    540

acccttgaag acatggtaaa acatggtgct aacttgattc gtttggatgc ctttgcgtat    600

gcagttaaaa aagttgacac aaatgacttc ttcgttgagc cagaaatctg ggacactttg    660

aatgaagtac gtgaaatttt gacaccatta aaggctgaaa ttttaccaga aattcatgaa    720

cattactcaa tccctaaaaa gatcaatgat catggttact tcacctatga ctttgcatta    780

ccaatgacaa cgctttacac attgtattca ggtaagacaa atcaattggc aaagtggttg    840

aagatgtcac caatgaagca attcacaaca ttggacacgc atgatggtat tggtgtcgtt    900

gatgcccgtg atattctaac tgatgatgaa attgactacg cttctgaaca actttacaag    960

gttggcgcga atgtcaaaaa gacatattca tctgcttcat acaacaacct tgatatttac   1020

caaattaact caacttatta ttcagcattg ggaaatgatg atgcagcata cttgttgagt   1080

cgtgtcttcc aagtctttgc gcctggaatt ccacaaattt attacgttgg tttgttggca   1140

ggtgaaaacg atatcgcgct tttggagtca actaaagaag gtcgtaatat taaccgtcat   1200

tactatacgc gtgaagaagt taagtcagaa gttaagcgac cagttgttgc taacttattg   1260

aagctattgt catggcgtaa tgaaagccct gcatttgatt tggctggctc aatcacagtt   1320

gacacgccaa ctgatacaac aattgtggtg acacgtcaag atgaaaatgg tcaaaacaaa   1380

gctgtattaa cagccgatgc ggccaacaaa acttttgaaa tcgttgagaa tggtcaaact   1440

gttatgagca gtgataattt gactcagaac taa                                1473


<210> SEQ ID NO 2
<211> LENGTH: 490
<212> TYPE: PRT
<213> ORGANISM: Leuconostoc mesenteroides

<400> SEQUENCE: 2
```

```
Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Val Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Ala Leu Leu Glu Ser Thr Lys Glu Gly Arg Asn Ile Asn Arg His
385                 390                 395                 400

Tyr Tyr Thr Arg Glu Glu Val Lys Ser Glu Val Lys Arg Pro Val Val
                405                 410                 415
```

```
Ala Asn Leu Leu Lys Leu Leu Ser Trp Arg Asn Glu Ser Pro Ala Phe
            420                 425                 430

Asp Leu Ala Gly Ser Ile Thr Val Asp Thr Pro Thr Asp Thr Thr Ile
        435                 440                 445

Val Val Thr Arg Gln Asp Glu Asn Gly Gln Asn Lys Ala Val Leu Thr
    450                 455                 460

Ala Asp Ala Ala Asn Lys Thr Phe Glu Ile Val Glu Asn Gly Gln Thr
465                 470                 475                 480

Val Met Ser Ser Asp Asn Leu Thr Gln Asn
                485                 490


<210> SEQ ID NO 3
<211> LENGTH: 1515
<212> TYPE: DNA
<213> ORGANISM: Bifidobacterium adolescentis

<400> SEQUENCE: 3

atgaaaaaca aggtgcagct catcacttac gccgaccgcc ttggcgacgg caccatcaag      60

tcgatgaccg acattctgcg cacccgcttc gacggcgtgt acgacggcgt tcacatcctg     120

ccgttcttca ccccgttcga cggcgccgac gcaggcttcg acccgatcga ccacaccaag     180

gtcgacgaac gtctcggcag ctgggacgac gtcgccgaac tctccaagac ccacaacatc     240

atggtcgacg ccatcgtcaa ccacatgagt tgggaatcca agcagttcca ggacgtgctg     300

gccaagggcg aggagtccga atactatccg atgttcctca ccatgagctc cgtgttcccg     360

aacggcgcca ccgaagagga cctggccggc atctaccgtc cgcgtccggg cctgccgttc     420

acccactaca agttcgccgg caagacccgc ctcgtgtggg tcagcttcac ccgcagcag      480

gtggacatcg acaccgattc cgacaagggt tgggaatacc tcatgtcgat tttcgaccag     540

atggccgcct ctcacgtcag ctacatccgc ctcgacgccg tcggctatgg cgccaaggaa     600

gccggcacca gctgcttcat gaccccgaag accttcaagc tgatctcccg tctgcgtgag     660

gaaggcgtca agcgcggtct ggaaatcctc atcgaagtgc actcctacta caagaagcag     720

gtcgaaatcg catccaaggt ggaccgcgtc tacgacttcg ccctgcctcc gctgctgctg     780

cacgcgctga gcaccggcca cgtcgagccc gtcgcccact ggaccgacat acgcccgaac     840

aacgccgtca ccgtgctcga tacgcacgac ggcatcggcg tgatcgacat cggctccgac     900

cagctcgacc gctcgctcaa gggtctcgtg ccggatgagg acgtggacaa cctcgtcaac     960

accatccacg ccaacaccca cggcgaatcc caggcagcca ctggcgccgc cgcatccaat    1020

ctcgacctct accaggtcaa cagcacctac tattcggcgc tcgggtgcaa cgaccagcac    1080

tacatcgccg cccgcgcggt gcagttcttc ctgccgggcg tgccgcaagt ctactacgtc    1140

ggcgcgctcg ccggcaagaa cgacatggag ctgctgcgta agacgaataa cggccgcgac    1200

atcaatcgcc attactactc caccgcggaa atcgacgaga acctcaagcg tccggtcgtc    1260

aaggccctga acgcgctcgc caagttccgc aacgagctcg acgcgttcga cggcacgttc    1320

tcgtacacca ccgatgacga cacgtccatc agcttcacct ggcgcggcga aaccagccag    1380

gccacgctga cgttcgagcc gaagcgcggt ctcggtgtgg acaacactac gccggtcgcc    1440

atgttggaat gggaggattc cgcgggagac caccgttcgg atgatctgat cgccaatccg    1500

cctgtcgtcg cctga                                                     1515


<210> SEQ ID NO 4
<211> LENGTH: 504
<212> TYPE: PRT
```

<213> ORGANISM: Bifidobacterium adolescentis

<400> SEQUENCE: 4

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
    370                 375                 380

Gly Lys Asn Asp Met Glu Leu Leu Arg Lys Thr Asn Asn Gly Arg Asp
385                 390                 395                 400
```

Ile Asn Arg His Tyr Tyr Ser Thr Ala Glu Ile Asp Glu Asn Leu Lys
405 410 415

Arg Pro Val Val Lys Ala Leu Asn Ala Leu Ala Lys Phe Arg Asn Glu
420 425 430

Leu Asp Ala Phe Asp Gly Thr Phe Ser Tyr Thr Thr Asp Asp Asp Thr
435 440 445

Ser Ile Ser Phe Thr Trp Arg Gly Glu Thr Ser Gln Ala Thr Leu Thr
450 455 460

Phe Glu Pro Lys Arg Gly Leu Gly Val Asp Asn Thr Thr Pro Val Ala
465 470 475 480

Met Leu Glu Trp Glu Asp Ser Ala Gly Asp His Arg Ser Asp Asp Leu
485 490 495

Ile Ala Asn Pro Pro Val Val Ala
500

<210> SEQ ID NO 5
<211> LENGTH: 1527
<212> TYPE: DNA
<213> ORGANISM: Bifidobacterium longum

<400> SEQUENCE: 5
atgaaaaaca aagtgcaact catcacatac gccgatcgtc tcggcgatgg cactcttagc 60
tcgatggccg acatcctgcg cacccgcttc gacggcgtgt atgacggcgt gcatatcctg 120
ccgttcttca ctccgttcga tggtgcggat gcaggcttcg acccgatcga ccataccaaa 180
gtcgacgaac gtctcggcag ctgggacgac gtcgccgaac tctccaagac ccacaacatc 240
atggtcgacg ccatcgtcaa ccacatgagt tgggaatcca agcagttcca agacgtgctt 300
gaaaaaggtg aggaatccga gtattacccg atgtttctga ccatgagctc cgtgttcccg 360
aacggcgcca ccgaagagga cctggccggc atctaccgtc cgcgtccggg cctgccgttc 420
acccactaca agttcgccgg caagacgcgc ctggtctggg tgagcttcac cccgcagcag 480
gttgatattg acaccgattc cgacaagggc tgggaatacc tcatgtccat cttcgatcag 540
atggccgcct cccatgtaag ctacatccgc ctcgacgccg tcggctacgg cgctaaggaa 600
gctggcacga gctgcttcat gaccccgaag acgttcaagc tgatctcccg cctacgtgag 660
gaaggcgtca agcgaggcct cgaaattctc attgaggtgc atagctacta caagaagcag 720
gtggaaatcg cctccaaggt ggaccgcgtc tacgatttcg ccctgccgcc gctgcttctg 780
cactcgctgt tcaccggtca cgtcgaaccc gtggcccact ggaccgagat ccgcccgaac 840
aacgccgtca ccgtgctcga tacgcacgat ggcatcggcg tgatcgacat cggctccgac 900
cagctcgacc gctccctcaa gggcctcgtg cccgacgagg acgtcgacaa cctggtcaac 960
accatccatg ccaacaccca cggcgaatcc caggccgcca ccggtgccgc cgcgtccaac 1020
ctcgacctct accaggtcaa ctccacgtac tactcggccc tcggctgcaa cgaccagcac 1080
tacttggccg cccgcgccgt gcagttcttc ctgccgggcg tgccgcaggt ctactacgtg 1140
ggcgcgctcg ccggccgcaa cgacatggaa ctgctgcgcc gcaccaacaa cggccgcgac 1200
atcaaccgcc actactactc caccgccgaa atcgatgaaa acctcgaacg cccggtggtc 1260
aaggccctga acgccctggc caagttccgc aacgaactgc ctgcattcga tggcgagttc 1320
agctacgagg tcgatggcga cacgtccatc accttccgct ggaccgccgc cgacggcacg 1380
tccacggccg ccctcacctt cgagcccgga cgcggcctcg gcacagacaa cgccaccccg 1440
gttgccagcc ttgcctggag cgatgccgcc ggcgaccacg aaacccgcga tctgctcgcc 1500

```
aacccgccga ttgccgatat cgactaa                                     1527


<210> SEQ ID NO 6
<211> LENGTH: 508
<212> TYPE: PRT
<213> ORGANISM: Bifidobacterium longum

<400> SEQUENCE: 6

Met Lys Asn Lys Val Gln Leu Ile Thr Tyr Ala Asp Arg Leu Gly Asp
1               5                   10                  15

Gly Thr Leu Ser Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Glu Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Glu Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Ser Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ser Leu Phe Thr Gly His Val Glu Pro Val Val
            260                 265                 270

His Trp Thr Glu Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Leu Ala Ala Arg Ala Val Gln
        355                 360                 365
```

```
Phe Phe Leu Pro Gly Val Pro Gln Val Tyr Tyr Val Gly Ala Leu Ala
    370                 375                 380

Gly Arg Asn Asp Met Glu Leu Leu Arg Arg Thr Asn Asn Gly Arg Asp
385                 390                 395                 400

Ile Asn Arg His Tyr Tyr Ser Thr Ala Glu Ile Asp Glu Asn Leu Glu
                405                 410                 415

Arg Pro Val Val Lys Ala Leu Asn Ala Leu Ala Lys Phe Arg Asn Glu
            420                 425                 430

Leu Pro Ala Phe Asp Gly Glu Phe Ser Tyr Glu Val Asp Gly Asp Thr
        435                 440                 445

Ser Ile Thr Phe Arg Trp Thr Ala Ala Asp Gly Thr Ser Thr Ala Ala
    450                 455                 460

Leu Thr Phe Glu Pro Gly Arg Gly Leu Gly Thr Asp Asn Thr Thr Pro
465                 470                 475                 480

Val Ala Ser Leu Ala Trp Ser Asp Ala Ala Gly Asp His Glu Thr His
                485                 490                 495

Asp Leu Leu Ala Asn Pro Pro Ile Ala Asp Ile Asp
            500                 505
```

```
<210> SEQ ID NO 7
<211> LENGTH: 1443
<212> TYPE: DNA
<213> ORGANISM: Lactobacillus amylovorus GRL1118

<400> SEQUENCE: 7

atgccaatta aaaataaagt aatgttgatt acctatccag atagtttagg taaaaacttg      60

caagaattaa gcgaagtctt agaaaatgat ttaaaaggtg cggttggcgg cattcattta     120

ctgccattct ttccttcaac gggtgatcgc ggatttgcac caactgatta cacgacagtt     180

gatcctaaat ttggtaattg gtcagatgtt gaaaagttgg gcgaaaaata ctacctgatg     240

tttgatttta tgatcaatca tatttctagg cattctaagt attacgaaga ttttcaaaag     300

aataaggaca aaagttcata tgcagatatg ttcttaagtt gggataagtt ttggccaaaa     360

ggtcgtccaa ctaaagaaga tgtggaccta atctataagc gtaaagatcg tgctccatat     420

caagagatta cttttgcgga tgggagcaag gagaaacttt ggaatacttt tggtcctgag     480

caaatcgatt tagatgtgcg caaaaaggtt acgcaaaagt ttattaagga cacgttggtt     540

agcctaatta agcacggagc agatatcatt cgtttggatg cttttgctta tgctgtgaaa     600

aaactagata ctaatgactt ctttgtagaa ccagaaatct ggaatttgct taagcaggta     660

caagatgata ttgctgatga aggagcaacg attttgccag aaatccatga gcattattct     720

atgccgttca agatttcaaa acatggctac tttatctacg actttgctct accaatggtt     780

actctgtatt cgctttattc aggtaaatcc aatcgtttgg cagcttggct aaagaaatgt     840

ccaatgaagc aattcactac cttggatact catgatggta ttggcgtagt tgatgcgcgt     900

gatattcttt ctccagaaga gatcgattac accagccaag aactttataa agttggtgct     960

aatgttaaga aaaagtattc aagtgctgaa tatcataatt tggatattta tcaaattaat    1020

actacttttt attcagcttt gggcgatgac gataaaagat acttcatggc aagattattg    1080

caggtctttg ctcctgggat tccgcaggtc tactatgttg ggatgttagc tggcaagaat    1140

gatattaagc tccttgaaga aactaaagag gggagaaata ttaatcgtca ttattacagc    1200

aaagctgaag ttgaacaaga aattcagcga cctgttgttg cctctttgtt gaaactcttt    1260

acttttagaa acaatgaacc tgcatttgac ttaaatggtt ctattgatat ctctacccct    1320
```

```
aatgaaaatg aaatccgtat tgttcgaatc aataaagaac aaaatcataa agcagaatta   1380

actgctaact tacaagattt aacttaccga gttttggtta acggtaagca aatcaacttt   1440

taa                                                                 1443


<210> SEQ ID NO 8
<211> LENGTH: 480
<212> TYPE: PRT
<213> ORGANISM: Lactobacillus amylovorus GRL1118

<400> SEQUENCE: 8

Met Pro Ile Lys Asn Lys Val Met Leu Ile Thr Tyr Pro Asp Ser Leu
1               5                   10                  15

Gly Lys Asn Leu Gln Glu Leu Ser Glu Val Leu Glu Asn Asp Leu Lys
            20                  25                  30

Gly Ala Val Gly Gly Ile His Leu Leu Pro Phe Phe Pro Ser Thr Gly
        35                  40                  45

Asp Arg Gly Phe Ala Pro Thr Asp Tyr Thr Thr Val Asp Pro Lys Phe
    50                  55                  60

Gly Asn Trp Ser Asp Val Glu Lys Leu Gly Glu Lys Tyr Tyr Leu Met
65                  70                  75                  80

Phe Asp Phe Met Ile Asn His Ile Ser Arg His Ser Lys Tyr Tyr Glu
                85                  90                  95

Asp Phe Gln Lys Asn Lys Asp Lys Ser Ser Tyr Ala Asp Met Phe Leu
            100                 105                 110

Ser Trp Asp Lys Phe Trp Pro Lys Gly Arg Pro Thr Lys Glu Asp Val
        115                 120                 125

Asp Leu Ile Tyr Lys Arg Lys Asp Arg Ala Pro Tyr Gln Glu Ile Thr
    130                 135                 140

Phe Ala Asp Gly Ser Lys Glu Lys Leu Trp Asn Thr Phe Gly Pro Glu
145                 150                 155                 160

Gln Ile Asp Leu Asp Val Arg Lys Lys Val Thr Gln Lys Phe Ile Lys
                165                 170                 175

Asp Thr Leu Val Ser Leu Ile Lys His Gly Ala Asp Ile Ile Arg Leu
            180                 185                 190

Asp Ala Phe Ala Tyr Ala Val Lys Lys Leu Asp Thr Asn Asp Phe Phe
        195                 200                 205

Val Glu Pro Glu Ile Trp Asn Leu Leu Lys Gln Val Gln Asp Asp Ile
    210                 215                 220

Ala Asp Glu Gly Ala Thr Ile Leu Pro Glu Ile His Glu His Tyr Ser
225                 230                 235                 240

Met Pro Phe Lys Ile Ser Lys His Gly Tyr Phe Ile Tyr Asp Phe Ala
                245                 250                 255

Leu Pro Met Val Thr Leu Tyr Ser Leu Tyr Ser Gly Lys Ser Asn Arg
            260                 265                 270

Leu Ala Ala Trp Leu Lys Lys Cys Pro Met Lys Gln Phe Thr Thr Leu
        275                 280                 285

Asp Thr His Asp Gly Ile Gly Val Val Asp Ala Arg Asp Ile Leu Ser
    290                 295                 300

Pro Glu Glu Ile Asp Tyr Thr Ser Gln Glu Leu Tyr Lys Val Gly Ala
305                 310                 315                 320

Asn Val Lys Lys Lys Tyr Ser Ser Ala Glu Tyr His Asn Leu Asp Ile
                325                 330                 335

Tyr Gln Ile Asn Thr Thr Phe Tyr Ser Ala Leu Gly Asp Asp Asp Lys
            340                 345                 350
```

```
Arg Tyr Phe Met Ala Arg Leu Leu Gln Val Phe Ala Pro Gly Ile Pro
        355                 360                 365

Gln Val Tyr Tyr Val Gly Met Leu Ala Gly Lys Asn Asp Ile Lys Leu
    370                 375                 380

Leu Glu Glu Thr Lys Glu Gly Arg Asn Ile Asn Arg His Tyr Tyr Ser
385                 390                 395                 400

Lys Ala Glu Val Glu Gln Glu Ile Gln Arg Pro Val Val Ala Ser Leu
                405                 410                 415

Leu Lys Leu Phe Thr Phe Arg Asn Asn Glu Pro Ala Phe Asp Leu Asn
            420                 425                 430

Gly Ser Ile Asp Ile Ser Thr Pro Asn Glu Asn Glu Ile Arg Ile Val
        435                 440                 445

Arg Ile Asn Lys Glu Gln Asn His Lys Ala Glu Leu Thr Ala Asn Leu
    450                 455                 460

Gln Asp Leu Thr Tyr Arg Val Leu Val Asn Gly Lys Gln Ile Asn Phe
465                 470                 475                 480
```

<210> SEQ ID NO 9
<211> LENGTH: 1500
<212> TYPE: DNA
<213> ORGANISM: Streptomyces sp.

<400> SEQUENCE: 9

```
gtgcagaacc aagtgcagct aatcacctac gtcgaccggc tggcaggcga tctgccggcg     60

ctgacgcggt tgctggaagg gccgctggac ggcatcttcg ggggtgtcca tctgctgccg    120

ttcttcgacc cgatcgacgg tgcagacgcc gggttcgacc cggtagacca cacgacggtg    180

gacgctcggc tcggcacgtg ggacgacgtc gaggcactcg gtgctcgagt accggtcatg    240

gccgacctga tcgtcaacca cgtctccgcg tcgtcgccgc agttcctcga ctggctcgag    300

cacggcagcg gctccgagta cgacgggatg ttcctgtcgc tcgacgccgt cttccccgat    360

ggggccaccg aagagctggt gacggcggtg taccgacctc gtccaggact gcctctgaca    420

ccggtgcaac tcgctgacgg caccaagcgg ctgatgtgga cgacgttcac gccgcagcag    480

atcgacatcg acgtgacgca cccgacgggg cgtgactacc tcgaaggcat cctggacacg    540

ttcgcggagc gggggatcac gagtgtccgg ctcgacgcgg tcggctacgc catcaagacg    600

gccggaacct cgtgcttcat gaccccggag acgttcgcgt tcatcgacga cctcgccgcg    660

agcgcccatc ggcgagacat cacgatcctc gtcgagatcc actcgtactg gcgcacgcag    720

gtcgagatcg cgtcgcgggt cgactgggtc tacgacttcg cgctcccgcc gttggtgctc    780

cacgcgctgt acagcggcga cgcatcgccg ttgcgccgct ggtgcgaggt ccgcccgcac    840

aacgcggtca acgtgctgga cacccacgac gggatcggcg tgatcgacgt cggcccgggc    900

ggcagcgacc cgaacaagcc agggctgctc gaccccgggc agctcgatgc gctcgtcgaa    960

ggcatccacg aggccagcgg tgggagcagc cgcgcggcga ccggtagtgc cgcgtccaac   1020

ctcgacctct accaggtcaa ctgcacctac ctcgacgcct gcggtcgcga cgaggccgcc   1080

tacctcatcg cgcgcctgct ccaggtgtgg ctgccgggta tcccgcagat gtattacgtc   1140

ggcctgctcg ccggcgagaa cgacctcgac ctgctggagc ggaccggcgt tgggcgtgac   1200

atcaaccgcc gctactacac gccagacgag gtcgagcagg cgctccagca gcccgtggtc   1260

gtcgggctct tacggctgct gcgcctgcgc aacgatcacc cggcgttcga cggcgcatgg   1320

gagctgttgg acggcgacgc ggcgtccggg cagctggcga tgcgctggtc gaacgccgac   1380
```

```
gagatcgcag agctcgccgt cgacgtccgt gcacgaacct atgagcttcg agtgaccatg   1440

gatggcgagc tgcgcagctt cgtcaacgtg ctcgacctgc cggagaccga ctcgacctga   1500


<210> SEQ ID NO 10
<211> LENGTH: 499
<212> TYPE: PRT
<213> ORGANISM: Streptomyces sp.

<400> SEQUENCE: 10

Met Gln Asn Gln Val Gln Leu Ile Thr Tyr Val Asp Arg Leu Ala Gly
1               5                   10                  15

Asp Leu Pro Ala Leu Thr Arg Leu Leu Glu Gly Pro Leu Asp Gly Ile
            20                  25                  30

Phe Gly Gly Val His Leu Leu Pro Phe Phe Asp Pro Ile Asp Gly Ala
        35                  40                  45

Asp Ala Gly Phe Asp Pro Val Asp His Thr Thr Val Asp Ala Arg Leu
    50                  55                  60

Gly Thr Trp Asp Asp Val Glu Ala Leu Gly Ala Arg Val Pro Val Met
65                  70                  75                  80

Ala Asp Leu Ile Val Asn His Val Ser Ala Ser Ser Pro Gln Phe Leu
                85                  90                  95

Asp Trp Leu Glu His Gly Ser Gly Ser Glu Tyr Asp Gly Met Phe Leu
            100                 105                 110

Ser Leu Asp Ala Val Phe Pro Asp Gly Ala Thr Glu Glu Leu Val Thr
        115                 120                 125

Ala Val Tyr Arg Pro Arg Pro Gly Leu Pro Leu Thr Pro Val Gln Leu
    130                 135                 140

Ala Asp Gly Thr Lys Arg Leu Met Trp Thr Thr Phe Thr Pro Gln Gln
145                 150                 155                 160

Ile Asp Ile Asp Val Thr His Pro Thr Gly Arg Asp Tyr Leu Glu Gly
                165                 170                 175

Ile Leu Asp Thr Phe Ala Glu Arg Gly Ile Thr Ser Val Arg Leu Asp
            180                 185                 190

Ala Val Gly Tyr Ala Ile Lys Thr Ala Gly Thr Ser Cys Phe Met Thr
        195                 200                 205

Pro Glu Thr Phe Ala Phe Ile Asp Asp Leu Ala Ala Ser Ala His Arg
    210                 215                 220

Arg Asp Ile Thr Ile Leu Val Glu Ile His Ser Tyr Trp Arg Thr Gln
225                 230                 235                 240

Val Glu Ile Ala Ser Arg Val Asp Trp Val Tyr Asp Phe Ala Leu Pro
                245                 250                 255

Pro Leu Val Leu His Ala Leu Tyr Ser Gly Asp Ala Ser Pro Leu Arg
            260                 265                 270

Arg Trp Cys Glu Val Arg Pro His Asn Ala Val Asn Val Leu Asp Thr
        275                 280                 285

His Asp Gly Ile Gly Val Ile Asp Val Gly Pro Gly Gly Ser Asp Pro
    290                 295                 300

Asn Lys Pro Gly Leu Leu Asp Pro Gly Gln Leu Asp Ala Leu Val Glu
305                 310                 315                 320

Gly Ile His Glu Ala Ser Gly Gly Ser Ser Arg Ala Ala Thr Gly Ser
                325                 330                 335

Ala Ala Ser Asn Leu Asp Leu Tyr Gln Val Asn Cys Thr Tyr Leu Asp
            340                 345                 350

Ala Cys Gly Arg Asp Glu Ala Ala Tyr Leu Ile Ala Arg Leu Leu Gln
```

```
        355                 360                 365

Val Trp Leu Pro Gly Ile Pro Gln Met Tyr Tyr Val Gly Leu Leu Ala
    370                 375                 380

Gly Glu Asn Asp Leu Asp Leu Leu Glu Arg Thr Gly Val Gly Arg Asp
385                 390                 395                 400

Ile Asn Arg Arg Tyr Tyr Thr Pro Asp Glu Val Glu Gln Ala Leu Gln
                405                 410                 415

Gln Pro Val Val Val Gly Leu Leu Arg Leu Leu Arg Leu Arg Asn Asp
            420                 425                 430

His Pro Ala Phe Asp Gly Ala Trp Glu Leu Leu Asp Gly Asp Ala Ala
        435                 440                 445

Ser Gly Gln Leu Ala Met Arg Trp Ser Asn Ala Asp Glu Ile Ala Glu
    450                 455                 460

Leu Ala Val Asp Val Arg Ala Arg Thr Tyr Glu Leu Arg Val Thr Met
465                 470                 475                 480

Asp Gly Glu Leu Arg Ser Phe Val Asn Val Leu Asp Leu Pro Glu Thr
                485                 490                 495

Asp Ser Thr


<210> SEQ ID NO 11
<211> LENGTH: 1491
<212> TYPE: DNA
<213> ORGANISM: Alkalimonas sp.

<400> SEQUENCE: 11

atgaacaatc agccaggcag caatcaaatt cagttaatca cctacgttga ccgcttaagc      60

ggcggcggtg tcacagagct gcatcagctg ctgcagcagg agctcggcgg cttgttcgat     120

ggggtgcatc tgctgccctt ttacacgccg attgatggcg aagatgccgg ttttgaccct     180

accgatcaca ccgccgtcga cagcaggctt ggcaactggc aggacatcgc gagccttgcc     240

agcgattacc cggtgatggc ggatatgatt gtcaaccacg tctcggcgca atcagcgcag     300

tttcaggatg tgctggctaa aggggaagcc tcgccttact ggccgttgtt tctgacccgt     360

gacaaggtgt ttggtcaagc accagagcct gctgaacttg cagccattta ccggccgagg     420

ccaaccagct gctttaccga gctaacactt gccgatggtc gcagccttcc cttttggacc     480

acctttaccg ccaaccagat cgacattgat gtgcaatccg agcccggcca ggcctatctg     540

gatgcgattt tgcagcgttt tactgaaaat ggcgtcaagt tgatccggct ggacgcggct     600

ggctacgcca ttaaaaaagc cggcaccagc tgctttatgc tgccggaaac ctttgaattt     660

attgccggtc ttagcagcaa agccaaagcg ctcggcatgc aatgcctggt cgagatccac     720

ggttaccatc aaacccaaat tgacattgcc aagcgctgcg attgggtgta cgacttcgcg     780

ctgccaccgc tggtgctgca taccctgttc agtcgcgatg ccaaggcact gaaacactgg     840

ctggatatcg ccccgcgcaa ctgcatcacc gtgctggata cccacgatgg catcggcatt     900

gtcgatgcgg ccgatcatca gggccagcct ggcttgttga ctgatccaga gctggatgca     960

ctggtggaac aaattcacca caacagcggc ggcagctcta aactggccac cggcaacgct    1020

gccaataacg tcgatttgta tcaggtgaac tgcagtttct acgatgcatt ggcacagcac    1080

gacgagcatt atctgctggc ccgtgccatt cagctgtttt gcccgggtat cagccagatc    1140

tattacggcg gcctgctggc agcagaaaac gatgtcgagt tactgaagcg cactcaggtc    1200

ggccgcgaca tcaaccggcc ctatttcacg gcggagaaag tgcgccaggc gctgcaaaaa    1260

ccggtggtga aagcgctgtg cgctttaatc aaactgcgcc gcagtctgca ggcctttgat    1320
```

ggcgacttta gccaacagct gatcgatggg ctgtaccagc tcaactggca gcatcagggc 1380
catagtgcca gtttgcggat ccagcttgct gatctgtcgg ccgaactggt ctggcagcac 1440
agcggtgagg tgcagcaaca atgtgcactc agcagtttgc tggcggaata a 1491

<210> SEQ ID NO 12
<211> LENGTH: 496
<212> TYPE: PRT
<213> ORGANISM: Alkalimonas sp.

<400> SEQUENCE: 12

```
Met Asn Asn Gln Pro Gly Ser Asn Gln Ile Gln Leu Ile Thr Tyr Val
1               5                   10                  15

Asp Arg Leu Ser Gly Gly Gly Val Thr Glu Leu His Gln Leu Leu Gln
            20                  25                  30

Gln Glu Leu Gly Gly Leu Phe Asp Gly Val His Leu Leu Pro Phe Tyr
        35                  40                  45

Thr Pro Ile Asp Gly Glu Asp Ala Gly Phe Asp Pro Thr Asp His Thr
    50                  55                  60

Ala Val Asp Ser Arg Leu Gly Asn Trp Gln Asp Ile Ala Ser Leu Ala
65                  70                  75                  80

Ser Asp Tyr Pro Val Met Ala Asp Met Ile Val Asn His Val Ser Ala
                85                  90                  95

Gln Ser Ala Gln Phe Gln Asp Val Leu Ala Lys Gly Glu Ala Ser Pro
            100                 105                 110

Tyr Trp Pro Leu Phe Leu Thr Arg Asp Lys Val Phe Gly Gln Ala Pro
        115                 120                 125

Glu Pro Ala Glu Leu Ala Ala Ile Tyr Arg Pro Arg Pro Thr Ser Cys
    130                 135                 140

Phe Thr Glu Leu Thr Leu Ala Asp Gly Arg Ser Leu Pro Phe Trp Thr
145                 150                 155                 160

Thr Phe Thr Ala Asn Gln Ile Asp Ile Asp Val Gln Ser Glu Pro Gly
                165                 170                 175

Gln Ala Tyr Leu Asp Ala Ile Leu Gln Arg Phe Thr Glu Asn Gly Val
            180                 185                 190

Lys Leu Ile Arg Leu Asp Ala Ala Gly Tyr Ala Ile Lys Lys Ala Gly
        195                 200                 205

Thr Ser Cys Phe Met Leu Pro Glu Thr Phe Glu Phe Ile Ala Gly Leu
    210                 215                 220

Ser Ser Lys Ala Lys Ala Leu Gly Met Gln Cys Leu Val Glu Ile His
225                 230                 235                 240

Gly Tyr His Gln Thr Gln Ile Asp Ile Ala Lys Arg Cys Asp Trp Val
                245                 250                 255

Tyr Asp Phe Ala Leu Pro Pro Leu Val Leu His Thr Leu Phe Ser Arg
            260                 265                 270

Asp Ala Lys Ala Leu Lys His Trp Leu Asp Ile Ala Pro Arg Asn Cys
        275                 280                 285

Ile Thr Val Leu Asp Thr His Asp Gly Ile Gly Ile Val Asp Ala Ala
    290                 295                 300

Asp His Gln Gly Gln Pro Gly Leu Leu Thr Asp Pro Glu Leu Asp Ala
305                 310                 315                 320

Leu Val Glu Gln Ile His His Asn Ser Gly Gly Ser Ser Lys Leu Ala
                325                 330                 335

Thr Gly Asn Ala Ala Asn Asn Val Asp Leu Tyr Gln Val Asn Cys Ser
```

```
            340                 345                 350

Phe Tyr Asp Ala Leu Ala Gln His Asp Glu His Tyr Leu Leu Ala Arg
        355                 360                 365

Ala Ile Gln Leu Phe Cys Pro Gly Ile Ser Gln Ile Tyr Tyr Gly Gly
    370                 375                 380

Leu Leu Ala Ala Glu Asn Asp Val Glu Leu Leu Lys Arg Thr Gln Val
385                 390                 395                 400

Gly Arg Asp Ile Asn Arg Pro Tyr Phe Thr Ala Glu Lys Val Arg Gln
                405                 410                 415

Ala Leu Gln Lys Pro Val Val Lys Ala Leu Cys Ala Leu Ile Lys Leu
            420                 425                 430

Arg Arg Ser Leu Gln Ala Phe Asp Gly Asp Phe Ser Gln Gln Leu Ile
        435                 440                 445

Asp Gly Leu Tyr Gln Leu Asn Trp Gln His Gln Gly His Ser Ala Ser
    450                 455                 460

Leu Arg Ile Gln Leu Ala Asp Leu Ser Ala Glu Leu Val Trp Gln His
465                 470                 475                 480

Ser Gly Glu Val Gln Gln Gln Cys Ala Leu Ser Ser Leu Leu Ala Glu
                485                 490                 495


<210> SEQ ID NO 13
<211> LENGTH: 1461
<212> TYPE: DNA
<213> ORGANISM: Bacillus sp.

<400> SEQUENCE: 13

atgactatta aaaatcaagt catgctgatt acatatgctg atagcatggg gaagaattta      60

caagagttaa acgaagttct tacgaaacac tttcgagaca cgattggcgg ggttcacctt     120

ttgccttttt atccatcgtc tgccgaccgt gggttcgctc caatgactta caaagaagtg     180

gatgaaccat ttggaacgtg ggaagatatt caggcgttat ctaataactt ctatcttatg     240

ttcgatttta tggtgaatca tatatctaaa agttcagagt actttcaaga tttcgttgaa     300

aagaaagatg aatcggatta tgccaaattg tttattcaat ataaagactt ttggccgaac     360

ggggagccaa ctcaagaaga cgtagataaa atttataaaa gaaagccaag agcgccttat     420

attgatgtga catttaacga tggatcgaaa gaaaaaatct ggtgtacgtt tgatgaagaa     480

cagatagatt tgaatgttta ccatgaacga acgaagcggt tcatccaaga taatttgcac     540

tatttatcaa aaaaaggcgc ctctattatg agattagatg ctttcgcata tgctacgaaa     600

caacctggga ccaattgctt ctttattgaa cctgatacgt gggaaatgct tgatgaaatc     660

aaggaaatat tagacccttta cggtgtagaa attcttcctg agattcatga gcattattcg    720

attcagctaa agcttgcaga gcggggatat tgggtatatg attttgcttt acctatgctt     780

gtactccatg ctctatatag tgggcgaact gataggctag ccaactggtt gcaaacatgc     840

ccgaaaaagc agtttacaac tcttgatact cacgatggca ttggtgtagt cgatgtggtc     900

gatcttttga gtaacgaaga aatggaagaa acacgagatg accttttttac aaaaggtgcg    960

aacgtaaaac gcgtttacaa tacaatggaa tataacaatt tagatattta tcaattaaat    1020

tgtacgtact attcagcttt aggaaacaga gatgatgctt atattttggc acgagcgatc    1080

caatttttca cgccaggtat tcctcaaata tattatgtgg gactcctagc gggagaaaat    1140

gatattgaat tacttgaaaa gacgaaagtg ggccgtaaca tcaatcgtca ttactataca    1200

aaagatgaaa tcgatgaaaa tatgacacgc ccaattatgt cacatctttc gaatttgatg    1260
```

```
aggtttagaa ataactatcc agcttttgat ggggagatcg aagtgatcga gcatgaagat   1320

tcctctgtca tggaaattat taggacccac ggggactatc aggcagtttt aacagccaac   1380

cttaaaactt atgcctatga aatcacttac aaagatctag aaacaggtga aaaaagaagc   1440

ttagaaaaca tatcaaagta a                                             1461


<210> SEQ ID NO 14
<211> LENGTH: 486
<212> TYPE: PRT
<213> ORGANISM: Bacillus sp.

<400> SEQUENCE: 14

Met Thr Ile Lys Asn Gln Val Met Leu Ile Thr Tyr Ala Asp Ser Met
1               5                   10                  15

Gly Lys Asn Leu Gln Glu Leu Asn Glu Val Leu Thr Lys His Phe Arg
            20                  25                  30

Asp Thr Ile Gly Gly Val His Leu Leu Pro Phe Tyr Pro Ser Ser Ala
        35                  40                  45

Asp Arg Gly Phe Ala Pro Met Thr Tyr Lys Glu Val Asp Glu Pro Phe
    50                  55                  60

Gly Thr Trp Glu Asp Ile Gln Ala Leu Ser Asn Asn Phe Tyr Leu Met
65                  70                  75                  80

Phe Asp Phe Met Val Asn His Ile Ser Lys Ser Ser Glu Tyr Phe Gln
                85                  90                  95

Asp Phe Val Glu Lys Lys Asp Glu Ser Asp Tyr Ala Lys Leu Phe Ile
            100                 105                 110

Gln Tyr Lys Asp Phe Trp Pro Asn Gly Glu Pro Thr Gln Glu Asp Val
        115                 120                 125

Asp Lys Ile Tyr Lys Arg Lys Pro Arg Ala Pro Tyr Ile Asp Val Thr
    130                 135                 140

Phe Asn Asp Gly Ser Lys Glu Lys Ile Trp Cys Thr Phe Asp Glu Glu
145                 150                 155                 160

Gln Ile Asp Leu Asn Val Tyr His Glu Arg Thr Lys Arg Phe Ile Gln
                165                 170                 175

Asp Asn Leu His Tyr Leu Ser Lys Lys Gly Ala Ser Ile Met Arg Leu
            180                 185                 190

Asp Ala Phe Ala Tyr Ala Thr Lys Gln Pro Gly Thr Asn Cys Phe Phe
        195                 200                 205

Ile Glu Pro Asp Thr Trp Glu Met Leu Asp Glu Ile Lys Glu Ile Leu
    210                 215                 220

Asp Pro Tyr Gly Val Glu Ile Leu Pro Glu Ile His Glu His Tyr Ser
225                 230                 235                 240

Ile Gln Leu Lys Leu Ala Glu Arg Gly Tyr Trp Val Tyr Asp Phe Ala
                245                 250                 255

Leu Pro Met Leu Val Leu His Ala Leu Tyr Ser Gly Arg Thr Asp Arg
            260                 265                 270

Leu Ala Asn Trp Leu Gln Thr Cys Pro Lys Lys Gln Phe Thr Thr Leu
        275                 280                 285

Asp Thr His Asp Gly Ile Gly Val Val Asp Val Val Asp Leu Leu Ser
    290                 295                 300

Asn Glu Glu Met Glu Glu Thr Arg Asp Asp Leu Phe Thr Lys Gly Ala
305                 310                 315                 320

Asn Val Lys Arg Val Tyr Asn Thr Met Glu Tyr Asn Asn Leu Asp Ile
                325                 330                 335
```

```
Tyr Gln Leu Asn Cys Thr Tyr Tyr Ser Ala Leu Gly Asn Arg Asp Asp
            340                 345                 350

Ala Tyr Ile Leu Ala Arg Ala Ile Gln Phe Phe Thr Pro Gly Ile Pro
        355                 360                 365

Gln Ile Tyr Tyr Val Gly Leu Leu Ala Gly Glu Asn Asp Ile Glu Leu
    370                 375                 380

Leu Glu Lys Thr Lys Val Gly Arg Asn Ile Asn Arg His Tyr Tyr Thr
385                 390                 395                 400

Lys Asp Glu Ile Asp Glu Asn Met Thr Arg Pro Ile Met Ser His Leu
                405                 410                 415

Ser Asn Leu Met Arg Phe Arg Asn Asn Tyr Pro Ala Phe Asp Gly Glu
            420                 425                 430

Ile Glu Val Ile Glu His Glu Asp Ser Ser Val Met Glu Ile Ile Arg
        435                 440                 445

Thr His Gly Asp Tyr Gln Ala Val Leu Thr Ala Asn Leu Lys Thr Tyr
    450                 455                 460

Ala Tyr Glu Ile Thr Tyr Lys Asp Leu Glu Thr Gly Glu Lys Arg Ser
465                 470                 475                 480

Leu Glu Asn Ile Ser Lys
                485
```

```
<210> SEQ ID NO 15
<211> LENGTH: 1446
<212> TYPE: DNA
<213> ORGANISM: Aerococcus sp.

<400> SEQUENCE: 15

atgacatttc aaaacaaaac catgttgatt acctattctg atagtttagg tagcaactta      60

aaagaattga agacgaatat cgaccaatat tttggtcaag ccatcggtgg tgtgcatcta     120

ctgccatttt ttccctctac aggcgataga gggtttgctc cggttgacta cggtcaagta     180

gatccagcat ttggtaactg ggatgatatc aaagccctag gtgacaaata ctatctaatg     240

ttcgatttta tgatcaatca catctcccgc cagtccacgt attacaaaga ctttcaggag     300

aaaaaggacg cttctgacta cgccgattta tttctaagat gggaaaaatt ctggccaagt     360

ggacgaccaa cacaggccga catcgactta atctataaaa gaaaagataa agctcccatg     420

caagccatca ccttcgctga tggtactacg gaacatttat ggaatacttt tggggaagag     480

caaatcgacc tagatatacg ccatcaagtc acaatggact tcatcaaaga tacgattgaa     540

cagctagtgg caaacggttg cgatttgatt cgacttgatg cctttgccta tgcaattaaa     600

aaactagata ccaatgattt tttcgtggaa ccagaaattt gggacttact agaccgagtg     660

caagcggttg cccaagaagc aggcgcggat attttacctg aaattcatga acactataca     720

attcctttta aacttgctga tcacggctac tttgtttatg actttgcttt accaatggtt     780

accttgtatt cactgttctc gggtaacaca gaccaattag ctaagtggtt gaagatgagc     840

cccatgaagc aatttaccac cttagatacc catgacggaa taggggtgt cgatgtaaag     900

gatattttaa ccgacgaaga aattgatttt acatccaaag ccctttataa ggtaggggct     960

aacgttaaac gtaagtattc ttctgcagaa tataataatt tagacatcta tcaaatcaat    1020

accacctatt attcagcgct aggtgactat gataagaaat atttcatcgc gcgattgatt    1080

caagctttcg caccaggaat tccacaagtg tattatgtgg gtctacttgc tggtaaaaat    1140

gatctagaac tcctagaaaa taccaaagag gggcgtaata tcaatcgcca ctattacact    1200

agtgatgaaa ttggacgtga aatacaacgt ccattggtcc aaaaattatt gcaattgttt    1260
```

```
accttccgta atgaaagtga agcttttgat ttagctggtg gtatcgaggt tgctacaccg   1320

gatgcacata cgataatcat tacacgctat aatgctgaca aatcagtaat tgctgaagca   1380

aacataaact tacttgattt acgctacagt atctttgaaa acgaccgtcc cgttcatttt   1440

gaatag                                                              1446


<210> SEQ ID NO 16
<211> LENGTH: 481
<212> TYPE: PRT
<213> ORGANISM: Aerococcus sp.

<400> SEQUENCE: 16

Met Thr Phe Gln Asn Lys Thr Met Leu Ile Thr Tyr Ser Asp Ser Leu
1               5                   10                  15

Gly Ser Asn Leu Lys Glu Leu Lys Thr Asn Ile Asp Gln Tyr Phe Gly
            20                  25                  30

Gln Ala Ile Gly Gly Val His Leu Leu Pro Phe Phe Pro Ser Thr Gly
        35                  40                  45

Asp Arg Gly Phe Ala Pro Val Asp Tyr Gly Gln Val Asp Pro Ala Phe
    50                  55                  60

Gly Asn Trp Asp Asp Ile Lys Ala Leu Gly Asp Lys Tyr Tyr Leu Met
65                  70                  75                  80

Phe Asp Phe Met Ile Asn His Ile Ser Arg Gln Ser Thr Tyr Tyr Lys
                85                  90                  95

Asp Phe Gln Glu Lys Lys Asp Ala Ser Asp Tyr Ala Asp Leu Phe Leu
            100                 105                 110

Arg Trp Glu Lys Phe Trp Pro Ser Gly Arg Pro Thr Gln Ala Asp Ile
        115                 120                 125

Asp Leu Ile Tyr Lys Arg Lys Asp Lys Ala Pro Met Gln Ala Ile Thr
    130                 135                 140

Phe Ala Asp Gly Thr Thr Glu His Leu Trp Asn Thr Phe Gly Glu Glu
145                 150                 155                 160

Gln Ile Asp Leu Asp Ile Arg His Gln Val Thr Met Asp Phe Ile Lys
                165                 170                 175

Asp Thr Ile Glu Gln Leu Val Ala Asn Gly Cys Asp Leu Ile Arg Leu
            180                 185                 190

Asp Ala Phe Ala Tyr Ala Ile Lys Lys Leu Asp Thr Asn Asp Phe Phe
        195                 200                 205

Val Glu Pro Glu Ile Trp Asp Leu Leu Asp Arg Val Gln Ala Val Ala
    210                 215                 220

Gln Glu Ala Gly Ala Asp Ile Leu Pro Glu Ile His Glu His Tyr Thr
225                 230                 235                 240

Ile Pro Phe Lys Leu Ala Asp His Gly Tyr Phe Val Tyr Asp Phe Ala
                245                 250                 255

Leu Pro Met Val Thr Leu Tyr Ser Leu Phe Ser Gly Asn Thr Asp Gln
            260                 265                 270

Leu Ala Lys Trp Leu Lys Met Ser Pro Met Lys Gln Phe Thr Thr Leu
        275                 280                 285

Asp Thr His Asp Gly Ile Gly Val Val Asp Val Lys Asp Ile Leu Thr
    290                 295                 300

Asp Glu Glu Ile Asp Phe Thr Ser Lys Ala Leu Tyr Lys Val Gly Ala
305                 310                 315                 320

Asn Val Lys Arg Lys Tyr Ser Ser Ala Glu Tyr Asn Asn Leu Asp Ile
                325                 330                 335
```

```
Tyr Gln Ile Asn Thr Thr Tyr Tyr Ser Ala Leu Gly Asp Tyr Asp Lys
            340                 345                 350

Lys Tyr Phe Ile Ala Arg Leu Ile Gln Ala Phe Ala Pro Gly Ile Pro
        355                 360                 365

Gln Val Tyr Tyr Val Gly Leu Leu Ala Gly Lys Asn Asp Leu Glu Leu
    370                 375                 380

Leu Glu Asn Thr Lys Glu Gly Arg Asn Ile Asn Arg His Tyr Tyr Thr
385                 390                 395                 400

Ser Asp Glu Ile Gly Arg Glu Ile Gln Arg Pro Leu Val Gln Lys Leu
                405                 410                 415

Leu Gln Leu Phe Thr Phe Arg Asn Glu Ser Glu Ala Phe Asp Leu Ala
            420                 425                 430

Gly Gly Ile Glu Val Ala Thr Pro Asp Ala His Thr Ile Ile Ile Thr
        435                 440                 445

Arg Tyr Asn Ala Asp Lys Ser Val Ile Ala Glu Ala Asn Ile Asn Leu
    450                 455                 460

Leu Asp Leu Arg Tyr Ser Ile Phe Glu Asn Asp Arg Pro Val His Phe
465                 470                 475                 480

Glu
```

<210> SEQ ID NO 17
<211> LENGTH: 1440
<212> TYPE: DNA
<213> ORGANISM: Artificial sequence
<220> FEATURE:
<223> OTHER INFORMATION: Metagenomic (composite) sequence for Sp277.

<400> SEQUENCE: 17

```
atgaagataa aaaacgaagc aatgctgatc acctatccgg acagtctggg aaataacctg     60

aaggacttgg aacatgtgct ggatacccat ctgaaagggg tcgtcggcgg cgtgcatatt    120

ctgccgttct tcccgtcatc cggcgaccgc ggcttttcgc cgatggacta cacgaaagtg    180

gatgagcggt tcggcggttg ggaggacatc aaacgcatca gcgaaaaata ctacatgatg    240

tatgaattca tgctgaacca catttccgcg caatcgccct attatttgga ctttttggag    300

aaaaaagaag agtctcccta caaagactac ttcatccgct acaacgacta ttggccggag    360

aaccgaccga ctgaagcgga catcgatctg atctataaac gcaaacccaa agcgcctttc    420

gtggacgccc atttcaagga cggtacgacg gaaaaagttt ggtgcacgtt ctcggaagag    480

caaatcgatc tgaatgtgaa gactgaagcg acgcgccggt tcatcaagga taccttgagt    540

ttcctggcgg acaaaggagc ctcgatcatc cgtttggacg cattcgccta tgccatcaaa    600

gaattggata cgaattgctt cttcgttgaa ccggaaattt gggagatgct ggaatacgca    660

gtggaaatcc tggagccata tggtgtgacg gtgcttccgg aaatccatga gcattacaca    720

atccaacaaa aaatcgcgga aaaaggctat ccggtctacg atttcgcctt gccgatgttg    780

gtgctgcacg ccctttacag cggcaaagcc gagaagctgc tgcactggct ggaaatctgt    840

ccgcgcaacc aattcaccac cttggacacg catgacggca tcggtgtcgt tgatgtgaag    900

gatctgctga cccaggaaga agtggacttc gcggtcgaag ccctttacga aaagggcgct    960

aacttgaagc ggatttatag ctcggaagcc tacaacaacc tggacatcta tcagatcaac   1020

tgcacgtact attcggcttt gggcaacaac gatgccgcct atctgttggc gcgggcaatc   1080

cagtgcttca ctccgggcat tccgcagatc tattacgtgg gcttgctggc cggcgaaaac   1140

gatctggaac tgctggagaa cagcaaggaa ggccgcaaca tcaaccgtca ctactatagc   1200
```

```
ctggatgaaa tcaatcagga aatcgaacgt ccggtcgtaa aagatctttt ccgcttgctg   1260

gctttccgca acacggccaa agcgttcgac ggcgacttgg agataacgat gctcgacgaa   1320

ggggccttca ctttgacgtg ggccactgcc gaagaatcgg ccagcctatc tgtcgacctg   1380

gctacgaaca aattctcggt cctgcaccgc actgcggcag gagacgaaca aatattttag   1440


<210> SEQ ID NO 18
<211> LENGTH: 479
<212> TYPE: PRT
<213> ORGANISM: Artificial sequence
<220> FEATURE:
<223> OTHER INFORMATION: Metagenomic (composite) sequence for Sp277.

<400> SEQUENCE: 18

Met Lys Ile Lys Asn Glu Ala Met Leu Ile Thr Tyr Pro Asp Ser Leu
1               5                   10                  15

Gly Asn Asn Leu Lys Asp Leu Glu His Val Leu Asp Thr His Leu Lys
            20                  25                  30

Gly Val Val Gly Gly Val His Ile Leu Pro Phe Phe Pro Ser Ser Gly
        35                  40                  45

Asp Arg Gly Phe Ser Pro Met Asp Tyr Thr Lys Val Asp Glu Arg Phe
    50                  55                  60

Gly Gly Trp Glu Asp Ile Lys Arg Ile Ser Glu Lys Tyr Tyr Met Met
65                  70                  75                  80

Tyr Glu Phe Met Leu Asn His Ile Ser Ala Gln Ser Pro Tyr Tyr Leu
                85                  90                  95

Asp Phe Leu Glu Lys Lys Glu Glu Ser Pro Tyr Lys Asp Tyr Phe Ile
            100                 105                 110

Arg Tyr Asn Asp Tyr Trp Pro Glu Asn Arg Pro Thr Glu Ala Asp Ile
        115                 120                 125

Asp Leu Ile Tyr Lys Arg Lys Pro Lys Ala Pro Phe Val Asp Ala His
    130                 135                 140

Phe Lys Asp Gly Thr Thr Glu Lys Val Trp Cys Thr Phe Ser Glu Glu
145                 150                 155                 160

Gln Ile Asp Leu Asn Val Lys Thr Glu Ala Thr Arg Arg Phe Ile Lys
                165                 170                 175

Asp Thr Leu Ser Phe Leu Ala Asp Lys Gly Ala Ser Ile Ile Arg Leu
            180                 185                 190

Asp Ala Phe Ala Tyr Ala Ile Lys Glu Leu Asp Thr Asn Cys Phe Phe
        195                 200                 205

Val Glu Pro Glu Ile Trp Glu Met Leu Glu Tyr Ala Val Glu Ile Leu
    210                 215                 220

Glu Pro Tyr Gly Val Thr Val Leu Pro Glu Ile His Glu His Tyr Thr
225                 230                 235                 240

Ile Gln Gln Lys Ile Ala Glu Lys Gly Tyr Pro Val Tyr Asp Phe Ala
                245                 250                 255

Leu Pro Met Leu Val Leu His Ala Leu Tyr Ser Gly Lys Ala Glu Lys
            260                 265                 270

Leu Leu His Trp Leu Glu Ile Cys Pro Arg Asn Gln Phe Thr Thr Leu
        275                 280                 285

Asp Thr His Asp Gly Ile Gly Val Val Asp Val Lys Asp Leu Leu Thr
    290                 295                 300

Gln Glu Glu Val Asp Phe Ala Val Glu Ala Leu Tyr Glu Lys Gly Ala
305                 310                 315                 320
```

```
Asn Leu Lys Arg Ile Tyr Ser Ser Glu Ala Tyr Asn Asn Leu Asp Ile
                325                 330                 335

Tyr Gln Ile Asn Cys Thr Tyr Tyr Ser Ala Leu Gly Asn Asn Asp Ala
            340                 345                 350

Ala Tyr Leu Leu Ala Arg Ala Ile Gln Cys Phe Thr Pro Gly Ile Pro
        355                 360                 365

Gln Ile Tyr Tyr Val Gly Leu Leu Ala Gly Glu Asn Asp Leu Glu Leu
    370                 375                 380

Leu Glu Asn Ser Lys Glu Gly Arg Asn Ile Asn Arg His Tyr Tyr Ser
385                 390                 395                 400

Leu Asp Glu Ile Asn Gln Glu Ile Glu Arg Pro Val Val Lys Asp Leu
                405                 410                 415

Phe Arg Leu Leu Ala Phe Arg Asn Thr Ala Lys Ala Phe Asp Gly Asp
            420                 425                 430

Leu Glu Ile Thr Met Leu Asp Glu Gly Ala Phe Thr Leu Thr Trp Ala
        435                 440                 445

Thr Ala Glu Glu Ser Ala Ser Leu Ser Val Asp Leu Ala Thr Asn Lys
    450                 455                 460

Phe Ser Val Leu His Arg Thr Ala Ala Gly Asp Glu Gln Ile Phe
465                 470                 475
```

<210> SEQ ID NO 19
<211> LENGTH: 1722
<212> TYPE: DNA
<213> ORGANISM: Clostridiaceae sp.

<400> SEQUENCE: 19

```
atgactaagc aaggattatt acaaaatgcc ggtcccatgt tcaatgctta tcctgacagc     60

ataggaggaa cattgaatga ttgtgtagaa cttcttaagc tgccggagtt tgaaaatgca    120

tttagggcat tttatatttt gccaagcctt ttcaatacag atcttgacag ggtttttcg    180

gtaattgatt atgagttgaa tgaggcatat gcctccaatg aagatttaaa aaatttaaaa    240

cagttgaata tagagcttaa gctggatttc attttaaacc attgttctgt actttcaaaa    300

cagtttcagg atattataaa aaacggggaa aaatcaaaat acacggattt cttcatcaac    360

tggaacaagt tttgggacgg gtacggagaa atgacagaag aaggatatat ccgcccttat    420

gacgaatata tcaaaaatat gtttttcaga aaacccggac ttccgatttt gatggtaagg    480

atgcctgacg gcagggaagt accctattgg aacacttttt atcaggaagt aaaatataat    540

aaaatcacaa gttatgaact cataaaaaac ctgaatatcc agtatgtaac tgctgaaaga    600

atagcaaatc tggtaaacag tgccctggat gaaggaaaga aaccgattga aattgatttt    660

acaggctttg aaaaatacaa agatgaggta atagatttac ttgaagcaaa caggcattat    720

ctaggccaga tggaccttaa tataaagtcg ccactggtat gggagttcta tgatgatacc    780

ttaaaaaaat taaaagagta cggagcgtcg ataattaggc ttgatgcatt tgcatatgct    840

ccaaaagaac cgggggaaaa aaacttcatg aatgaaccgg gaacatggga gctgcttgaa    900

cgggtaagag aattggctga taaatatcaa ttaacgcttt tacctgaaat acattccaga    960

tacgaagaaa aagttcatga aaaattagcc gaaaaagggt atcttaccta tgatttcttt   1020

ttacccggcc taattattga cgctttggag cggcacaata acaaatatat aattaaatgg   1080

ttttatgata ttattgaaaa gaatataaaa acagtcaata tgctgggttg tcatgacgga   1140

attcctctgc tggatttaaa gggcctgatt ccggatgatg agattgacca attaataagt   1200

actattgtat caagaggcgg actggtaaaa gacctgcacg gtaagaaaaa tatatattat   1260
```

```
caggttaatt ctacgtattt cagcgccctt ggagaagacg aaagaaaact tcttttggcc   1320

agagccattc aaatttttac tcccggaata ccccaggtat ggtatcttga tttatttgca   1380

ggaagaaatg actatgaggc ggttaaaaag gcaggaccgg gagggcataa ggaaattaac   1440

cgtaccaatt tgactatgga tcaggcaaaa gacggactta aaacagatat tgtaagacgg   1500

cagttagaac tgctaagatt cagaaatact tttcctgcat ttggctttaa tgccaaattg   1560

caagttatag aatcagaacc gcatatattg aaactcaggt gggaaaaaga ctcctgcagt   1620

gcaacactca cagccaattt gaaggattat tcctttgaaa tatcgggtgt agatgaaaat   1680

aataatatta taaattttaa ttcaaataac aataattggt ag                       1722


<210> SEQ ID NO 20
<211> LENGTH: 573
<212> TYPE: PRT
<213> ORGANISM: Clostridiaceae sp.

<400> SEQUENCE: 20

Met Thr Lys Gln Gly Leu Leu Gln Asn Ala Gly Pro Met Phe Asn Ala
1               5                   10                  15

Tyr Pro Asp Ser Ile Gly Gly Thr Leu Asn Asp Cys Val Glu Leu Leu
            20                  25                  30

Lys Leu Pro Glu Phe Glu Asn Ala Phe Arg Ala Phe Tyr Ile Leu Pro
        35                  40                  45

Ser Leu Phe Asn Thr Asp Leu Asp Arg Gly Phe Ser Val Ile Asp Tyr
    50                  55                  60

Glu Leu Asn Glu Ala Tyr Ala Ser Asn Glu Asp Leu Lys Asn Leu Lys
65                  70                  75                  80

Gln Leu Asn Ile Glu Leu Lys Leu Asp Phe Ile Leu Asn His Cys Ser
                85                  90                  95

Val Leu Ser Lys Gln Phe Gln Asp Ile Ile Lys Asn Gly Glu Lys Ser
            100                 105                 110

Lys Tyr Thr Asp Phe Phe Ile Asn Trp Asn Lys Phe Trp Asp Gly Tyr
        115                 120                 125

Gly Glu Met Thr Glu Glu Gly Tyr Ile Arg Pro Tyr Asp Glu Tyr Ile
    130                 135                 140

Lys Asn Met Phe Phe Arg Lys Pro Gly Leu Pro Ile Leu Met Val Arg
145                 150                 155                 160

Met Pro Asp Gly Arg Glu Val Pro Tyr Trp Asn Thr Phe Tyr Gln Glu
                165                 170                 175

Val Lys Tyr Asn Lys Ile Thr Ser Tyr Glu Leu Ile Lys Asn Leu Asn
            180                 185                 190

Ile Gln Tyr Val Thr Ala Glu Arg Ile Ala Asn Leu Val Asn Ser Ala
        195                 200                 205

Leu Asp Glu Gly Lys Lys Pro Ile Glu Ile Asp Phe Thr Gly Phe Glu
    210                 215                 220

Lys Tyr Lys Asp Glu Val Ile Asp Leu Leu Glu Ala Asn Arg His Tyr
225                 230                 235                 240

Leu Gly Gln Met Asp Leu Asn Ile Lys Ser Pro Leu Val Trp Glu Phe
                245                 250                 255

Tyr Asp Asp Thr Leu Lys Lys Leu Lys Glu Tyr Gly Ala Ser Ile Ile
            260                 265                 270

Arg Leu Asp Ala Phe Ala Tyr Ala Pro Lys Glu Pro Gly Glu Lys Asn
        275                 280                 285
```

```
Phe Met Asn Glu Pro Gly Thr Trp Glu Leu Leu Glu Arg Val Arg Glu
    290                 295                 300

Leu Ala Asp Lys Tyr Gln Leu Thr Leu Leu Pro Glu Ile His Ser Arg
305                 310                 315                 320

Tyr Glu Glu Lys Val His Glu Lys Leu Ala Glu Lys Gly Tyr Leu Thr
                325                 330                 335

Tyr Asp Phe Phe Leu Pro Gly Leu Ile Ile Asp Ala Leu Glu Arg His
            340                 345                 350

Asn Asn Lys Tyr Ile Ile Lys Trp Phe Tyr Asp Ile Ile Glu Lys Asn
        355                 360                 365

Ile Lys Thr Val Asn Met Leu Gly Cys His Asp Gly Ile Pro Leu Leu
    370                 375                 380

Asp Leu Lys Gly Leu Ile Pro Asp Asp Glu Ile Asp Gln Leu Ile Ser
385                 390                 395                 400

Thr Ile Val Ser Arg Gly Gly Leu Val Lys Asp Leu His Gly Lys Lys
                405                 410                 415

Asn Ile Tyr Tyr Gln Val Asn Ser Thr Tyr Phe Ser Ala Leu Gly Glu
            420                 425                 430

Asp Glu Arg Lys Leu Leu Leu Ala Arg Ala Ile Gln Ile Phe Thr Pro
        435                 440                 445

Gly Ile Pro Gln Val Trp Tyr Leu Asp Leu Phe Ala Gly Arg Asn Asp
    450                 455                 460

Tyr Glu Ala Val Lys Lys Ala Gly Pro Gly Gly His Lys Glu Ile Asn
465                 470                 475                 480

Arg Thr Asn Leu Thr Met Asp Gln Ala Lys Asp Gly Leu Lys Thr Asp
                485                 490                 495

Ile Val Arg Arg Gln Leu Glu Leu Leu Arg Phe Arg Asn Thr Phe Pro
            500                 505                 510

Ala Phe Gly Phe Asn Ala Lys Leu Gln Val Ile Glu Ser Glu Pro His
        515                 520                 525

Ile Leu Lys Leu Arg Trp Glu Lys Asp Ser Cys Ser Ala Thr Leu Thr
    530                 535                 540

Ala Asn Leu Lys Asp Tyr Ser Phe Glu Ile Ser Gly Val Asp Glu Asn
545                 550                 555                 560

Asn Asn Ile Ile Asn Phe Asn Ser Asn Asn Asn Asn Trp
                565                 570
```

<210> SEQ ID NO 21
<211> LENGTH: 1506
<212> TYPE: DNA
<213> ORGANISM: Actinotalea sp.

<400> SEQUENCE: 21

```
gtgaccacat ccccgtccgc cccgggcggc ccccagctga tcgcctacgc cgaccgcttc      60

ggcggctccg tcgcggggct caccgagctg ctccgcggcc cgctcgccgg agcgttcgac     120

ggcgtgcacg tgctgccctt cttcaccccg ttcgacggcg ccgatgcggg gttcgacccg     180

gtggaccaca cccaggtcga cccccgtctg ggcacctggc aggacgtcgc cgagctcgcc     240

acggaccaca cggtcatggc cgacgtcatc gtcaaccacg tgtcgagcga ctcaccggcc     300

ttccaggacg tggtcgagcg gggacgggac tccccgtggg caccgatgtt cctgaccttc     360

gacgcggtct tccccgaggg ggcgaccgag gcccagctcg ccgccatcta ccgtccgcgc     420

cctggcctgc ccttcaccgc gatgaccctg ggtggggagc gtcggctggt ctggacgacc     480

ttcaccccgc agcaggtcga cctcgacatc cgcgcccccc aggcgtggcg gtacctgacc     540
```

```
gaggtgatcg acaaccagac cggtgccggg gtgggcatgc tgcgcctgga cgcggtgggc     600

tacgtcgcga aggtcccggg cacgagctgc ttcatgctcc ccgaggcggc cgacgtggtc     660

accagggtcc gtgagcacgc ccacgggcgc ggggcccagg tgctcctgga gatccacggc     720

tactaccgcc agcagatcga gatcgcgaag accgtggaca tggtctatga cttcgcgctg     780

ccgcccctgc tgctgcacgc cttcgcggcg gccgacctcg ccccgctcgc gcactggctc     840

gaggtgcgtc cgaccaactg cgtcacggtg ctcgataccc acgacggcat cgggatcatc     900

gacgcgggtc gtgggccggc gggtgagccg ggcctgctcg aggacgcgca gatcgacgcc     960

ctggtcgagt ggatccacga gcagagctcg ggggagagcc ggcgcgcgac cggcggcgcg    1020

gcgtcgaacc tcgacctcta ccaggtgaac tgcaccttct tcgcggccct cggcgagcac    1080

gaggaccgct acctgctcgc gcggctcgtg cagctgttcc tgccgggcat cccgcaggtc    1140

tactacgtcg ggctgctcgc cggtcgcaac gacatggacc tcctcgaacg caccggcgtg    1200

ggtcgtgaca tcaaccgcca ccactacacg cgccccgaga tcgacgccga gctcgagcga    1260

cccgtcgtgc gggaccagct cgcggccctg cggctgcgcg cgcagcaccc ggccttcgcc    1320

ggggaggtca cctgggccgt cgacggcccc gagctgaccg tgcgctgggt cgcgggggag    1380

cacacggccg agctcgaggt cgacgtcgcg gccgtgcgtg gcgtcgtgcg ggtgagtgcg    1440

gccgggcagg tccaggaggt cgacgcccgg gccctcgccg cgacggtccc cgacctgctg    1500

ccgtga                                                               1506
```

```
<210> SEQ ID NO 22
<211> LENGTH: 501
<212> TYPE: PRT
<213> ORGANISM: Actinotalea sp.

<400> SEQUENCE: 22

Met Thr Thr Ser Pro Ser Ala Pro Gly Gly Pro Gln Leu Ile Ala Tyr
1               5                   10                  15

Ala Asp Arg Phe Gly Gly Ser Val Ala Gly Leu Thr Glu Leu Leu Arg
            20                  25                  30

Gly Pro Leu Ala Gly Ala Phe Asp Gly Val His Val Leu Pro Phe Phe
        35                  40                  45

Thr Pro Phe Asp Gly Ala Asp Ala Gly Phe Asp Pro Val Asp His Thr
    50                  55                  60

Gln Val Asp Pro Arg Leu Gly Thr Trp Gln Asp Val Ala Glu Leu Ala
65                  70                  75                  80

Thr Asp His Thr Val Met Ala Asp Val Ile Val Asn His Val Ser Ser
                85                  90                  95

Asp Ser Pro Ala Phe Gln Asp Val Val Glu Arg Gly Arg Asp Ser Pro
            100                 105                 110

Trp Ala Pro Met Phe Leu Thr Phe Asp Ala Val Phe Pro Glu Gly Ala
        115                 120                 125

Thr Glu Ala Gln Leu Ala Ala Ile Tyr Arg Pro Arg Pro Gly Leu Pro
    130                 135                 140

Phe Thr Ala Met Thr Leu Gly Gly Glu Arg Arg Leu Val Trp Thr Thr
145                 150                 155                 160

Phe Thr Pro Gln Gln Val Asp Leu Asp Ile Arg Ala Pro Gln Ala Trp
                165                 170                 175

Arg Tyr Leu Thr Glu Val Ile Asp Asn Gln Thr Gly Ala Gly Val Gly
            180                 185                 190
```

```
Met Leu Arg Leu Asp Ala Val Gly Tyr Val Ala Lys Val Pro Gly Thr
        195                 200                 205

Ser Cys Phe Met Leu Pro Glu Ala Ala Asp Val Val Thr Arg Val Arg
    210                 215                 220

Glu His Ala His Gly Arg Gly Ala Gln Val Leu Leu Glu Ile His Gly
225                 230                 235                 240

Tyr Tyr Arg Gln Gln Ile Glu Ile Ala Lys Thr Val Asp Met Val Tyr
                245                 250                 255

Asp Phe Ala Leu Pro Pro Leu Leu Leu His Ala Phe Ala Ala Ala Asp
            260                 265                 270

Leu Ala Pro Leu Ala His Trp Leu Glu Val Arg Pro Thr Asn Cys Val
        275                 280                 285

Thr Val Leu Asp Thr His Asp Gly Ile Gly Ile Ile Asp Ala Gly Arg
    290                 295                 300

Gly Pro Ala Gly Glu Pro Gly Leu Leu Glu Asp Ala Gln Ile Asp Ala
305                 310                 315                 320

Leu Val Glu Trp Ile His Glu Gln Ser Ser Gly Glu Ser Arg Arg Ala
                325                 330                 335

Thr Gly Gly Ala Ala Ser Asn Leu Asp Leu Tyr Gln Val Asn Cys Thr
            340                 345                 350

Phe Phe Ala Ala Leu Gly Glu His Glu Asp Arg Tyr Leu Leu Ala Arg
        355                 360                 365

Leu Val Gln Leu Phe Leu Pro Gly Ile Pro Gln Val Tyr Tyr Val Gly
    370                 375                 380

Leu Leu Ala Gly Arg Asn Asp Met Asp Leu Leu Glu Arg Thr Gly Val
385                 390                 395                 400

Gly Arg Asp Ile Asn Arg His His Tyr Thr Arg Pro Glu Ile Asp Ala
                405                 410                 415

Glu Leu Glu Arg Pro Val Val Arg Asp Gln Leu Ala Ala Leu Arg Leu
            420                 425                 430

Arg Ala Gln His Pro Ala Phe Ala Gly Glu Val Thr Trp Ala Val Asp
        435                 440                 445

Gly Pro Glu Leu Thr Val Arg Trp Val Ala Gly Glu His Thr Ala Glu
    450                 455                 460

Leu Glu Val Asp Val Ala Ala Val Arg Gly Val Val Arg Val Ser Ala
465                 470                 475                 480

Ala Gly Gln Val Gln Glu Val Asp Ala Arg Ala Leu Ala Ala Thr Val
                485                 490                 495

Pro Asp Leu Leu Pro
            500
```

<210> SEQ ID NO 23
<211> LENGTH: 1500
<212> TYPE: DNA
<213> ORGANISM: Paenibacillus sp.

<400> SEQUENCE: 23

```
atgaaaaaaa ttacaaatca ggtcatgctc attacgtatg ccgacagcat ggggagcaat      60

ttggacgagc tgaaccaggt gcttgaaacg cattttgagg gcgttatcga agggcttcac     120

atccttcctt tcttcccgtc ctccggtgat cgcggctttg cggtcatcca ttatgacgag     180

gtagatccag ccttcggcga ttggaatgac atccagcgac tatcggacaa gtattatctg     240

atggcggact tcatgatcaa tcacgtctcg atccgctcgg aagagttcat cgactacatg     300

cagcggggcg acgagtcacc attcaaggag atgttcattc actgggatga gttctggccc     360
```

```
ggcggggaac caaccgaagc cgagatggaa gcgctatatc ggagaaaaat gcatggaccc    420

tataaggaat ttacgcgtgc ggacggtaaa acggttaagc tgtggaacac gttcttcgag    480

gagcaggtgg atatcgatcc atgggcgacg gctacgcaaa gctactacga gcgtaatctg    540

gagcggctcg ccgggtacgt gccactgatc cgattcgatg ccttcgcgta tgcttccaaa    600

aagccgggca ccagctgctt cttcgtcgaa ccggaagtgt gggacgtgct ggatatcggc    660

atgcgtccgc ttaacaaata cggtacggaa atgctgcctg agattcatga gaactacaag    720

atccagctca agatggcgga gcagggtcat tgggtgtacg atttcgcgct gccgatgctg    780

ctcctgcacg cgctgatgac ggggtgctcg gaccggctca tccactggat gcagatctgc    840

cctcgcaagc agttcacaac gctcgacacc catgacggga tcggcgtcgt cgatgtggca    900

ggattgctga gcgacgagga aatcgatctg gtgcgtgatc gtgtgaatac gaaggttgaa    960

ccgttgcagc agtacatcaa tttcccgcca ggcattgtca aaatgtccgg tgcaaaagcg   1020

agacaatatc agctgatgtg cacgtactat tcggcattgg atgaggatga tcatgcttac   1080

acgctggccc gaattatcca gctgtacgcg ccgggaattc cgcaagtcta ctatgtgggc   1140

ctgctggctg gcgagaatga tgaggaatcg ctgaagcgtt tgggcgagcc gcggagcctc   1200

aatcggcaca actactcgat ggaggaaatc gctgagcggg tgcagacccc gatgctgcag   1260

cacttatatg cagttatgaa attccgcaac agccatcctg ccttcggcgg cgatgtcgag   1320

attggcgaac cggctggcga cggccagctt gccatcgcct ggcgtcaggg cgatgcttgg   1380

accaccctgg aggcggatct gcggacgaag gcttatacaa tcgtcgccag taacgccgaa   1440

ggcgctgcag agagactgtt ccactctaac ggcgtggccg tcccggaggg atcacaatga   1500
```

```
<210> SEQ ID NO 24
<211> LENGTH: 499
<212> TYPE: PRT
<213> ORGANISM: Paenibacillus sp.

<400> SEQUENCE: 24

Met Lys Lys Ile Thr Asn Gln Val Met Leu Ile Thr Tyr Ala Asp Ser
1               5                   10                  15

Met Gly Ser Asn Leu Asp Glu Leu Asn Gln Val Leu Glu Thr His Phe
            20                  25                  30

Glu Gly Val Ile Glu Gly Leu His Ile Leu Pro Phe Phe Pro Ser Ser
        35                  40                  45

Gly Asp Arg Gly Phe Ala Val Ile His Tyr Asp Glu Val Asp Pro Ala
    50                  55                  60

Phe Gly Asp Trp Asn Asp Ile Gln Arg Leu Ser Asp Lys Tyr Tyr Leu
65                  70                  75                  80

Met Ala Asp Phe Met Ile Asn His Val Ser Ile Arg Ser Glu Glu Phe
                85                  90                  95

Ile Asp Tyr Met Gln Arg Gly Asp Glu Ser Pro Phe Lys Glu Met Phe
            100                 105                 110

Ile His Trp Asp Glu Phe Trp Pro Gly Gly Glu Pro Thr Glu Ala Glu
        115                 120                 125

Met Glu Ala Leu Tyr Arg Arg Lys Met His Gly Pro Tyr Lys Glu Phe
    130                 135                 140

Thr Arg Ala Asp Gly Lys Thr Val Lys Leu Trp Asn Thr Phe Phe Glu
145                 150                 155                 160

Glu Gln Val Asp Ile Asp Pro Trp Ala Thr Ala Thr Gln Ser Tyr Tyr
                165                 170                 175
```

```
Glu Arg Asn Leu Glu Arg Leu Ala Gly Tyr Val Pro Leu Ile Arg Phe
            180                 185                 190

Asp Ala Phe Ala Tyr Ala Ser Lys Lys Pro Gly Thr Ser Cys Phe Phe
        195                 200                 205

Val Glu Pro Glu Val Trp Asp Val Leu Asp Ile Gly Met Arg Pro Leu
    210                 215                 220

Asn Lys Tyr Gly Thr Glu Met Leu Pro Glu Ile His Glu Asn Tyr Lys
225                 230                 235                 240

Ile Gln Leu Lys Met Ala Glu Gln Gly His Trp Val Tyr Asp Phe Ala
                245                 250                 255

Leu Pro Met Leu Leu Leu His Ala Leu Met Thr Gly Cys Ser Asp Arg
            260                 265                 270

Leu Ile His Trp Met Gln Ile Cys Pro Arg Lys Gln Phe Thr Thr Leu
        275                 280                 285

Asp Thr His Asp Gly Ile Gly Val Val Asp Val Ala Gly Leu Leu Ser
    290                 295                 300

Asp Glu Glu Ile Asp Leu Val Arg Asp Arg Val Asn Thr Lys Val Glu
305                 310                 315                 320

Pro Leu Gln Gln Tyr Ile Asn Phe Pro Pro Gly Ile Val Lys Met Ser
                325                 330                 335

Gly Ala Lys Ala Arg Gln Tyr Gln Leu Met Cys Thr Tyr Tyr Ser Ala
            340                 345                 350

Leu Asp Glu Asp Asp His Ala Tyr Thr Leu Ala Arg Ile Ile Gln Leu
        355                 360                 365

Tyr Ala Pro Gly Ile Pro Gln Val Tyr Tyr Val Gly Leu Leu Ala Gly
    370                 375                 380

Glu Asn Asp Glu Glu Ser Leu Lys Arg Leu Gly Glu Pro Arg Ser Leu
385                 390                 395                 400

Asn Arg His Asn Tyr Ser Met Glu Glu Ile Ala Glu Arg Val Gln Thr
                405                 410                 415

Pro Met Leu Gln His Leu Tyr Ala Val Met Lys Phe Arg Asn Ser His
            420                 425                 430

Pro Ala Phe Gly Gly Asp Val Glu Ile Gly Glu Pro Ala Gly Asp Gly
        435                 440                 445

Gln Leu Ala Ile Ala Trp Arg Gln Gly Asp Ala Trp Thr Thr Leu Glu
    450                 455                 460

Ala Asp Leu Arg Thr Lys Ala Tyr Thr Ile Val Ala Ser Asn Ala Glu
465                 470                 475                 480

Gly Ala Ala Glu Arg Leu Phe His Ser Asn Gly Val Ala Val Pro Glu
                485                 490                 495

Gly Ser Gln
```

<210> SEQ ID NO 25
<211> LENGTH: 2079
<212> TYPE: DNA
<213> ORGANISM: Aquifex aeolicus

<400> SEQUENCE: 25

```
atggaagaag aaaaagtaaa agagggattg tgggagttag cttacaacct gtggtggacg     60

tggaatccgc cggctaagga attattcaga agcattgacc cgcttttgtg gaaggaaact    120

aaggaaaacc ccattgagtt attgaggaaa accaaactcc ttgaaaacaa gctcaaagac    180

gaagatttta tatctcactt caagtacgtt tattcccttt acaaaaccta catgaacagg    240
```

```
cattcgaaat acgaggatac gtataagaag cctatagttt tcctgtctcc cgagtacgga    300

cttcaccaca cactacttat atacgcgggg ggactgggct ttttagcagg agatatactc    360

aaggagagca gtgacttggg atttccgctt ataggtgtcg ggtttatgta ccctcagggc    420

tacgtaaagc agaggataag ggttgacgga tggcaggaag accttgacgc acaaaatcaa    480

aaggaattaa tgcccgttaa aaaagttctg gacaaagaag gaaaatggct caagtgctac    540

gtttacgtaa gggatgaaaa ggtttacttt ggagtctggg aagttaacgt gggaaagaca    600

aagctctacc ttcttgacac gaacgtagag gaaaatactc cctggaacag ggaaatatcc    660

tcaagactct acgttccgga caaagacctg aggttaagac aacagatagt tcttggtttt    720

ggcaccgtaa tactccttga aaagctgggc attgatgcag gaggttttca cataaacgaa    780

gattatccct cgttcgtgtt ccttgcagaa atatttaaac ttctaaaaaa aggtctgacc    840

tgggataagg cgatagaaga agtaagaaag atttctctct ttaccacgca cacaccacta    900

cgggttgccg taaatactta tcccttccac atgatagagg aacagtttct attcgttaag    960

gatgtttacg gaatagacgt aaagaaagtt ctggaactcg gaacgaatcc tgaagaccct   1020

tcggagggtt ttaacagtac gattatgtcc ctcagactcg caaagtacgt aaacgcagtg   1080

agtaaaagac atcaagaagt ttcaagcaag atgtggagtt ttttatttaa agaaaaggag   1140

aatccaatag attacgtaac gaacggtgtt cactttccca catggatttg ttcagatttg   1200

agaagactgt acgaggagta tttgggagag aactttgtgg aacttcacga ccacaagtct   1260

ctgtgggaat taataagaga catacccgac gaagaactgt gggaatatca cataagaaat   1320

aaagaaagac ttattgagca cataaaagac agggcaaggg aaaggtgggt caaggaaaaa   1380

gcggatcctt caatccttat ggccgaaggt ctgttccttg attctgacgt tcttacggtc   1440

ggttttgcga ggaggatgac cggttacaaa agaccggatc ttatattcac ggatgtagaa   1500

cgcttaaaaa agatagtgaa tgattcggaa agacctgttc agataatatt cgcgggaaag   1560

gctcatccgg ctgatatcga agggaaaaag ataatccaga gaatatttaa ctttgcgaaa   1620

gatccggaat ttgggggaag aatagctttc gttgaagatt acgacgaact ccttgcccat   1680

tacatggtga ggggtgtgga cgtatggttg aacaaccctc ttcctcccct tgaagcctgc   1740

gggacaagcg gtatgaaagc ttctatgaac ggagtgcttc acctttcaat acttgacggt   1800

tggtggattg agggttataa cggaaagaac ggttgggctt tcggagatta cgaagttgaa   1860

ggagacagga acagagcgga tgcggaggcc atttacaaca tccttgagaa tgaagtaatc   1920

ccccttatt acgaaaggga cgagagggga gtgccagtta agtggataag tatgatgaag     1980

gaagctataa aaagcattac ccctaacttt tgctccagaa ggatgttaaa agattacata   2040

aataagttct attcaaaaat tttaaaggag gagggatga                           2079
```

<210> SEQ ID NO 26
<211> LENGTH: 692
<212> TYPE: PRT
<213> ORGANISM: Aquifex aeolicus

<400> SEQUENCE: 26

```
Met Glu Glu Glu Lys Val Lys Glu Gly Leu Trp Glu Leu Ala Tyr Asn
1               5                   10                  15

Leu Trp Trp Thr Trp Asn Pro Pro Ala Lys Glu Leu Phe Arg Ser Ile
            20                  25                  30

Asp Pro Leu Leu Trp Lys Glu Thr Lys Glu Asn Pro Ile Glu Leu Leu
        35                  40                  45
```

```
Arg Lys Thr Lys Leu Leu Glu Asn Lys Leu Lys Asp Glu Asp Phe Ile
    50                  55                  60

Ser His Phe Lys Tyr Val Tyr Ser Leu Tyr Lys Thr Tyr Met Asn Arg
65                  70                  75                  80

His Ser Lys Tyr Glu Asp Thr Tyr Lys Lys Pro Ile Val Phe Leu Ser
                85                  90                  95

Pro Glu Tyr Gly Leu His His Thr Leu Leu Ile Tyr Ala Gly Gly Leu
            100                 105                 110

Gly Phe Leu Ala Gly Asp Ile Leu Lys Glu Ser Ser Asp Leu Gly Phe
        115                 120                 125

Pro Leu Ile Gly Val Gly Phe Met Tyr Pro Gln Gly Tyr Val Lys Gln
    130                 135                 140

Arg Ile Arg Val Asp Gly Trp Gln Glu Asp Leu Asp Ala Gln Asn Gln
145                 150                 155                 160

Lys Glu Leu Met Pro Val Lys Lys Val Leu Asp Lys Glu Gly Lys Trp
                165                 170                 175

Leu Lys Cys Tyr Val Tyr Val Arg Asp Glu Lys Val Tyr Phe Gly Val
            180                 185                 190

Trp Glu Val Asn Val Gly Lys Thr Lys Leu Tyr Leu Leu Asp Thr Asn
        195                 200                 205

Val Glu Glu Asn Thr Pro Trp Asn Arg Glu Ile Ser Ser Arg Leu Tyr
    210                 215                 220

Val Pro Asp Lys Asp Leu Arg Leu Arg Gln Gln Ile Val Leu Gly Phe
225                 230                 235                 240

Gly Thr Val Ile Leu Leu Glu Lys Leu Gly Ile Asp Ala Gly Gly Phe
                245                 250                 255

His Ile Asn Glu Asp Tyr Pro Ser Phe Val Phe Leu Ala Glu Ile Phe
            260                 265                 270

Lys Leu Leu Lys Lys Gly Leu Thr Trp Asp Lys Ala Ile Glu Glu Val
        275                 280                 285

Arg Lys Ile Ser Leu Phe Thr Thr His Thr Pro Leu Arg Val Ala Val
    290                 295                 300

Asn Thr Tyr Pro Phe His Met Ile Glu Glu Gln Phe Leu Phe Val Lys
305                 310                 315                 320

Asp Val Tyr Gly Ile Asp Val Lys Lys Val Leu Glu Leu Gly Thr Asn
                325                 330                 335

Pro Glu Asp Pro Ser Glu Gly Phe Asn Ser Thr Ile Met Ser Leu Arg
            340                 345                 350

Leu Ala Lys Tyr Val Asn Ala Val Ser Lys Arg His Gln Glu Val Ser
        355                 360                 365

Ser Lys Met Trp Ser Phe Leu Phe Lys Glu Lys Glu Asn Pro Ile Asp
    370                 375                 380

Tyr Val Thr Asn Gly Val His Phe Pro Thr Trp Ile Cys Ser Asp Leu
385                 390                 395                 400

Arg Arg Leu Tyr Glu Glu Tyr Leu Gly Glu Asn Phe Val Glu Leu His
                405                 410                 415

Asp His Lys Ser Leu Trp Glu Leu Ile Arg Asp Ile Pro Asp Glu Glu
            420                 425                 430

Leu Trp Glu Tyr His Ile Arg Asn Lys Glu Arg Leu Ile Glu His Ile
        435                 440                 445

Lys Asp Arg Ala Arg Glu Arg Trp Val Lys Glu Lys Ala Asp Pro Ser
    450                 455                 460

Ile Leu Met Ala Glu Gly Leu Phe Leu Asp Ser Asp Val Leu Thr Val
```

```
465                 470                 475                 480

Gly Phe Ala Arg Arg Met Thr Gly Tyr Lys Arg Pro Asp Leu Ile Phe
                485                 490                 495

Thr Asp Val Glu Arg Leu Lys Lys Ile Val Asn Asp Ser Glu Arg Pro
            500                 505                 510

Val Gln Ile Ile Phe Ala Gly Lys Ala His Pro Ala Asp Ile Glu Gly
        515                 520                 525

Lys Lys Ile Ile Gln Arg Ile Phe Asn Phe Ala Lys Asp Pro Glu Phe
    530                 535                 540

Gly Gly Arg Ile Ala Phe Val Glu Asp Tyr Asp Glu Leu Leu Ala His
545                 550                 555                 560

Tyr Met Val Arg Gly Val Asp Val Trp Leu Asn Asn Pro Leu Pro Pro
                565                 570                 575

Leu Glu Ala Cys Gly Thr Ser Gly Met Lys Ala Ser Met Asn Gly Val
            580                 585                 590

Leu His Leu Ser Ile Leu Asp Gly Trp Trp Ile Glu Gly Tyr Asn Gly
        595                 600                 605

Lys Asn Gly Trp Ala Phe Gly Asp Tyr Glu Val Glu Gly Asp Arg Asn
    610                 615                 620

Arg Ala Asp Ala Glu Ala Ile Tyr Asn Ile Leu Glu Asn Glu Val Ile
625                 630                 635                 640

Pro Leu Tyr Tyr Glu Arg Asp Glu Arg Gly Val Pro Val Lys Trp Ile
                645                 650                 655

Ser Met Met Lys Glu Ala Ile Lys Ser Ile Thr Pro Asn Phe Cys Ser
            660                 665                 670

Arg Arg Met Leu Lys Asp Tyr Ile Asn Lys Phe Tyr Ser Lys Ile Leu
        675                 680                 685

Lys Glu Glu Gly
    690
```

<210> SEQ ID NO 27
<211> LENGTH: 2460
<212> TYPE: DNA
<213> ORGANISM: Thermus caldophilus GK24

<400> SEQUENCE: 27

```
atgaacgttc tcggacggat caccgccatg cccgacctcc ccgagcccct ggaggggctt     60

aaggagatcg cctacaacct ctggtggagc tggaacccgg aggcggccga gcttttccag    120

gagctggacc ccgccctttg gaagcggttc cgcgggaacc cggtgaagct ccttctggag    180

ctggaccccg cccgcctcga ggccttaagc gcctcgggct acgccgcccg ggtccaggcc    240

acccgggagg cgcttagggc ctacctcgag gcccgcagga cgaagcgggg ccccctggtg    300

gcctacttct cggcggagta cggcttccac agctccctgc ccatctacgc cggggggctt    360

ggggtcctcg ccggggacca cgtcaaggcg gcgagcgacc tcggcctcaa cctcgtgggg    420

gtggggctct tctaccacga ggggtacttc caccagcgcc tctccccgga aggggagcag    480

gtggaggtct acgagcccct ccgccccgag gagcttcccc tcgtcccggt ccaggacgcc    540

gaggggaggc ccgtgcgggt ggccgtggag ttcccgggcc gcctggtcca cgtgggggg    600

taccgggtgc aggtgggggc ggtgcccgtc tacctcctca ccacagacct cccggagaac    660

gcccccgagg accggcagat cacggcccgg ctctacgccg cgggcctcga ggcccgcatc    720

cagcaggagc tcgtcctggg cctcgggggg gtgcggttcc tcagggcctt gggcctcgcc    780

cccgccttct tccacatgaa cgaggggcac tcggccttcc tgggccttga gcgcctccgg    840
```

```
gagcttgtgg ccgaggggta ccccttccgg gaggccctgg agctcgtccg ggcctcggcc    900

ctcttcacca cccacacccc cgtgcccgcc gggcacgacg tcttccccct ggacctcgtg    960

gaccgctacc tggggggtt ttgggagaag ctcggggtgg accgggacac cttcctcggg   1020

cttggcctgg aggagaagcc ttgggggccc gtcttctcca tgtccaacct cgccctgcgc   1080

acggcggccc aggccaacgg ggtctcccgc ctccacgggg aggtttcccg gaacatgttc   1140

cgccacctct ggccgggcct cctgggggag gaggtgccca tcggccacgt caccaacggg   1200

gtgcacacct ggaccttcct ccaccccagg cttcgccgcc actacgccga ggtcttcggg   1260

cccgagtggg tggagcgtcc cgaggacccc gagacctggc gggtggaggg gctcggggag   1320

gccttctggc gcatccggca ggacctgaag ctcttcttgg tgcgggaggt gcgccagcgc   1380

ctctacgagc agcgccgccg caacggggag gggcccgccc gcttgcggga ggcggagaag   1440

gccctggacc ccgaggccct caccatcggg ttcgcccgcc gcttcgccac ctacaagcgg   1500

gccgtcctcc tcttcaagga ccccgagcgg cttttgcgca tcctcaaggg gccctacccc   1560

gtgcagttcg tcttcgccgg gaaggcccac cccaaggacg aggcggggaa ggcctacctc   1620

aaggagcttg tgagcaagat ccgggagtac ggcctggagg accggatggt ggtcctcgag   1680

gactacgaca tgtacctggc ccgggtgctc acccacgggt ccgacgtctg gctcaacacc   1740

ccgaggcggc cgatggaggc ctcgggcacg agcggcatga aggccgccct caacggggcc   1800

ctcaacctca gcgtcttgga cggctggtgg gccgaggcct acaacggcaa aaacggcttc   1860

gccatcgggg acgagcgcgt ctacgagagc gaggaggccc aggacgtggc cgacgcccag   1920

gccctctacg acctcctgga gtccgaggtc atccccctct tctacgccaa gggcctggag   1980

gggtactcct cgggctggat gtccatggtc cacgagagcc tccgcaccgt ggggccctac   2040

ttcagcgcgg ggcggatggt ccgggactac ctcgccctct acgagcgggg cgccctttgg   2100

gagaaggagg cccgggcccg cctcgaggcc ctaaaggcct tcgccgaggc cctccccgcc   2160

ttccacgccc tgggggtcag gcccgaggtc cccggggacc tcaccctgaa cggggggcgg   2220

ctggaggtgg gggcggtcct cgagggggag gtgccggagg gcctccgccc ccacctccgg   2280

gtccagctcg tggtgcgccg cttgggcggc ggcctggagg tggtggacct ggaggaggtg   2340

gccccggggc ggtaccgcac cgccttccgc cccacaaggc ccgggagcta cacctacggc   2400

ctccgcctcg ccctcctcca ccccgtgacg ggccgggtgg agtgggtgcg ctgggcctag   2460
```

<210> SEQ ID NO 28
<211> LENGTH: 819
<212> TYPE: PRT
<213> ORGANISM: Thermus caldophilus GK24

<400> SEQUENCE: 28

```
Met Asn Val Leu Gly Arg Ile Thr Ala Met Pro Asp Leu Pro Glu Pro
1               5                   10                  15

Leu Glu Gly Leu Lys Glu Ile Ala Tyr Asn Leu Trp Trp Ser Trp Asn
            20                  25                  30

Pro Glu Ala Ala Glu Leu Phe Gln Glu Leu Asp Pro Ala Leu Trp Lys
        35                  40                  45

Arg Phe Arg Gly Asn Pro Val Lys Leu Leu Leu Glu Leu Asp Pro Ala
    50                  55                  60

Arg Leu Glu Ala Leu Ser Ala Ser Gly Tyr Ala Ala Arg Val Gln Ala
65                  70                  75                  80

Thr Arg Glu Ala Leu Arg Ala Tyr Leu Glu Ala Arg Arg Thr Lys Arg
```

```
                85                  90                  95

Gly Pro Leu Val Ala Tyr Phe Ser Ala Glu Tyr Gly Phe His Ser Ser
            100                 105                 110

Leu Pro Ile Tyr Ala Gly Gly Leu Gly Val Leu Ala Gly Asp His Val
        115                 120                 125

Lys Ala Ala Ser Asp Leu Gly Leu Asn Leu Val Gly Val Gly Leu Phe
    130                 135                 140

Tyr His Glu Gly Tyr Phe His Gln Arg Leu Ser Pro Glu Gly Glu Gln
145                 150                 155                 160

Val Glu Val Tyr Glu Pro Leu Arg Pro Glu Glu Leu Pro Leu Val Pro
                165                 170                 175

Val Gln Asp Ala Glu Gly Arg Pro Val Arg Val Ala Val Glu Phe Pro
            180                 185                 190

Gly Arg Leu Val His Val Gly Gly Tyr Arg Val Gln Val Gly Ala Val
        195                 200                 205

Pro Val Tyr Leu Leu Thr Thr Asp Leu Pro Glu Asn Ala Pro Glu Asp
    210                 215                 220

Arg Gln Ile Thr Ala Arg Leu Tyr Ala Ala Gly Leu Glu Ala Arg Ile
225                 230                 235                 240

Gln Gln Glu Leu Val Leu Gly Leu Gly Gly Val Arg Phe Leu Arg Ala
                245                 250                 255

Leu Gly Leu Ala Pro Ala Phe Phe His Met Asn Glu Gly His Ser Ala
            260                 265                 270

Phe Leu Gly Leu Glu Arg Leu Arg Glu Leu Val Ala Glu Gly Tyr Pro
        275                 280                 285

Phe Arg Glu Ala Leu Glu Leu Val Arg Ala Ser Ala Leu Phe Thr Thr
    290                 295                 300

His Thr Pro Val Pro Ala Gly His Asp Val Phe Pro Leu Asp Leu Val
305                 310                 315                 320

Asp Arg Tyr Leu Gly Gly Phe Trp Glu Lys Leu Gly Val Asp Arg Asp
                325                 330                 335

Thr Phe Leu Gly Leu Gly Leu Glu Glu Lys Pro Trp Gly Pro Val Phe
            340                 345                 350

Ser Met Ser Asn Leu Ala Leu Arg Thr Ala Ala Gln Ala Asn Gly Val
        355                 360                 365

Ser Arg Leu His Gly Glu Val Ser Arg Asn Met Phe Arg His Leu Trp
    370                 375                 380

Pro Gly Leu Leu Gly Glu Glu Val Pro Ile Gly His Val Thr Asn Gly
385                 390                 395                 400

Val His Thr Trp Thr Phe Leu His Pro Arg Leu Arg Arg His Tyr Ala
                405                 410                 415

Glu Val Phe Gly Pro Glu Trp Val Glu Arg Pro Glu Asp Pro Glu Thr
            420                 425                 430

Trp Arg Val Glu Gly Leu Gly Glu Ala Phe Trp Arg Ile Arg Gln Asp
        435                 440                 445

Leu Lys Leu Phe Leu Val Arg Glu Val Arg Gln Arg Leu Tyr Glu Gln
    450                 455                 460

Arg Arg Arg Asn Gly Glu Gly Pro Ala Arg Leu Arg Glu Ala Glu Lys
465                 470                 475                 480

Ala Leu Asp Pro Glu Ala Leu Thr Ile Gly Phe Ala Arg Arg Phe Ala
                485                 490                 495

Thr Tyr Lys Arg Ala Val Leu Leu Phe Lys Asp Pro Glu Arg Leu Leu
            500                 505                 510
```

```
Arg Ile Leu Lys Gly Pro Tyr Pro Val Gln Phe Val Phe Ala Gly Lys
        515                 520                 525

Ala His Pro Lys Asp Glu Ala Gly Lys Ala Tyr Leu Lys Glu Leu Val
    530                 535                 540

Ser Lys Ile Arg Glu Tyr Gly Leu Glu Asp Arg Met Val Val Leu Glu
545                 550                 555                 560

Asp Tyr Asp Met Tyr Leu Ala Arg Val Leu Thr His Gly Ser Asp Val
                565                 570                 575

Trp Leu Asn Thr Pro Arg Arg Pro Met Glu Ala Ser Gly Thr Ser Gly
            580                 585                 590

Met Lys Ala Ala Leu Asn Gly Ala Leu Asn Leu Ser Val Leu Asp Gly
        595                 600                 605

Trp Trp Ala Glu Ala Tyr Asn Gly Lys Asn Gly Phe Ala Ile Gly Asp
    610                 615                 620

Glu Arg Val Tyr Glu Ser Glu Glu Ala Gln Asp Val Ala Asp Ala Gln
625                 630                 635                 640

Ala Leu Tyr Asp Leu Leu Glu Ser Glu Val Ile Pro Leu Phe Tyr Ala
                645                 650                 655

Lys Gly Leu Glu Gly Tyr Ser Ser Gly Trp Met Ser Met Val His Glu
            660                 665                 670

Ser Leu Arg Thr Val Gly Pro Tyr Phe Ser Ala Gly Arg Met Val Arg
        675                 680                 685

Asp Tyr Leu Ala Leu Tyr Glu Arg Gly Ala Leu Trp Glu Lys Glu Ala
    690                 695                 700

Arg Ala Arg Leu Glu Ala Leu Lys Ala Phe Ala Glu Ala Leu Pro Ala
705                 710                 715                 720

Phe His Ala Leu Gly Val Arg Pro Glu Val Pro Gly Asp Leu Thr Leu
                725                 730                 735

Asn Gly Gly Arg Leu Glu Val Gly Ala Val Leu Glu Gly Glu Val Pro
            740                 745                 750

Glu Gly Leu Arg Pro His Leu Arg Val Gln Leu Val Val Arg Arg Leu
        755                 760                 765

Gly Gly Gly Leu Glu Val Val Asp Leu Glu Glu Val Ala Pro Gly Arg
    770                 775                 780

Tyr Arg Thr Ala Phe Arg Pro Thr Arg Pro Gly Ser Tyr Thr Tyr Gly
785                 790                 795                 800

Leu Arg Leu Ala Leu Leu His Pro Val Thr Gly Arg Val Glu Trp Val
                805                 810                 815

Arg Trp Ala
```

<210> SEQ ID NO 29
<211> LENGTH: 1623
<212> TYPE: DNA
<213> ORGANISM: Thermoanaerobacter tengcongensis MB4

<400> SEQUENCE: 29

```
atggaaaaca aaaaactgcc aagagtagct tatttctgca tggaatacgg ccttgaatct      60

aacttcaagc tttacgctgg aggtttaggc attctagcag gggattacct taaagccgca     120

aaggaaatgg gtcttccagt cgtagggata ggaatacttt ggaaacaggg ttacactgaa     180

cagcatatcg gtgaagacgg ctatccttac gatgcatacc gcaattatac ccgcaattac     240

gactttttaa aagacacagg ggtaaaggtc aaagtaaaga taagaaataa agatgtctac     300

tgcaaagtct ggctagtgga tagttttgac aatgcccctt tatacctctt agacacagac     360
```

```
attcctgaaa acggcgacag atggataaca ggccagcttt acggatggtt tggtgaggaa    420

agggttgcgc aggagattgt gctaggaatt ggcggtgtaa gagctttaag agccttagga    480

attgatgttg acatctacca cttcaacgaa gggcatgcag ttctggctgg tattgagctt    540

ataagagaaa aaatggaaaa tcaagggatg tcttttgaag aggcttggga agccacccgc    600

aaagaaatag tttttacaac tcacacccct gtaaaagaag gaaacgaatc tcacgacttg    660

gaacttttaa tgtacatggg agcaaacaac gggcttacta tagaacagtt ggctcaaata    720

ggtggggtac cttttaacat gactgtagca ggactaagac tttctaaaat tgcaaacggt    780

gtatcaaaat tgcatggcca aactgctaac aaaatgtggc aacatataga gaacaaagcc    840

cccatcattt ctataaccaa cggaattcat agaggtacgt gggtggacaa gaggataaca    900

gaagcttaca aaaaaggaac aggtcttttg gaaacccaca acctttttgaa aaaagagtta    960

atagattttg tatataaaaa gacaggagtg aaactagacg cagacaaact ccttataggt   1020

ttttcaagaa gagctgctcc ttataaaaga agcgacctta tcttcacaaa tgaaaaggcc   1080

atcggtgaat atttgagaga cagaaaaata caaattgtct tttcaggaaa aggccatcca   1140

ttggacgacg tgggcaaaga aattgtcgca agaattgtta agatgacaaa gaaatacccct  1200

gaaagtgtag tatttttgga agactatgat atgacgatcg ggaaaatgct cactcgcggc   1260

gcagacgtat ggcttaacaa cccaagaagg cctcttgagg caagcggtac atcgggcatg   1320

aaggctgcaa tgaacggcgt tttaaatttg agcatcctcg atggctggtg gccagaagcc   1380

tgcattgatg gagtaaatgg ttggcaattc ggagatgggt ttgaatcaga caactttgag   1440

gaacttgaca agcacgatgc agaagctcta tatgatgtgc ttctcaataa agtagtaccc   1500

acctactaca acgataagaa aaaatgggaa gaaatgatga aagaaagtat aagaactact   1560

tttgaagcct tttctgcaaa cagaatgctt caagaatatt atgacctcat gtataccaaa   1620

taa                                                                 1623
```

<210> SEQ ID NO 30
<211> LENGTH: 540
<212> TYPE: PRT
<213> ORGANISM: Thermoanaerobacter tengcongensis MB4

<400> SEQUENCE: 30

```
Met Glu Asn Lys Lys Leu Pro Arg Val Ala Tyr Phe Cys Met Glu Tyr
1               5                   10                  15

Gly Leu Glu Ser Asn Phe Lys Leu Tyr Ala Gly Gly Leu Gly Ile Leu
            20                  25                  30

Ala Gly Asp Tyr Leu Lys Ala Ala Lys Glu Met Gly Leu Pro Val Val
        35                  40                  45

Gly Ile Gly Ile Leu Trp Lys Gln Gly Tyr Thr Glu Gln His Ile Gly
    50                  55                  60

Glu Asp Gly Tyr Pro Tyr Asp Ala Tyr Arg Asn Tyr Thr Arg Asn Tyr
65                  70                  75                  80

Asp Phe Leu Lys Asp Thr Gly Val Lys Val Lys Val Lys Ile Arg Asn
                85                  90                  95

Lys Asp Val Tyr Cys Lys Val Trp Leu Val Asp Ser Phe Asp Asn Ala
            100                 105                 110

Pro Leu Tyr Leu Leu Asp Thr Asp Ile Pro Glu Asn Gly Asp Arg Trp
        115                 120                 125

Ile Thr Gly Gln Leu Tyr Gly Trp Phe Gly Glu Glu Arg Val Ala Gln
    130                 135                 140
```

```
Glu Ile Val Leu Gly Ile Gly Gly Val Arg Ala Leu Arg Ala Leu Gly
145                 150                 155                 160

Ile Asp Val Asp Ile Tyr His Phe Asn Glu Gly His Ala Val Leu Ala
                165                 170                 175

Gly Ile Glu Leu Ile Arg Glu Lys Met Glu Asn Gln Gly Met Ser Phe
            180                 185                 190

Glu Glu Ala Trp Glu Ala Thr Arg Lys Glu Ile Val Phe Thr Thr His
        195                 200                 205

Thr Pro Val Lys Glu Gly Asn Glu Ser His Asp Leu Glu Leu Leu Met
    210                 215                 220

Tyr Met Gly Ala Asn Asn Gly Leu Thr Ile Glu Gln Leu Ala Gln Ile
225                 230                 235                 240

Gly Gly Val Pro Phe Asn Met Thr Val Ala Gly Leu Arg Leu Ser Lys
                245                 250                 255

Ile Ala Asn Gly Val Ser Lys Leu His Gly Gln Thr Ala Asn Lys Met
            260                 265                 270

Trp Gln His Ile Glu Asn Lys Ala Pro Ile Ile Ser Ile Thr Asn Gly
        275                 280                 285

Ile His Arg Gly Thr Trp Val Asp Lys Arg Ile Thr Glu Ala Tyr Lys
    290                 295                 300

Lys Gly Thr Gly Leu Leu Glu Thr His Asn Leu Leu Lys Lys Glu Leu
305                 310                 315                 320

Ile Asp Phe Val Tyr Lys Lys Thr Gly Val Lys Leu Asp Ala Asp Lys
                325                 330                 335

Leu Leu Ile Gly Phe Ser Arg Arg Ala Ala Pro Tyr Lys Arg Ser Asp
            340                 345                 350

Leu Ile Phe Thr Asn Glu Lys Ala Ile Gly Glu Tyr Leu Arg Asp Arg
        355                 360                 365

Lys Ile Gln Ile Val Phe Ser Gly Lys Gly His Pro Leu Asp Asp Val
    370                 375                 380

Gly Lys Glu Ile Val Ala Arg Ile Val Lys Met Thr Lys Lys Tyr Pro
385                 390                 395                 400

Glu Ser Val Val Phe Leu Glu Asp Tyr Asp Met Thr Ile Gly Lys Met
                405                 410                 415

Leu Thr Arg Gly Ala Asp Val Trp Leu Asn Asn Pro Arg Arg Pro Leu
            420                 425                 430

Glu Ala Ser Gly Thr Ser Gly Met Lys Ala Ala Met Asn Gly Val Leu
        435                 440                 445

Asn Leu Ser Ile Leu Asp Gly Trp Trp Pro Glu Ala Cys Ile Asp Gly
    450                 455                 460

Val Asn Gly Trp Gln Phe Gly Asp Gly Phe Glu Ser Asp Asn Phe Glu
465                 470                 475                 480

Glu Leu Asp Lys His Asp Ala Glu Ala Leu Tyr Asp Val Leu Leu Asn
                485                 490                 495

Lys Val Val Pro Thr Tyr Tyr Asn Asp Lys Lys Lys Trp Glu Glu Met
            500                 505                 510

Met Lys Glu Ser Ile Arg Thr Thr Phe Glu Ala Phe Ser Ala Asn Arg
        515                 520                 525

Met Leu Gln Glu Tyr Tyr Asp Leu Met Tyr Thr Lys
    530                 535                 540
```

<210> SEQ ID NO 31
<211> LENGTH: 2607

<212> TYPE: DNA
<213> ORGANISM: Artificial sequence
<220> FEATURE:
<223> OTHER INFORMATION: Metagenomic (composite) sequence for GP-006.

<400> SEQUENCE: 31

```
atgaagccat tacgcacctt taaggtcacc ccttacctac ctgctgctct ggaaagtctg     60

cgctttttgg cctacaacct gcatttcagt tggaatgtag agacccgtaa tgtgtttaac    120

cgcatggatc ccgatctttg ggatgcctgt gcccacaacc cgattgccct tctaggccag    180

atccggcagg aacggctgga tgaattggcg gaggatcccg gctttttggc ccaattggaa    240

cgagcctatc aacagctgca cacttactta caagaagaca cctggtaccg caaacatcac    300

tctgcccact ctgtagaggg ggaatgttat gcctattttt ccgccgagtt cggtctggcg    360

gattgcctgc ccatttattc cggggggcta gggattttgg ctggggatca cctgaaagcc    420

gccagcgacc tgggcttacc cttggtgggg gtgggcttgc tctatcagaa ggggtatttt    480

cgccagtacc tcaacccgga tggttggcag caggaacgct acccaatcaa cgagtttttt    540

aacatgccct tggagctgca aaaggatgcc gaggggcggg agattcgcat tgaagtggac    600

tatcccaacc gcaaggtgtt tgcccgcatc tggaaggtga acgtgggccg ggtgcccctc    660

tatcttttgg ataccaacat cgagcccaac agccaatacg accaagacat caccgatgaa    720

ctgtacggtg gcgaccaaga tctgcgcatt caccaagaga tcatgctggg gattggcggg    780

gtgcgggcgc tgcgagccct cgggatccaa cccaccgttt accacatgaa cgaagggcac    840

tcagcctttt tggcggtgga gcgaattcgt ctgttcatga ctgagcaggg gctgagtttt    900

gaagaagcct ggcaagtggc caaatccagc caaatgttca ccacccacac gccggtgccc    960

gccggaatcg acctgtttcc ccccgataaa atcgactact acctcggctc ctactacagc   1020

caactgggcc taggtcggga gcgctttttg gccttaggcc gagagaacac tggcgatttt   1080

cagtcgcagt tcagcatggc ggtgctggcc attaatatgg cctcttttgt gaatggggtg   1140

agcaagttac acggggcggt ctcccgtaaa atgttcagtc agctgtggcc ggggatccct   1200

ctcgaagaag tgccgatcac ctccatcacc aatggtgtcc atgcccgtac ctgggtggga   1260

gaagaaaatc aatccctcta cgatcgctac ttagggcccg attggccaga agcccccccct   1320

ttcgacccga tctggcagaa ggtggatcgg atcccggata gtgagctgtg gcgcacccac   1380

gagcggagcc gttcccgctt ggtcagcttt acccgcgaac ggctaatggc gcagctacag   1440

aaacgggcgg cctcgactat tgaaatccag cgggcctccg aagccctcaa tccggaggtg   1500

ctcacgattg ggtttgcccg ccgctttgct acctacaagc gcgccaccct gctgttccgg   1560

gatcccgaac gcttcaaagc cttggtgacc catcctcacc acccgatgca gttcatcttc   1620

gcgggtaagg cccacccccg cgataccccc ggcaaagagc tgatccggca gattgtgcag   1680

ttgtcgcggc agccggagtt tcggcatcac ctggtcttta tcgaagacta cgacatgcac   1740

gtcacaagca tgatggtggc cggggtggat gtgtggctaa acaaccctct acgcccccgc   1800

gaggccagtg gcaccagtgg catgaaggcc gccgccaatg gtggacaaaa cctgagcatt   1860

ttggatggat ggtgggatga ggccgactac taccaaaccg gctggccgat cggtcgtggc   1920

gaggaatacg aggatcgggc ttaccaagat gaggtggagt cgaacgctct ctacgacttg   1980

ctggagaaag aggtggcacc cactttttat cagcgcacca gcgatggtct accccacccg   2040

tggatccagc gcatgaagca gtcgattcgc ctcaatgcac ctctgtttag cacccagcgc   2100

atggtacagg aatatgccga gcgggcttat atccctctca gtggctacta cgcccgcatg   2160
```

```
cgcagcgaaa actttgaatc ggcccgacgc tttacccgtt ggcaaagcca tgtgcaggag   2220

aactggtatg gtattcaggt gctgagcgtc cacgttgcgg atcaagaggg ttctttgcac   2280

cctgccccca gtgtttccgc cgcgccggat agcagtgccg tgatggctcg cgcccccctc   2340

accgtgaccg ccgagctccg cctgggagcc ctaaaaccac aggatgtgat cttgcaagcc   2400

taccagggcc ccgtggacga tagcggccat atccagcagg ggcaagccac cccgatgcgt   2460

tacgtggaga tggtggagga tcgagcgatt ttctcggggc aaattcgcta tgatgccagt   2520

ggcctgcagg ggctggcatt gcgggtgatg ccgttccacc cagatatgca cgatccttac   2580

gaactgcggc tgatgctctg ggcttag                                       2607
```

<210> SEQ ID NO 32
<211> LENGTH: 868
<212> TYPE: PRT
<213> ORGANISM: Artificial sequence
<220> FEATURE:
<223> OTHER INFORMATION: Metagenomic (composite) sequence for GP-006.

<400> SEQUENCE: 32

```
Met Lys Pro Leu Arg Thr Phe Lys Val Thr Pro Tyr Leu Pro Ala Ala
1               5                   10                  15

Leu Glu Ser Leu Arg Phe Leu Ala Tyr Asn Leu His Phe Ser Trp Asn
            20                  25                  30

Val Glu Thr Arg Asn Val Phe Asn Arg Met Asp Pro Asp Leu Trp Asp
        35                  40                  45

Ala Cys Ala His Asn Pro Ile Ala Leu Leu Gly Gln Ile Arg Gln Glu
    50                  55                  60

Arg Leu Asp Glu Leu Ala Glu Asp Pro Gly Phe Leu Ala Gln Leu Glu
65                  70                  75                  80

Arg Ala Tyr Gln Gln Leu His Thr Tyr Leu Gln Glu Asp Thr Trp Tyr
                85                  90                  95

Arg Lys His His Ser Ala His Ser Val Glu Gly Glu Cys Tyr Ala Tyr
            100                 105                 110

Phe Ser Ala Glu Phe Gly Leu Ala Asp Cys Leu Pro Ile Tyr Ser Gly
        115                 120                 125

Gly Leu Gly Ile Leu Ala Gly Asp His Leu Lys Ala Ala Ser Asp Leu
    130                 135                 140

Gly Leu Pro Leu Val Gly Val Gly Leu Leu Tyr Gln Lys Gly Tyr Phe
145                 150                 155                 160

Arg Gln Tyr Leu Asn Pro Asp Gly Trp Gln Gln Glu Arg Tyr Pro Ile
                165                 170                 175

Asn Glu Phe Phe Asn Met Pro Leu Glu Leu Gln Lys Asp Ala Glu Gly
            180                 185                 190

Arg Glu Ile Arg Ile Glu Val Asp Tyr Pro Asn Arg Lys Val Phe Ala
        195                 200                 205

Arg Ile Trp Lys Val Asn Val Gly Arg Val Pro Leu Tyr Leu Leu Asp
    210                 215                 220

Thr Asn Ile Glu Pro Asn Ser Gln Tyr Asp Gln Asp Ile Thr Asp Glu
225                 230                 235                 240

Leu Tyr Gly Gly Asp Gln Asp Leu Arg Ile His Gln Glu Ile Met Leu
                245                 250                 255

Gly Ile Gly Gly Val Arg Ala Leu Arg Ala Leu Gly Ile Gln Pro Thr
            260                 265                 270

Val Tyr His Met Asn Glu Gly His Ser Ala Phe Leu Ala Val Glu Arg
        275                 280                 285
```

```
Ile Arg Leu Phe Met Thr Glu Gln Gly Leu Ser Phe Glu Glu Ala Trp
    290                 295                 300

Gln Val Ala Lys Ser Ser Gln Met Phe Thr Thr His Thr Pro Val Pro
305                 310                 315                 320

Ala Gly Ile Asp Leu Phe Pro Pro Asp Lys Ile Asp Tyr Tyr Leu Gly
                325                 330                 335

Ser Tyr Tyr Ser Gln Leu Gly Leu Gly Arg Glu Arg Phe Leu Ala Leu
            340                 345                 350

Gly Arg Glu Asn Thr Gly Asp Phe Gln Ser Gln Phe Ser Met Ala Val
        355                 360                 365

Leu Ala Ile Asn Met Ala Ser Phe Val Asn Gly Val Ser Lys Leu His
    370                 375                 380

Gly Ala Val Ser Arg Lys Met Phe Ser Gln Leu Trp Pro Gly Ile Pro
385                 390                 395                 400

Leu Glu Glu Val Pro Ile Thr Ser Ile Thr Asn Gly Val His Ala Arg
                405                 410                 415

Thr Trp Val Gly Glu Glu Asn Gln Ser Leu Tyr Asp Arg Tyr Leu Gly
            420                 425                 430

Pro Asp Trp Pro Glu Ala Pro Pro Phe Asp Pro Ile Trp Gln Lys Val
        435                 440                 445

Asp Arg Ile Pro Asp Ser Glu Leu Trp Arg Thr His Glu Arg Ser Arg
    450                 455                 460

Ser Arg Leu Val Ser Phe Thr Arg Glu Arg Leu Met Ala Gln Leu Gln
465                 470                 475                 480

Lys Arg Ala Ala Ser Thr Ile Glu Ile Gln Arg Ala Ser Glu Ala Leu
                485                 490                 495

Asn Pro Glu Val Leu Thr Ile Gly Phe Ala Arg Arg Phe Ala Thr Tyr
            500                 505                 510

Lys Arg Ala Thr Leu Leu Phe Arg Asp Pro Glu Arg Phe Lys Ala Leu
        515                 520                 525

Val Thr His Pro His His Pro Met Gln Phe Ile Phe Ala Gly Lys Ala
    530                 535                 540

His Pro Arg Asp Thr Pro Gly Lys Glu Leu Ile Arg Gln Ile Val Gln
545                 550                 555                 560

Leu Ser Arg Gln Pro Glu Phe Arg His His Leu Val Phe Ile Glu Asp
                565                 570                 575

Tyr Asp Met His Val Thr Ser Met Met Val Ala Gly Val Asp Val Trp
            580                 585                 590

Leu Asn Asn Pro Leu Arg Pro Arg Glu Ala Ser Gly Thr Ser Gly Met
        595                 600                 605

Lys Ala Ala Ala Asn Gly Gly Gln Asn Leu Ser Ile Leu Asp Gly Trp
    610                 615                 620

Trp Asp Glu Ala Asp Tyr Tyr Gln Thr Gly Trp Pro Ile Gly Arg Gly
625                 630                 635                 640

Glu Glu Tyr Glu Asp Arg Ala Tyr Gln Asp Glu Val Glu Ser Asn Ala
                645                 650                 655

Leu Tyr Asp Leu Leu Glu Lys Glu Val Ala Pro Thr Phe Tyr Gln Arg
            660                 665                 670

Thr Ser Asp Gly Leu Pro His Pro Trp Ile Gln Arg Met Lys Gln Ser
        675                 680                 685

Ile Arg Leu Asn Ala Pro Leu Phe Ser Thr Gln Arg Met Val Gln Glu
    690                 695                 700
```

```
Tyr Ala Glu Arg Ala Tyr Ile Pro Leu Ser Gly Tyr Tyr Ala Arg Met
705                 710                 715                 720

Arg Ser Glu Asn Phe Glu Ser Ala Arg Arg Phe Thr Arg Trp Gln Ser
                725                 730                 735

His Val Gln Glu Asn Trp Tyr Gly Ile Gln Val Leu Ser Val His Val
            740                 745                 750

Ala Asp Gln Glu Gly Ser Leu His Pro Ala Pro Ser Val Ser Ala Ala
        755                 760                 765

Pro Asp Ser Ser Ala Val Met Ala Arg Ala Pro Leu Thr Val Thr Ala
    770                 775                 780

Glu Leu Arg Leu Gly Ala Leu Lys Pro Gln Asp Val Ile Leu Gln Ala
785                 790                 795                 800

Tyr Gln Gly Pro Val Asp Asp Ser Gly His Ile Gln Gln Gly Gln Ala
                805                 810                 815

Thr Pro Met Arg Tyr Val Glu Met Val Glu Asp Arg Ala Ile Phe Ser
            820                 825                 830

Gly Gln Ile Arg Tyr Asp Ala Ser Gly Leu Gln Gly Leu Ala Leu Arg
        835                 840                 845

Val Met Pro Phe His Pro Asp Met His Asp Pro Tyr Glu Leu Arg Leu
    850                 855                 860

Met Leu Trp Ala
865
```

<210> SEQ ID NO 33
<211> LENGTH: 2571
<212> TYPE: DNA
<213> ORGANISM: Paenibacillus sp.

<400> SEQUENCE: 33

```
atgactatgg cagcagcctt ccctcaaggg gcgaacgaca tgcccgcagc aatataccgc     60

ttgcgcgagc ttgcgtacaa tgtttggtgg agctggaacg acgatgcgct gcaactattc    120

gaacatatcg atccaaaacg ctttgccgcg tccggctaca atccggtgcg ccttctgaac    180

gagctggaac cgggtcagct ggcatctctc agcgagaacg cttccttcct ggagagctat    240

cggaaggtca tggcccgatt cgacgactac ctgcagggcg catcctggta cagcaccaac    300

tatgaaagct ccagcaacgc ccgcatcgcc tacttctccg ccgaattcgg ttttcatgaa    360

tccctgccga tctactccgg cggtctcggc attctggccg gtgatcatat caaatcggcg    420

agcgatcttg gcatcccgtt aatcgggatc ggcctcttgt acaagaaagg ctattttacg    480

caaaaaatag acgcactcgg caatcagcaa agcgagatgg cggactacga ttttacgcag    540

ctcccgctgc agcctgtgct gctggacgat cgtcagctca cggtgtcgat acagctgccg    600

ttccgcagca tcaccctgct cgtgtggtcg gtgcaggtcg ggcgcacccg ggtctgcctg    660

ctcgacagcg accacgaggc aaacgcgccg gaggaccggg ccattacggc ccaactgtac    720

ggcggcgacc aggatatgcg catcgtgcag gagatcgccc tcggcatcgg ggggatcaaa    780

gcgctgcgtg cgctgggggt ttacccgaac gtgtaccata tcaacgaggg ccacgcggct    840

tttctcacac tggaacgact taaagagctg attcagctcg ggctgccgtt ccatgtagcc    900

gttgaaaccg tgcgctcggc gacggtgttt acgacgcata ccccggtgcc ggcggggcat    960

gatgctttta acatcgggat ggtggaacat tatctcggtc cctatttcag cgaagtagct   1020

gcgcacaagc aagcgattat cgcgctcggt caggatcaga agaccggcct gttcaatatg   1080

acccacctgg cgatgaatac cgccgggctc cgcaacggcg tcagcaagct gcacggccag   1140
```

```
gtgtcgcgcg aaatgttcaa agaattccac ggtcacacgg atgcgaatga agtcccgatc   1200

ggttcgatca ccaacggtgt gcaccttgac tcctggaccg caccggcgtg gaaagagctt   1260

tttgatcgtt ttctcccggg aacgtggcgc gaggagcagg cgaacaccca tcaatgggca   1320

caggtcgagg tcattccgga cgaatcgatc tggaaggtgc atatgcagtt aaaagagcgg   1380

ttgattacct acgcgcgcaa aaacctcgct gcacagcgag cccgcaacgg tgagtcgcag   1440

gagcggattg acgaagtgcg ggctacctc aatccaagag cgctgaccat cgggtttgct   1500

cggcgttttg cgacctacaa gcgggcgaac atgattttca acgacctcca tcggctgaaa   1560

aaattggtaa atgacccgga tcgcccgatc cagctcattt tcgcgggcaa ggcgcacccc   1620

gccgattacc cggggcagga tttgattcgc gacatttacc gcatttcgca gatgaaggag   1680

tttctcggga aaatcgtcat cctcgaaaac tacgatattc atatggcccg ctatctcgtg   1740

caaggcgtcg atgtgtggct caataacccg cgcagaccgt tggaagcgag cggaaccagc   1800

ggccagaagg cggcgatgaa cggcgttctc aatttcagtg tgctcgacgg ctggtgggag   1860

gaaggctaca acggcacgaa cggctgggcg atcggatcga ccgggcaggc ggactgggcc   1920

caacaggaaa gggaaaacac ccgatccctc taccatctgc tcgaaaatga aatcattccc   1980

ctctactaca accagggggc gctgccgcat caatggatca gccggatgaa gcgttccatc   2040

cagtcgctag ctccggtgta caacacccat cggatggtgc aggattacac cgttcagtcg   2100

tatttgccga ccgctgagcg cgcaacgctg ttcgtggcaa accagtacga tgtggcgacc   2160

aaagtcgccg actacaagca gttcattcgc aacaactggc atcaagtccg aattttggcg   2220

attgaggata aattgccgcc atcctccgaa gcggagatca gcccttatga tgccgcccct   2280

tcgaccaaga aggtccgggc gcacatccat ttcggcccga tctggccgca ggatacggct   2340

gttgagatta tttattacga ggaaattgac gaatcctggc accaaaaaac ggtgcacatg   2400

gaacccgtcg gcgaactgat cggcaggcg cagtacttcg aagcttccat tcccggacat   2460

ttgttccacg gtccgcactt ctccattcgt gtgcggccga tctcggccaa ttttgcccac   2520

tcgttcgagc tatccttagt aaccagcacg ctggcctggc aggagggcta a            2571
```

<210> SEQ ID NO 34
<211> LENGTH: 856
<212> TYPE: PRT
<213> ORGANISM: Paenibacillus sp.

<400> SEQUENCE: 34

```
Met Thr Met Ala Ala Ala Phe Pro Gln Gly Ala Asn Asp Met Pro Ala
1               5                   10                  15

Ala Ile Tyr Arg Leu Arg Glu Leu Ala Tyr Asn Val Trp Trp Ser Trp
            20                  25                  30

Asn Asp Asp Ala Leu Gln Leu Phe Glu His Ile Asp Pro Lys Arg Phe
        35                  40                  45

Ala Ala Ser Gly Tyr Asn Pro Val Arg Leu Leu Asn Glu Leu Glu Pro
    50                  55                  60

Gly Gln Leu Ala Ser Leu Ser Glu Asn Ala Ser Phe Leu Glu Ser Tyr
65                  70                  75                  80

Arg Lys Val Met Ala Arg Phe Asp Asp Tyr Leu Gln Gly Ala Ser Trp
                85                  90                  95

Tyr Ser Thr Asn Tyr Glu Ser Ser Ser Asn Ala Arg Ile Ala Tyr Phe
            100                 105                 110

Ser Ala Glu Phe Gly Phe His Glu Ser Leu Pro Ile Tyr Ser Gly Gly
        115                 120                 125
```

```
Leu Gly Ile Leu Ala Gly Asp His Ile Lys Ser Ala Ser Asp Leu Gly
    130                 135                 140

Ile Pro Leu Ile Gly Ile Gly Leu Leu Tyr Lys Lys Gly Tyr Phe Thr
145                 150                 155                 160

Gln Lys Ile Asp Ala Leu Gly Asn Gln Gln Ser Glu Met Ala Asp Tyr
                165                 170                 175

Asp Phe Thr Gln Leu Pro Leu Gln Pro Val Leu Leu Asp Asp Arg Gln
            180                 185                 190

Leu Thr Val Ser Ile Gln Leu Pro Phe Arg Ser Ile Thr Leu Leu Val
        195                 200                 205

Trp Ser Val Gln Val Gly Arg Thr Arg Val Cys Leu Leu Asp Ser Asp
    210                 215                 220

His Glu Ala Asn Ala Pro Glu Asp Arg Ala Ile Thr Ala Gln Leu Tyr
225                 230                 235                 240

Gly Gly Asp Gln Asp Met Arg Ile Val Gln Glu Ile Ala Leu Gly Ile
                245                 250                 255

Gly Gly Ile Lys Ala Leu Arg Ala Leu Gly Val Tyr Pro Asn Val Tyr
            260                 265                 270

His Ile Asn Glu Gly His Ala Ala Phe Leu Thr Leu Glu Arg Leu Lys
        275                 280                 285

Glu Leu Ile Gln Leu Gly Leu Pro Phe His Val Ala Val Glu Thr Val
    290                 295                 300

Arg Ser Ala Thr Val Phe Thr Thr His Thr Pro Val Pro Ala Gly His
305                 310                 315                 320

Asp Ala Phe Asn Ile Gly Met Val Glu His Tyr Leu Gly Pro Tyr Phe
                325                 330                 335

Ser Glu Val Ala Ala His Lys Gln Ala Ile Ile Ala Leu Gly Gln Asp
            340                 345                 350

Gln Lys Thr Gly Leu Phe Asn Met Thr His Leu Ala Met Asn Thr Ala
        355                 360                 365

Gly Leu Arg Asn Gly Val Ser Lys Leu His Gly Gln Val Ser Arg Glu
    370                 375                 380

Met Phe Lys Glu Phe His Gly His Thr Asp Ala Asn Glu Val Pro Ile
385                 390                 395                 400

Gly Ser Ile Thr Asn Gly Val His Leu Asp Ser Trp Thr Ala Pro Ala
                405                 410                 415

Trp Lys Glu Leu Phe Asp Arg Phe Leu Pro Gly Thr Trp Arg Glu Glu
            420                 425                 430

Gln Ala Asn Thr His Gln Trp Ala Gln Val Glu Val Ile Pro Asp Glu
        435                 440                 445

Ser Ile Trp Lys Val His Met Gln Leu Lys Glu Arg Leu Ile Thr Tyr
    450                 455                 460

Ala Arg Lys Asn Leu Ala Ala Gln Arg Ala Arg Asn Gly Glu Ser Gln
465                 470                 475                 480

Glu Arg Ile Asp Glu Val Arg Gly Tyr Leu Asn Pro Arg Ala Leu Thr
                485                 490                 495

Ile Gly Phe Ala Arg Arg Phe Ala Thr Tyr Lys Arg Ala Asn Met Ile
            500                 505                 510

Phe Asn Asp Leu His Arg Leu Lys Lys Leu Val Asn Asp Pro Asp Arg
        515                 520                 525

Pro Ile Gln Leu Ile Phe Ala Gly Lys Ala His Pro Ala Asp Tyr Pro
    530                 535                 540
```

```
Gly Gln Asp Leu Ile Arg Asp Ile Tyr Arg Ile Ser Gln Met Lys Glu
545                 550                 555                 560

Phe Leu Gly Lys Ile Val Ile Leu Glu Asn Tyr Asp Ile His Met Ala
                565                 570                 575

Arg Tyr Leu Val Gln Gly Val Asp Val Trp Leu Asn Asn Pro Arg Arg
            580                 585                 590

Pro Leu Glu Ala Ser Gly Thr Ser Gly Gln Lys Ala Ala Met Asn Gly
        595                 600                 605

Val Leu Asn Phe Ser Val Leu Asp Gly Trp Trp Glu Glu Gly Tyr Asn
    610                 615                 620

Gly Thr Asn Gly Trp Ala Ile Gly Ser Thr Gly Gln Ala Asp Trp Ala
625                 630                 635                 640

Gln Gln Glu Arg Glu Asn Thr Arg Ser Leu Tyr His Leu Leu Glu Asn
                645                 650                 655

Glu Ile Ile Pro Leu Tyr Tyr Asn Gln Gly Ala Leu Pro His Gln Trp
            660                 665                 670

Ile Ser Arg Met Lys Arg Ser Ile Gln Ser Leu Ala Pro Val Tyr Asn
        675                 680                 685

Thr His Arg Met Val Gln Asp Tyr Thr Val Gln Ser Tyr Leu Pro Thr
    690                 695                 700

Ala Glu Arg Ala Thr Leu Phe Val Ala Asn Gln Tyr Asp Val Ala Thr
705                 710                 715                 720

Lys Val Ala Asp Tyr Lys Gln Phe Ile Arg Asn Asn Trp His Gln Val
                725                 730                 735

Arg Ile Leu Ala Ile Glu Asp Lys Leu Pro Pro Ser Ser Glu Ala Glu
            740                 745                 750

Ile Ser Pro Tyr Asp Ala Ala Pro Ser Thr Lys Lys Val Arg Ala His
        755                 760                 765

Ile His Phe Gly Pro Ile Trp Pro Gln Asp Thr Ala Val Glu Ile Ile
    770                 775                 780

Tyr Tyr Glu Glu Ile Asp Glu Ser Trp His Gln Lys Thr Val His Met
785                 790                 795                 800

Glu Pro Val Gly Glu Leu Ile Gly Gln Ala Gln Tyr Phe Glu Ala Ser
                805                 810                 815

Ile Pro Gly His Leu Phe His Gly Pro His Phe Ser Ile Arg Val Arg
            820                 825                 830

Pro Ile Ser Ala Asn Phe Ala His Ser Phe Glu Leu Ser Leu Val Thr
        835                 840                 845

Ser Thr Leu Ala Trp Gln Glu Gly
    850                 855
```

<210> SEQ ID NO 35
<211> LENGTH: 2559
<212> TYPE: DNA
<213> ORGANISM: Artificial sequence
<220> FEATURE:
<223> OTHER INFORMATION: Metagenomic (composite) sequence for GP-017.

<400> SEQUENCE: 35

```
atgcgaattc gtccgttgaa agttctcacg gttgcctccg tcctgccgga ggagctctcc     60

tttcttgagc gcttagccta taacttctgg tggtcctgga atcggaaagc tgaatcactc    120

ttttcgaccg ttgacccagt ccgatgggaa aggattcgac gcaatcctgt tcgattgctc    180

aaagaaacgc cgcaagaacg ctttcgtgag cttgtcgagg attctgcata ccggaagttg    240

cttagggagg tggagaaaga gttcgatgcg tatcttggcc aagcgcccca gctaagctgg    300
```

```
ccctctccaa ggccgatagc gtatttctgt gccgaatacg gcatcagcga gtgctttcag    360
aactacagcg gcggtttagg ggttcttgca ggggaccatc tcaaaaccgc atcggatgtt    420
ggattgccaa tggtcgctgt ggggctgctc taccagcaag gatacttcca tcagcatgtt    480
acctacaacg gctggcagca ggagaatttc ctcgactacg atttttccct cttgccgatt    540
cagcttgtcc gtgccgagag tggagcgccg ctcatcattc gcgtagagct tcccgatggc    600
gacgttgctg ctcaagtctg gaaagccgat gttggacgga ttccgctcta ccttctcgat    660
acgaacattg ccgataatag cacgaacccc acttaccaaa acatcaccga ccagctctac    720
ggcggcaccc acgagacgcg gatcatgcag gaaatgttgc tcggaattgg tggagtccgc    780
gtgcttgcag cgctagggat tgaaccttca gtccttcata tcaacgaagg gcatgctgcg    840
ttctgcacgc ttgagtggac acgtcatctg gcgcaacagc ttggtctgag ttttcacgaa    900
gccgccgaga ttactcgtgc gcagacgtgc tttacaacgc acacgccagt tcccgctgga    960
aatgagatat tctcgctcgg gttactccag agatatttct cgcgctacat gccggtgctc   1020
ggtatagaat gggaagagtt tctcaagctc ggtcaggcaa acaacggctc cagcgatgag   1080
ggtttttcca tgacgattct ggggctgcgg atgagcaacc accgcaatgg cgtcagcgag   1140
ctgcacggcc acgttgcgcg tacaatgtgg caatcactct ggccacatgt cgcaagtgat   1200
gaagtcccca tccgtagcat cactaatggt gtgcatattc ctacgtgggt ttcgagcgat   1260
tttgctgcac tctatgatcg agcgcttggt ccaggatggc gtcagcgccc gagcgaaccc   1320
acccagtggg atgcgattgc ggcaatcccg gatgcggagc tctgggcagt tcatgttcgc   1380
cgccgtcagc gcttgcttga agcagttcgg gagcatatcc ggcagcgggg cggatattac   1440
gacgaggagc atcggcagcg agccattgct gcgttgcacc ccaactgcct catcattggt   1500
tttgcacggc gctttgcaac ctataagcgc tcggatttgc tcttccgaaa ttgggatcgg   1560
cttgcatcaa ttcttcgcaa cccttcgcgg ccggtcatca tcctgctggc gggaaaagca   1620
cacccgcaag acattgccag caaggaaatg atgcaacgca tcctgacggg aattcgcaat   1680
gccgggctag aacagcacgt gatttttctg gaagattacg atcttggcat tgcacgcgca   1740
ctcgtcaagg gagccgacgt atggctcaac acaccacgtc gcccgtacga agcatcgggt   1800
acgagcggaa tgaaagctgc gctcaacggt gtgctgcact gcagcgttct cgatggctgg   1860
tgggcagaag ctgccctgag cgacaacggc tttaccattg gccacggcga agtcttcgct   1920
actgcggatg aacaagacgc acacgagagc gaaagcctct accagctttt ggaaaacgac   1980
atcatcccaa tgttctacga acgggacgcg gccggtgtcc cacgtcggtg ggtcaagcgg   2040
atgaagtctg ccattgcaac gcttgcagcg cgctattcaa cccatcgcat gctcgatgaa   2100
tatcggatgg cgttctacga acctgctgct gcactcggcg ctgtgctggc agagcaacaa   2160
gggcgcgcag cacgggagct tagccgctgg aaacgcacac ttccagagcg ctggaaaact   2220
ctccggatca ttagtgccga cgtcccagac cgcggcgtta tccacgtcgg agagccagtt   2280
cctgtgcgtc ttgtactcga ctgcggcgca atgaatcccg acgagttgct cgcacaggtg   2340
tactatggcc cgctgaccgc acgcggtgag ttcatgcagg cgcgcgttgc gaacctttcg   2400
ctgtcgcatg tcgagggtgc acgtgcgacg ttcgagggaa cctacacaac gcccgacagt   2460
ggccagcacg gcgtcgcgtt acgtgtgctc ccacaccatc cgcatgtgcc agatccagtg   2520
gacttgcagc tggtcgtttg ggtgcaaggc gagcagtag                          2559
```

<210> SEQ ID NO 36

```
<211> LENGTH: 852
<212> TYPE: PRT
<213> ORGANISM: Artificial sequence
<220> FEATURE:
<223> OTHER INFORMATION: Metagenomic (composite) sequence for GP-017.

<400> SEQUENCE: 36

Met Arg Ile Arg Pro Leu Lys Val Leu Thr Val Ala Ser Val Leu Pro
1               5                   10                  15

Glu Glu Leu Ser Phe Leu Glu Arg Leu Ala Tyr Asn Phe Trp Trp Ser
            20                  25                  30

Trp Asn Arg Lys Ala Glu Ser Leu Phe Ser Thr Val Asp Pro Val Arg
        35                  40                  45

Trp Glu Arg Ile Arg Arg Asn Pro Val Arg Leu Leu Lys Glu Thr Pro
    50                  55                  60

Gln Glu Arg Phe Arg Glu Leu Val Glu Asp Ser Ala Tyr Arg Lys Leu
65                  70                  75                  80

Leu Arg Glu Val Glu Lys Glu Phe Asp Ala Tyr Leu Gly Gln Ala Pro
                85                  90                  95

Gln Leu Ser Trp Pro Ser Pro Arg Pro Ile Ala Tyr Phe Cys Ala Glu
            100                 105                 110

Tyr Gly Ile Ser Glu Cys Phe Gln Asn Tyr Ser Gly Gly Leu Gly Val
        115                 120                 125

Leu Ala Gly Asp His Leu Lys Thr Ala Ser Asp Val Gly Leu Pro Met
    130                 135                 140

Val Ala Val Gly Leu Leu Tyr Gln Gln Gly Tyr Phe His Gln His Val
145                 150                 155                 160

Thr Tyr Asn Gly Trp Gln Gln Glu Asn Phe Leu Asp Tyr Asp Phe Ser
                165                 170                 175

Leu Leu Pro Ile Gln Leu Val Arg Ala Glu Ser Gly Ala Pro Leu Ile
            180                 185                 190

Ile Arg Val Glu Leu Pro Asp Gly Asp Val Ala Ala Gln Val Trp Lys
        195                 200                 205

Ala Asp Val Gly Arg Ile Pro Leu Tyr Leu Leu Asp Thr Asn Ile Ala
    210                 215                 220

Asp Asn Ser Thr Asn Pro Thr Tyr Gln Asn Ile Thr Asp Gln Leu Tyr
225                 230                 235                 240

Gly Gly Thr His Glu Thr Arg Ile Met Gln Glu Met Leu Leu Gly Ile
                245                 250                 255

Gly Gly Val Arg Val Leu Ala Ala Leu Gly Ile Glu Pro Ser Val Leu
            260                 265                 270

His Ile Asn Glu Gly His Ala Ala Phe Cys Thr Leu Glu Trp Thr Arg
        275                 280                 285

His Leu Ala Gln Gln Leu Gly Leu Ser Phe His Glu Ala Ala Glu Ile
    290                 295                 300

Thr Arg Ala Gln Thr Cys Phe Thr Thr His Thr Pro Val Pro Ala Gly
305                 310                 315                 320

Asn Glu Ile Phe Ser Leu Gly Leu Leu Gln Arg Tyr Phe Ser Arg Tyr
                325                 330                 335

Met Pro Val Leu Gly Ile Glu Trp Glu Glu Phe Leu Lys Leu Gly Gln
            340                 345                 350

Ala Asn Asn Gly Ser Ser Asp Glu Gly Phe Ser Met Thr Ile Leu Gly
        355                 360                 365

Leu Arg Met Ser Asn His Arg Asn Gly Val Ser Glu Leu His Gly His
    370                 375                 380
```

```
Val Ala Arg Thr Met Trp Gln Ser Leu Trp Pro His Val Ala Ser Asp
385                 390                 395                 400

Glu Val Pro Ile Arg Ser Ile Thr Asn Gly Val His Ile Pro Thr Trp
                405                 410                 415

Val Ser Ser Asp Phe Ala Ala Leu Tyr Asp Arg Ala Leu Gly Pro Gly
            420                 425                 430

Trp Arg Gln Arg Pro Ser Glu Pro Thr Gln Trp Asp Ala Ile Ala Ala
        435                 440                 445

Ile Pro Asp Ala Glu Leu Trp Ala Val His Val Arg Arg Arg Gln Arg
    450                 455                 460

Leu Leu Glu Ala Val Arg Glu His Ile Arg Gln Arg Gly Gly Tyr Tyr
465                 470                 475                 480

Asp Glu Glu His Arg Gln Arg Ala Ile Ala Ala Leu His Pro Asn Cys
                485                 490                 495

Leu Ile Ile Gly Phe Ala Arg Arg Phe Ala Thr Tyr Lys Arg Ser Asp
            500                 505                 510

Leu Leu Phe Arg Asn Trp Asp Arg Leu Ala Ser Ile Leu Arg Asn Pro
        515                 520                 525

Ser Arg Pro Val Ile Ile Leu Leu Ala Gly Lys Ala His Pro Gln Asp
    530                 535                 540

Ile Ala Ser Lys Glu Met Met Gln Arg Ile Leu Thr Gly Ile Arg Asn
545                 550                 555                 560

Ala Gly Leu Glu Gln His Val Ile Phe Leu Glu Asp Tyr Asp Leu Gly
                565                 570                 575

Ile Ala Arg Ala Leu Val Lys Gly Ala Asp Val Trp Leu Asn Thr Pro
            580                 585                 590

Arg Arg Pro Tyr Glu Ala Ser Gly Thr Ser Gly Met Lys Ala Ala Leu
        595                 600                 605

Asn Gly Val Leu His Cys Ser Val Leu Asp Gly Trp Trp Ala Glu Ala
    610                 615                 620

Ala Leu Ser Asp Asn Gly Phe Thr Ile Gly His Gly Glu Val Phe Ala
625                 630                 635                 640

Thr Ala Asp Glu Gln Asp Ala His Glu Ser Glu Ser Leu Tyr Gln Leu
                645                 650                 655

Leu Glu Asn Asp Ile Ile Pro Met Phe Tyr Glu Arg Asp Ala Ala Gly
            660                 665                 670

Val Pro Arg Arg Trp Val Lys Arg Met Lys Ser Ala Ile Ala Thr Leu
        675                 680                 685

Ala Ala Arg Tyr Ser Thr His Arg Met Leu Asp Glu Tyr Arg Met Ala
    690                 695                 700

Phe Tyr Glu Pro Ala Ala Ala Leu Gly Ala Val Leu Ala Glu Gln Gln
705                 710                 715                 720

Gly Arg Ala Ala Arg Glu Leu Ser Arg Trp Lys Arg Thr Leu Pro Glu
                725                 730                 735

Arg Trp Lys Thr Leu Arg Ile Ile Ser Ala Asp Val Pro Asp Arg Gly
            740                 745                 750

Val Ile His Val Gly Glu Pro Val Pro Val Arg Leu Val Leu Asp Cys
        755                 760                 765

Gly Ala Met Asn Pro Asp Glu Leu Leu Ala Gln Val Tyr Tyr Gly Pro
    770                 775                 780

Leu Thr Ala Arg Gly Glu Phe Met Gln Ala Arg Val Ala Asn Leu Ser
785                 790                 795                 800
```

```
Leu Ser His Val Glu Gly Ala Arg Ala Thr Phe Glu Gly Thr Tyr Thr
                805                 810                 815

Thr Pro Asp Ser Gly Gln His Gly Val Ala Leu Arg Val Leu Pro His
            820                 825                 830

His Pro His Val Pro Asp Pro Val Asp Leu Gln Leu Val Val Trp Val
        835                 840                 845

Gln Gly Glu Gln
    850


<210> SEQ ID NO 37
<211> LENGTH: 2547
<212> TYPE: DNA
<213> ORGANISM: Artificial sequence
<220> FEATURE:
<223> OTHER INFORMATION: Metagenomic (composite) sequence for GP-022.

<400> SEQUENCE: 37

atgagtgagc aggtttatat ggatccgtcc ttgtaccgtc aactgcctgc cgatatcgac     60

ggctttgacg agttggtcga actggcgctg gacatgcgct ggtcgtggaa tcatgccaca    120

gatcagatct ggcggcagat ggaccccgtg ttgtgggcgt ttacgcacag cccgtggagc    180

atcctgcaga ccgtttcgcg cgacaagatc gagcgggtgt gcgccgatcc ggtgttccgc    240

aagaatctcg acgaactgat acagaccaag cgtcagggat cggaactgcc cacctggttt    300

cagcaggccc atgccgaatc acagctgaag gcggtggctt atttcagtat ggaattcatg    360

ctgagtgagg cattgcccat ttattcaggt ggtctgggta atgtggccgg cgatcaactc    420

aaggcggcca gcgatctggg tgtgccggtc atcggtgtcg ggttgttgta ccagcaaggc    480

tattttcgcc agatcatcga caacgacggt gcgcagcagg ccatctttcc gtataacgat    540

cccggacaat tgccgatcac gccgttgcgt caggcaaatg gggagtggct gcgctttcag    600

atcgacctgc ccggctatgc cgtctggttg cgcgcgtggc aggttcaggt cgggcgagtc    660

aaattgtatt tgctggacag caatgacgcc gccaattttc cggtgcatcg gggcattacc    720

agcgaacttt acggcggtgg tgccgaattg cgcatcaaac aggaaattct gctcggtatc    780

ggcggctggc ggttgctgga ggcgctcggc atccagccgg aagtgtgtca tctgaatgaa    840

gggcatgcgg cctttgcagt attggagcgc gcgcgcagct tcatggaaaa aaccggtcag    900

ccgttcgatg tggcgctgac cgtaacccgt gccggcaacc tttttaccac ccacaccgcc    960

gtggcggccg gtttcgaccg ttttgcaccg gcgttgatcg aacaatacct cggcggttat   1020

gtcgaacaaa agctgggcat cacctgccat gatttgctgg ccatgggacg tcaacatccc   1080

gaggatgcgt ccgagccttt caacatggct tatctggcca ttcgcggcag cggtgccgtc   1140

aatggcgtga gccgtttgca cggcgaagtc agtcgccagt tgttcggttc gctgtttccg   1200

cgctggtcga cgcaagaggt gccggtcggt catgtaacca acggcgttca cacgccgacc   1260

tgggattcag ccgccgccga caacctgtgg accaatgcgt gcggcaaggg gcgctggagc   1320

ggggaagtcg aggctctgga gcaggagatt cgccagcttt ccgatacccg gttgtggcaa   1380

ttccgcaccg aaggcagtca ggcactggtg gactacgcac gcacgcgcct gtcgcagcaa   1440

ttggcatcgt ccggcgcctc gcgcgaagcg gctgaacatg cgcagcacct gtttgacagc   1500

aatacgctga cattgggatt tgcgcgacgt ttcgccagct acaagcggcc caatctgctg   1560

ttgcatgacc cggaacggct gttgcgtctg ttgaccaacc cccggcgtcc ggtgcagatc   1620

atcatggccg gcaaggcgca tcctgacgac agggacgggc aggccatgat ccggcagtgg   1680

gtacaattca tccgtcggcc cgaagtgcgc ccgcacgcga tctttctcag cgattacgac   1740
```

```
atgctgctga ccgaacacct ggtgcagggt gtggatgtct ggctcaatac accgcgccga   1800

ccatgggaag cctgcggcac cagcggcatg aaggtgctgg tcaacggcgg catcaatctg   1860

tcggaactgg acggttggtg ggcggaagcc tatacgcccg aagtgggctg ggcgctgggc   1920

gacggacagg agcatgatga agaccccgcc tgggacgcca gggaggctga tgcgctgtac   1980

accctgctgg aaaacgaagt gataccggag ttttataccc gcaacgaaca gggcattcct   2040

gttgcctggg tgacccggat gcgcgaaagc atggcgcagc tgacaccgcg tttttccagc   2100

aatcgcgccg tacgcgaata caccgggcaa ctgtatctgc cattggcatc ggcgtatctt   2160

gcgcgcgccg aaaacaacgc tgagcgtggc gccgacatgg tgcgctggcg acaggatctg   2220

gcgcaaaagt gggcgggtct gcgctttggc gaagtgaccc tgagcagcga ggatggacag   2280

cacagctttg aagtgcagat ttatctggac gatgtcgatc ccggtgcatt gcgggtcgag   2340

ctttttgcca atgatgtgga tggtggcgga ccggagcgca tcgagatgca gcgcgtgcgc   2400

caactggtgg gctcgaccag cggttatgcc taccgggcca cagtgccggc agaccgcgcc   2460

gcatcgagct acaccgcccg gctggttcca taccatgagg gggtggcgat tccgctggaa   2520

gaggcgcata ttctttggca acgatga                                       2547
```

<210> SEQ ID NO 38
<211> LENGTH: 848
<212> TYPE: PRT
<213> ORGANISM: Artificial sequence
<220> FEATURE:
<223> OTHER INFORMATION: Metagenomic (composite) sequence for GP-022.

<400> SEQUENCE: 38

```
Met Ser Glu Gln Val Tyr Met Asp Pro Ser Leu Tyr Arg Gln Leu Pro
1               5                   10                  15

Ala Asp Ile Asp Gly Phe Asp Glu Leu Val Glu Leu Ala Leu Asp Met
            20                  25                  30

Arg Trp Ser Trp Asn His Ala Thr Asp Gln Ile Trp Arg Gln Met Asp
        35                  40                  45

Pro Val Leu Trp Ala Phe Thr His Ser Pro Trp Ser Ile Leu Gln Thr
    50                  55                  60

Val Ser Arg Asp Lys Ile Glu Arg Val Cys Ala Asp Pro Val Phe Arg
65                  70                  75                  80

Lys Asn Leu Asp Glu Leu Ile Gln Thr Lys Arg Gln Gly Ser Glu Leu
                85                  90                  95

Pro Thr Trp Phe Gln Gln Ala His Ala Glu Ser Gln Leu Lys Ala Val
            100                 105                 110

Ala Tyr Phe Ser Met Glu Phe Met Leu Ser Glu Ala Leu Pro Ile Tyr
        115                 120                 125

Ser Gly Gly Leu Gly Asn Val Ala Gly Asp Gln Leu Lys Ala Ala Ser
    130                 135                 140

Asp Leu Gly Val Pro Val Ile Gly Val Gly Leu Leu Tyr Gln Gln Gly
145                 150                 155                 160

Tyr Phe Arg Gln Ile Ile Asp Asn Asp Gly Ala Gln Gln Ala Ile Phe
                165                 170                 175

Pro Tyr Asn Asp Pro Gly Gln Leu Pro Ile Thr Pro Leu Arg Gln Ala
            180                 185                 190

Asn Gly Glu Trp Leu Arg Phe Gln Ile Asp Leu Pro Gly Tyr Ala Val
        195                 200                 205

Trp Leu Arg Ala Trp Gln Val Gln Val Gly Arg Val Lys Leu Tyr Leu
```

```
    210                 215                 220

Leu Asp Ser Asn Asp Ala Ala Asn Phe Pro Val His Arg Gly Ile Thr
225                 230                 235                 240

Ser Glu Leu Tyr Gly Gly Gly Ala Glu Leu Arg Ile Lys Gln Glu Ile
                245                 250                 255

Leu Leu Gly Ile Gly Gly Trp Arg Leu Leu Glu Ala Leu Gly Ile Gln
            260                 265                 270

Pro Glu Val Cys His Leu Asn Glu Gly His Ala Ala Phe Ala Val Leu
        275                 280                 285

Glu Arg Ala Arg Ser Phe Met Glu Lys Thr Gly Gln Pro Phe Asp Val
    290                 295                 300

Ala Leu Thr Val Thr Arg Ala Gly Asn Leu Phe Thr Thr His Thr Ala
305                 310                 315                 320

Val Ala Ala Gly Phe Asp Arg Phe Ala Pro Ala Leu Ile Glu Gln Tyr
                325                 330                 335

Leu Gly Gly Tyr Val Glu Gln Lys Leu Gly Ile Thr Cys His Asp Leu
            340                 345                 350

Leu Ala Met Gly Arg Gln His Pro Glu Asp Ala Ser Glu Pro Phe Asn
        355                 360                 365

Met Ala Tyr Leu Ala Ile Arg Gly Ser Gly Ala Val Asn Gly Val Ser
    370                 375                 380

Arg Leu His Gly Glu Val Ser Arg Gln Leu Phe Gly Ser Leu Phe Pro
385                 390                 395                 400

Arg Trp Ser Thr Gln Glu Val Pro Val Gly His Val Thr Asn Gly Val
                405                 410                 415

His Thr Pro Thr Trp Asp Ser Ala Ala Ala Asp Asn Leu Trp Thr Asn
            420                 425                 430

Ala Cys Gly Lys Gly Arg Trp Ser Gly Glu Val Glu Ala Leu Glu Gln
        435                 440                 445

Glu Ile Arg Gln Leu Ser Asp Thr Arg Leu Trp Gln Phe Arg Thr Glu
    450                 455                 460

Gly Ser Gln Ala Leu Val Asp Tyr Ala Arg Thr Arg Leu Ser Gln Gln
465                 470                 475                 480

Leu Ala Ser Ser Gly Ala Ser Arg Glu Ala Ala Glu His Ala Gln His
                485                 490                 495

Leu Phe Asp Ser Asn Thr Leu Thr Leu Gly Phe Ala Arg Arg Phe Ala
            500                 505                 510

Ser Tyr Lys Arg Pro Asn Leu Leu Leu His Asp Pro Glu Arg Leu Leu
        515                 520                 525

Arg Leu Leu Thr Asn Pro Arg Arg Pro Val Gln Ile Ile Met Ala Gly
    530                 535                 540

Lys Ala His Pro Asp Asp Arg Asp Gly Gln Ala Met Ile Arg Gln Trp
545                 550                 555                 560

Val Gln Phe Ile Arg Arg Pro Glu Val Arg Pro His Ala Ile Phe Leu
                565                 570                 575

Ser Asp Tyr Asp Met Leu Leu Thr Glu His Leu Val Gln Gly Val Asp
            580                 585                 590

Val Trp Leu Asn Thr Pro Arg Arg Pro Trp Glu Ala Cys Gly Thr Ser
        595                 600                 605

Gly Met Lys Val Leu Val Asn Gly Gly Ile Asn Leu Ser Glu Leu Asp
    610                 615                 620

Gly Trp Trp Ala Glu Ala Tyr Thr Pro Glu Val Gly Trp Ala Leu Gly
625                 630                 635                 640
```

```
Asp Gly Gln Glu His Asp Glu Asp Pro Ala Trp Asp Ala Arg Glu Ala
                645                 650                 655

Asp Ala Leu Tyr Thr Leu Leu Glu Asn Glu Val Ile Pro Glu Phe Tyr
            660                 665                 670

Thr Arg Asn Glu Gln Gly Ile Pro Val Ala Trp Val Thr Arg Met Arg
        675                 680                 685

Glu Ser Met Ala Gln Leu Thr Pro Arg Phe Ser Ser Asn Arg Ala Val
    690                 695                 700

Arg Glu Tyr Thr Gly Gln Leu Tyr Leu Pro Leu Ala Ser Ala Tyr Leu
705                 710                 715                 720

Ala Arg Ala Glu Asn Asn Ala Glu Arg Gly Ala Asp Met Val Arg Trp
                725                 730                 735

Arg Gln Asp Leu Ala Gln Lys Trp Ala Gly Leu Arg Phe Gly Glu Val
            740                 745                 750

Thr Leu Ser Ser Glu Asp Gly Gln His Ser Phe Glu Val Gln Ile Tyr
        755                 760                 765

Leu Asp Asp Val Asp Pro Gly Ala Leu Arg Val Glu Leu Phe Ala Asn
    770                 775                 780

Asp Val Asp Gly Gly Gly Pro Glu Arg Ile Glu Met Gln Arg Val Arg
785                 790                 795                 800

Gln Leu Val Gly Ser Thr Ser Gly Tyr Ala Tyr Arg Ala Thr Val Pro
                805                 810                 815

Ala Asp Arg Ala Ala Ser Ser Tyr Thr Ala Arg Leu Val Pro Tyr His
            820                 825                 830

Glu Gly Val Ala Ile Pro Leu Glu Glu Ala His Ile Leu Trp Gln Arg
        835                 840                 845
```

<210> SEQ ID NO 39
<211> LENGTH: 2610
<212> TYPE: DNA
<213> ORGANISM: Mycobacterium sp.

<400> SEQUENCE: 39

```
gtgaaagccc tgcgccggtt caccgtccgt gcccaccttc ccgagcgcct cgccgcgcta     60

gaacggctgt cgatcaacct ccgctggtcg tgggacaagc cgacccagga cctgttcgcc    120

gacatcgatc ccaacttgtg gaagcacgtc ggctgcgacc ccgtcgcgct gctcggcggc    180

gtcgacccca agcggctcga ccaactggcc ggcgacgagg acttcctgcg ccgcctcgag    240

gcgctggccg ccgatctcga cgactacctg agtcggccac tgtggtacca gcagcaactc    300

gagcaggggc aggcgctgcc caacggcatc gcgtacttct cgatggagtt cggggtcgcc    360

gaggtgctgc ccaactactc cggcggcctc ggcatcctgg ccggtgacca cctcaagtcg    420

gcgtccgacc tcgggctccc gctcatcgcg gtgggcctgt actaccgctc cggatacttc    480

cggcagtcgc tgaccgccga cggctggcag cacgagaact acccctcgct ggatccgcag    540

ggtctgccgc tgcgtctgct caccggcgcc gattccgatc cggtgctggt ggagctggcg    600

atgcccgacg acgccacgct gtgggcccgg gtgtgggtgg cgcaggtcgg caggatcccg    660

ctgctgctgc tggactccga catcccggag aacgagcacg acctgcgcgg cgtgaccgat    720

cggctctacg gcggcgacca ggagcaccgc atcaagcagg agatcctggc cggtatcggc    780

ggcgtgcggg cgatccgggc gttcaccgag gtcgagggcc tgcccgcacc ggaggtcttc    840

cacatgaacg agggccatgc cggtttcctc ggtgtggagc gcatccgcga gctcatcgac    900

gccgggctgg acttcgacac cgcgctgacc gtggtgcggt catcgacggt gttcaccacg    960
```

```
cacaccccgg tgcccgcggg catcgaccgg ttcccggtcg agatggtcaa gcggtacttc   1020
ggcaaccctc ccggcagccc ctcgggcgcg agctcgcgtc tgctgcccgg cgtcccgctg   1080
gaccgcatca ccggcttcgg tgccgaggac gatccggcga agttcaacat ggcgcacatg   1140
ggcctgcggc tggcgcagcg ggccaacggg gtgtcgctgc tgcacggccg ggtcagccgc   1200
gagatgttca acgagttgtg gcccggattc gacgccaccg aggtgccgat cggctcgatc   1260
accaacggtg tgcacgcccc gagctgggcc gcgccgcagt ggatggaact cgggcgcgag   1320
ctgctcggca gcaccgatct gagctcgctc agcgaaccgg agacatggga gcgtctgcac   1380
caggtcgacc ccggccacct gtggaggatc cgctccgagc tgcgccgcga gctcgtcgag   1440
gacgtgcggg tgcgcctgcg tcgcagctgg acccaacgcg gcgccgccga cgccgaactc   1500
ggttggacgg caaccgcttt cgaccccaat gtgctgacca tcggattcgc ccgccgagtg   1560
ccgacctaca agcggctcac gctgatgctg cgtgaccccg aacggctgca gaggttgctg   1620
ctcgacgagc aacggccggt gcagctgatc gtggccggca aatcgcaccc tgccgacgac   1680
ggcggtaagg cgctgatcca gcaggtggtg cggttcgccg accgccacga cgtccggcac   1740
cgcatcgcgt tcctgcccga ctacgacatg tcgatggcgc gccagctcta ctgggggtgc   1800
gacgtctggc tgaacaatcc gctgcgcccg ctggaggcct gcggcacgtc ggggatgaag   1860
agcgcgctca acggcgggct gaacctgtcg atccgcgacg gctggtggga cgagtggtac   1920
gacggcgaga acggctggga gatcccgacc gccaacggcc tgaccgacga ggcgcgccgc   1980
gacgatctcg aggcgtccgc gctctacgac ctgatcgagc agtcggtggc cccgaagttc   2040
tacgagcgtg acgagcacgg cgtgccgatc cgctgggtgg agatggtccg gcacacgctc   2100
aaggtgctcg ggccgaaggt gctggcctct cggatggtgc gtgattacac cgagaggtac   2160
tacgccccgg ccgcgcagtc gctgcgccgc accgtcgaag ccgtcgacgg catgccgttc   2220
gcggccgccg ccgggcttgc cgactaccgc cgccgggtcc aggaggcgtg gccgaagatc   2280
cagatcaccg acgtggacag ctacgggttg cccgacaccc cgctgctcgg gtcgaagctg   2340
acgctgaccg cgacggtgcg gctggccggg ctgcggcccg acgaggtgtc ggtgcaggcc   2400
gtgctgggcc gggtcgacgc cgggaacatc ctgctcgacc ccaccacggt gccgatgacg   2460
cacaccggca ccgccgacgg cggcaacgag gtcttctcga ccaccgcgcc gttgccggtg   2520
gccgggccgg tgggctacac cgtgcgggtg ctgccgcacc acccgctgtt ggccgcggac   2580
aacgagctgg gtctggtcac gctggcgtga                                    2610
```

```
<210> SEQ ID NO 40
<211> LENGTH: 869
<212> TYPE: PRT
<213> ORGANISM: Mycobacterium sp.

<400> SEQUENCE: 40

Met Lys Ala Leu Arg Arg Phe Thr Val Arg Ala His Leu Pro Glu Arg
1               5                   10                  15

Leu Ala Ala Leu Glu Arg Leu Ser Ile Asn Leu Arg Trp Ser Trp Asp
            20                  25                  30

Lys Pro Thr Gln Asp Leu Phe Ala Asp Ile Asp Pro Asn Leu Trp Lys
        35                  40                  45

His Val Gly Cys Asp Pro Val Ala Leu Leu Gly Gly Val Asp Pro Lys
    50                  55                  60

Arg Leu Asp Gln Leu Ala Gly Asp Glu Asp Phe Leu Arg Arg Leu Glu
65                  70                  75                  80
```

```
Ala Leu Ala Ala Asp Leu Asp Asp Tyr Leu Ser Arg Pro Leu Trp Tyr
                85                  90                  95

Gln Gln Gln Leu Glu Gln Gly Gln Ala Leu Pro Asn Gly Ile Ala Tyr
            100                 105                 110

Phe Ser Met Glu Phe Gly Val Ala Glu Val Leu Pro Asn Tyr Ser Gly
        115                 120                 125

Gly Leu Gly Ile Leu Ala Gly Asp His Leu Lys Ser Ala Ser Asp Leu
    130                 135                 140

Gly Leu Pro Leu Ile Ala Val Gly Leu Tyr Tyr Arg Ser Gly Tyr Phe
145                 150                 155                 160

Arg Gln Ser Leu Thr Ala Asp Gly Trp Gln His Glu Asn Tyr Pro Ser
                165                 170                 175

Leu Asp Pro Gln Gly Leu Pro Leu Arg Leu Leu Thr Gly Ala Asp Ser
            180                 185                 190

Asp Pro Val Leu Val Glu Leu Ala Met Pro Asp Asp Ala Thr Leu Trp
        195                 200                 205

Ala Arg Val Trp Val Ala Gln Val Gly Arg Ile Pro Leu Leu Leu Leu
    210                 215                 220

Asp Ser Asp Ile Pro Glu Asn Glu His Asp Leu Arg Gly Val Thr Asp
225                 230                 235                 240

Arg Leu Tyr Gly Gly Asp Gln Glu His Arg Ile Lys Gln Glu Ile Leu
                245                 250                 255

Ala Gly Ile Gly Gly Val Arg Ala Ile Arg Ala Phe Thr Glu Val Glu
            260                 265                 270

Gly Leu Pro Ala Pro Glu Val Phe His Met Asn Glu Gly His Ala Gly
        275                 280                 285

Phe Leu Gly Val Glu Arg Ile Arg Glu Leu Ile Asp Ala Gly Leu Asp
    290                 295                 300

Phe Asp Thr Ala Leu Thr Val Val Arg Ser Ser Thr Val Phe Thr Thr
305                 310                 315                 320

His Thr Pro Val Pro Ala Gly Ile Asp Arg Phe Pro Val Glu Met Val
                325                 330                 335

Lys Arg Tyr Phe Gly Asn Pro Pro Gly Ser Pro Ser Gly Ala Ser Ser
            340                 345                 350

Arg Leu Leu Pro Gly Val Pro Leu Asp Arg Ile Thr Gly Phe Gly Ala
        355                 360                 365

Glu Asp Asp Pro Ala Lys Phe Asn Met Ala His Met Gly Leu Arg Leu
    370                 375                 380

Ala Gln Arg Ala Asn Gly Val Ser Leu Leu His Gly Arg Val Ser Arg
385                 390                 395                 400

Glu Met Phe Asn Glu Leu Trp Pro Gly Phe Asp Ala Thr Glu Val Pro
                405                 410                 415

Ile Gly Ser Ile Thr Asn Gly Val His Ala Pro Ser Trp Ala Ala Pro
            420                 425                 430

Gln Trp Met Glu Leu Gly Arg Glu Leu Leu Gly Ser Thr Asp Leu Ser
        435                 440                 445

Ser Leu Ser Glu Pro Glu Thr Trp Glu Arg Leu His Gln Val Asp Pro
    450                 455                 460

Gly His Leu Trp Arg Ile Arg Ser Glu Leu Arg Arg Glu Leu Val Glu
465                 470                 475                 480

Asp Val Arg Val Arg Leu Arg Arg Ser Trp Thr Gln Arg Gly Ala Ala
                485                 490                 495
```

```
Asp Ala Glu Leu Gly Trp Thr Ala Thr Ala Phe Asp Pro Asn Val Leu
            500                 505                 510

Thr Ile Gly Phe Ala Arg Arg Val Pro Thr Tyr Lys Arg Leu Thr Leu
        515                 520                 525

Met Leu Arg Asp Pro Glu Arg Leu Gln Arg Leu Leu Leu Asp Glu Gln
    530                 535                 540

Arg Pro Val Gln Leu Ile Val Ala Gly Lys Ser His Pro Ala Asp Asp
545                 550                 555                 560

Gly Gly Lys Ala Leu Ile Gln Gln Val Val Arg Phe Ala Asp Arg His
                565                 570                 575

Asp Val Arg His Arg Ile Ala Phe Leu Pro Asp Tyr Asp Met Ser Met
            580                 585                 590

Ala Arg Gln Leu Tyr Trp Gly Cys Asp Val Trp Leu Asn Asn Pro Leu
        595                 600                 605

Arg Pro Leu Glu Ala Cys Gly Thr Ser Gly Met Lys Ser Ala Leu Asn
    610                 615                 620

Gly Gly Leu Asn Leu Ser Ile Arg Asp Gly Trp Trp Asp Glu Trp Tyr
625                 630                 635                 640

Asp Gly Glu Asn Gly Trp Glu Ile Pro Thr Ala Asn Gly Leu Thr Asp
                645                 650                 655

Glu Ala Arg Arg Asp Asp Leu Glu Ala Ser Ala Leu Tyr Asp Leu Ile
            660                 665                 670

Glu Gln Ser Val Ala Pro Lys Phe Tyr Glu Arg Asp Glu His Gly Val
        675                 680                 685

Pro Ile Arg Trp Val Glu Met Val Arg His Thr Leu Lys Val Leu Gly
    690                 695                 700

Pro Lys Val Leu Ala Ser Arg Met Val Arg Asp Tyr Thr Glu Arg Tyr
705                 710                 715                 720

Tyr Ala Pro Ala Ala Gln Ser Leu Arg Arg Thr Val Glu Ala Val Asp
                725                 730                 735

Gly Met Pro Phe Ala Ala Ala Ala Gly Leu Ala Asp Tyr Arg Arg Arg
            740                 745                 750

Val Gln Glu Ala Trp Pro Lys Ile Gln Ile Thr Asp Val Asp Ser Tyr
        755                 760                 765

Gly Leu Pro Asp Thr Pro Leu Leu Gly Ser Lys Leu Thr Leu Thr Ala
    770                 775                 780

Thr Val Arg Leu Ala Gly Leu Arg Pro Asp Glu Val Ser Val Gln Ala
785                 790                 795                 800

Val Leu Gly Arg Val Asp Ala Gly Asn Ile Leu Leu Asp Pro Thr Thr
                805                 810                 815

Val Pro Met Thr His Thr Gly Thr Ala Asp Gly Gly Asn Glu Val Phe
            820                 825                 830

Ser Thr Thr Ala Pro Leu Pro Val Ala Gly Pro Val Gly Tyr Thr Val
        835                 840                 845

Arg Val Leu Pro His His Pro Leu Leu Ala Ala Asp Asn Glu Leu Gly
    850                 855                 860

Leu Val Thr Leu Ala
865
```

<210> SEQ ID NO 41
<211> LENGTH: 2598
<212> TYPE: DNA
<213> ORGANISM: Paenibacillus sp.

<400> SEQUENCE: 41

```
atgtccacgt tgttcccggc accatccttc cgccttcctg cggctattgc cagactgtcg     60
gatctcgccc tgaatctgtg gtttagctgg aacggcagcg cccaggccct atttgccgat    120
attgatgcag agctctggct gcagacacgc cataaccccg tagagctatt aaccaaggta    180
tcggaggaca cgctcgaacg gctggctgca gacgaatcct tcttgaatcg ctatgaggct    240
gtgctcaggc aattcgacga atatatgggc gccggaacct ggtttagccg ccattatccg    300
catcagtccc ggcatgcaat cgcttatttc tccgcggagt tcggcttcca tgaatcgctg    360
cccatctact ccggcgggtt gggtatcctc gcgggggatc attgtaaatc cgccagtgac    420
ctcggcattc ctctgatcgg agtaggcttg ctatacaaaa agggctactt tcgccagaag    480
ctggattcca aggggcatca actggccgaa agcgtcccct atcacttccg cacactgcca    540
attacaccgg ctttggcttt acatgcggag aaagccaatg tttcagacga agatgcgggg    600
acgccacggg acgctgaaca accggaacct caagagctgt acgtcaccgt ggatgtagcc    660
gatcgtactg tccgcttgaa ggtgtggcag gctcgggtcg ggcgtatccg ggtgctgctg    720
ctggatgccg acctggagga gaacagctcc tgggaccgcg acttgaccgc acagctatac    780
ggagggacgc aggatgtccg gattgctcag gaaatgctgc tcggtatcgg aggcatccgc    840
gccctacggg cgcttaacgt ccctacaggg gcctatcata tcaatgaagg tcatgccgcc    900
ttcctgtcgt tcgaaaggct aaaagaacag cttgagctgg gactcccctt ccatgtcgcg    960
ctggaggtcg tccgcgccag cactgtgttt accacacata cgccagtggc ggcaggacat   1020
gatgcatttc ctctggcgat gttcgattat tatttcacca gactgttcac cgatcatccg   1080
gccttgcgcc acgatctgac acggctcggc tttgacgaat ccagtcagac cttcaacatg   1140
acccatctgg cgctgaacac ctccgctctt cgcaacggcg tgagtaagct gcacgggcat   1200
gtgtcccgcc agatgttccg ggactttcat ggccatatcg acattcgcga ggttcccatc   1260
ggccacatca ctaatggcgt acatctcagc acctggcttg ctccgcagct caaggagctg   1320
ttcgaccggt tcctgcctgg caactggaca ctcaatcaga tgaacccgga cgtatggcgg   1380
ggtatcgatc tgatccctag cgaatcgttg tggaaggtgc acgaggagct gaaggaaacg   1440
atgattcgcc tggcgcgggc caacctggcc gagcagcgcc gccgaaacgg acagtccgat   1500
catcagatcg gggaagcccg tggctatctg tccaaacacg ccctcacgat cggctttgcc   1560
cgccggttcg ctacgtacaa acgggctacg ctgatcttca atgacctcaa acgtctggat   1620
cgactcgtca atgatccgga gcgccccgtg cagttcattt ttgccggcaa ggctcatccc   1680
gccgaccgtc ccggtcagga tatgcttcgt gaaatctatc aggtgtccca actcgagcgg   1740
ttcaagggca agatcgttct gctggaaaat tatgatatca atgtagcgcg ggccctcgtc   1800
caaggcgtag acatctggct taacaatcca cgtcgtccgt acgaggcgag tggtacgagc   1860
gggcagaagg ctgcgctgaa cggcgtcatt aatttcagcg tgctggacgg ttggtgggag   1920
gaaggctatg acgggagcaa cggctggagc attgactcag acctgaatgc tgatgaggag   1980
acccagggac gccagaatac tcaatctctc taccaggtgc tggagcaaga aatcgtcccg   2040
ctgtactaca atcaaggccc cctgccggtc caatggatcg agcggatgaa acgttcgatc   2100
cagacgctgt ctcccgtcta taacacggac cggatggtcg ccgactatac ggcgggcgcc   2160
tacattccct ctctggagcg gacccagcgg ttcatcacca attcatacga agaggcccgg   2220
aaagtcgcgg actttaaaaa attcatctcg gacaactggc atcacgtccg cgtgatcgag   2280
gttagcgatt cgcttcaaag cggcaaaacc gcccggactg ccgagcctgt caaggaagtg   2340
```

```
tcggtcactg tacagttcgg acctgtctgg taccaggata cggcggttga cctgatctac   2400

tacgaggaca ccgcaagcgg ctgggagcag gtggtcgtcc cgatggaacc ttcccgccag   2460

ttaggcgaag gcctattcat ctatcgtgcc attgtcccgt cccatctccg tcacggcccc   2520

catttcagtg tcagggtgca tccagtcagc acgaatttcg ccacttcgtt cgagctgccc   2580

ctcgtcaaaa cctattga                                                 2598
```

```
<210> SEQ ID NO 42
<211> LENGTH: 865
<212> TYPE: PRT
<213> ORGANISM: Paenibacillus sp.

<400> SEQUENCE: 42

Met Ser Thr Leu Phe Pro Ala Pro Ser Phe Arg Leu Pro Ala Ala Ile
1               5                   10                  15

Ala Arg Leu Ser Asp Leu Ala Leu Asn Leu Trp Phe Ser Trp Asn Gly
            20                  25                  30

Ser Ala Gln Ala Leu Phe Ala Asp Ile Asp Ala Glu Leu Trp Leu Gln
        35                  40                  45

Thr Arg His Asn Pro Val Glu Leu Leu Thr Lys Val Ser Glu Asp Thr
    50                  55                  60

Leu Glu Arg Leu Ala Ala Asp Glu Ser Phe Leu Asn Arg Tyr Glu Ala
65                  70                  75                  80

Val Leu Arg Gln Phe Asp Glu Tyr Met Gly Ala Gly Thr Trp Phe Ser
                85                  90                  95

Arg His Tyr Pro His Gln Ser Arg His Ala Ile Ala Tyr Phe Ser Ala
            100                 105                 110

Glu Phe Gly Phe His Glu Ser Leu Pro Ile Tyr Ser Gly Gly Leu Gly
        115                 120                 125

Ile Leu Ala Gly Asp His Cys Lys Ser Ala Ser Asp Leu Gly Ile Pro
    130                 135                 140

Leu Ile Gly Val Gly Leu Leu Tyr Lys Lys Gly Tyr Phe Arg Gln Lys
145                 150                 155                 160

Leu Asp Ser Lys Gly His Gln Leu Ala Glu Ser Val Pro Tyr His Phe
                165                 170                 175

Arg Thr Leu Pro Ile Thr Pro Ala Leu Ala Leu His Ala Glu Lys Ala
            180                 185                 190

Asn Val Ser Asp Glu Asp Ala Gly Thr Pro Arg Asp Ala Glu Gln Pro
        195                 200                 205

Glu Pro Gln Glu Leu Tyr Val Thr Val Asp Val Ala Asp Arg Thr Val
    210                 215                 220

Arg Leu Lys Val Trp Gln Ala Arg Val Gly Arg Ile Arg Val Leu Leu
225                 230                 235                 240

Leu Asp Ala Asp Leu Glu Glu Asn Ser Ser Trp Asp Arg Asp Leu Thr
                245                 250                 255

Ala Gln Leu Tyr Gly Gly Thr Gln Asp Val Arg Ile Ala Gln Glu Met
            260                 265                 270

Leu Leu Gly Ile Gly Gly Ile Arg Ala Leu Arg Ala Leu Asn Val Pro
        275                 280                 285

Thr Gly Ala Tyr His Ile Asn Glu Gly His Ala Ala Phe Leu Ser Phe
    290                 295                 300

Glu Arg Leu Lys Glu Gln Leu Glu Leu Gly Leu Pro Phe His Val Ala
305                 310                 315                 320

Leu Glu Val Val Arg Ala Ser Thr Val Phe Thr Thr His Thr Pro Val
```

```
                325                 330                 335

Ala Ala Gly His Asp Ala Phe Pro Leu Ala Met Phe Asp Tyr Tyr Phe
            340                 345                 350

Thr Arg Leu Phe Thr Asp His Pro Ala Leu Arg His Asp Leu Thr Arg
        355                 360                 365

Leu Gly Phe Asp Glu Ser Ser Gln Thr Phe Asn Met Thr His Leu Ala
    370                 375                 380

Leu Asn Thr Ser Ala Leu Arg Asn Gly Val Ser Lys Leu His Gly His
385                 390                 395                 400

Val Ser Arg Gln Met Phe Arg Asp Phe His Gly His Ile Asp Ile Arg
                405                 410                 415

Glu Val Pro Ile Gly His Ile Thr Asn Gly Val His Leu Ser Thr Trp
            420                 425                 430

Leu Ala Pro Gln Leu Lys Glu Leu Phe Asp Arg Phe Leu Pro Gly Asn
        435                 440                 445

Trp Thr Leu Asn Gln Met Asn Pro Asp Val Trp Arg Gly Ile Asp Leu
    450                 455                 460

Ile Pro Ser Glu Ser Leu Trp Lys Val His Glu Glu Leu Lys Glu Thr
465                 470                 475                 480

Met Ile Arg Leu Ala Arg Ala Asn Leu Ala Glu Gln Arg Arg Arg Asn
                485                 490                 495

Gly Gln Ser Asp His Gln Ile Gly Glu Ala Arg Gly Tyr Leu Ser Lys
            500                 505                 510

His Ala Leu Thr Ile Gly Phe Ala Arg Arg Phe Ala Thr Tyr Lys Arg
        515                 520                 525

Ala Thr Leu Ile Phe Asn Asp Leu Lys Arg Leu Asp Arg Leu Val Asn
    530                 535                 540

Asp Pro Glu Arg Pro Val Gln Phe Ile Phe Ala Gly Lys Ala His Pro
545                 550                 555                 560

Ala Asp Arg Pro Gly Gln Asp Met Leu Arg Glu Ile Tyr Gln Val Ser
                565                 570                 575

Gln Leu Glu Arg Phe Lys Gly Lys Ile Val Leu Leu Glu Asn Tyr Asp
            580                 585                 590

Ile Asn Val Ala Arg Ala Leu Val Gln Gly Val Asp Ile Trp Leu Asn
        595                 600                 605

Asn Pro Arg Arg Pro Tyr Glu Ala Ser Gly Thr Ser Gly Gln Lys Ala
    610                 615                 620

Ala Leu Asn Gly Val Ile Asn Phe Ser Val Leu Asp Gly Trp Trp Glu
625                 630                 635                 640

Glu Gly Tyr Asp Gly Ser Asn Gly Trp Ser Ile Asp Ser Asp Leu Asn
                645                 650                 655

Ala Asp Glu Glu Thr Gln Gly Arg Gln Asn Thr Gln Ser Leu Tyr Gln
            660                 665                 670

Val Leu Glu Gln Glu Ile Val Pro Leu Tyr Tyr Asn Gln Gly Pro Leu
        675                 680                 685

Pro Val Gln Trp Ile Glu Arg Met Lys Arg Ser Ile Gln Thr Leu Ser
    690                 695                 700

Pro Val Tyr Asn Thr Asp Arg Met Val Ala Asp Tyr Thr Ala Gly Ala
705                 710                 715                 720

Tyr Ile Pro Ser Leu Glu Arg Thr Gln Arg Phe Ile Thr Asn Ser Tyr
                725                 730                 735

Glu Glu Ala Arg Lys Val Ala Asp Phe Lys Lys Phe Ile Ser Asp Asn
            740                 745                 750
```

```
Trp His His Val Arg Val Ile Glu Val Ser Asp Ser Leu Gln Ser Gly
        755                 760                 765

Lys Thr Ala Arg Thr Ala Glu Pro Val Lys Glu Val Ser Val Thr Val
    770                 775                 780

Gln Phe Gly Pro Val Trp Tyr Gln Asp Thr Ala Val Asp Leu Ile Tyr
785                 790                 795                 800

Tyr Glu Asp Thr Ala Ser Gly Trp Glu Gln Val Val Val Pro Met Glu
                805                 810                 815

Pro Ser Arg Gln Leu Gly Glu Gly Leu Phe Ile Tyr Arg Ala Ile Val
            820                 825                 830

Pro Ser His Leu Arg His Gly Pro His Phe Ser Val Arg Val His Pro
        835                 840                 845

Val Ser Thr Asn Phe Ala Thr Ser Phe Glu Leu Pro Leu Val Lys Thr
    850                 855                 860

Tyr
865
```

<210> SEQ ID NO 43
<211> LENGTH: 2592
<212> TYPE: DNA
<213> ORGANISM: Microbacterium sp.

<400> SEQUENCE: 43

```
gtggcccgtt cgatcgactc ccctatactg ccgcgcgtga aggccatccg cacgttcacc     60

gtccgccccg tcctcgcacc cgccctggag ccgctccacc gcctcgcggc gaattggcgg    120

tggtcgtgga gccggtcgac acacgccctg ttctcctcga tggatccgac ccagtggagc    180

gaggtcggtg agaaccccgc acgcatgctc ggcgcgctcg gccaggagcg cctggacgcc    240

ctcgcgcacg acgagtcctt cgtcgcgcgg gtgcgcgagg aggacgagcg cctggaggcc    300

tacctctccg gcgaccggtg gtatcagagc ctcgacggcg gcgacaatcc ccgcgccatc    360

gcgtacttct ctcccgagtt cggagtcgac ggctccctcc cccagtactc cggcgggctc    420

ggcatcctgg ccggcgatca cctcaaaagc gcctcggacc tgggagtccc cctcctgggc    480

gtcggtctgt tctaccgcgc cggctacttc cggcaggcca tcggcgacga cggctggcag    540

cgcgagagct atccgctcct cgatccgtac ggactcggcc tcaccctcct gcgcgaggtc    600

gacggctccc ccgtcgagat cacgctcgac ctctccggcg ggcgtcgtct cgccgcgcgc    660

gtatggcagg ccgacatcgg ccgcgtcccc ctgctgctcc tcgactccga gactccgtcg    720

aatcccgagg accttcgtca cgtgaccgac cggctctacg gcggcggcgg cgagcaccgg    780

ttgctgcagg agctgctcct gggcgtcggc ggcgttcggg cggtgcgtgc gtggacgcgg    840

ctgaccggcg cgccggaacc ggatgtcttc cacacgaacg aaggccatgc cggattccag    900

ggtctcgagc ggatgtccga gctgatcgtc ggcgagggcc tcgatttcga cgtcgccctc    960

gcccaggtgc ggtcctccac ggtgttcact acgcacaccc ccgtcccggc gggcatcgac   1020

cggttcccgc gcagcctcat cgatcagatg ctcacggccg gtctgttccg cggcctcgat   1080

cccgaccgag ccctgcgtct cggcctcgaa gggtatgacg gaggcgaccc gcacaccttc   1140

aacatggcgg tgctgggcct gcacctcggg cagcacgcca acggcgtctc gcgcctgcac   1200

ggccgcgtga gccgggagat gttcgggccg ctgtggcccg gcgtggacgc cgacgaagtg   1260

ccgatcatct ccatcaccaa cggcgtgcac gccccgacgt gggtgcatcc ggagttgaag   1320

gcgctcagcg agcgcgcctt cggcgacgcc ctcacgacca cccacgactg gcgagatccc   1380
```

```
gcccgcgtgg ccgacgagga gctgtgggag tcccggcgcc gcatgaaggc cggtctcgtc   1440
gccgaggcac gccgccgact cagggcgggc gaggagtccg gcacgggcgc gccgtggatc   1500
gatgacgcgc tcgaccccga cgtcctcacc atcggattcg cccggcgcgt gccgacctac   1560
aaacggctga ccctcatgct ccgcgacccg gaacggctca cgcagctgct caccgatgcc   1620
caccgtccgg ttcagatcgt cgtggccggc aagtcccacc cagccgacga ctcggggaag   1680
atcctcatcc agcagctcgt gcgcttcagc caggaccccc gggtccgtgg gcgcatcgtc   1740
ttcctccccg actatgacat caccctcgcc aagcacctct acccgggatg cgatgtctgg   1800
ctgaacaatc cgctgcgccc gctcgaggcg tgcggaacga gcggcatgaa ggcggccctg   1860
aacggtgcgc tgaacctgtc gatcctcgac ggctggtggg acgagtggtt cgacgggagg   1920
aacggctggg cgatcccgtc ggccgacagg gcggccgacg acgacgaacg cgacgacgcc   1980
gaggcgagcg cactgtacga cctgatcgag aaccgtctcg tgccgacctt ctacgaccgt   2040
gaggacgggc ttcccgcccc ctggctggag atggttcgtc acaccatgac gaccctcggc   2100
ggcaaggcga ccagcgaccg catggtgcgc gactacgtca ccgagctcta cgtcccagcc   2160
gctcgtcaca acgccgagct cgctgccgac ggccacgctc gcgcccgcga gctggcgcga   2220
tacatctcgc gggtgaagga tgcctggccc ggcgtgcgga tcgacagcgt cgacgcgaac   2280
ggggccaccg cccacccccg caccggcgag acggtcacgg tgacggcacg cgtgcgcctc   2340
gcccatctct cccccgacga cgtggccgtc gaactcgtct acggccacgc cgacagcgac   2400
gggcgcctcg accgcacccg caccgcgatt ccgctctccg cccagcccgg cggcgaagat   2460
gggatgaccg tcttcgccgg agcgctgcgg ctgacgatga ccgggccgtt cggctacacc   2520
gtgcgcgtgg tcccgcggca cgaccacctc gtgtcccccc tcgaactggg gctcgtctcg   2580
ctcgcttcct ga                                                       2592
```

```
<210> SEQ ID NO 44
<211> LENGTH: 863
<212> TYPE: PRT
<213> ORGANISM: Microbacterium sp.

<400> SEQUENCE: 44

Met Ala Arg Ser Ile Asp Ser Pro Ile Leu Pro Arg Val Lys Ala Ile
1               5                   10                  15

Arg Thr Phe Thr Val Arg Pro Val Leu Ala Pro Ala Leu Glu Pro Leu
            20                  25                  30

His Arg Leu Ala Ala Asn Trp Arg Trp Ser Trp Ser Arg Ser Thr His
        35                  40                  45

Ala Leu Phe Ser Ser Met Asp Pro Thr Gln Trp Ser Glu Val Gly Glu
    50                  55                  60

Asn Pro Ala Arg Met Leu Gly Ala Leu Gly Gln Glu Arg Leu Asp Ala
65                  70                  75                  80

Leu Ala His Asp Glu Ser Phe Val Ala Arg Val Arg Glu Glu Asp Glu
                85                  90                  95

Arg Leu Glu Ala Tyr Leu Ser Gly Asp Arg Trp Tyr Gln Ser Leu Asp
            100                 105                 110

Gly Gly Asp Asn Pro Arg Ala Ile Ala Tyr Phe Ser Pro Glu Phe Gly
        115                 120                 125

Val Asp Gly Ser Leu Pro Gln Tyr Ser Gly Gly Leu Gly Ile Leu Ala
    130                 135                 140

Gly Asp His Leu Lys Ser Ala Ser Asp Leu Gly Val Pro Leu Leu Gly
145                 150                 155                 160
```

```
Val Gly Leu Phe Tyr Arg Ala Gly Tyr Phe Arg Gln Ala Ile Gly Asp
                165                 170                 175

Asp Gly Trp Gln Arg Glu Ser Tyr Pro Leu Leu Asp Pro Tyr Gly Leu
            180                 185                 190

Gly Leu Thr Leu Leu Arg Glu Val Asp Gly Ser Pro Val Glu Ile Thr
        195                 200                 205

Leu Asp Leu Ser Gly Gly Arg Arg Leu Ala Ala Arg Val Trp Gln Ala
    210                 215                 220

Asp Ile Gly Arg Val Pro Leu Leu Leu Leu Asp Ser Glu Thr Pro Ser
225                 230                 235                 240

Asn Pro Glu Asp Leu Arg His Val Thr Asp Arg Leu Tyr Gly Gly Gly
                245                 250                 255

Gly Glu His Arg Leu Leu Gln Glu Leu Leu Leu Gly Val Gly Gly Val
            260                 265                 270

Arg Ala Val Arg Ala Trp Thr Arg Leu Thr Gly Ala Pro Glu Pro Asp
        275                 280                 285

Val Phe His Thr Asn Glu Gly His Ala Gly Phe Gln Gly Leu Glu Arg
    290                 295                 300

Met Ser Glu Leu Ile Val Gly Glu Gly Leu Asp Phe Asp Val Ala Leu
305                 310                 315                 320

Ala Gln Val Arg Ser Ser Thr Val Phe Thr Thr His Thr Pro Val Pro
                325                 330                 335

Ala Gly Ile Asp Arg Phe Pro Arg Ser Leu Ile Asp Gln Met Leu Thr
            340                 345                 350

Ala Gly Leu Phe Arg Gly Leu Asp Pro Asp Arg Ala Leu Arg Leu Gly
        355                 360                 365

Leu Glu Gly Tyr Asp Gly Gly Asp Pro His Thr Phe Asn Met Ala Val
    370                 375                 380

Leu Gly Leu His Leu Gly Gln His Ala Asn Gly Val Ser Arg Leu His
385                 390                 395                 400

Gly Arg Val Ser Arg Glu Met Phe Gly Pro Leu Trp Pro Gly Val Asp
                405                 410                 415

Ala Asp Glu Val Pro Ile Ile Ser Ile Thr Asn Gly Val His Ala Pro
            420                 425                 430

Thr Trp Val His Pro Glu Leu Lys Ala Leu Ser Glu Arg Ala Phe Gly
        435                 440                 445

Asp Ala Leu Thr Thr Thr His Asp Trp Arg Asp Pro Ala Arg Val Ala
    450                 455                 460

Asp Glu Glu Leu Trp Glu Ser Arg Arg Arg Met Lys Ala Gly Leu Val
465                 470                 475                 480

Ala Glu Ala Arg Arg Arg Leu Arg Ala Gly Glu Glu Ser Gly Thr Gly
                485                 490                 495

Ala Pro Trp Ile Asp Asp Ala Leu Asp Pro Asp Val Leu Thr Ile Gly
            500                 505                 510

Phe Ala Arg Arg Val Pro Thr Tyr Lys Arg Leu Thr Leu Met Leu Arg
        515                 520                 525

Asp Pro Glu Arg Leu Thr Gln Leu Leu Thr Asp Ala His Arg Pro Val
    530                 535                 540

Gln Ile Val Val Ala Gly Lys Ser His Pro Ala Asp Asp Ser Gly Lys
545                 550                 555                 560

Ile Leu Ile Gln Gln Leu Val Arg Phe Ser Gln Asp Pro Arg Val Arg
                565                 570                 575
```

```
Gly Arg Ile Val Phe Leu Pro Asp Tyr Asp Ile Thr Leu Ala Lys His
            580                 585                 590

Leu Tyr Pro Gly Cys Asp Val Trp Leu Asn Asn Pro Leu Arg Pro Leu
        595                 600                 605

Glu Ala Cys Gly Thr Ser Gly Met Lys Ala Ala Leu Asn Gly Ala Leu
    610                 615                 620

Asn Leu Ser Ile Leu Asp Gly Trp Trp Asp Glu Trp Phe Asp Gly Arg
625                 630                 635                 640

Asn Gly Trp Ala Ile Pro Ser Ala Asp Arg Ala Ala Asp Asp Asp Glu
                645                 650                 655

Arg Asp Asp Ala Glu Ala Ser Ala Leu Tyr Asp Leu Ile Glu Asn Arg
            660                 665                 670

Leu Val Pro Thr Phe Tyr Asp Arg Glu Asp Gly Leu Pro Ala Pro Trp
        675                 680                 685

Leu Glu Met Val Arg His Thr Met Thr Thr Leu Gly Gly Lys Ala Thr
    690                 695                 700

Ser Asp Arg Met Val Arg Asp Tyr Val Thr Glu Leu Tyr Val Pro Ala
705                 710                 715                 720

Ala Arg His Asn Ala Glu Leu Ala Ala Asp Gly His Ala Arg Ala Arg
                725                 730                 735

Glu Leu Ala Arg Tyr Ile Ser Arg Val Lys Asp Ala Trp Pro Gly Val
            740                 745                 750

Arg Ile Asp Ser Val Asp Ala Asn Gly Ala Thr Ala His Pro Arg Thr
        755                 760                 765

Gly Glu Thr Val Thr Val Thr Ala Arg Val Arg Leu Ala His Leu Ser
    770                 775                 780

Pro Asp Asp Val Ala Val Glu Leu Val Tyr Gly His Ala Asp Ser Asp
785                 790                 795                 800

Gly Arg Leu Asp Arg Thr Arg Thr Ala Ile Pro Leu Ser Ala Gln Pro
                805                 810                 815

Gly Gly Glu Asp Gly Met Thr Val Phe Ala Gly Ala Leu Arg Leu Thr
            820                 825                 830

Met Thr Gly Pro Phe Gly Tyr Thr Val Arg Val Val Pro Arg His Asp
        835                 840                 845

His Leu Val Ser Pro Leu Glu Leu Gly Leu Val Ser Leu Ala Ser
    850                 855                 860
```

<210> SEQ ID NO 45
<211> LENGTH: 2562
<212> TYPE: DNA
<213> ORGANISM: Artificial sequence
<220> FEATURE:
<223> OTHER INFORMATION: Metagenomic (composite) sequence for GP-013.

<400> SEQUENCE: 45

```
atggctggta ccttgttcca actcgaaatc aatcccaagc tcccggcgcg tcttgcgcgc     60

ctcgaagagc tcgccaacaa cctctggtat agctgggatc gtcccacgcg caccctgttt    120

gcccgcctgg gcacccggct gtggggtgcg gtcggccaca gcccgaaggc ctttctcaag    180

cgcgtcgacc agcaccgtct cgaagaggcg gcggaagacc cagtgtttct cggcgcgctc    240

gcgcatgtgc tgtcggccta cgacacttat cacgacaacc tgcgtcgcga gccggggcat    300

cagttgccgg aaggcgcatt gatcgcctat ttctgcgccg aattcggttt tcatgagagt    360

ctgccgatct attccggcgg cctgggcatc ctcgccggcg atcactgcaa gacggcaagc    420

gacatgaacc tgcccttcgt cggcgttggc ctgctctacc ggcaaggtta tttcctgcag    480
```

```
agcatcgacg gcgagggacg tcagcatgcg ctctacaacg acgccgattt cgacgacctg    540
ccggtcaccc cggtcgccgc gcccgggggga ggcgacctga aggtagccgt gcgcctgccg    600
ggccgcgatg tctgggtcaa ggtctggaag gcgcgcgtcg gccacgtatc gatctatctg    660
ctcgataccg atctcgagga aaactcgccg catgaccgcg acatcaccca ccagctctat    720
ggcggcgatc gcaccacacg catcgagcag gagatcgtgc tcggcatggg cggcgtgcgg    780
gcgctcgctg cgttgaatct caaacccacc gtctggcaca tcaacgaagg ccatgcggcg    840
tttttggtgc tcgaacgcat gcgcgatctg atcaagagcg gtctcgattt cgatgctgcg    900
atcgaagtcg tcgcctgcaa tacggtgttt accacccata cgccggtacc agccggacac    960
gatcatttcg ccgacgaaat gatccgccag tatttcgagg agtgctgcca cgacatgggt   1020
tgcgaggtcg gcagcttgct ggcattgggg cgcatcgacg acacgccaga attcaacatg   1080
accggcctgg cgatccgcgg ctcgcgtttc cagaacggcg tctcgcgcat ccacggggac   1140
gtctccgcgg aaatctgccg tcagttgtgg ccacagatcg atcccgaaga aaacccgatg   1200
gactatgtca ccaacggggt gcatgtgccg acgttcctgt ctgaccactg gcatgacacc   1260
ttcgatcgcg tgctcggacc ggcctggcgc cagcggctca ccgatgcgca gacctggtcg   1320
caagtgcatg cgattcccga tcacacgttc tggagcatcc gccagtcgat caaggcggag   1380
atgctctact tggtgcggca tcggatcacc gagcaataca cgcgcaacca atgttcgcag   1440
gcgcatatcg accggctgct gcagctcgcc gatccggaaa accccaacgt gctgacggtc   1500
ggcttcgcgc gccgtttcgc cacctacaag cgcgccacgc tcttgttcag cgatttggag   1560
ctgttgcggc gcatgatctg caatcccgaa cgtccggtgc tgttcatctt cgccggcaag   1620
gcgcatccgg ccgaccagcc cgggcaggcg ttgatccggc gcgtccacga agtggcgcag   1680
atgccggaat tcgaaggtca catcctgctc gtcgaaggct atgacctgcg cctggcgcgc   1740
cggctcgtct cgggcgtcga tgtctggctg aacaatccgg tctatccgct cgaagcctcc   1800
ggcacttccg gcatgaaggc ggcgatgaat ggcgtcatca acctgtcggt gctcgacggc   1860
tggtggggtg agggtttcca tcaagacgat ggcggtgcca atggctgggc gatcaagccg   1920
gcttcgcgaa cgctcgacga ggcgcggcgc gatcaggagg aaggtcgctc gctctacgag   1980
accctccagg acaaggtgat cccgttgtat tacgcgcgcg gcccgatggg ctattcaccc   2040
ggctggatcg cgatggccaa gcgttcgatc gcgacgatca cgccgcgctt caattcccag   2100
cgcatggtcg gtgagtatct gcacaagttc tatgcacccg ccgatctaca gtggcgcaag   2160
aaaagcgccg atggttacgc cgccgcgcgc acgctggcgg cttggaagca gaaagtgcgt   2220
caggcttggc caaaagtccg gctacggcgc ctcgatatgc cggtgaagcg tatcccctat   2280
ggcgccagtc tgcacttcga actggccgtg catctggatg gcctggcgcc gcaggacgtg   2340
gcggtggaat tgctgctgtc gcgtcccggc accgacagcc gcacgcggcc gccacgcaag   2400
ctattgctcg aataccgcgg cccaggcgag cagggtgaca gcatcttcgc gctcgatttc   2460
acgcccgacg tgtgcggtaa gctcgactat cggctgcgcg tctatcctca tcacgagcta   2520
ctcacccatc ccttcgagat gggcatgatg ctgtggttgt ga                      2562
```

<210> SEQ ID NO 46
<211> LENGTH: 853
<212> TYPE: PRT
<213> ORGANISM: Artificial sequence
<220> FEATURE:
<223> OTHER INFORMATION: Metagenomic (composite) sequence for GP-013.

<400> SEQUENCE: 46

```
Met Ala Gly Thr Leu Phe Gln Leu Glu Ile Asn Pro Lys Leu Pro Ala
1               5                   10                  15

Arg Leu Ala Arg Leu Glu Glu Leu Ala Asn Asn Leu Trp Tyr Ser Trp
            20                  25                  30

Asp Arg Pro Thr Arg Thr Leu Phe Ala Arg Leu Gly Thr Arg Leu Trp
        35                  40                  45

Gly Ala Val Gly His Ser Pro Lys Ala Phe Leu Lys Arg Val Asp Gln
    50                  55                  60

His Arg Leu Glu Glu Ala Ala Glu Asp Pro Val Phe Leu Gly Ala Leu
65                  70                  75                  80

Ala His Val Leu Ser Ala Tyr Asp Thr Tyr His Asp Asn Leu Arg Arg
                85                  90                  95

Glu Pro Gly His Gln Leu Pro Glu Gly Ala Leu Ile Ala Tyr Phe Cys
            100                 105                 110

Ala Glu Phe Gly Phe His Glu Ser Leu Pro Ile Tyr Ser Gly Gly Leu
        115                 120                 125

Gly Ile Leu Ala Gly Asp His Cys Lys Thr Ala Ser Asp Met Asn Leu
    130                 135                 140

Pro Phe Val Gly Val Gly Leu Leu Tyr Arg Gln Gly Tyr Phe Leu Gln
145                 150                 155                 160

Ser Ile Asp Gly Glu Gly Arg Gln His Ala Leu Tyr Asn Asp Ala Asp
                165                 170                 175

Phe Asp Asp Leu Pro Val Thr Pro Val Ala Ala Pro Gly Gly Gly Asp
            180                 185                 190

Leu Lys Val Ala Val Arg Leu Pro Gly Arg Asp Val Trp Val Lys Val
        195                 200                 205

Trp Lys Ala Arg Val Gly His Val Ser Ile Tyr Leu Leu Asp Thr Asp
    210                 215                 220

Leu Glu Glu Asn Ser Pro His Asp Arg Asp Ile Thr His Gln Leu Tyr
225                 230                 235                 240

Gly Gly Asp Arg Thr Thr Arg Ile Glu Gln Glu Ile Val Leu Gly Met
                245                 250                 255

Gly Gly Val Arg Ala Leu Ala Ala Leu Asn Leu Lys Pro Thr Val Trp
            260                 265                 270

His Ile Asn Glu Gly His Ala Ala Phe Leu Val Leu Glu Arg Met Arg
        275                 280                 285

Asp Leu Ile Lys Ser Gly Leu Asp Phe Asp Ala Ala Ile Glu Val Val
    290                 295                 300

Ala Cys Asn Thr Val Phe Thr Thr His Thr Pro Val Pro Ala Gly His
305                 310                 315                 320

Asp His Phe Ala Asp Glu Met Ile Arg Gln Tyr Phe Glu Glu Cys Cys
                325                 330                 335

His Asp Met Gly Cys Glu Val Gly Ser Leu Leu Ala Leu Gly Arg Ile
            340                 345                 350

Asp Asp Thr Pro Glu Phe Asn Met Thr Gly Leu Ala Ile Arg Gly Ser
        355                 360                 365

Arg Phe Gln Asn Gly Val Ser Arg Ile His Gly Asp Val Ser Ala Glu
    370                 375                 380

Ile Cys Arg Gln Leu Trp Pro Gln Ile Asp Pro Glu Glu Asn Pro Met
385                 390                 395                 400

Asp Tyr Val Thr Asn Gly Val His Val Pro Thr Phe Leu Ser Asp His
                405                 410                 415
```

```
Trp His Asp Thr Phe Asp Arg Val Leu Gly Pro Ala Trp Arg Gln Arg
            420                 425                 430

Leu Thr Asp Ala Gln Thr Trp Ser Gln Val His Ala Ile Pro Asp His
        435                 440                 445

Thr Phe Trp Ser Ile Arg Gln Ser Ile Lys Ala Glu Met Leu Tyr Leu
    450                 455                 460

Val Arg His Arg Ile Thr Glu Gln Tyr Thr Arg Asn Gln Cys Ser Gln
465                 470                 475                 480

Ala His Ile Asp Arg Leu Leu Gln Leu Ala Asp Pro Glu Asn Pro Asn
                485                 490                 495

Val Leu Thr Val Gly Phe Ala Arg Arg Phe Ala Thr Tyr Lys Arg Ala
            500                 505                 510

Thr Leu Leu Phe Ser Asp Leu Glu Leu Leu Arg Arg Met Ile Cys Asn
        515                 520                 525

Pro Glu Arg Pro Val Leu Phe Ile Phe Ala Gly Lys Ala His Pro Ala
    530                 535                 540

Asp Gln Pro Gly Gln Ala Leu Ile Arg Arg Val His Glu Val Ala Gln
545                 550                 555                 560

Met Pro Glu Phe Glu Gly His Ile Leu Leu Val Glu Gly Tyr Asp Leu
                565                 570                 575

Arg Leu Ala Arg Arg Leu Val Ser Gly Val Asp Val Trp Leu Asn Asn
            580                 585                 590

Pro Val Tyr Pro Leu Glu Ala Ser Gly Thr Ser Gly Met Lys Ala Ala
        595                 600                 605

Met Asn Gly Val Ile Asn Leu Ser Val Leu Asp Gly Trp Trp Gly Glu
    610                 615                 620

Gly Phe His Gln Asp Asp Gly Gly Ala Asn Gly Trp Ala Ile Lys Pro
625                 630                 635                 640

Ala Ser Arg Thr Leu Asp Glu Ala Arg Arg Asp Gln Glu Glu Gly Arg
                645                 650                 655

Ser Leu Tyr Glu Thr Leu Gln Asp Lys Val Ile Pro Leu Tyr Tyr Ala
            660                 665                 670

Arg Gly Pro Met Gly Tyr Ser Pro Gly Trp Ile Ala Met Ala Lys Arg
        675                 680                 685

Ser Ile Ala Thr Ile Thr Pro Arg Phe Asn Ser Gln Arg Met Val Gly
    690                 695                 700

Glu Tyr Leu His Lys Phe Tyr Ala Pro Ala Asp Leu Gln Trp Arg Lys
705                 710                 715                 720

Lys Ser Ala Asp Gly Tyr Ala Ala Ala Arg Thr Leu Ala Ala Trp Lys
                725                 730                 735

Gln Lys Val Arg Gln Ala Trp Pro Lys Val Arg Leu Arg Arg Leu Asp
            740                 745                 750

Met Pro Val Lys Arg Ile Pro Tyr Gly Ala Ser Leu His Phe Glu Leu
        755                 760                 765

Ala Val His Leu Asp Gly Leu Ala Pro Gln Asp Val Ala Val Glu Leu
    770                 775                 780

Leu Leu Ser Arg Pro Gly Thr Asp Ser Arg Thr Arg Pro Pro Arg Lys
785                 790                 795                 800

Leu Leu Leu Glu Tyr Arg Gly Pro Gly Glu Gln Gly Asp Ser Ile Phe
                805                 810                 815

Ala Leu Asp Phe Thr Pro Asp Val Cys Gly Lys Leu Asp Tyr Arg Leu
            820                 825                 830
```

```
Arg Val Tyr Pro His His Glu Leu Leu Thr His Pro Phe Glu Met Gly
        835                 840                 845

Met Met Leu Trp Leu
    850


<210> SEQ ID NO 47
<211> LENGTH: 2127
<212> TYPE: DNA
<213> ORGANISM: Artificial sequence
<220> FEATURE:
<223> OTHER INFORMATION: Metagenomic (composite) sequence for GP-043.

<400> SEQUENCE: 47

atgcagaaaa cattgacgat tgatgaagtt atcaactcgc tttatgaact tgcgtataat     60

ctctggtgga cttacaatcc caaagcacag gaaatttttg agatgctttc accgatgctt    120

tggaaattga caaatcataa tgcagtgcaa acattgaaat caatttcaaa gtttgagtta    180

aaggcaagat tgtcaaatcc agatttttta tcaaaagttg aaaatgtcct caacgagttc    240

aaacagtata ttagaacaag acaggagctt tcaaaaaata aatttcctga tttcatcaat    300

cgtccagttg cttattttac agctgaattt ggcttacacg aatgccttcc aatttattct    360

ggtgggttgg gaattttatc cggagaccac gcaaaatccg caagtgatat aggtcttcca    420

ttcgttgggg tgagcttgtt ttacaggcac ggttattttg atcaaaaaat agccgacaat    480

ggatggcaaa ttgaggaata taatccagtt caaccaaatt ttttgcctgt taaacttgtg    540

ctggaccaac agaatcaacc tttaaaagta aaacttaaca tcgggcattc tgagatttca    600

attcaggcgt gggaagtcaa tgttgggata tcaaaaattt atcttcttga tacgaatttg    660

cccgaaaatg attttcatta tcgtgatata acgagcaagg tttacggcgg tgatgcaaca    720

acgagaattt ttcaggagat agtcctcggg attggtggcg taagattttt aaaagctctt    780

ggaattgaac catctgttta tcatctaaac gagggacaca gtgccttttt gacgcttgaa    840

cttatgagag aagaacttaa caaaggtaaa acgaaagagg aagccgaaag gtcggtccgt    900

gaaaaatgtg tcttcacaac gcacacgcct gtccccgcag ggcacgatag attttcaccc    960

gatttaattg aatatgctct tggcagtttt atccaatcgc ttggtatgag cttaaaagag   1020

tttctcgctt acgggaggat tcatcctgac aatgaacagg agacattttg tatgacagtt   1080

cttgcgctta aactttcaag aaatgcaaac gctgtaagcg agctcaacgg gattgtgagc   1140

agaaaaatgt ggcaacccct tttcaaaagc aaatcagaaa aagatgtccc tatcggacat   1200

ataacaaacg gcgttcattc acttacatgg cttaacaaaa ttgcatttga attctggacg   1260

aaaaagcttg gcgataaatg gtatgaagag attgaaaacc cgaaactctg ggaaaatgtt   1320

cttgatgaaa atttcatcac agatgaagag atatggtcaa taaggtatga gttgaggcgg   1380

agtttgattg agtttgtcag ggagaaaatt ttaaatctgc tttttaaatc cgggcttgat   1440

tcaaaagtga acataaattc aattttatcg cccgatgctt taacaatcgg attttcaaga   1500

agatttgcaa cttacaaaag ggcaccgttg attttttacg atcttgaaag agcgaagaaa   1560

atttttaacg ataggtcaaa acctgttcaa ataattttct ctgggaaggc acatccacga   1620

gacgacgccg ggaaagaatt tctacaacga attgttcaaa tatcaaaaat gccggaattt   1680

tacggcaaag ttatcttcat tgaaaactat gatatgaaca tcgcacgaca tttaatttct   1740

ggatgtgacc tctggctcaa taatccgaga agacctcttg aggcgagtgg aacgagcggt   1800

caaaaaattg ttttgaactt tggtttgaat ttcagcatac ttgatggatg gtggcgtgaa   1860

gcatacaacg ggaaaatgg atgggctatc ggtaaagatg aatcagttga agacccaaat   1920
```

atacaggata aacttgacgc tgaatttctc tatcaaacgc ttgaaaatga aatcatccca 1980
gcattttaca atcgcaacga aaatggaatc ccaaaagaat ggataaaaag aatcaggaaa 2040
tcaatcgcaa ctgtaactta tttctttaac acgaacagaa tggtcagaga atatgtcaag 2100
aagtattaca ggaaaagcga aaattag 2127

<210> SEQ ID NO 48
<211> LENGTH: 708
<212> TYPE: PRT
<213> ORGANISM: Artificial sequence
<220> FEATURE:
<223> OTHER INFORMATION: Metagenomic (composite) sequence for GP-043.

<400> SEQUENCE: 48

Met Gln Lys Thr Leu Thr Ile Asp Glu Val Ile Asn Ser Leu Tyr Glu
1 5 10 15

Leu Ala Tyr Asn Leu Trp Trp Thr Tyr Asn Pro Lys Ala Gln Glu Ile
20 25 30

Phe Glu Met Leu Ser Pro Met Leu Trp Lys Leu Thr Asn His Asn Ala
35 40 45

Val Gln Thr Leu Lys Ser Ile Ser Lys Phe Glu Leu Lys Ala Arg Leu
50 55 60

Ser Asn Pro Asp Phe Leu Ser Lys Val Glu Asn Val Leu Asn Glu Phe
65 70 75 80

Lys Gln Tyr Ile Arg Thr Arg Gln Glu Leu Ser Lys Asn Lys Phe Pro
85 90 95

Asp Phe Ile Asn Arg Pro Val Ala Tyr Phe Thr Ala Glu Phe Gly Leu
100 105 110

His Glu Cys Leu Pro Ile Tyr Ser Gly Gly Leu Gly Ile Leu Ser Gly
115 120 125

Asp His Ala Lys Ser Ala Ser Asp Ile Gly Leu Pro Phe Val Gly Val
130 135 140

Ser Leu Phe Tyr Arg His Gly Tyr Phe Asp Gln Lys Ile Ala Asp Asn
145 150 155 160

Gly Trp Gln Ile Glu Glu Tyr Asn Pro Val Gln Pro Asn Phe Leu Pro
165 170 175

Val Lys Leu Val Leu Asp Gln Gln Asn Gln Pro Leu Lys Val Lys Leu
180 185 190

Asn Ile Gly His Ser Glu Ile Ser Ile Gln Ala Trp Glu Val Asn Val
195 200 205

Gly Ile Ser Lys Ile Tyr Leu Leu Asp Thr Asn Leu Pro Glu Asn Asp
210 215 220

Phe His Tyr Arg Asp Ile Thr Ser Lys Val Tyr Gly Gly Asp Ala Thr
225 230 235 240

Thr Arg Ile Phe Gln Glu Ile Val Leu Gly Ile Gly Gly Val Arg Phe
245 250 255

Leu Lys Ala Leu Gly Ile Glu Pro Ser Val Tyr His Leu Asn Glu Gly
260 265 270

His Ser Ala Phe Leu Thr Leu Glu Leu Met Arg Glu Glu Leu Asn Lys
275 280 285

Gly Lys Thr Lys Glu Glu Ala Glu Arg Ser Val Arg Glu Lys Cys Val
290 295 300

Phe Thr Thr His Thr Pro Val Pro Ala Gly His Asp Arg Phe Ser Pro
305 310 315 320

```
Asp Leu Ile Glu Tyr Ala Leu Gly Ser Phe Ile Gln Ser Leu Gly Met
                325                 330                 335

Ser Leu Lys Glu Phe Leu Ala Tyr Gly Arg Ile His Pro Asp Asn Glu
            340                 345                 350

Gln Glu Thr Phe Cys Met Thr Val Leu Ala Leu Lys Leu Ser Arg Asn
        355                 360                 365

Ala Asn Ala Val Ser Glu Leu Asn Gly Ile Val Ser Arg Lys Met Trp
    370                 375                 380

Gln Pro Leu Phe Lys Ser Lys Ser Glu Lys Asp Val Pro Ile Gly His
385                 390                 395                 400

Ile Thr Asn Gly Val His Ser Leu Thr Trp Leu Asn Lys Ile Ala Phe
                405                 410                 415

Glu Phe Trp Thr Lys Lys Leu Gly Asp Lys Trp Tyr Glu Glu Ile Glu
            420                 425                 430

Asn Pro Lys Leu Trp Glu Asn Val Leu Asp Glu Asn Phe Ile Thr Asp
        435                 440                 445

Glu Glu Ile Trp Ser Ile Arg Tyr Glu Leu Arg Arg Ser Leu Ile Glu
    450                 455                 460

Phe Val Arg Glu Lys Ile Leu Asn Leu Leu Phe Lys Ser Gly Leu Asp
465                 470                 475                 480

Ser Lys Val Asn Ile Asn Ser Ile Leu Ser Pro Asp Ala Leu Thr Ile
                485                 490                 495

Gly Phe Ser Arg Arg Phe Ala Thr Tyr Lys Arg Ala Pro Leu Ile Phe
            500                 505                 510

Tyr Asp Leu Glu Arg Ala Lys Lys Ile Phe Asn Asp Arg Ser Lys Pro
        515                 520                 525

Val Gln Ile Ile Phe Ser Gly Lys Ala His Pro Arg Asp Asp Ala Gly
    530                 535                 540

Lys Glu Phe Leu Gln Arg Ile Val Gln Ile Ser Lys Met Pro Glu Phe
545                 550                 555                 560

Tyr Gly Lys Val Ile Phe Ile Glu Asn Tyr Asp Met Asn Ile Ala Arg
                565                 570                 575

His Leu Ile Ser Gly Cys Asp Leu Trp Leu Asn Asn Pro Arg Arg Pro
            580                 585                 590

Leu Glu Ala Ser Gly Thr Ser Gly Gln Lys Ile Val Leu Asn Phe Gly
        595                 600                 605

Leu Asn Phe Ser Ile Leu Asp Gly Trp Trp Arg Glu Ala Tyr Asn Gly
    610                 615                 620

Glu Asn Gly Trp Ala Ile Gly Lys Asp Glu Ser Val Glu Asp Pro Asn
625                 630                 635                 640

Ile Gln Asp Lys Leu Asp Ala Glu Phe Leu Tyr Gln Thr Leu Glu Asn
                645                 650                 655

Glu Ile Ile Pro Ala Phe Tyr Asn Arg Asn Glu Asn Gly Ile Pro Lys
            660                 665                 670

Glu Trp Ile Lys Arg Ile Arg Lys Ser Ile Ala Thr Val Thr Tyr Phe
        675                 680                 685

Phe Asn Thr Asn Arg Met Val Arg Glu Tyr Val Lys Lys Tyr Tyr Arg
    690                 695                 700

Lys Ser Glu Asn
705


<210> SEQ ID NO 49
<211> LENGTH: 2118
<212> TYPE: DNA
```

<213> ORGANISM: Artificial sequence
<220> FEATURE:
<223> OTHER INFORMATION: Metagenomic (composite) sequence for GP-044.

<400> SEQUENCE: 49

```
gtggagaaat acaagaccaa gaacaacatc tttccccata ttccggaacg catttcccgc     60
ttgggagaac tggcggaaaa cctgtggtgg agctggaacc cccaagcccg catgctattc    120
aagatgctgg acaggcaggc ctggaaggag agcggtcaca atccggacgc aatgctcaag    180
aagctgcccc agcatctgct ccaggaagcc gcccaggacc ggaactacct gcgccactat    240
gatctggtca tgtcccagtt cgaccaacag gccaaccacg acaacgtgga ggacagatcg    300
ccagtggcct atttcagcgc cgaatacggc ctgcatcact ccctgccctt ctttgccggg    360
ggattgggtc ttctggccgg ggatcacctc aaggaatgca gcgacatgcg actgcccctg    420
gtggcagtgg gtttcatgta tccctccgga tacctgaagc agaccatcaa taaggacggt    480
tggcaggaaa gcgtcaccca gaccgtggac cgcgaatccg cttccatcaa tcaaatcttc    540
gataccagcg gcgaacggat cataatcgaa atcccccatc tggagccccg cattcgggca    600
gcggtgtgga aggtcgcggt aggcagggta agcctcttcc taatcgatac ggaaatcgag    660
gaaaacccgg agtggatcca gcatatcgcc cgtcagctct ataccagcga ccaggagcat    720
cgcctcctgc aggaagcggt gctgggcctg ggaggataca ccttgctgcg caggctgggg    780
atcgatccct atatgataca cctcaacgag ggacaccccg cttttgccct cctggaagcc    840
atgcgggacc tgatgcagca gggaaggagc tttgaccagg ccaaaaaaga aatacgggaa    900
aagagcctgt tcactaccca cactccggtt ccggccgggc acgatgtttt cccggcggag    960
ctgatggaca agtatttccc ttcctattgg caggccctgg gtttggacag ggaatccttt   1020
ctggaactgg gtaagcatcc ggagaaaccg gaatccggat ttaacatgac cgtgctggcc   1080
atgcgcctta ccgggcagtg caatgcggta agccgacgac acggagaggt gaccaggcag   1140
atgtggcaag gcctctggcc ggataagcaa gcggaggata tccccataga ccacgtcacc   1200
aatggagtgc acctgcccac ttggctggac cccaagatcc ggctcctgta caaccagcac   1260
tttgacgagg gctggatcat ggagcacgac aatcccgcta tctgggagtt catagaggaa   1320
ataccggacg agaagctctg gcagacccat tatctgctca aggtaaaact cctgaaccac   1380
attcgacagc tcgcccgaga gaactggagg cagcggcaaa ccccggatct tattcccgca   1440
ctggggacca tgctcgagcc ctccatcctg accatcggct tcgggaggcg ttttgccacc   1500
tacaaaaggg cggatctcat attgcaggac ccggagcgcc tgaaacagct ggtgaacgat   1560
tcctggcgcc ccattcagat catatttgcc ggcaaggccc atcccgcgga ccacgagggg   1620
caacgcttga tgcagcgggt gatccacttt gcccaggatc cggagttcag cggcaggata   1680
gcctttgtgg aaaacttcaa cgaacagctt gcccagtaca tggtccacgg agtggacgtg   1740
tggctgaaca ctccccagcc tcccatggaa gcgagcggaa ctagcggaat gaaggcctcg   1800
atcaacggag tgcccaacct gagcattccc gacggttggt ggctggaggg agcctccccg   1860
ggcaacggct ggaccattcc cctccaccaa gatgccgaac caggagagca ggactggttg   1920
gaggcccggg aactctacca cttaatcgag gaaaggctaa tccccaaata ctattccagc   1980
tcggagacag gagtgcccca cgagtgggtg cgcatcatga aggaggccat caagacagtg   2040
gcccccccact tctccgctcg ccgcatggtc aaggaatacc agcaaaagca ctatcaaaag   2100
caaagccggc acgaataa                                                 2118
```

<210> SEQ ID NO 50
<211> LENGTH: 705
<212> TYPE: PRT
<213> ORGANISM: Artificial sequence
<220> FEATURE:
<223> OTHER INFORMATION: Metagenomic (composite) sequence for GP-044.

<400> SEQUENCE: 50

```
Met Glu Lys Tyr Lys Thr Lys Asn Asn Ile Phe Pro His Ile Pro Glu
1               5                   10                  15

Arg Ile Ser Arg Leu Gly Glu Leu Ala Glu Asn Leu Trp Trp Ser Trp
            20                  25                  30

Asn Pro Gln Ala Arg Met Leu Phe Lys Met Leu Asp Arg Gln Ala Trp
        35                  40                  45

Lys Glu Ser Gly His Asn Pro Asp Ala Met Leu Lys Lys Leu Pro Gln
    50                  55                  60

His Leu Leu Gln Glu Ala Ala Gln Asp Arg Asn Tyr Leu Arg His Tyr
65                  70                  75                  80

Asp Leu Val Met Ser Gln Phe Asp Gln Gln Ala Asn His Asp Asn Val
                85                  90                  95

Glu Asp Arg Ser Pro Val Ala Tyr Phe Ser Ala Glu Tyr Gly Leu His
            100                 105                 110

His Ser Leu Pro Phe Phe Ala Gly Gly Leu Gly Leu Leu Ala Gly Asp
        115                 120                 125

His Leu Lys Glu Cys Ser Asp Met Arg Leu Pro Leu Val Ala Val Gly
    130                 135                 140

Phe Met Tyr Pro Ser Gly Tyr Leu Lys Gln Thr Ile Asn Lys Asp Gly
145                 150                 155                 160

Trp Gln Glu Ser Val Thr Gln Thr Val Asp Arg Glu Ser Ala Ser Ile
                165                 170                 175

Asn Gln Ile Phe Asp Thr Ser Gly Glu Arg Ile Ile Ile Glu Ile Pro
            180                 185                 190

His Leu Glu Pro Arg Ile Arg Ala Ala Val Trp Lys Val Ala Val Gly
        195                 200                 205

Arg Val Ser Leu Phe Leu Ile Asp Thr Glu Ile Glu Glu Asn Pro Glu
    210                 215                 220

Trp Ile Gln His Ile Ala Arg Gln Leu Tyr Thr Ser Asp Gln Glu His
225                 230                 235                 240

Arg Leu Leu Gln Glu Ala Val Leu Gly Leu Gly Gly Tyr Thr Leu Leu
                245                 250                 255

Arg Arg Leu Gly Ile Asp Pro Tyr Met Ile His Leu Asn Glu Gly His
            260                 265                 270

Pro Ala Phe Ala Leu Leu Glu Ala Met Arg Asp Leu Met Gln Gln Gly
        275                 280                 285

Arg Ser Phe Asp Gln Ala Lys Lys Glu Ile Arg Glu Lys Ser Leu Phe
    290                 295                 300

Thr Thr His Thr Pro Val Pro Ala Gly His Asp Val Phe Pro Ala Glu
305                 310                 315                 320

Leu Met Asp Lys Tyr Phe Pro Ser Tyr Trp Gln Ala Leu Gly Leu Asp
                325                 330                 335

Arg Glu Ser Phe Leu Glu Leu Gly Lys His Pro Glu Lys Pro Glu Ser
            340                 345                 350

Gly Phe Asn Met Thr Val Leu Ala Met Arg Leu Thr Gly Gln Cys Asn
        355                 360                 365

Ala Val Ser Arg Arg His Gly Glu Val Thr Arg Gln Met Trp Gln Gly
```

```
    370                 375                 380

Leu Trp Pro Asp Lys Gln Ala Glu Asp Ile Pro Ile Asp His Val Thr
385                 390                 395                 400

Asn Gly Val His Leu Pro Thr Trp Leu Asp Pro Lys Ile Arg Leu Leu
                405                 410                 415

Tyr Asn Gln His Phe Asp Glu Gly Trp Ile Met Glu His Asp Asn Pro
            420                 425                 430

Ala Ile Trp Glu Phe Ile Glu Glu Ile Pro Asp Glu Lys Leu Trp Gln
        435                 440                 445

Thr His Tyr Leu Leu Lys Val Lys Leu Leu Asn His Ile Arg Gln Leu
    450                 455                 460

Ala Arg Glu Asn Trp Arg Gln Arg Gln Thr Pro Asp Leu Ile Pro Ala
465                 470                 475                 480

Leu Gly Thr Met Leu Glu Pro Ser Ile Leu Thr Ile Gly Phe Gly Arg
                485                 490                 495

Arg Phe Ala Thr Tyr Lys Arg Ala Asp Leu Ile Leu Gln Asp Pro Glu
            500                 505                 510

Arg Leu Lys Gln Leu Val Asn Asp Ser Trp Arg Pro Ile Gln Ile Ile
        515                 520                 525

Phe Ala Gly Lys Ala His Pro Ala Asp His Glu Gly Gln Arg Leu Met
    530                 535                 540

Gln Arg Val Ile His Phe Ala Gln Asp Pro Glu Phe Ser Gly Arg Ile
545                 550                 555                 560

Ala Phe Val Glu Asn Phe Asn Glu Gln Leu Ala Gln Tyr Met Val His
                565                 570                 575

Gly Val Asp Val Trp Leu Asn Thr Pro Gln Pro Pro Met Glu Ala Ser
            580                 585                 590

Gly Thr Ser Gly Met Lys Ala Ser Ile Asn Gly Val Pro Asn Leu Ser
        595                 600                 605

Ile Pro Asp Gly Trp Trp Leu Glu Gly Ala Ser Pro Gly Asn Gly Trp
    610                 615                 620

Thr Ile Pro Leu His Gln Asp Ala Glu Pro Gly Glu Gln Asp Trp Leu
625                 630                 635                 640

Glu Ala Arg Glu Leu Tyr His Leu Ile Glu Glu Arg Leu Ile Pro Lys
                645                 650                 655

Tyr Tyr Ser Ser Ser Glu Thr Gly Val Pro His Glu Trp Val Arg Ile
            660                 665                 670

Met Lys Glu Ala Ile Lys Thr Val Ala Pro His Phe Ser Ala Arg Arg
        675                 680                 685

Met Val Lys Glu Tyr Gln Gln Lys His Tyr Gln Lys Gln Ser Arg His
    690                 695                 700

Glu
705


<210> SEQ ID NO 51
<211> LENGTH: 2109
<212> TYPE: DNA
<213> ORGANISM: Streptomyces sp.

<400> SEQUENCE: 51

atggcctcgc acgcgcacct gcgcgacgac ctggaccgtc tcgcacgcaa cgtccgctgg      60

gcgtggacgc cgccagcacg tcgcgtgctc gaggagctcg atccggccgc ctggcgccgc     120

accggtggga acccggccgc catcctcagc gacctgaccg atgagcggct cgaagcggct     180
```

```
gccgcacagc ccgactacct ggggcgcgtg cacgacgcct ccgaggaact cgcccgctac    240

ctcgacgacg gggacacctg gtacgcacgc agtggaggcg accccgaccg gcgtgtggtc    300

tacctgtccg cggagtacgg gctgacggac tgcctgcgca tctactccgg cgggctcggc    360

gtgctcgccg gcgaccatct gcgctcggct tcggacctcg gcctgccgct gaccgcgatc    420

ggcctcgcgt accgcaacgg ctacttccgc cagcacctcg acggctcggg ctggcagatc    480

gccgaggtgg cgtccaacga cttcgagcgg tcgccggcga ccctcgtgct cgacgatgag    540

ggcgcaccgc tcgaggtgca cgtcgagatg gggacggcg aggtgacggt ccgggcgtgg    600

caggtccacg tcggacgtgt gccgctctac ctgctcgaca ccgacgttga gggcaacggc    660

gaccaccacc gggcgatcac cgggcagctg tacggcggag acagcgacac gcgcttgcgt    720

caggagctga tcctcggcgt cggcgggatg cgcctgctcg acgcgctggg cgtgcacgcg    780

gacgtcatcc acctgaacga gggccacgcg gcgttcgcga ccctggagtt gctgcgcggc    840

cacctcgacg ggagtgccgg tctcgacgac gccgtggccg aggtcagcga gcgcctcgtc    900

ttcacgaccc acaccccggt gcccgcaggg catgacgtgt tcgacggggg gctggcgtcg    960

tggcacctgg gtccgctcgc gcagcgcatc ggcgtcccgt tcgagcagct gtggcgcctg   1020

gcctgcgccg aaggcgacaa catctggtcg cagaccgtgc tggcgctgac gttcgcccgc   1080

cgcacgaacg gtgtcgcccg cctccatggc gaggtgtcgc gccggatgtg ggcgcgcctg   1140

tggccggacc gcgacgtcga tgacgtgccg atcacccaca tcaccaacgg cgtccacccg   1200

gcgatgtggg tgggcgagga cctcgcccgc atcctcgact ggtcgctggg gccagggtgg   1260

cggatggacg acgacgccga acgctgggag cgggtccgcg aggtggcgcc ggcggagctg   1320

tggcgggtcc acgacgacgc ccgctatcgg ctgatccgcg aggtgcgccg ccgcctgcgc   1380

gcgcagagcc gccgcttcgg catcgggccc gatggtgcag ggctcgaccc ggatgcgctg   1440

acgatcggct tcgctcggcg gttcgcgacc tacaagcgcg caacgctcct cgcccacgac   1500

ctggaccgtc tggcggccat cctcggctcc gacgaccggc cggtgcaggt cgtcgtcgcc   1560

ggcaaggcac acccgcagga tgaggggggc aagcacctga tccagcagct cgtcggtctc   1620

tcccgcgacc cgcagcttcg aggtcggttg gcgttcgtcg agggctacga cctcgaactc   1680

gcccacgcgc tcgtcaccgg cgtcgacgtg tggctgaaca acccgctgcg cccgatggag   1740

gcgtccggca cctcggggat gaaggccgcg atgaacgggg tgttgaacct ctccgtgctg   1800

gacggatggt gggacgaggc ggtggcggat ctgacaccgc tcgcacgtga aggcttcggt   1860

tgggccatcg gcgaccgcac cgagggcgac gaccgtggtg cccgtgacgc ggccgacgcg   1920

gcgagcttct acgaccttct cgagcagcgg gtcgtcccga ccttctacga gcgcggcgcc   1980

gacgatgtgc cgcagcgctg ggtcacgatg atgcaggacg cgatcgccat cctcgcgccc   2040

cgcttctcga cccatcggat ggtcgccgac tacgcatcgt cggtgtacgc gcactcgaag   2100

ggcgcgtag                                                           2109
```

<210> SEQ ID NO 52
<211> LENGTH: 702
<212> TYPE: PRT
<213> ORGANISM: Streptomyces sp.

<400> SEQUENCE: 52

```
Met Ala Ser His Ala His Leu Arg Asp Asp Leu Asp Arg Leu Ala Arg
1               5                   10                  15

Asn Val Arg Trp Ala Trp Thr Pro Pro Ala Arg Arg Val Leu Glu Glu
            20                  25                  30
```

```
Leu Asp Pro Ala Ala Trp Arg Arg Thr Gly Gly Asn Pro Ala Ala Ile
        35                  40                  45

Leu Ser Asp Leu Thr Asp Glu Arg Leu Glu Ala Ala Ala Ala Gln Pro
    50                  55                  60

Asp Tyr Leu Gly Arg Val His Asp Ala Ser Glu Glu Leu Ala Arg Tyr
65                  70                  75                  80

Leu Asp Asp Gly Asp Thr Trp Tyr Ala Arg Ser Gly Gly Asp Pro Asp
                85                  90                  95

Arg Arg Val Val Tyr Leu Ser Ala Glu Tyr Gly Leu Thr Asp Cys Leu
            100                 105                 110

Arg Ile Tyr Ser Gly Gly Leu Gly Val Leu Ala Gly Asp His Leu Arg
        115                 120                 125

Ser Ala Ser Asp Leu Gly Leu Pro Leu Thr Ala Ile Gly Leu Ala Tyr
    130                 135                 140

Arg Asn Gly Tyr Phe Arg Gln His Leu Asp Gly Ser Gly Trp Gln Ile
145                 150                 155                 160

Ala Glu Val Ala Ser Asn Asp Phe Glu Arg Ser Pro Ala Thr Leu Val
                165                 170                 175

Leu Asp Asp Glu Gly Ala Pro Leu Glu Val His Val Glu Met Gly Asp
            180                 185                 190

Gly Glu Val Thr Val Arg Ala Trp Gln Val His Val Gly Arg Val Pro
        195                 200                 205

Leu Tyr Leu Leu Asp Thr Asp Val Glu Gly Asn Gly Asp His His Arg
    210                 215                 220

Ala Ile Thr Gly Gln Leu Tyr Gly Gly Asp Ser Asp Thr Arg Leu Arg
225                 230                 235                 240

Gln Glu Leu Ile Leu Gly Val Gly Gly Met Arg Leu Leu Asp Ala Leu
                245                 250                 255

Gly Val His Ala Asp Val Ile His Leu Asn Glu Gly His Ala Ala Phe
            260                 265                 270

Ala Thr Leu Glu Leu Leu Arg Gly His Leu Asp Gly Ser Ala Gly Leu
        275                 280                 285

Asp Asp Ala Val Ala Glu Val Ser Glu Arg Leu Val Phe Thr Thr His
    290                 295                 300

Thr Pro Val Pro Ala Gly His Asp Val Phe Asp Gly Gly Leu Ala Ser
305                 310                 315                 320

Trp His Leu Gly Pro Leu Ala Gln Arg Ile Gly Val Pro Phe Glu Gln
                325                 330                 335

Leu Trp Arg Leu Ala Cys Ala Glu Gly Asp Asn Ile Trp Ser Gln Thr
            340                 345                 350

Val Leu Ala Leu Thr Phe Ala Arg Arg Thr Asn Gly Val Ala Arg Leu
        355                 360                 365

His Gly Glu Val Ser Arg Arg Met Trp Ala Arg Leu Trp Pro Asp Arg
    370                 375                 380

Asp Val Asp Asp Val Pro Ile Thr His Ile Thr Asn Gly Val His Pro
385                 390                 395                 400

Ala Met Trp Val Gly Glu Asp Leu Ala Arg Ile Leu Asp Trp Ser Leu
                405                 410                 415

Gly Pro Gly Trp Arg Met Asp Asp Asp Ala Glu Arg Trp Glu Arg Val
            420                 425                 430

Arg Glu Val Ala Pro Ala Glu Leu Trp Arg Val His Asp Asp Ala Arg
        435                 440                 445
```

```
Tyr Arg Leu Ile Arg Glu Val Arg Arg Arg Leu Arg Ala Gln Ser Arg
    450                 455                 460

Arg Phe Gly Ile Gly Pro Asp Gly Ala Gly Leu Asp Pro Asp Ala Leu
465                 470                 475                 480

Thr Ile Gly Phe Ala Arg Arg Phe Ala Thr Tyr Lys Arg Ala Thr Leu
                485                 490                 495

Leu Ala His Asp Leu Asp Arg Leu Ala Ala Ile Leu Gly Ser Asp Asp
            500                 505                 510

Arg Pro Val Gln Val Val Val Ala Gly Lys Ala His Pro Gln Asp Glu
        515                 520                 525

Gly Gly Lys His Leu Ile Gln Gln Leu Val Gly Leu Ser Arg Asp Pro
    530                 535                 540

Gln Leu Arg Gly Arg Leu Ala Phe Val Glu Gly Tyr Asp Leu Glu Leu
545                 550                 555                 560

Ala His Ala Leu Val Thr Gly Val Asp Val Trp Leu Asn Asn Pro Leu
                565                 570                 575

Arg Pro Met Glu Ala Ser Gly Thr Ser Gly Met Lys Ala Ala Met Asn
            580                 585                 590

Gly Val Leu Asn Leu Ser Val Leu Asp Gly Trp Trp Asp Glu Ala Val
        595                 600                 605

Ala Asp Leu Thr Pro Leu Ala Arg Glu Gly Phe Gly Trp Ala Ile Gly
    610                 615                 620

Asp Arg Thr Glu Gly Asp Asp Arg Gly Ala Arg Asp Ala Ala Asp Ala
625                 630                 635                 640

Ala Ser Phe Tyr Asp Leu Leu Glu Gln Arg Val Val Pro Thr Phe Tyr
                645                 650                 655

Glu Arg Gly Ala Asp Asp Val Pro Gln Arg Trp Val Thr Met Met Gln
            660                 665                 670

Asp Ala Ile Ala Ile Leu Ala Pro Arg Phe Ser Thr His Arg Met Val
        675                 680                 685

Ala Asp Tyr Ala Ser Ser Val Tyr Ala His Ser Lys Gly Ala
    690                 695                 700
```

<210> SEQ ID NO 53
<211> LENGTH: 2073
<212> TYPE: DNA
<213> ORGANISM: Artificial sequence
<220> FEATURE:
<223> OTHER INFORMATION: Metagenomic (composite) sequence for GP-048.

<400> SEQUENCE: 53

```
atgacaagcc gtgacaaact ggaggccatt gccgctaacc tgtggtggag ctggaatcca     60

gaagctttag cactttttga gcagcttaac cctgaagctt ttcgagcctc gcagcacaat    120

ccgctggcgg cgctacgcac cgccgaccca gccttgctca cagatcgacc ttttatcaaa    180

gccgtcgata aagtttacga ggcctttaca gcctatctga atgctcctcc ccgcattaca    240

gatgcccccc gaacggccta cttttgcatg gagtatgggc tgcacgaaag cttgcccttc    300

tatgcgggcg gcctaggtgt gctggcggga gatcacatca aagcggcctc agacctgggc    360

cttccgatga cggctgtggg tctgtttctg cgcgagggtt acttccgcca gcgctttgag    420

cctaacggct ggcagattgc ggaatatcca gccatggacc ctgccgacca tccgatgacg    480

ctggtgcacg gccccgacgg ctatccgtta gtgatcacgg tgcatctagg ccggcaaccc    540

ttttatctgc gtgcttggaa actcgacgta ggccgcgtgc ccctttactt actcgatgga    600

gccttcgatg cgaatccaga gcccctgcgt agcctaacgc gccgccttta ccaaggcgat    660
```

```
cggcgcttgc gactgcagca ggaaatcatc ctgggcattg gggtgtgcg gcttttgcgt    720

gctttagatc tagatttcga gacgtaccat ctgaatgaag gacactgtgc ctttgttgcc    780

ctagagctgc tgcgtgagcg cttggcagct ggcgaagcgc gcgaagccgc cgaagcttgg    840

gtccgtgatc actgcgtctt taccacgcat acaccggtca tggcaggcca tgaccgcttt    900

agcccggaac tgttcttaga acaaatggaa acgttccggc accagcttgg gctttcagag    960

accgaactgc tggcctacgg ccgtgtcaat ccaaacgaca gcaccgaggc ctttacgatg   1020

acagtgctgg gcctaaagct ttcgcgcaaa accaatggcg tgtcggctat caacagtgtg   1080

gtggctcgcc ggcaatggca ccatttgtac ccagatcgcc ctttgaacga agtacctatt   1140

ggctacatta ccaatggcgt gcatttgccg acctggaccg ttgcgcacgc acgcccgttc   1200

ttagcacagc atctaggcga ctggctcgaa ggtcgcttta acccagatct ttggcgcaaa   1260

atcgactcca tctccgacgc ggaactatgg cagtaccgct gcatgctgcg ccgacggctg   1320

gtggagtttg tcaacgaata cgtcaaacac caatcgctcc cccaagaagc gcacctcagc   1380

cctgaggtac taaccatcgg ctttgcccgc cgctttgcca cctacaagcg tgccccctt    1440

ttgtttgagg acatggagcg agcgattcag cttttctccc gacaagaccg tcccattcag   1500

ctgatttacg cgggcaaggc gcatcctgca gacgacggtg gcaaacggtt cattcagcag   1560

atttatgaga tcacgcagca cccagcgttc cggggtaaag tcgtctttgt agaagactac   1620

gacatgcaca ttgcgcgcat gttggtttca ggatgtgacg tttggctaaa caatcctcgg   1680

cgaccgcttg aggctagcgg aaccagcggc cagaaaacag ccatacatgg gggactaaac   1740

ctgtcggtgt ttgacggctg gtggcctgaa ggctataacg gacaaaacgg ctgggctttt   1800

ggtcgcgagg ccacgggact ctacgaagat ccgatcacgc aggatgtcga agatcgcgaa   1860

gccctctatc gcgtgctcga atacgaggtg atcccagctt tttacgatcg caacggcgaa   1920

ggactaccgt tgcgatggct aacgcgcatg cgccaagcca tgcgcaccat tcctgcacag   1980

tttaacgcgg tacgtatggt gcgggagtac gtggagcaaa tgtaccgacc tgccgcaatg   2040

ccagcaaccg taaccgcagc tgctgctcaa tag                                2073
```

<210> SEQ ID NO 54
<211> LENGTH: 690
<212> TYPE: PRT
<213> ORGANISM: Artificial sequence
<220> FEATURE:
<223> OTHER INFORMATION: Metagenomic (composite) sequence for GP-048.

<400> SEQUENCE: 54

```
Met Thr Ser Arg Asp Lys Leu Glu Ala Ile Ala Ala Asn Leu Trp Trp
1               5                   10                  15

Ser Trp Asn Pro Glu Ala Leu Ala Leu Phe Glu Gln Leu Asn Pro Glu
            20                  25                  30

Ala Phe Arg Ala Ser Gln His Asn Pro Leu Ala Ala Leu Arg Thr Ala
        35                  40                  45

Asp Pro Ala Leu Leu Thr Asp Arg Pro Phe Ile Lys Ala Val Asp Lys
    50                  55                  60

Val Tyr Glu Ala Phe Thr Ala Tyr Leu Asn Ala Pro Pro Arg Ile Thr
65                  70                  75                  80

Asp Ala Pro Arg Thr Ala Tyr Phe Cys Met Glu Tyr Gly Leu His Glu
                85                  90                  95

Ser Leu Pro Phe Tyr Ala Gly Gly Leu Gly Val Leu Ala Gly Asp His
            100                 105                 110
```

```
Ile Lys Ala Ala Ser Asp Leu Gly Leu Pro Met Thr Ala Val Gly Leu
        115                 120                 125

Phe Leu Arg Glu Gly Tyr Phe Arg Gln Arg Phe Glu Pro Asn Gly Trp
    130                 135                 140

Gln Ile Ala Glu Tyr Pro Ala Met Asp Pro Ala Asp His Pro Met Thr
145                 150                 155                 160

Leu Val His Gly Pro Asp Gly Tyr Pro Leu Val Ile Thr Val His Leu
                165                 170                 175

Gly Arg Gln Pro Phe Tyr Leu Arg Ala Trp Lys Leu Asp Val Gly Arg
            180                 185                 190

Val Pro Leu Tyr Leu Leu Asp Gly Ala Phe Asp Ala Asn Pro Glu Pro
        195                 200                 205

Leu Arg Ser Leu Thr Arg Arg Leu Tyr Gln Gly Asp Arg Arg Leu Arg
    210                 215                 220

Leu Gln Gln Glu Ile Ile Leu Gly Ile Gly Gly Val Arg Leu Leu Arg
225                 230                 235                 240

Ala Leu Asp Leu Asp Phe Glu Thr Tyr His Leu Asn Glu Gly His Cys
                245                 250                 255

Ala Phe Val Ala Leu Glu Leu Leu Arg Glu Arg Leu Ala Ala Gly Glu
            260                 265                 270

Ala Arg Glu Ala Ala Glu Ala Trp Val Arg Asp His Cys Val Phe Thr
        275                 280                 285

Thr His Thr Pro Val Met Ala Gly His Asp Arg Phe Ser Pro Glu Leu
    290                 295                 300

Phe Leu Glu Gln Met Glu Thr Phe Arg His Gln Leu Gly Leu Ser Glu
305                 310                 315                 320

Thr Glu Leu Leu Ala Tyr Gly Arg Val Asn Pro Asn Asp Ser Thr Glu
                325                 330                 335

Ala Phe Thr Met Thr Val Leu Gly Leu Lys Leu Ser Arg Lys Thr Asn
            340                 345                 350

Gly Val Ser Ala Ile Asn Ser Val Val Ala Arg Arg Gln Trp His His
        355                 360                 365

Leu Tyr Pro Asp Arg Pro Leu Asn Glu Val Pro Ile Gly Tyr Ile Thr
    370                 375                 380

Asn Gly Val His Leu Pro Thr Trp Thr Val Ala His Ala Arg Pro Phe
385                 390                 395                 400

Leu Ala Gln His Leu Gly Asp Trp Leu Glu Gly Arg Phe Asn Pro Asp
                405                 410                 415

Leu Trp Arg Lys Ile Asp Ser Ile Ser Asp Ala Glu Leu Trp Gln Tyr
            420                 425                 430

Arg Cys Met Leu Arg Arg Arg Leu Val Glu Phe Val Asn Glu Tyr Val
        435                 440                 445

Lys His Gln Ser Leu Pro Gln Glu Ala His Leu Ser Pro Glu Val Leu
    450                 455                 460

Thr Ile Gly Phe Ala Arg Arg Phe Ala Thr Tyr Lys Arg Ala Pro Leu
465                 470                 475                 480

Leu Phe Glu Asp Met Glu Arg Ala Ile Gln Leu Phe Ser Arg Gln Asp
                485                 490                 495

Arg Pro Ile Gln Leu Ile Tyr Ala Gly Lys Ala His Pro Ala Asp Asp
            500                 505                 510

Gly Gly Lys Arg Phe Ile Gln Gln Ile Tyr Glu Ile Thr Gln His Pro
        515                 520                 525
```

```
Ala Phe Arg Gly Lys Val Val Phe Val Glu Asp Tyr Asp Met His Ile
    530                 535                 540

Ala Arg Met Leu Val Ser Gly Cys Asp Val Trp Leu Asn Asn Pro Arg
545                 550                 555                 560

Arg Pro Leu Glu Ala Ser Gly Thr Ser Gly Gln Lys Thr Ala Ile His
                565                 570                 575

Gly Gly Leu Asn Leu Ser Val Phe Asp Gly Trp Trp Pro Glu Gly Tyr
            580                 585                 590

Asn Gly Gln Asn Gly Trp Ala Phe Gly Arg Glu Ala Thr Gly Leu Tyr
        595                 600                 605

Glu Asp Pro Ile Thr Gln Asp Val Glu Asp Arg Glu Ala Leu Tyr Arg
    610                 615                 620

Val Leu Glu Tyr Glu Val Ile Pro Ala Phe Tyr Asp Arg Asn Gly Glu
625                 630                 635                 640

Gly Leu Pro Leu Arg Trp Leu Thr Arg Met Arg Gln Ala Met Arg Thr
                645                 650                 655

Ile Pro Ala Gln Phe Asn Ala Val Arg Met Val Arg Glu Tyr Val Glu
            660                 665                 670

Gln Met Tyr Arg Pro Ala Ala Met Pro Ala Thr Val Thr Ala Ala Ala
        675                 680                 685

Ala Gln
    690
```

<210> SEQ ID NO 55
<211> LENGTH: 1473
<212> TYPE: DNA
<213> ORGANISM: Artificial sequence
<220> FEATURE:
<223> OTHER INFORMATION: Codon-optimized sequence encoding version of Sp14.

<400> SEQUENCE: 55

```
gtggctgaaa ttcagaataa agccatgctg atcacgtatg cagatagcct gggcaaaaat     60

ctgaaagatg ttcatcaagt cctgaaagaa gatattggcg acgcaattgg cggagttcat    120

ctgctgccgt tttttccgtc aacaggcgat agaggctttg caccggcaga ttatacaaga    180

gttgatgcag catttggcga ttgggcagat gttgaagcac tgggcgaaga atattatctg    240

atgtttgact tcatgattaa ccatatcagc cgtgaaagcg tcatgtacca ggatttcaaa    300

aaaaaccatg acgatagcaa atacaaagac ttctttatcc gctgggaaaa gttttgggcg    360

aaagcaggcg aaaatagacc gacacaagca gatgtcgatc tgatctataa acgcaaagat    420

aaagcaccga cgcaagaaat cacatttgat gatggcacaa cagaaaacct gtggaacaca    480

tttggagaag aacaaattga tatcgatgtg aatagcgcga ttgcgaaaga atttatcaaa    540

acgacactgg aagatatggt gaaacatggc gcaaatctga ttagactgga tgcatttgca    600

tacgcggtta aaaaagtcga tacgaacgat ttttttgtcg agccggaaat ttgggataca    660

ctgaatgaag ttcgcgaaat tctgacaccg ctgaaagcag aaattcttcc ggaaatccat    720

gaacattata gcattccgaa aaagatcaac gaccatggct attttacgta tgattttgca    780

ctgccgatga cgacacttta tacactgtat tcaggcaaaa caaaccaact ggcaaaatgg    840

ctgaaaatgt caccgatgaa acagtttaca acactggata cacatgatgg aattggcgtt    900

gttgatgcga gagatattct tacggatgac gaaattgatt atgcgagcga acaactgtac    960

aaagttggag cgaatgtgaa aaaaacatat agcagcgcga gctataacaa cctggacatt   1020

tatcagatca acagcacgta ttatagcgct ctgggcaatg atgatgcggc atatctgctg   1080
```

```
tcaagagtct ttcaagtgtt tgctccggga attccgcaga tctattatgt tggcctgctg   1140

gctggcgaaa acgatattgc acttctggaa tcaacaaaag aaggacgcaa tattaaccgc   1200

cattattaca cacgcgaaga agttaaaagc gaggttaaaa gaccggttgt tgcgaatctg   1260

cttaaactgc tgtcttggag aaatgaatca ccggcatttg atctggcagg ctcaattaca   1320

gttgatacac cgacagatac aacaattgtc gtcacaagac aagatgaaaa cggccaaaat   1380

aaagcggttc tgacagcgga tgcagcgaat aaaacatttg aaattgtcga aaatggccag   1440

acagttatgt caagcgataa tctgacacag aac                                1473
```

```
<210> SEQ ID NO 56
<211> LENGTH: 1515
<212> TYPE: DNA
<213> ORGANISM: Artificial sequence
<220> FEATURE:
<223> OTHER INFORMATION: Codon-optimized sequence encoding version of
      Sp15.

<400> SEQUENCE: 56

gtggctaaaa acaaagtcca gctgattacg tatgcagata gactgggaga tggcacaatt     60

aaaagcatga cagatattct gcgcacaaga tttgatggcg tttatgacgg cgttcatatc    120

ctgccgtttt ttacaccgtt tgatggtgca gatgcaggct ttgatccgat tgatcataca    180

aaagttgatg aaagactggg ctcatgggat gatgttgcag aactgtcaaa aacgcataac    240

attatggttg atgcgatcgt gaatcacatg agctgggaaa gcaaacaatt tcaagatgtt    300

ctggcaaaag gcgaagaaag cgaatactat ccgatgtttc tgacaatgtc aagcgttttt    360

ccgaatggcg caacagaaga agatctggca ggcatttata gaccgcgtcc gggacttccg    420

tttacacatt acaaatttgc aggcaaaaca agactggttt gggtttcatt tacacctcaa    480

caggtcgata ttgatacgga ttcagataaa ggctgggaat acctgatgag catttttgat    540

cagatggcag catcacatgt tagctatatt agactggatg cagttggcta tggcgctaaa    600

gaagctggca caagctgctt tatgacaccg aaaacattta aactgatttc acgcctgaga    660

gaagaaggcg ttaaaagagg cctggaaatt ctgattgaag tccacagcta ttacaaaaag    720

caagtcgaaa ttgcgtcaaa agtcgatcgc gtctatgatt ttgcactgcc tccgctgctg    780

cttcatgcac tgtcaacagg acatgttgaa ccggttgcac attggacaga cattagaccg    840

aataatgcag ttacagtcct ggatacacat gatggcattg gcgttattga tattggctca    900

gatcaactgg atagatcact gaaaggcctg gttccggatg aagatgttga taatctggtc    960

aatacaatcc atgcaaacac acatggcgaa tcacaagcag caacaggcgc agcagcaagc   1020

aatctggatc tttatcaagt caacagcacg tattattcag cactgggctg caatgatcaa   1080

cattatattg cagcaagagc ggtccaattt tttctgcctg gcgttccgca agtttattat   1140

gttggcgcac ttgcgggaaa aaatgatatg gaactgctgc ggaaaacaaa taatggacgc   1200

gatattaacc gccattacta tagcacagca gaaatcgatg aaaacctgaa aagaccggtt   1260

gttaaagcac tgaatgcact ggcgaaattt agaaatgaac tggacgcttt tgatgggaca   1320

ttttcatata caacggatga tgatacgagc atcagcttta catggcgtgg cgaaacaagc   1380

caagcaacac tgacgtttga accgaaaaga ggacttggcg tcgataatac aacaccggtc   1440

gcaatgctgg aatgggaaga ttcagcaggc gatcatcgtt cagatgatct tattgcaaat   1500

ccgcctgtcg ttgcg                                                    1515
```

<210> SEQ ID NO 57
<211> LENGTH: 1527
<212> TYPE: DNA
<213> ORGANISM: Artificial sequence
<220> FEATURE:
<223> OTHER INFORMATION: Codon-optimized sequence encoding version of Sp16.

<400> SEQUENCE: 57

```
gtggctaaaa acaaagtcca gctgattacg tatgcagata gactgggaga tggcacactg     60

tcatcaatga cagatattct gagaacaaga tttgacggcg tttatgatgg cgttcatatt    120

ctgccgtttt ttacaccgtt tgatggcgca gatgcaggct ttgatccgat tgatcataca    180

aaagttgatg aaagactggg ctcatgggat gatgttgcag aactgtcaaa aacgcataac    240

attatggttg atgcgatcgt gaatcacatg agctgggaaa gcaaacaatt tcaggatgtt    300

ctggaaaaag gcgaagaaag cgaatactat ccgatgtttc tgacaatgtc aagcgttttt    360

ccgaatggcg caacagaaga agatctggca ggcatttata gaccgcgtcc gggacttccg    420

tttacacatt acaaatttgc aggcaaaaca agactggttt gggtttcatt tacacctcaa    480

caggtcgata ttgatacaga ttcagatgaa ggctgggaat acctgatgag catttttgat    540

cagatggcag catcacatgt tagctatatt agactggatg cagttggcta tggcgctaaa    600

gaagcatcaa caagctgctt tatgacaccg aaaacgttta aactgattag cagactgaga    660

gaagaaggcg ttaaaagagg cctggaaatt ctgattgaag tccacagcta ttacaaaaag    720

caagtcgaaa ttgcgtcaaa agtcgatcgc gtctatgatt ttgcactgcc tccgctgctg    780

ctgcattcac tgtttacagg ccatgttgaa ccggttgttc attggacaga aattcgtccg    840

aataatgcag ttacagtcct ggatacacat gatggcattg gcgttattga tattggctca    900

gatcaactgg atagatcact gaaaggcctg gttccggatg aagatgttga taatctggtc    960

aatacaatcc atgcaaacac acatggcgaa tcacaagcag caacaggcgc agcggcatca   1020

aatctggatc tttatcaggt taacagcacg tattattcag cactgggctg caatgatcaa   1080

cattatcttg cagcgagagc ggtccaattt tttctgcctg gcgttccgca agtttattat   1140

gttggcgcac tggctggcag aaatgatatg gaactgctga gaagaacaaa caatggacgc   1200

gatattaacc gccattatta ctcaacagcg gaaatcgatg aaaacctgga aagaccggtc   1260

gttaaagcac tgaatgcact ggcaaaattt cgcaatgaac ttccggcatt tgatggggaa   1320

tttagctatg aagtcgatgg cgatacatca attacattta gatggacagc ggcagatgga   1380

acatcaacag cagcactgac atttgaacct ggcagaggcc ttggcacaga taatacaaca   1440

ccggttgcat cactggcatg gtcagatgcg gcaggcgatc atgaaacgca tgatctgctg   1500

gcaaatccgc ctattgcaga tattgac                                       1527
```

<210> SEQ ID NO 58
<211> LENGTH: 1443
<212> TYPE: DNA
<213> ORGANISM: Artificial sequence
<220> FEATURE:
<223> OTHER INFORMATION: Codon-optimized sequence encoding version of Sp17.

<400> SEQUENCE: 58

```
gtggctccga ttaaaaacaa agtcatgctg atcacatatc cggattcact gggcaaaaat     60

ctgcaagaac tgagcgaagt tctggaaaat gatctgaaag gcgcagttgg cggaattcat    120

ctgctgccgt tttttccgtc aacaggcgat agaggctttg caccgacaga ttatacaaca    180
```

```
gttgatccga aatttggcaa ctggtcagat gttgaaaaac tgggcgaaaa gtactacctg    240

atgtttgact ttatgattaa ccacatctca cgccatagca aatactatga ggacttccag    300

aaaaacaagg acaaaagcag ctatgcggac atgtttctgt catgggacaa attttggccg    360

aaaggcagac cgacaaaaga agatgtcgat ctgatctata aacgcaaaga tagagcaccg    420

tatcaagaaa tcacatttgc agatggcagc aaagaaaaac tctggaatac atttggaccg    480

gaacaaattg atctggacgt cagaaaaaaa gtcacgcaga aatttatcaa ggacacactg    540

gtgtctctga ttaaacatgg cgcagatatt attcgcctgg atgcatttgc gtatgcagtc    600

aaaaaacttg acacgaacga tttttttgtc gagccggaaa tctggaatct gctgaaacaa    660

gttcaagatg atattgcgga tgaaggcgca acaattcttc cggaaattca tgaacattat    720

agcatgccgt tcaaaatcag caaacacggc tattttatct acgattttgc actgccgatg    780

gtcacactgt attcacttta ttcaggcaaa agcaatagac tggcagcatg gctgaaaaaa    840

tgcccgatga aacaatttac aacgctggat acacatgatg gcattggcgt tgttgatgca    900

agagatattc tgagccctga agaaattgat tacacgagcc aagagctgta taaagttggc    960

gcaaatgtca aaaagaaata cagcagcgct gaataccata acctggatat ttatcagatc   1020

aacacgacgt tttatagcgc actgggagat gatgataaac gctactttat ggcaagactg   1080

ctgcaagtgt ttgcacctgg cattccgcaa gtttattatg ttggcatgct tgctggcaaa   1140

aacgatatta aactgctgga agaaacgaaa gaaggccgta acattaatcg ccattattac   1200

agcaaagcgg aagtcgaaca agaaattcaa agaccggttg ttgcatcact gcttaaactg   1260

tttacatttc gcaataacga accggcattt gatcttaacg gctcaattga tattagcacg   1320

ccgaacgaaa atgaaattcg cattgttcgc attaacaaag aacagaacca taaagcagaa   1380

ctgacagcga atcttcagga tctgacatat agagttctgg tcaacggcaa acaaattaac   1440

ttc                                                                 1443
```

<210> SEQ ID NO 59
<211> LENGTH: 1497
<212> TYPE: DNA
<213> ORGANISM: Artificial sequence
<220> FEATURE:
<223> OTHER INFORMATION: Codon-optimized sequence encoding Sp157.

<400> SEQUENCE: 59

```
gtgcagaatc aggtgcagct gatcacctat gtagatcgtt tggcgggcga cctgccggcc     60

ctgactcgcc tgctggaggg cccgctcgac ggcatcttcg gcggtgtcca cctgctcccg    120

ttcttcgacc cgatcgacgg cgccgacgcg ggcttcgacc cggtcgacca caccaccgtc    180

gacgcgcgcc tggggacctg ggacgacgtc gaggccctgg gcgcccgcgt gccggttatg    240

gccgacctca tcgtgaacca cgtgagcgcg tcctcgccgc agttcctgga ctggctggag    300

catggctcgg gctcggagta cgacggcatg ttcttaagcc tggacgcggt gttccccgac    360

ggcgccaccg aggaactggt cacggccgtg taccgccccc gccccggcct gcccctgacc    420

ccggtccagc tggctgacgg caccaagcgt ttaatgtgga ccaccttcac gccgcagcaa    480

atcgacatcg acgtcaccca cccgaccggc cgcgactacc tggagggcat cctggacacc    540

ttcgccgagc ggggcatcac cagcgtgcgt ctggacgccg tgggctacgc catcaagacc    600

gccggcacca gctgctttat gaccccggag accttcgcct tcatcgacga cctggccgcc    660

tcggcccacc gccgcgatat caccatcctg gtggaaatcc acagctactg gcgcacgcag    720

gtggaaatcg ccagtcgtgt ggactgggtg tacgacttcg ccctgccgcc gctggtcctg    780
```

```
cacgccctgt acagcgggga cgccagcccg ctgcgccgtt ggtgcgaagt ccgcccgcac    840

aacgcggtga atgtgctgga cacccacgac ggcatcgggg tgatcgacgt gggccccggc    900

ggctccgacc cgaacaagcc cggcctgctg gaccccggcc agctcgacgc cctggtcgag    960

ggcatccacg aggccagcgg cggcagctcg cgcgcggcca ccggctccgc cgcgagcaac   1020

ctggacctct accaggtgaa ctgcacctac ctggacgcct gcgggcggga cgaggccgcg   1080

tacctgatcg cccggctgct gcaggtgtgg ctgccgggca tcccgcagat gtactacgtc   1140

ggcctcctgg cgggcgagaa cgacctggac ctgctggaac gcaccggtgt cggccgcgac   1200

atcaaccgtc gctactacac cccggatgag gtggagcagg ccctgcagca gcccgtggtg   1260

gtggggctgc tccgcctgct gcgcctgcgc aacgaccatc cggccttcga cggcgcctgg   1320

gagctgctgg acggcgacgc cgccagcggc cagctggcga tgcgctggag caacgccgac   1380

gagatcgccg agcttgccgt cgacgtccgc gcccgcacat acgaactgcg cgtgacgatg   1440

gacggcgagc tgcgcagctt cgtgaacgtg ctggacctgc cggagaccga cagcacc      1497
```

<210> SEQ ID NO 60
<211> LENGTH: 1488
<212> TYPE: DNA
<213> ORGANISM: Artificial sequence
<220> FEATURE:
<223> OTHER INFORMATION: Codon-optimized sequence encoding Sp159.

<400> SEQUENCE: 60

```
gtgaataacc agccgggcag caaccagatc cagctgatca cctacgtcga ccgcctgagc     60

ggcggcggcg tgacagagct gcaccagctg ctgcagcagg agctgggcgg cctgttcgac    120

ggcgtgcacc tgctcccgtt ctacaccccg atcgacggcg aggacgccgg cttcgacccg    180

accgaccaca ccgctgtgga cagccgcctg ggcaactggc aggacatcgc cagcctcgcg    240

agcgattacc cggtgatggc cgacatgatc gtgaaccacg tgagcgcgca gtcggcccag    300

ttccaggacg tcctggccaa gggcgaggcc tcgccgtact ggcccctgtt cctgacgcgc    360

gacaaggtct tcggccaggc cccgagcccc gccgagctgg ccgccatcta ccgcccgcgt    420

cccaccagct gcttcaccga gctgaccctc gcggacggcc gcagcctgcc cttctggacc    480

accttcaccg ccaaccagat cgacattgac gtccagagcg agccgggcca ggcgtacctg    540

gacgccatcc tgcagagatt cactgagaac ggcgtcaagc tgatccgcct ggacgccgcc    600

ggctacgcca tcaagaaggc cgggacgtcg tgcttcatgc tgccggaaac cttcgagttc    660

atcgccggcc tgagctccaa ggccaaggcc ttgggcatgc agtgcctggt ggagatccac    720

ggctaccacc agacgcagat cgacatcgct aagcgctgcg actgggtgta cgacttcgcc    780

ctgccgccgc tggtgctgca caccctgttc agccgcgacg ccaaggccct gaagcactgg    840

ctggacatcg ccccccgcaa ctgcatcacc gtgctggaca cccacgacgg catcggcatc    900

gtggacgccg cggaccacca gggccagccg ggtctgctga ccgacccgga gctggacgcg    960

ctcgtggagc agatccacca caactccggg ggcagctcga agctggcgac cggtaacgcc   1020

gcgaacaacg tggacctgta ccaggtgaac tgcagcttct acgacgcgct ggcccagcat   1080

gatgaacatt accttttggc acgcgcgatc cagttgttct gccctgggat cagccagatc   1140

tattacggcg gtctgctcgc cgcggagaac gacgtcgaac tcctcaagcg cacccaggtc   1200

ggccgcgata tcaaccgccc ctacttcacc gccgaaaagg tgcgtcaagc cctgcagaag   1260

ccggtcgtga aagcactctg cgccctgatc aagctgcgcc gtagtctgca ggccttcgac   1320
```

```
ggcgacttca gtcaacagct catagacggc ctgtaccagc tgaattggca gcatcagggc   1380

cattcggcga gcctgcgcat ccagctggcc gacctgagcg ccgaactggt gtggcagcac   1440

agcggcgaag tgcagcagca gtgcgccctg agcagcctgc tggctgag                 1488


<210> SEQ ID NO 61
<211> LENGTH: 1458
<212> TYPE: DNA
<213> ORGANISM: Artificial sequence
<220> FEATURE:
<223> OTHER INFORMATION: Codon-optimized sequence encoding Sp236.

<400> SEQUENCE: 61

gtgaccatca agaaccaagt aatgctgatc acctacgcgg actcgatggg caagaacctg     60

caagagctga acgaggtgct gaccaagcac ttccgcgaca ccatcggcgg cgtgcacctg    120

ctcccgttct acccgtcgtc cgccgaccgc ggcttcgccc cgatgaccta caaggaagtt    180

gatgagccgt tcggcacctg ggaggacatt caggccctga gcaataactt ctatctgatg    240

ttcgacttca tggtgaatca tatcagcaag agctcggagt acttccagga tttcgtcgaa    300

aagaaagatg agtcggacta tgccaaattg ttcattcaat ataaggactt ctggcctaac    360

ggcgaaccca cccaggaaga cgtggataaa atctataagc ggaagccgcg cgccccgtac    420

attgatgtga ccttcaacga cggctcaaaa gaaaagattt ggtgcacctt cgatgaagaa    480

cagattgacc tgaatgtgta ccatgaacgc accaagcgct tcatccagga taacctgcat    540

tacctgagca agaagggcgc ttccatcatg cgccttgatg cattcgcgta cgccaccaag    600

cagccaggga ccaactgctt cttcatcgaa cctgacacct gggagatgct ggacgagatc    660

aaggagatcc tggacccgta tggcgtggag atcctgccgg agatccacga acactacagc    720

atccagctga agctggccga gcgcggctac tgggtctacg acttcgccct gccgatgctg    780

gtcctgcacg ccctgtactc gggccggacc gaccggctgg ccaactggct gcagacctgc    840

ccgaaaaagc agttcaccac cctggatacc cacgacggca tcggcgtcgt cgacgtggtg    900

gacctgctga gcaacgagga gatggaggag acccgtgacg acctgttcac caagggcgcc    960

aacgtgaagc gcgtctacaa cacgatggag tacaacaacc tggacatcta ccagctgaac   1020

tgcacctact acagcgccct gggcaaccgt gacgacgcct acatcctggc gcgcgccatc   1080

cagttcttca cccccggcat cccgcagatc tactacgtgg gcctgctggc cggcgagaac   1140

gacatcgagc tcctggagaa gaccaaggtc ggccgcaaca tcaaccgcca ctactacacc   1200

aaggacgaga tcgacgagaa catgacccgc cccatcatgt cgcacctgag caacctgatg   1260

cgcttccgca acaactaccc cgccttcgac ggcgagatcg aggtgatcga acacgaggac   1320

agcagcgtga tggagatcat ccgcacccac ggcgactacc aggccgtgct gactgccaac   1380

ctgaagacct acgcctacga gatcacctac aaggacctgg agaccggcga gaagcgcagc   1440

ctggagaaca tcagcaag                                                 1458


<210> SEQ ID NO 62
<211> LENGTH: 1443
<212> TYPE: DNA
<213> ORGANISM: Artificial sequence
<220> FEATURE:
<223> OTHER INFORMATION: Codon-optimized sequence encoding Sp254.

<400> SEQUENCE: 62

gtgacgttcc agaacaagac catgctgatc acctacagcg actcgctggg cagcaacctg     60

aaggaactga agaccaacat cgaccagtac ttcggccagg ccatcggcgg cgtccacctg    120
```

```
ctgccgttct tcccgagcac cggcgatcgt ggcttcgcgc ctgtggatta cggccaggta    180
gaccctgcct tcggcaattg ggatgatatt aaggccttgg gtgataagta ttacctgatg    240
ttcgatttta tgatcaacca catcagccgc cagtcgacct actacaagga cttccaggag    300
aagaaggacg cctccgacta cgccgacctg ttcctgcgct gggagaagtt ctggcccagc    360
ggccggccga cccaggccga catcgacctg atctacaagc gcaaggacaa ggcccccgatg    420
caggccatca ccttcgccga cggcaccacc gagcacctgt ggaacacctt cggcgaagag    480
cagatcgacc tggacatccg ccaccaggtg acgatggact tcatcaagga caccatcgag    540
cagctcgtgg ccaacggctg cgacctgatc cgcctggatg ccttcgccta cgcgatcaag    600
aagctggaca ccaacgactt cttcgtggag ccggaaatct gggacctgct ggaccgcgtc    660
caggccgtgg cccaggaagc gggcgccgac atcctgcccg agatccatga gcactacacc    720
atcccgttca agctggccga ccacggctac ttcgtgtacg acttcgcgct gccgatggtg    780
accctctaca gcctgttctc gggcaacacc gaccagctgg ccaagtggct gaagatgagc    840
cccatgaagc agttcaccac cctggatacc catgacggca tcggcgtcgt cgacgtgaag    900
gacatcctga cggacgagga gatcgacttc acctcgaagg ccctgtacaa ggtgggggca    960
aacgtgaagc gcaagtactc tagcgcggag tacaacaacc tcgacatcta tcagatcaac   1020
accacctact acagcgcact gggcgactac gataagaagt actttatcgc ccgcctgatc   1080
caggcgttcg cccccggcat accgcaggtc tactacgtgg gcctgctggc cgggaagaac   1140
gacctggaac tgcttgaaaa caccaaggaa gggcgtaaca tcaaccgcca ctactacacc   1200
agcgatgaga tcggccggga gatccagcgt ccgctggtcc agaaactgct gcagttgttc   1260
accttccgca acgagtccga ggccttcgat ctggcgggcg gaattgaggt ggccaccccg   1320
gatgcccaca ccatcatcat cacccggtac aatgccgaca agagcgtgat cgccgaggcg   1380
aacatcaacc tgcttgatct gcgctacagc atcttcgaga acgaccgccc agtccacttt   1440
gag                                                                 1443
```

<210> SEQ ID NO 63
<211> LENGTH: 1437
<212> TYPE: DNA
<213> ORGANISM: Artificial sequence
<220> FEATURE:
<223> OTHER INFORMATION: Codon-optimized sequence encoding Sp277.

<400> SEQUENCE: 63

```
gtgaagatta agaatgaggc catgctgatc acctacccgg atagcctggg taacaacctc     60
aaggacctgg aacacgtgtt ggacacccat ctgaagggcg ttgtgggcgg ggtgcacatc    120
ctgccgttct tcccaagttc gggcgaccgt ggcttcagcc cgatggatta cactaaggtc    180
gacgagcgct tcggcggctg ggaggacatc aagcgcatct cggagaagta ctacatgatg    240
tacgagttca tgctgaacca catctcggcc cagagcccgt actatctgga cttcctggag    300
aagaaggaag agagccccta caaggactac ttcatccggt acaacgacta ctggcccgag    360
aaccgcccga cggaggctga cattgacttg atctataagc ggaagccgaa ggccccgttc    420
gtggacgccc acttcaagga cggaaccacc gagaaggtct ggtgcacctt cagcgaggag    480
cagatcgacc tgaacgtaaa aaccgaagcg acgcgccgct tcatcaaaga taccctcagc    540
ttcctggccg acaagggcgc cagcatcatc cgcttggacg cattcgcgta cgccatcaag    600
gaactggaca ctaactgctt tttcgtagag ccggaaatct gggagatgct ggagtacgcg    660
```

gtcgaaatcc ttgagcccta cggcgtgacc gtgctgccag aaatccatga gcattacacc 720
atccagcaga agatcgcgga gaagggctac cccgtgtacg acttcgcgtt gcctatgctg 780
gtgctgcacg cgctgtacag cggcaaggcc gagaagctgc ttcactggct ggagatctgc 840
ccgcgcaacc agttcaccac cctcgacacc cacgacggca tcggcgtggt ggacgtgaag 900
gacttgctga cgcaagagga agtggacttc gccgtggagg cgctgtacga gaagggcgcc 960
aacctgaagc gcatctacag cagtgaggcc tacaacaacc tggacatcta ccagatcaac 1020
tgcacgtact acagcgccct gggcaataac gacgccgcgt acctgctcgc ccgcgccatc 1080
cagtgcttca cgcccggcat cccgcagatc tactacgtcg gcctgctggc cggcgagaac 1140
gacctggagc tgctggagaa cagcaaggaa ggccgcaaca tcaaccgcca ctactactcg 1200
ctggacgaga tcaaccagga gatcgagcgc ccggtggtca aggacctgtt ccgcctgctg 1260
gccttccgca acaccgccaa ggccttcgac ggcgacctgg agatcaccat gctggacgag 1320
ggcgcgttca ccctgacctg ggcgaccgcc gaggagagcg cctcgctgag cgtggacctg 1380
gccaccaaca agttcagcgt gctgcaccgc accgccgccg gcgacgagca gatcttc 1437

<210> SEQ ID NO 64
<211> LENGTH: 1719
<212> TYPE: DNA
<213> ORGANISM: Artificial sequence
<220> FEATURE:
<223> OTHER INFORMATION: Codon-optimized sequence encoding Sp75.

<400> SEQUENCE: 64
gtgactaagc agggcctgct gcagaacgcc ggcccgatgt tcaacgccta cccggacagc 60
atcggcggca ccctgaacga ttgcgtggag ctgctgaagc tgccggaatt cgagaatgcc 120
ttccgcgcct tctacatctt gcctagcctg ttcaacacgg acctcgaccg cggcttttcc 180
gtgatcgact acgagctgaa cgaggcctac gccagcaacg aagacctgaa gaacctgaag 240
cagctgaaca tcgaactgaa actggacttc atcctgaacc attgcagcgt gcttagcaag 300
cagttccagg acatcatcaa gaacggcgag aagagcaagt atactgattt cttcatcaac 360
tggaataagt tttgggacgg gtacggtgag atgaccgaag aaggctacat ccgcccgtat 420
gatgagtaca ttaagaacat gttcttccgt aagccaggcc tcccaatcct gatggtccgc 480
atgcccgatg gccgtgaagt cccctattgg aacaccttct accaagaggt gaagtacaac 540
aagatcacgt cgtacgagct gatcaagaac ctgaacatcc agtacgtgac cgccgagcgc 600
atcgccaacc tagtgaacag cgccctggac gagggcaaga agccgatcga aatcgacttc 660
accggcttcg agaagtacaa ggacgaggtc atcgacctgc tggaagccaa ccggcactac 720
ctgggccaga tggatttaaa catcaagagc ccgctggtct gggagttcta cgacgacacc 780
ctgaagaagc tgaaggagta cggggcctcg atcatccgcc tggacgcgtt cgcctacgcg 840
ccgaaggaac cgggcgagaa gaactttatg aacgagccgg gcacctggga gctgctggag 900
cgcgtgcgcg agctcgccga caagtaccag ctgaccctgc tcccggaaat ccacagccgc 960
tacgaggaga aggtccacga gaagctggcc gagaagggct acctgaccta cgacttcttc 1020
ctgccgggcc tgatcatcga cgccctggag cgccacaaca acaagtacat catcaagtgg 1080
ttctacgaca tcatcgaaaa gaacatcaag accgtcaaca tgctgggctg ccacgacggc 1140
atcccgctcc tggacctgaa gggcctgatc ccggacgacg agatcgacca gctgatctcc 1200
accatcgtga gccggggcgg cctggtgaag gacctgcacg gcaagaagaa catctactac 1260
caggtcaaca gcacctactt ctccgccctg ggcgaggacg agcgcaagct gctgctggcg 1320

```
cgcgcgatcc agatcttcac ccccggcatc ccccaagtgt ggtacctgga cctgttcgcg   1380

ggccgcaacg actatgaagc cgtgaagaag gccggaccgg gcggccacaa ggagatcaac   1440

aggaccaacc tgacgatgga ccaggcgaag gatggcctga agaccgacat cgtgcgccgc   1500

cagctggagc tgctgcgctt ccgcaacacc ttcccggcct tcggcttcaa cgccaagctg   1560

caggtgatcg agagcgagcc ccacatcctg aaactgaggt gggaaaagga tagctgtagc   1620

gccaccctga ccgccaacct gaaggactac tcgttcgaaa tcagcggcgt ggacgagaac   1680

aacaacatca tcaacttcaa cagcaacaat aataactgg                           1719
```

<210> SEQ ID NO 65
<211> LENGTH: 1503
<212> TYPE: DNA
<213> ORGANISM: Artificial sequence
<220> FEATURE:
<223> OTHER INFORMATION: Codon-optimized sequence encoding Sp156.

<400> SEQUENCE: 65

```
gtgaccacct cccccagcgc ccccggcggc ccgcagctga tcgcctacgc cgaccggttc     60

ggcggcagcg tggccggcct gaccgagctg ctgcggggcc ccctggccgg cgccttcgac    120

ggggtgcacg tgctgccgtt cttcaccccc ttcgacggcg ccgacgccgg gttcgacccg    180

gtcgaccaca cccaggtgga cccgcgcctg ggtacctggc aggacgtggc ggaactggcc    240

acggaccaca ccgtcatggc cgacgtgatc gtgaaccacg tgtcgtcgga ctccccggcg    300

ttccaggacg tcgtggagcg cggccgtgac tcgccgtggg cccccatgtt cctgaccttc    360

gacgccgtct tcccggaggg cgccaccgag gcccaactgg ccgccatcta ccgcccgcgt    420

ccgggcctcc cgttcaccgc gatgaccctg ggcggcgagc gccggctggt gtggaccacc    480

ttcaccccgc agcaggtgga cctggacatc cgcgccccgc aggcctggcg ctacctgacc    540

gaggtgattg acaaccagac gggcgccggc gtgggcatgc tgcgcctcga cgccgtgggc    600

tacgtggcga aggtgccggg cacgagctgc ttcatgctgc cggaggcggc cgacgtcgtg    660

acccgcgtgc gcgagcacgc ccacggccgg ggcgcccagg tgctgctgga gatccacggc    720

tactatcgtc agcagattga gatcgccaag accgtggaca tggtgtatga cttcgccctc    780

ccgcccctgc tgctgcacgc gttcgccgcc gccgacctgg cgccgctcgc ccactggctt    840

gaggtccgcc ccaccaactg cgtgaccgtc ttggacaccc atgacggcat cggcatcatc    900

gacgccggcc gcgggcccgc cggcgagccg ggcctcctgg aggacgcgca gatcgacgcg    960

ctcgtcgaat ggatccatga gcagagtagc ggcgagagcc gccgcgccac cggcggcgcc   1020

gcgtcgaatc tggacctgta ccaggtgaac tgcaccttct tcgccgccct gggcgagcac   1080

gaggaccgct acctgctggc ccgcctggtc cagctgttcc tgccgggcat cccgcaggtc   1140

tactacgtgg ggctgctggc cggccgcaac gacatggacc tgctggaacg caccggcgtg   1200

ggccgcgata tcaaccgcca ccattacacc cgccccgaaa tcgacgccga actggagcgc   1260

ccggtggtcc gcgaccagct ggccgccctg cgcctgcggg cccagcaccc ggccttcgcc   1320

ggcgaagtga cctgggccgt ggacggcccc gagctgaccg tgcgctgggt cgcgggcgag   1380

cacaccgccg agctggaagt ggacgtggcc gccgtgcgcg gcgtcgtgcg ggtgagcgcc   1440

gctggtcaag tgcaagaagt agatgcacgt gccttggcgg ccaccgtccc tgatctgctg   1500

cca                                                                  1503
```

<210> SEQ ID NO 66

<211> LENGTH: 1497
<212> TYPE: DNA
<213> ORGANISM: Artificial sequence
<220> FEATURE:
<223> OTHER INFORMATION: Codon-optimized sequence encoding Sp158.

<400> SEQUENCE: 66

```
gtgaagaaga tcaccaacca ggtgatgctg atcacctacg ccgatagcat gggtagtaac      60
ttggatgaat taaatcaagt gttggaaact cacttcgaag gcgtgattga gggtctgcat     120
atcctgccat tctttccgag cagcggtgac cgcggtttcg cagtgatcca ctatgatgaa     180
gtcgaccccg ccttcggtga ttggaacgac atccagcgcc tgagcgataa atattatctg     240
atggcagact ttatgattaa tcatgtgagc atccgtagtg aagaattcat cgattatatg     300
cagcgcggcg atgaaagccc gttcaaggaa atgttcatcc attgggatga attctggccc     360
ggcggcgagc cgaccgaggc cgagatggag gccctgtatc gccggaagat gcacggcccc     420
tacaaggagt tcacccgcgc cgacggcaag acggtcaagc tgtggaacac cttcttcgag     480
gaacaggtgg acatcgaccc gtgggccacc gccacccaga gctactacga gcgcaacttg     540
gagcgcctgg ccggctacgt gccgctgatc cgcttcgacg ccttcgccta cgccagcaag     600
aagccgggca cctcgtgctt cttcgtggag cccgaggtct gggacgtgct ggacatcggc     660
atgcgcccgc tgaacaagta cggcaccgaa atgctcccgg agatccacga gaactacaag     720
atccagctga agatggccga gcagggccat tgggtgtacg acttcgccct gccgatgctg     780
ctgctgcacg ccctgatgac cggctgctcg gaccgcctca tccactggat gcagatctgc     840
ccgcgcaaac agttcaccac cctggacacc cacgatggca tcggcgtggt ggacgtcgcg     900
ggcctcctgt ccgacgaaga aatcgacctg gtgcgtgacc gcgtcaacac caaggtcgag     960
ccgctgcagc agtacatcaa cttcccgccg ggcatcgtga agatgagcgg cgccaaggcc    1020
cgccagtacc agctgatgtg cacctactac agcgccctcg acgaggacga ccacgcgtac    1080
accctggcgc gcatcatcca gctgtacgcg ccgggcatcc cgcaggtgta ctacgtgggc    1140
ctgctggccg gcgagaacga cgaggaatcg ctgaagcgcc tgggcgagcc ccgctcgctg    1200
aaccggcaca actacagcat ggaggaaatc gccgagcgcg tccagacccc catgctgcag    1260
catctgtacg ccgtgatgaa gttccgcaac agccacccgg ccttcggcgg cgacgtggag    1320
atcggcgagc ccgccggcga cggccagctg gccatcgcct ggcgccaggg cgacgcctgg    1380
accaccctgg aggccgacct gcgcaccaag gcctacacca tcgtggcgtc gaacgccgag    1440
ggcgccgccg agcgcctgtt ccacagcaac ggcgtggccg tgccggaggg cagccag        1497
```

<210> SEQ ID NO 67
<211> LENGTH: 2079
<212> TYPE: DNA
<213> ORGANISM: Artificial sequence
<220> FEATURE:
<223> OTHER INFORMATION: Codon-optimized sequence encoding version of GP-3.

<400> SEQUENCE: 67

```
gtggctgaag aagaaaaagt taaagaaggc ctttgggaac tggcatataa tctgtggtgg      60
acatggaatc cgcctgcaaa agaactgttt agaagcattg atccgctgct gtggaaagaa     120
acaaaagaaa atccgattga actgctgcgc aaaacaaaac tgctggaaaa taaactgaaa     180
gatgaagatt ttatcagcca tttcaaatat gtctatagcc tgtataaaac atatatgaac     240
cgccatagca aatatgaaga tacgtacaaa aaaccgattg tctttctgtc accggaatat     300
```

```
ggcctgcatc atacactgct gatttatgct ggcggactgg gctttctggc tggcgatatt    360

ctgaaagaat catcagatct tggctttccg ctgattggcg ttggctttat gtatccgcaa    420

ggctatgtta aacagagaat tagagttgat ggctggcaag aagatctgga cgcacaaaat    480

cagaaagaac ttatgccggt taaaaaagtc ctggacaaag agggtaaatg gctcaagtgc    540

tatgtgtatg ttcgggacga aaaagtctat tttggcgttt gggaagttaa cgtcggaaaa    600

acgaaactgt atctgctgga tacaaacgtc gaagaaaata caccgtggaa tagagaaatt    660

agcagcagac tgtatgtccc ggataaagat cttagactga gacaacaaat tgtcctggga    720

tttggcacag ttatcctgct tgaaaaactg ggcattgatg cgggtggctt tcatattaac    780

gaagattatc cgagctttgt gtttctggcg gaaatcttta aactcctgaa aaaaggcctg    840

acatgggata aagcaattga agaagtccgc aaaattagcc tgtttacaac acatacaccg    900

cttagagtcg cagttaatac atatccgttt cacatgatcg aggaacagtt tctgttcgtc    960

aaagatgttt atggcatcga cgtcaaaaaa gttcttgaac ttggcacaaa tccggaagat   1020

ccgtcagaag gctttaattc aacaattatg agcctgcgcc tggcgaaata tgttaatgca   1080

gtttcaaaac gccatcaaga ggtcagctca aaaatgtggt cctttctttt caaagagaaa   1140

gaaaacccta tcgattatgt cacaaacggc gttcactttc cgacatggat ttgcagcgat   1200

cttcgcagac tttatgaaga atatctgggc gaaaattttg tcgaactgca tgatcataaa   1260

agcctgtggg aattgattag agatatccct gatgaagagt tgtgggagta tcatattcgc   1320

aataaagaac gcctgatcga gcatattaaa gatagagcaa gagaacgctg ggtcaaagaa   1380

aaggcagatc cgagcattct gatggcagaa ggactgtttc ttgattcaga tgttctgaca   1440

gtcggctttg cgagaagaat gacaggatat aaaagaccgg atctgatctt tacagatgtc   1500

gaacgcctta aaaagatcgt caatgatagc gaacgtccgg tccaaattat ctttgctggc   1560

aaagcacatc cggcagatat tgaaggcaaa aaaatcattc agcgcatctt caacttcgcg   1620

aaagatccgg aatttggcgg aagaattgca tttgtggaag attacgatga acttctggca   1680

cattatatgg ttagaggcgt tgatgtttgg ctgaataatc cgcttccgcc tctggaagca   1740

tgcggcacat caggcatgaa agcaagcatg aatggcgttc tgcatctttc tattctggat   1800

ggatggtgga tcgaaggcta taatggcaaa aatggatggg catttggcga ctatgaagtc   1860

gaaggcgata gaaatagagc agatgctgaa gcgatttata acatcctgga aaacgaagtc   1920

atcccgctgt attatgaaag agatgaacgc ggagttccgg tcaaatggat tagcatgatg   1980

aaagaagcga tcaaaagcat cacaccgaat ttttgctcaa gacgtatgct gaaagactat   2040

attaacaaat tttacagcaa aatcttaaaa gaagaaggc                         2079
```

<210> SEQ ID NO 68
<211> LENGTH: 2460
<212> TYPE: DNA
<213> ORGANISM: Artificial sequence
<220> FEATURE:
<223> OTHER INFORMATION: Codon-optimized sequence encoding version of GP-4.

<400> SEQUENCE: 68

```
gtggctaatg ttctgggcag aattacagca atgccggatc tgccggaacc gctggaaggc     60

ctgaaagaaa ttgcatataa tctgtggtgg tcatggaatc cggaagcagc agaactgttt    120

caagaactgg atccggctct gtggaaaaga tttagaggca atccggttaa actgctgctg    180

gaacttgatc ctgcaagact ggaagcactg tcagcatcag gctatgcagc aagagttcaa    240
```

```
gcaacaagag aagcacttag agcatatctt gaagcaagaa gaacaaaaag aggaccgctg    300
gttgcatatt tttcagcaga atatggcttt cattcaagcc tgccgattta tgcaggcgga    360
ctgggcgttc tggcaggcga tcatgttaaa gcagcaagcg atctgggcct gaatctggtt    420
ggcgttggcc tgttttatca tgaaggctat tttcatcaac gcctgtcacc ggaaggcgaa    480
caagttgaag tttatgaacc gcttagaccg gaagaactgc cgcttgttcc ggttcaagat    540
gcagaaggca gaccggttag agttgcagtt gaatttccgg gacgcctggt tcatgttggc    600
ggatatagag tccaagttgg cgcagttccg gtgtatctgc tgacaacaga ccttccggaa    660
aatgctccgg aagatagaca gattacagcg agactgtatg cggcaggcct ggaagcgaga    720
attcaacaag aacttgtcct tggcctggga ggcgttagat ttctgagagc actgggcctt    780
gcaccggcat tttttcacat gaatgaagga cattcagcat ttctgggact ggaaagactt    840
agagaactgg ttgcggaagg atatccgttt agagaagctc ttgaacttgt tagagcaagc    900
gcactgttta caacacatac acctgttccg gctggccatg atgtttttcc gctggatctg    960
gtcgatagat atcttggagg cttttgggaa aaactgggag ttgatagaga tacgtttctt   1020
ggccttggac ttgaagaaaa accgtgggga ccggtttttt caatgtcaaa tctggcactg   1080
agaacagcag cacaagcaaa tggcgttagc agactgcatg gcgaagtctc aagaaatatg   1140
tttagacatc tgtggcctgg cctgctgggc gaagaggttc cgattggcca tgttacaaac   1200
ggcgttcata catggacatt tcttcatccg agactgcgca gacattatgc ggaagttttt   1260
ggaccggaat gggttgaaag acctgaagat ccggaaacat ggcgtgttga aggccttggc   1320
gaagcatttt ggagaattag acaagatctg aaactttttc tggtcagaga agtcagacaa   1380
agactgtacg aacagagaag aagaaacggc gaaggaccgg ctagactgcg tgaagccgaa   1440
aaagctctgg atcctgaagc gctgacaatt ggctttgcga gaagatttgc aacatataaa   1500
agagccgtcc tgctgtttaa agacccggaa cgcctgctga gaattctgaa aggaccgtat   1560
ccggtgcagt ttgtttttgc aggcaaagca catccgaaag atgaagcggg aaaagcgtat   1620
cttaaagagc tggttagcaa aatccgcgaa tatggattag aagatcgcat ggttgttctg   1680
gaagattatg atatgtatct ggcaagagtc ctgacacatg gctcagatgt ttggctgaat   1740
acaccgcgtc gtccgatgga agcgtcaggc acatcaggca tgaaagcagc gctgaatggc   1800
gcactgaatc tttcagttct ggatggatgg tgggctgaag cgtataatgg caaaaatgga   1860
tttgcgattg gagatgaacg cgtctatgaa tctgaagaag cacaagacgt tgcagatgca   1920
caagcgctgt atgatctgct tgaatcagaa gttatcccgc tgttttacgc aaaaggctta   1980
gaaggttatt caagcggctg gatgtcaatg gtccatgaat ctcttagaac agtcggacct   2040
tatttttctg ctggcagaat ggttagagat tatctggcgt tatatgaaag aggcgcactt   2100
tgggagaaag aagctagagc acgccttgaa gctctgaaag catttgctga agcattaccg   2160
gcttttcatg cacttggcgt tcgtccggaa gttcctggcg atctgacact taatggcgga   2220
cgtctggaag ttggagcggt gcttgaaggt gaagtgccgg aaggacttcg tccgcatctg   2280
agagttcagc tggttgttag acgtcttggc ggaggcttgg aagtcgttga tttagaagaa   2340
gtcgcaccgg gaagatatag aacagcgttt agaccgacaa gaccgggatc atatacgtat   2400
ggcctgagac tggcgctgtt acatccggtc acaggacgcg ttgaatgggt cagatgggct   2460
```

<210> SEQ ID NO 69
<211> LENGTH: 1623
<212> TYPE: DNA
<213> ORGANISM: Artificial sequence

```
<220> FEATURE:
<223> OTHER INFORMATION: Codon-optimized sequence encoding version of
      GP-5.

<400> SEQUENCE: 69

gtggctgaaa acaaaaaact gccgagagtt gcgtatttct gcatggaata tggcctggaa     60

tcaaacttta aactgtatgc aggcggactg ggcattctgg caggcgatta tctgaaagca    120

gcaaaagaaa tgggcctgcc ggttgttggc attggcattc tttggaaaca aggctataca    180

gaacaacaca ttggcgaaga tggctatccg tatgatgcgt atagaaatta tacgcgcaac    240

tatgacttcc tgaaagatac aggcgttaaa gtcaaagtga aatccgcaa caaagacgtc    300

tattgcaaag tttggctggt cgattcattt gataatgcac cgctgtatct gctggataca    360

gatattccgg aaaatggcga tcgctggatt acaggccaac tttatggctg gtttggagaa    420

gaaagagtcg cacaagaaat tgttctggga attggcggag ttagagcact gagagcactt    480

ggaattgatg tcgatatcta ccattttaat gaaggccatg cagttcttgc aggcattgaa    540

ctgattcgcg aaaaaatgga aaatcagggc atgagctttg aagaagcatg ggaagcaaca    600

cgcaaagaaa tcgtttttac aacgcataca ccggtcaaag aaggcaacga atcacacgat    660

ctggaactgc tgatgtatat gggagcaaat aatggcctga caattgaaca actggcacaa    720

attggaggcg ttccgtttaa tatgacagtt gcaggcctga gacttagcaa aattgcaaat    780

ggcgtttcaa aacttcatgg ccagacagcg aataaaatgt ggcagcatat tgaaaataag    840

gcaccgatta tcagcatcac aaacggcatt catagaggca catgggtcga taaaagaatt    900

acagaggcat acaaaaaagg cacaggactg ctggaaacac ataacctgct taaaaaagaa    960

ctgatcgatt ttgtctataa aaagacaggc gtcaaactgg atgcggataa actgcttatt   1020

ggcttttcaa gacgcgcagc accgtataaa cgcagcgatc tgatctttac aaacgaaaaa   1080

gcgatcggcg aatatcttcg tgatcgcaaa attcagattg tgtttagcgg caaaggccat   1140

ccgctggatg atgttggcaa agagattgtt gcacgcattg tcaaaatgac gaagaaatat   1200

ccggaaagcg ttgtgtttct ggaagattat gatatgacga tcggcaaaat gctgacaaga   1260

ggcgcagatg tttggcttaa taatccgcgt agaccgctgg aagcatcagg cacaagcggc   1320

atgaaagctg caatgaatgg cgtcctgaat ctgtcaattc tggatggatg gtggcctgaa   1380

gcatgcattg atggcgttaa tggctggcaa tttggagatg gctttgaaag cgataatttt   1440

gaggaactgg ataaacatga tgcggaagca ctgtatgatg tcctgctgaa taaagtcgtt   1500

ccgacgtatt ataacgacaa aaaaaagtgg gaagaaatga tgaaagaaag catccgcaca   1560

acgtttgaag catttagcgc aaatcgcatg ctccaagagt attatgatct gatgtacaca   1620

aag                                                                  1623


<210> SEQ ID NO 70
<211> LENGTH: 2604
<212> TYPE: DNA
<213> ORGANISM: Artificial sequence
<220> FEATURE:
<223> OTHER INFORMATION: Codon-optimized sequence encoding GP-006.

<400> SEQUENCE: 70

gtgaagccgc tgcgcacctt caaggtgacc ccgtacctgc ccgccgccct ggagagcctg     60

cgcttcctgg cctataacct gcacttcagc tggaacgtgg aaacccgcaa cgtgttcaac    120

cgcatggacc cggacctgtg ggacgcgtgc gcccataacc cgatcgccct gctgggccag    180

atccgccagg aacgcctgga cgagctcgcc gaggaccccg gcttcctggc ccagctggag    240
```

```
cgcgcctacc agcagctgca cacctacctg caggaagaca cctggtaccg caagcaccac    300
agcgcccact ccgtggaggg cgagtgctac gcctacttca gcgccgagtt cgggctggcc    360
gactgcctgc cgatctacag cggcggcctg gggatcctgg ccggggacca cctgaaggcc    420
gccagcgact tgggcctgcc gctcgtgggc gtcggcctgc tgtaccagaa gggctacttc    480
aggcagtacc tgaaccccga tggctggcag caggaacgct accccatcaa cgagttcttc    540
aacatgccgc tggagctcca gaaggatgcc gagggccgcg agatccgcat cgaggtcgat    600
tacccgaacc gcaaggtgtt cgcccggatc tggaaggtga acgtgggccg ggtgcccctg    660
tacctgctgg atacgaacat cgagccgaac tcccagtacg accaggacat taccgacgag    720
ctgtacggcg gcgaccagga cctgcgcatc caccaggaaa tcatgctggg catcggcggc    780
gtccgcgccc tgcgcgcctt gggcatccag ccgacagtgt accacatgaa cgagggccac    840
agcgccttcc tggccgtgga gcgcatccgc ctgtttatga ccgagcaggg cctgagcttc    900
gaagaagcct ggcaggtcgc caagagcagc cagatgttca ccacccatac cccggtgccg    960
gccgggatcg acctcttccc cccggacaag atcgactact acctgggctc ctactactcg   1020
caactgggcc tgggccgcga acgcttcttg gccctggggc gcgagaacac cggtgacttc   1080
cagagccagt tcagcatggc ggtcctggcg atcaacatgg cgtcgttcgt gaacggcgtg   1140
tccaagctgc acggcgccgt gagccgtaag atgttctcgc agctctggcc aggcatcccg   1200
ctggaggaag tcccgatcac cagcatcacc aatggcgtgc acgcccgcac ctgggtgggc   1260
gaggagaacc agtccctgta tgatcggtac ctgggccccg actggccgga ggcccccgccg   1320
ttcgacccga tctggcagaa ggtcgaccgc atcccggact cggagctgtg gcgcacccac   1380
gagcggagcc ggagccgctt ggtgtcgttc acccgcgagc gcctgatggc ccagctgcag   1440
aagcgcgcgg cgtccaccat cgagatccag cgcgcctcgg aagcactgaa tcccgaagtc   1500
ctgactatcg gtttcgcgcg ccgcttcgcc acgtacaagc gggccaccct cctgttccgt   1560
gacccggaac gcttcaaggc cctggtgacc cacccgcacc accccatgca gttcatcttc   1620
gccggcaagg cccacccgcg cgacacgccg ggcaaggagc tgatccggca gatcgtccag   1680
ctgtcgcggc agcccgagtt ccgtcatcac ctggtcttca tcgaggacta cgacatgcac   1740
gtcacctcga tgatggtggc cggcgtggac gtgtggctga acaacccgct gcgcccacgc   1800
gaggccagcg gcacgagcgg catgaaagcc gcggcgaacg gcggccagaa tctcagcatc   1860
ctcgacgggt ggtgggacga agccgactat taccagaccg gctggcccat cggtcgcggc   1920
gaagagtacg aggaccgcgc ataccaggac gaggtggaga gcaacgcgtt gtacgacctc   1980
ttggagaagg aagtggcccc gaccttctac cagcgcacgt cggacgggct gccgcatccc   2040
tggatccagc gcatgaagca gagcatccgc ctgaacgcgc cgttgttcag cacccagcgg   2100
atggtccagg agtacgccga acgcgcgtac atcccgctga gcggctacta cgcccgcatg   2160
cgtagcgaga acttcgaatc ggcccgccgg ttcactcgtt ggcagagcca tgtccaggag   2220
aactggtacg gcatccaggt gctgagcgtg catgtcgccg accaggaagg cagcctccac   2280
ccggcgccgt ccgtgagcgc cgcccccgac tccagcgccg tcatggcccg cgcgcccctg   2340
accgtgaccg cggagctgcg gctcggcgcg ctgaagcccc aggacgtgat cctgcaggcg   2400
taccagggcc cggtcgacga ctcgggtcac atccagcagg ggcaggccac cccgatgcgc   2460
tacgtggaga tggtcgaaga ccgcgccatc ttcagcggcc agatacgtta cgacgcgtcg   2520
ggcctgcagg gcctggcgct gcgcgtgatg ccgttccatc ccgatatgca tgatccatat   2580
```

gaactgagac tgatgctgtg ggcc 2604

<210> SEQ ID NO 71
<211> LENGTH: 2568
<212> TYPE: DNA
<213> ORGANISM: Artificial sequence
<220> FEATURE:
<223> OTHER INFORMATION: Codon-optimized sequence encoding GP-011.

<400> SEQUENCE: 71
gtgactatgg ccgccgcctt cccgcagggc gccaacgaca tgccggcggc catctaccgc 60
ctgcgcgagc tggcctacaa cgtgtggtgg tcgtggaacg acgacgccct gcagctgttc 120
gagcacatcg accctaagcg cttcgccgcg agcggctaca acccggtccg cctgctgaac 180
gagctggaac ccggccagct ggcctcgctg agcgagaacg ccagcttcct ggagagctac 240
cggaaggtga tggcccgctt cgatgactac ctgcagggcg cctcctggta cagcaccaac 300
tacgagagct ccagcaacgc ccgcatcgcc tacttcagcg cggaattcgg cttccacgag 360
tccctgccga tctactcggg cgggctcggc atcctggccg gggaccacat caagtccgcc 420
agcgacctgg gcatccccct gatcgggatc ggcctgctgt acaagaaggg ctacttcacc 480
cagaagatcg acgccttggg caaccagcag agcgaaatgg ccgactacga cttcacccag 540
ctgccgctgc agccggtgct gctggatgac cgccagctga ccgtctccat ccagctgccg 600
ttccgctcca tcactctcct ggtgtggtcg gtgcaggtgg gccgtacccg cgtgtgcctg 660
ctggattcgg accatgaggc caacgcccct gaggaccggg ccatcacggc ccagctgtac 720
ggcggcgacc aggacatgcg catcgtgcag gaaatcgccc tgggcatcgg cgggatcaag 780
gcgctgcgcg ccctgggcgt ataccccaac gtgtaccaca tcaacgaggg ccacgcggcc 840
ttcctgaccc tggagcgcct gaaggagctg atccagctgg gcctgccgtt ccacgtcgcc 900
gtcgagaccg tgcggagcgc caccgtcttc accacccaca ccccggtgcc cgccggccac 960
gacgcgttca atattgggat ggtcgagcac tacctgggcc cgtatttcag cgaagtcgcc 1020
gcccacaagc aggcgatcat cgccctgggt caggaccaga agaccggcct gttcaacatg 1080
acccatctgg ccatgaacac ggcgggcctc cgcaacggcg tgagcaagct gcacggccag 1140
gtgtcgcgcg agatgttcaa ggagttccac ggccacaccg acgccaacga ggtgccgatc 1200
ggctccatca ccaacggcgt gcacctggac tcctggacgg cccctgcctg gaaggagctg 1260
ttcgaccgct tcctgccagg cacctggcgc gaggagcagg ccaacaccca ccagtgggcg 1320
caggtcgagg tgatcccgga cgagagcatc tggaaggtcc acatgcagtt gaaggagcgc 1380
ctgatcacct acgcgcgcaa gaatctggcc gcgcagcgcg cccgcaacgg ggagtcgcag 1440
gagcgcatcg acgaggtgcg tggctatctc aacccgcggg ccctgaccat cggcttcgcg 1500
cgccgcttcg ccacctataa gcgggcgaac atgatcttca atgacctcca ccgcttgaag 1560
aagttggtga acgatccgga ccggcccatc cagctgatct tcgccggcaa ggcgcatccg 1620
gccgactacc ccggccagga cctgatccgc gacatctacc gcatctcgca gatgaaggag 1680
ttcctcggca agatcgtcat cctggagaac tatgacatcc acatggcgcg ctacctggtg 1740
cagggcgtgg acgtctggct gaacaacccg cgccgccccc tggaggcctc cggcaccagc 1800
ggccagaagg cggccatgaa cggtgtgctg aacttcagcg tgctggacgg ttggtgggag 1860
gaaggctata acggcaccaa cggctgggcg atcggttcga cgggccaggc cgattgggcc 1920
cagcaggagc gcgagaatac gcgctcgttg taccacctgt tggagaacga gatcatcccg 1980
ctgtactata accagggcgc cctcccgcat cagtggatca gccgtatgaa gcgcagcatc 2040

```
cagagcctgg ccccggtgta caacacccat cgtatggtgc aagactacac cgtgcagagc   2100

tacctgccga ccgcggagcg ggccaccctc ttcgtcgcca accagtacga cgtggccacc   2160

aaggtcgccg actacaagca gttcatccgc aataattggc atcaggtacg tattttagcg   2220

attgaagata agttaccgcc aagttcggag gccgaaatca gcccatatga cgccgcgccg   2280

agcaccaaga aggtgcgtgc gcacatccac ttcggcccga tctggcccca ggacaccgcc   2340

gtggagatca tctactacga ggagatcgac gaaagctggc atcagaagac cgtgcacatg   2400

gagccggtgg gcgagctgat cggccaggcc cagtacttcg aagccagcat cccaggccac   2460

ctgttccacg gcccgcattt cagcatccgc gtgcgcccga tcagcgccaa cttcgcccac   2520

tcgttcgagc tgagcctggt caccagcacc ctggcctggc aagaaggc                 2568
```

<210> SEQ ID NO 72
<211> LENGTH: 2556
<212> TYPE: DNA
<213> ORGANISM: Artificial sequence
<220> FEATURE:
<223> OTHER INFORMATION: Codon-optimized sequence encoding GP-017.

<400> SEQUENCE: 72

```
gtgcgcatcc gcccgctgaa ggtgctgacc gtggcctcgg tgctgccgga ggagctgagc     60

ttcctggagc gcctggccta caacttctgg tggtcctgga accgcaaggc cgagtcgctg    120

ttcagcaccg tcgacccggt gcgctgggag cgcatccgtc gcaacccggt gcgcctgctg    180

aaggagacgc cgcaggaacg cttccgcgag ctggtagagg acagcgccta ccgcaagctg    240

ctgcgcgaag tggaaaagga gttcgacgcc tacctgggcc aggcccccca gctgagttgg    300

cccagcccgc gcccgatagc ctacttctgc gccgagtacg gcatctccga gtgcttccag    360

aactatagcg gcggcctggg cgtgctggcg ggcgaccacc tgaagaccgc cagcgacgtg    420

ggcctgccga tggtggccgt ggggctcctg taccagcagg ggtacttcca ccagcacgtg    480

acctataacg gctggcagca ggagaacttc ctggactacg acttcagcct cctgccgatc    540

cagctggtcc gggcggaatc gggcgccccg ctgatcatcc gggtcgaact gccggatggc    600

gatgtggccg cgcaggtgtg gaaagccgac gtcggtcgca tccccctgta cctcctggac    660

accaatatcg ccgacaacag caccaacccg acttaccaga acatcaccga ccagctgtac    720

ggtgggaccc acgagacgcg tatcatgcag gagatgctgc tgggcattgg cggcgtgcgc    780

gtcctggccg ctctgggcat tgaaccgagc gtgctgcaca tcaacgaggg ccacgccgcg    840

ttctgcacgc tggagtggac ccgccacctg gcgcagcagc tgggcctgtc cttccacgaa    900

gccgccgaga tcacgcgtgc ccagacctgc ttcaccaccc acacgccggt cccggccggc    960

aacgagatct tcagcctggg cctgttgcag cgctacttca gccgctacat gcccgtgctc   1020

ggtatcgagt gggaggagtt cctcaagctc ggccaggcga acaacggcag ctcggacgag   1080

ggcttcagca tgaccatcct gggcctccgc atgagcaacc accgcaacgg cgtctcggag   1140

ctgcatggcc acgtcgcccg gaccatgtgg cagtccctct ggccgcacgt cgcgagcgat   1200

gaggtcccga tccgctcgat cacgaacggc gtgcacatcc cgacctgggt gagcagcgac   1260

ttcgcggccc tgtacgaccg ggccttgggc cccggctggc gtcagcgccc gagcgagccc   1320

acgcagtggg acgccatcgc cgcgatcccc gacgccgagc tgtgggccgt tcatgtgcgt   1380

cgccggcagc gcttgctgga ggccgtccgc gagcacatca ggcagcgtgg cggctactac   1440

gacgaggagc accgccagcg cgccatcgcg gccctgcacc cgaactgtct gatcatcggg   1500
```

```
ttcgcccggc gcttcgccac ctacaagcgt agcgacctgc tgttccgcaa ttgggatcgc   1560

ctggcaagca tcctgcgcaa ccccagtcgc ccggtcatca tcctgctggc cggcaaggcg   1620

catccgcagg acatcgcgag caaggagatg atgcagcgta tcctcaccgg gatccgcaac   1680

gccggcctgg agcagcacgt catcttcctg gaggactatg acctcggcat cgcgcgcgcg   1740

ctggtgaaag gcgcggatgt gtggctgaac accccgcgcc gcccctacga agcctccggc   1800

accagcggca tgaaggccgc gctgaacggg gtgctgcact gcagcgtgct ggacggttgg   1860

tgggccgagg ccgccctgtc ggacaacggc ttcacgatcg gccacggtga ggtgttcgcc   1920

accgccgacg aacaggacgc ccatgagagc gagtccctct accagctgct ggagaacgac   1980

atcatcccga tgttctacga acgcgacgcg gccggcgtcc cccgccgttg ggtgaagcgg   2040

atgaagtcgg ccatcgcgac cctcgccgcc cgctactcga cccaccggat gctggacgag   2100

taccgcatgg ccttctacga gccggccgcc gccctgggcg ccgtgctggc ggagcaacag   2160

ggccgcgccg cgcgcgagct gtcgcgctgg aagcgtaccc tgccggagcg ctggaagacc   2220

ctgcgcatca tctcggccga cgtgcctgac cggggcgtga tccacgtcgg tgagccggtc   2280

ccggtgcgtc tggtcctgga ctgcggcgcc atgaacccgg atgagctgct cgcccaggtg   2340

tactacgggc cgctgaccgc gcgcggcgaa tttatgcagg cccgcgtggc caacctgtcc   2400

ctgtcgcacg tcgagggcgc ccgcgccacc ttcgaaggca cctacaccac ccccgacagc   2460

ggccagcacg gcgtcgccct gcgcgtcctg ccccatcacc cccacgtgcc ggacccggtg   2520

gacctgcagc tggtcgtgtg ggtgcagggc gagcag                             2556
```

<210> SEQ ID NO 73
<211> LENGTH: 2544
<212> TYPE: DNA
<213> ORGANISM: Artificial sequence
<220> FEATURE:
<223> OTHER INFORMATION: Codon-optimized sequence encoding GP-022.

<400> SEQUENCE: 73

```
gtgagtgagc aggtgtacat ggacccgtcc ctgtatcgcc agctgccggc cgacatcgac     60

ggtttcgacg agttggtgga gctggccctg gacatgcgct ggagctggaa ccacgccacc    120

gaccagatct ggcgccagat ggatccggtc ctgtgggcct tcacccacag cccgtggtcg    180

atcctgcaga ccgtcagccg cgacaagatc gagcgcgtgt gcgccgaccc cgtcttccgc    240

aagaacctgg acgagctgat ccagacgaag cgccagggca gcgagctgcc gacctggttc    300

cagcaggccc acgccgagtc gcagctgaaa gccgtggcct acttcagcat ggagttcatg    360

ctgagcgagg ccctgccgat ctactccggc ggcctgggga acgtggcggg cgaccagctg    420

aaggcggcgt ccgacctggg cgtccccgtg atcggcgtcg gcctgctgta tcagcagggc    480

tacttccggc agatcatcga taacgacggc gcccagcagg ccatcttccc gtacaacgac    540

cccggccagc tcccgatcac cccgctccgt caggccaacg gcgagtggct gcgcttccag    600

atcgacctgc ctggctacgc cgtctggctg cgcgcctggc aggtgcaggt gggccgcgtg    660

aagctctacc tcctggatag caacgacgcc gccaacttcc cggtgcaccg gggcatcacc    720

agcgagttgt acggcggcgg ggccgagctg cggatcaagc aggagatcct gctgggcatc    780

ggcggctggc gcttgctgga agcgctgggg atccagcccg aggtgtgcca tctgaacgag    840

ggccacgccg ccttcgcggt cctggagcgt gcgcgcagct tcatggagaa gaccggtcag    900

ccgttcgacg tggccctgac cgtgacgcgc gcgggcaact tgttcaccac ccacaccgcc    960

gtcgccgccg gcttcgatcg cttcgccccg gcgctgatcg agcagtatct cggcggctac   1020
```

```
gtggagcaga agctcgggat cacctgccac gacttgctgg cgatgggtcg ccagcaccca   1080

gaagacgcct cggagccgtt caacatggcg tacctcgcga tccggggctc cggcgccgtc   1140

aacggcgtgt cgcgcctgca cggcgaggtc tcgcgccagc tgttcggcag cctcttccca   1200

cgctggagca cccaggaagt gcccgtgggc catgtcacga acggcgtgca cacccccacc   1260

tgggacagcg ccgccgcgga caacctgtgg accaacgcct gcggcaaggg gcgctggtcg   1320

ggcgaggtgg aggccctgga gcaagagatc cgccagctga gcgacacccg cctgtggcag   1380

ttccgcaccg agggcagcca ggccctggtg gactacgccc gcacccgcct gtcgcagcag   1440

ctggccagta gcggggccag ccgggaggcg gccgagcatg cgcagcacct gttcgacagc   1500

aacaccctga ccctgggctt tgcccggcgc ttcgcctcgt acaagcgccc gaacctcctg   1560

ctccacgacc ccgagcgcct gttgcgtctc ctgaccaacc cgcggcgccc cgtgcagatc   1620

ataatggccg gtaaggccca cccggacgac cgtgacgggc aggccatgat ccgccagtgg   1680

gtgcagttca tccgccgtcc cgaggtgcgg ccccacgcga tcttcctgtc ggactatgac   1740

atgctgctga ccgagcacct ggtgcagggc gtggacgtgt ggctgaacac cccgcgccgc   1800

ccgtgggaag cctgcggcac cagcggcatg aaggtgctgg tgaacggcgg catcaacctg   1860

agcgaattgg acggttggtg ggcggaggcg tacacgccag aggtgggttg ggccctgggt   1920

gacggccagg aacacgacga agacccggcc tgggacgccc gcgaagccga cgccctgtac   1980

accttgctgg agaacgaagt gatcccggaa ttctacaccc ggaatgaaca gggcatcccg   2040

gtggcctggg tgacccgcat gcgcgagagc atggcccagc tgacgccgcg cttcagcagc   2100

aaccgcgcgg tgcgcgagta cactggccag ctctacctgc cgctggcctc ggcctacctg   2160

gcgcgcgcgg agaacaacgc cgagcgtggc gccgacatgg tccgttggcg ccaggacttg   2220

gcgcagaagt gggccggcct ccgcttcggc gaggtcaccc tcagcagtga ggacgggcag   2280

cactcgttcg aggtccagat ctacctggat gacgtcgacc ccggcgccct gcgggtcgaa   2340

ctgttcgcga acgacgtgga cggcggcggc cccgaacgca tcgagatgca gcgtgtccgg   2400

cagctggtag gctcgacctc gggctacgcg taccgcgcga cggtcccggc cgaccgtgcc   2460

gccagcagct acaccgcgcg tctggtcccg taccatgagg gcgtggccat ccccctggaa   2520

gaagcccaca tcctgtggca gcgc                                          2544
```

<210> SEQ ID NO 74
<211> LENGTH: 2607
<212> TYPE: DNA
<213> ORGANISM: Artificial sequence
<220> FEATURE:
<223> OTHER INFORMATION: Codon-optimized sequence encoding GP-005.

<400> SEQUENCE: 74

```
gtgaaggccc tgcgccgctt caccgtgcgc gcccacctgc cggaacgcct ggccgccctg     60

gagcgcctga gcatcaacct gcgctggagc tgggacaagc ccacccagga cctgttcgcc    120

gacatcgacc cgaacctctg gaagcacgtg ggctgcgacc cggtcgccct gctgggcggc    180

gtggatccca agcgcctgga ccagctcgcg ggtgacgagg acttcctgcg ccgcctggag    240

gccctggcgg ccgacctgga cgactacctg tctcggccgc tgtggtacca gcagcagctg    300

gaacagggcc aggccctgcc gaacggcatc gcgtacttca gcatggagtt cggcgtggcc    360

gaggtcctgc cgaactacag cggcggcctg ggcatcctcg ccggcgacca cctgaagtcg    420

gccagcgacc tgggtctgcc cctcatcgcc gtggggctgt actaccgcag cggctacttc    480
```

```
cgccagagcc tgaccgcgga tggctggcaa cacgagaact acccgagcct ggacccgcag    540
ggcctgccgc tgcgcctgtt gaccggcgcc gactcggacc cggtcctggt ggagctcgcg    600
atgcctgatg acgcaaccct gtgggcgcgc gtctgggtcg cgcaggtggg ccgcatcccg    660
ctgctgctgc tggactcgga catcccggag aacgagcacg acctccgcgg cgtgacggac    720
cgcctgtacg gcggggacca ggagcatcgc atcaagcagg agatcctggc cgggatcggg    780
ggcgtgcgcg cgatccgcgc cttcaccgaa gtggagggtc tcccggcccc tgaagtcttc    840
cacatgaacg agggccacgc cggcttcctg ggcgtggagc gcatccgcga actgatcgac    900
gccggcctgg acttcgacac ggccctgacc gtggtgcggt cgagcacggt cttcacgacc    960
catacccccg tccccgccgg gatcgaccgc ttcccggtgg aaatggtgaa acgctacttc   1020
ggcaacccgc cgggctcgcc cagcggcgcc tcctcccgct tgctgccggg cgtccccctg   1080
gaccgcatca ccggtttcgg cgcggaagac gacccggcca agttcaacat ggcccatatg   1140
ggcctccgcc tggcccagcg cgcgaacggc gtgagcttgc tgcacggccg cgtaagccgt   1200
gagatgttca acgaactgtg gccgggcttc gacgcgaccg aggtcccgat cggctcgatc   1260
accaacggcg tccacgcgcc gtcgtgggcc gcgccccagt ggatggagct ggggcgcgag   1320
ctgctgggtt ccaccgacct gagctccctc tccgaacccg agacctggga acgcctgcac   1380
caagtggacc ctggccatct ctggcgcatc cgctcggagc tgcgccgtga gctggtagag   1440
gacgtccgcg tgcgcctgcg gcgctcctgg acccagcgcg gcgccgccga cgccgagctg   1500
ggctggaccg cgaccgcctt cgaccccaac gtgttgacca tcggcttcgc ccgtcgggtg   1560
ccgacctata agcgcctgac gctgatgctc cgggacccgg agcggctgca acgtctgctc   1620
ctggacgaac agcgcccggt ccagttgatc gtcgccggca agagccaccc ggccgacgac   1680
ggggggaagg cgctcattca gcaagtggtg cgcttcgccg accgccacga tgtgcgccat   1740
cgcatcgcgt tcctgcccga ctatgacatg agcatggccc gtcagctgta ctggggctgc   1800
gacgtctggc tgaataaccc gctccggccg ctggaagcgt gcgggaccag cggcatgaag   1860
agcgccctga acggcggctt gaacctgagc atccgcgacg gttggtggga cgagtggtac   1920
gacggcgaga acggctggga gatcccgacc gccaacggcc tgaccgacga agcgcgccgc   1980
gacgacctgg aagccagtgc cctctacgac ttgatcgaac agagcgtcgc cccgaagttc   2040
tacgagcgcg acgagcacgg cgtgcccatt cggtgggtcg agatggtgcg ccacacgttg   2100
aaggtcctgg gccccaaggt actggccagc cgcatggtgc gcgattacac ggaacgctat   2160
tacgcgcccg cggcacaaag cctgcgccgg accgtggagg cggtggacgg tatgccattc   2220
gcggctgccg cgggcctggc cgactaccgg cgccgtgtgc aggaagcctg gccgaagatc   2280
cagatcaccg acgtggactc ctacggcctc cccgacaccc cgctgctcgg cagcaagctg   2340
accctgaccg cgaccgtgcg cttggccggc ctgcgcccag acgaggtctc ggtgcaggcc   2400
gtcctcggcc gcgtggacgc gggcaacatc ctgttggacc ccaccaccgt cccgatgacc   2460
cacaccggga ccgccgacgg cggcaatgag gtcttctcga ccaccgcccc cctgccggtg   2520
gccggccccg tgggctacac cgtgcgcgtc ctgccgcacc acccgctcct ggccgccgac   2580
aacgagctgg gcctggtgac cctggcc                                       2607
```

```
<210> SEQ ID NO 75
<211> LENGTH: 2595
<212> TYPE: DNA
<213> ORGANISM: Artificial sequence
<220> FEATURE:
<223> OTHER INFORMATION: Codon-optimized sequence encoding GP-007.
```

<400> SEQUENCE: 75
gtgtcgaccc tgttcccggc cccgagcttc cgcctgccgg ccgcgatcgc gcgcctgagc 60
gacctggccc tcaacctgtg gttcagctgg aacggtagcg cccaggcgct tttcgccgac 120
atcgacgccg agctgtggct gcagacccgc cataacccgg tcgagctgct gaccaaggtg 180
tccgaggaca ccctggagcg cctggccgcg gacgagtcgt tcctgaaccg ctacgaagcg 240
gtcctccgcc agttcgacga gtacatgggc gcgggcacct ggtttagccg tcactacccg 300
catcaatcgc ggcacgccat cgcctacttc agcgccgagt tcggcttcca tgagagcctg 360
cccatctact ccggcggcct gggcatcctc gccggcgacc actgcaagtc cgccagcgac 420
ctgggcatcc cgttgatcgg cgtgggcttg ctgtacaaga agggctactt ccgtcagaag 480
ctggatagca agggtcacca gctggccgaa tcggtcccgt accacttccg caccctgccg 540
atcacccccg ccctggccct gcacgccgag aaagccaacg tcagcgacga ggacgcgggc 600
accccccgcg atgccgagca gccggagccg caggagctct atgtgaccgt ggacgtggcc 660
gatcgcaccg ttcgcctgaa ggtgtggcag gcccgcgtgg gccgcatccg cgtgctgctg 720
ctcgacgccg acctggagga aaacagcagc tgggaccgcg acctgaccgc ccagctgtac 780
ggcgggactc aggacgtccg catcgcccag gagatgctgc tgggcatcgg tggcatccgc 840
gcgctgcgcg ccctgaacgt gcccaccggc gcctaccata tcaatgaggg ccacgccgcg 900
ttcctcagct tcgagcgcct caaggagcag ctggagctgg gcttgccgtt ccacgtggcc 960
ttggaagtgg tgcgcgcctc gacggtgttc accacccaca ctcccgtcgc cgccgggcac 1020
gacgcgttcc cactggccat gttcgactac tacttcaccc gtctgttcac ggaccacccg 1080
gccctccgcc atgacctgac gcggctgggc ttcgacgaga gctcccagac cttcaatatg 1140
acccacctgg ccctgaacac gtcggccctg cgcaacggcg tgagcaaact gcatggccac 1200
gtcagccggc agatgttccg tgacttccac ggccacatcg acatccgtga agtcccgatc 1260
ggtcacatta cgaacggcgt ccacctgtcc acctggctgg ccccgcagct gaaggagctg 1320
ttcgaccggt tcttgccggg gaactggacc ctgaaccaga tgaaccccga tgtgtggcgc 1380
ggcatcgacc tgatcccgag cgagagcctc tggaaggtcc acgaagaact caaggagacc 1440
atgatccggc tcgcgcgcgc caacctggcc gagcagcgcc gccgcaacgg ccagagcgac 1500
catcagatcg gcgaggcgcg cggctacctg agcaaacacg ccctgaccat cggcttcgcg 1560
cgccgcttcg ccacctataa gcgcgccacc ctgatcttca acgacctgaa gcgcctggac 1620
cgcctggtga atgacccgga acggccggtg cagttcatct tcgccggcaa ggcccaccca 1680
gccgaccgtc cgggccagga catgctgcgc gagatctacc aggtgtcgca actggaacgc 1740
ttcaagggta agatcgtgct gttggaaaac tacgacatca acgtggcccg cgccctcgtg 1800
cagggcgtgg acatctggct gaacaacccg cgccgcccct acgaagcctc gggcaccagc 1860
gggcagaagg ccgccctgaa cggggtgatc aacttcagcg tcctggacgg gtggtgggaa 1920
gaaggctatg acgggagcaa cggctggagc atcgacagcg acctgaacgc cgatgaagag 1980
acccagggcc ggcagaacac ccagtcgctg taccaggtgc tggaacagga gatcgtcccc 2040
ctgtattaca accagggtcc gctgccggtg cagtggatcg agcgcatgaa gcgcagcatc 2100
cagaccctga gcccggtcta caacacggac cgcatggtgg cggactacac cgccggcgcg 2160
tacatcccat ccctggagcg tacgcagcgc ttcatcacca actcctacga ggaagcccgc 2220
aaggtggcgg acttcaagaa attcatcagc gataattggc accacgtccg ggtgatcgag 2280
gtgagcgaca gcctgcaatc gggcaagacc gcccgtaccg cggagccggt gaaggaagtc 2340
agcgtgaccg tccagttcgg cccggtgtgg taccaggaca ccgccgtcga cctgatctac 2400
tatgaagaca ccgcctcggg ttgggaacaa gtcgtggtcc cgatggagcc gtcgcgccag 2460
ctgggtgagg gcctgttcat ctaccgcgcc atcgtcccca gccacctgcg ccacggcccc 2520
cacttctcgg tgcgtgtgca cccggtgagc accaacttcg ccaccagctt cgagctgccg 2580
ttggtgaaga cctac 2595

<210> SEQ ID NO 76
<211> LENGTH: 2589
<212> TYPE: DNA
<213> ORGANISM: Artificial sequence
<220> FEATURE:
<223> OTHER INFORMATION: Codon-optimized sequence encoding GP-009.

<400> SEQUENCE: 76
gtggcccgta gcatcgatag cccgatcctg ccgcgggtga aagccatccg caccttcacc 60
gtccgcccgg tgctggcccc ggccctggag ccgctgcacc gtctggccgc caactggcgc 120
tggagctggt cgcgcagtac gcacgccctg ttcagctcga tggaccccac ccagtggagc 180
gaggtgggcg aaaacccggc ccgcatgctg ggggccctgg gccaggagcg tctggacgcc 240
ctggcccacg acgaatcgtt cgtggcccgc gtccgcgagg aagacgagcg tctggaggcc 300
tacctgtcgg gcgaccgctg gtaccagagc ctggacggcg gcgataaccc gcgcgcgatc 360
gcctacttca gcccggagtt cggtgtggac ggcagcctgc cccagtacag cggcggcctg 420
ggcatcctgg ccggcgacca tctgaagtcg gcctcggacc tcggcgtgcc cctcctgggc 480
gtcggcctgt tctaccgcgc cggttacttc cgccaagcga tcggcgacga cggctggcag 540
cgtgaatcgt acccccctgct cgacccgtat ggcctgggcc tgaccctgct gcgcgaggtt 600
gacggctcgc ccgtcgagat caccctggac ctctccggcg gccgtcgtct cgccgcccgc 660
gtgtggcagg ccgacatcgg ccgggtgccc ttgctcctgc tggacagcga gaccccgtcg 720
aacccggagg acctgcgcca tgtcaccgac cggctgtacg gcggcggcgg tgagcatcgg 780
ctgctgcagg aactgctgct gggcgtgggc ggcgtccgcg ccgtccgcgc gtggacccgc 840
ctcaccggcg cccccgagcc cgacgtgttc catacgaacg agggccacgc cgggttccag 900
ggcctggagc gcatgagcga gctgattgtg ggcgaaggcc tggacttcga cgtggccctg 960
gcccaggtcc gcagctccac cgtgttcacc acgcacaccc cggtgccggc cgggatcgac 1020
cgcttcccgc gctccctgat cgaccagatg ctgaccgccg gcctcttccg cggcctggac 1080
cctgaccgcg cgttgcggct ggggctggag ggctacgacg gcggcgaccc gcacaccttc 1140
aacatggccg tgctgggcct ccacttgggc cagcatgcca acggcgttag ccgcttgcac 1200
gggcgcgtga gccgcgagat gttcggcccg ttgtggccgg gcgtcgatgc ggacgaggtg 1260
cccatcatca gcatcaccaa cggcgtccac gccccgacct gggtgcaccc ggagctgaag 1320
gccctgtcgg agcgggcctt cggcgacgcc ctgaccacca cccacgactg gcgcgacccg 1380
gcgcgcgtgg cggatgaaga actctgggag tcccgccggc gtatgaaggc gggcctggtc 1440
gccgaagccc gtcgccgcct ccgggcgggc gaggagtcgg gcaccggcgc tccgtggatc 1500
gacgacgcgc tggaccccga tgtcctgacg atcggcttcg cccgtcgggt gccgacgtac 1560
aagcgcctga ccctgatgct gcgcgacccc gaacgtctga cccagctgct gacggatgcc 1620
caccgccctg tccagatcgt cgtggccggc aagagccacc cggccgacga ctcgggcaag 1680
atcctgatcc agcagctggt gcggttctcg caggaccccc gagtgcgtgg ccgcatcgtg 1740

```
ttcttgcctg actacgacat caccttggcc aagcacctgt acccaggctg cgacgtgtgg   1800

ctgaacaacc cgctgcgccc gctggaggcg tgcggcacca gcgggatgaa agccgcgctg   1860

aacggcgccc tgaacctgag catcctggac ggttggtggg acgagtggtt cgacgggcgg   1920

aacgggtggg ccatcccgtc ggccgaccgg gccgcggacg acgacgagcg cgacgacgcc   1980

gaggcctcgg ccctctacga tctcatcgaa aaccgcctgg tgcccacctt ctatgaccgc   2040

gaggacggcc tgccggcgcc gtggctggaa atggtccgcc acaccatgac gaccctgggt   2100

gggaaggcga cctccgaccg catggtgcgc gactacgtga ccgaactcta cgtcccggcc   2160

gcccgtcata acgcggaact cgccgccgac ggccacgccc gcgcccgtga gctggcgcgc   2220

tacatcagcc gcgtgaagga cgcgtggccg ggtgtgcgca ttgatagcgt cgacgctaac   2280

ggcgccaccg cgcacccgcg caccggtgag accgtcacgg tgaccgcccg cgtgcgcctg   2340

gcccacctgt cgcccgacga cgtcgcggtg gagctggtgt acggccacgc cgacagcgac   2400

ggccgcctgg accgcacccg gaccgccatc ccgctgagcg cgcagccggg cggcgaggac   2460

ggcatgaccg tgttcgccgg cgcgctgcgc ctgaccatga ccggcccgtt cggctacacc   2520

gtccgcgtgg tgccccgcca cgaccacctg gtgagccccc tggagctggg cctggtgagc   2580

ctggccagc                                                           2589
```

<210> SEQ ID NO 77
<211> LENGTH: 2559
<212> TYPE: DNA
<213> ORGANISM: Artificial sequence
<220> FEATURE:
<223> OTHER INFORMATION: Codon-optimized sequence encoding GP-013.

<400> SEQUENCE: 77

```
gtggcgggca ccctgttcca gctggaaatc aacccgaagc tgccggcccg cttggcccgt     60

ctggaggaac tggccaacaa cctgtggtac tcgtgggacc gccccacccg tacgctgttc    120

gcccgcctgg gcacccgcct ctggggcgcc gtgggccact ccccgaaggc cttcctgaag    180

cgtgtggacc agcaccgtct ggaagaggcg gccgaagacc cggtgttcct gggcgccctg    240

gcccatgtgc tctcggccta cgacacctac catgacaacc tgcgccgcga gccgggccac    300

cagctgcctg aaggcgccct gatcgcctac ttctgcgccg aattcggctt ccacgaaagc    360

ctgcccatct atagcggcgg cctgggcatc ctcgccggcg atcactgcaa gaccgccagc    420

gacatgaacc tgccgttcgt gggcgtgggg ctcctgtacc gccagggcta cttcctgcag    480

agcatcgatg gcgaggggcg ccagcatgcc ctgtacaacg acgccgactt cgacgacctt    540

ccggtgaccc ccgtcgccgc gccgggcggc ggtgacctga aagtggccgt ccgcctgccg    600

ggccgcgatg tctgggtgaa ggtgtggaag gcccgcgtgg gccacgtgag catctacctg    660

ctggacaccg acttggaaga gaacagtccg cacgaccgtg acatcactca tcagctgtac    720

ggcggcgacc gcaccacgcg catcgagcag gagatcgtcc tgggcatggg cggggtccgc    780

gccctggccg ccctgaacct gaagcccacc gtgtggcaca tcaacgaagg ccacgccgcc    840

ttcctggtgc tggaacggat gcgtgacctg atcaagtcgg gcctggactt cgacgccgcc    900

atcgaggtcg tggcctgcaa cacggtgttc accacccaca cccccgtgcc cgccggccac    960

gaccacttcg ccgatgagat gatccgccag tacttcgagg agtgctgcca tgacatgggg   1020

tgcgaggtcg gcagcctgct ggcgctcggc cgcatcgacg ataccccgga attcaacatg   1080

accggtttgg cgattcgcgg ttcccgattc cagaacggcg tgtcccggat ccacggcgac   1140
```

```
gtgagcgcgg agatctgtcg ccagctgtgg ccgcagattg atcccgagga gaaccccgatg   1200

gactacgtta ccaacggcgt gcacgtaccg accttcctga gtgaccactg gcacgacacg   1260

ttcgaccgcg tcctgggccc ggcgtggcgc cagcgcctga ccgacgccca gacttggtcg   1320

caggtgcacg cgatccccga ccacaccttc tggagcatcc gccagagcat caaggcggag   1380

atgctgtact tggtgcgcca ccgcatcacc gagcagtaca cccgcaacca gtgcagccag   1440

gcccacatcg atcgcctgct ccagctggcc gaccccgaaa acccgaacgt gctgaccgtg   1500

ggcttcgccc gccgcttcgc cacctacaag cgggccaccc tgctcttcag cgacctggag   1560

ctgctgcgcc gcatgatctg caacccggag cgcccggtcc tgttcatctt cgccggcaag   1620

gcgcacccgg ccgaccagcc gggccaggcc ctgatccggc gcgtccacga ggtggcgcag   1680

atgcccgagt ttgagggcca catcctgctg gtcgagggtt acgaccttcg cctggcccgc   1740

cgcctggtca gcggcgtcga cgtctggctg aacaacccgg tctacccgct ggaggcgagc   1800

ggcacctccg gcatgaaggc cgccatgaac ggcgtgatca acctgagcgt gctggacggt   1860

tggtggggcg agggcttcca ccaggacgac ggcggcgcca acggctgggc catcaagccg   1920

gcctcgcgca ccctggacga agcccgtcgt gaccaggaag agggccgcag cctgtacgaa   1980

accttgcaag acaaggtcat ccccctgtac tacgcccgcg gcccgatggg ctatagccca   2040

ggctggatcg cgatggccaa gcgctccatc gcgacgatca ccccgcgctt caactcgcag   2100

cgtatggtgg gggagtacct gcataagttc tacgcgccgg cggacctgca gtggcggaag   2160

aaatcggcgg acggctacgc cgcggcgcgc acactggccg cttggaagca gaaggtccgc   2220

caggcctggc ctaaggtccg cctgcgtcgc ctcgacatgc cggtgaaacg gatcccgtac   2280

ggcgccagcc tgcatttcga gctggcggtg cacctggacg ggctggcccc ccaggacgtg   2340

gccgtggaac tgctgctgag ccgtccgggt accgacagtc gcacgcgccc gccccgcaag   2400

ctgttgttgg aataccgcgg ccccggtgag cagggcgaca gcatcttcgc cctggacttc   2460

acgccggacg tgtgcggcaa actggactat cgcctgcggg tctacccgca ccacgagctg   2520

ctgacccacc cgttcgagat gggcatgatg ctgtggctg                          2559
```

<210> SEQ ID NO 78
<211> LENGTH: 2124
<212> TYPE: DNA
<213> ORGANISM: Artificial sequence
<220> FEATURE:
<223> OTHER INFORMATION: Codon-optimized sequence encoding GP-043.

<400> SEQUENCE: 78

```
gtgcagaaga ccctgaccat cgacgaggtg atcaacagcc tgtacgagct ggcgtacaac     60

ctgtggtgga cctacaaccc gaaggcgcag gagatcttcg agatgctgag cccgatgctc    120

tggaagctga ccaaccataa cgccgtccag accctgaaga gcatctcgaa gttcgagctg    180

aaggcccgcc tgagcaaccc ggacttcctg agcaaggtgg agaacgtcct gaacgaattc    240

aagcagtaca tcagaacccg ccaggaactg agcaagaaca agttccccga cttcatcaac    300

cgcccggtcg cctacttcac cgccgagttc ggcctgcacg aatgcctgcc gatctatagc    360

ggcggcctgg gcatcctgag cggcgaccac gccaaatcgg ccagcgacat cggcctgccg    420

ttcgtcggcg tgtcgctctt ctaccgccac ggctacttcg accagaagat cgcagacaac    480

ggctggcaga tcgaggagta caacccggtg cagccgaact tcctgccggt gaagctggtc    540

ctggaccagc agaaccagcc gctgaaggtg aagctgaaca tcggccattc cgagatctcg    600

atccaggcct gggaagtgaa cgtcggcatc agcaagatct acctgctgga caccaacctg    660
```

```
ccggagaacg acttccacta tcgggacatc acgtcgaagg tctacggcgg tgacgccacc    720

acccgcatct tccaggagat cgtgctcggc atcggcggcg tgcggttcct gaaggccctg    780

ggcatcgaac ccagcgtcta ccacctgaac gaaggccact cggccttcct gaccctggag    840

ctgatgcgcg aggaactcaa caagggcaag accaaggaag aggcggagcg gagcgtgcgt    900

gagaagtgcg tgttcaccac ccacaccccc gtgcccgccg gccatgaccg cttcagcccc    960

gatctgatcg agtacgccct gggctccttc atccagagcc tcggcatgag cctgaaggag   1020

ttcttggcct acggccgcat ccacccggac aacgagcagg agaccttctg catgaccgtc   1080

ctggccctga agctcagccg caacgccaac gccgtgagcg agctgaacgg catcgtgagc   1140

cgcaagatgt ggcagccgct gttcaagtcc aaaagcgaga aggacgtccc gatcggccac   1200

atcacgaacg gcgtgcactc cttgacctgg ctgaataaga ttgcgttcga gttctggacg   1260

aaaaagctgg gtgacaagtg gtacgaggaa atcgagaacc cgaagctgtg ggagaacgtg   1320

ctggacgaga acttcatcac ggacgaggag atctggtcca tccgctacga gctgcgccgc   1380

agcctcatcg agttcgtgcg cgagaagatc ctgaacctcc tgtttaagag cggcctggac   1440

tccaaggtga acatcaacag catcctgagc ccggacgcgc tgaccatcgg cttcagccgg   1500

cgcttcgcca cgtacaagcg cgccccgctg atcttctacg accttgaacg cgccaagaag   1560

atcttcaacg accgtagcaa gccggtgcag atcatcttca gcggcaaggc ccacccgcgc   1620

gacgacgcgg gcaaagaatt cctccagcgc atcgtccaga tctcgaagat gcccgaattc   1680

tacggcaagg tgatcttcat cgagaactac gatatgaaca tcgcacgtca cctgattagc   1740

ggctgcgatt tatggctgaa caacccgcgc cgcccattgg aagcctcggg cacctcgggg   1800

cagaagatcg tgctgaattt tggcctgaac ttctctatcc tggacgggtg gtggcgtgaa   1860

gcctataacg gtgagaacgg ctgggccatc ggtaaggacg aaagcgtgga ggatccgaac   1920

atccaggaca aactggatgc cgaattcctg taccaaacgc ttgaaaatga gatcatcccg   1980

gccttctaca ataggaatga gaacggcatc ccgaaggaat ggattaaacg catccgcaag   2040

agcattgcca ccgtgaccta cttcttcaat accaaccgca tggtgcgcga atacgtgaag   2100

aaatactacc gtaagagtga gaac                                          2124
```

<210> SEQ ID NO 79
<211> LENGTH: 2115
<212> TYPE: DNA
<213> ORGANISM: Artificial sequence
<220> FEATURE:
<223> OTHER INFORMATION: Codon-optimized sequence encoding GP-044.

<400> SEQUENCE: 79

```
gtggaaaagt acaagaccaa gaacaacatc ttcccgcaca tcccggagcg catcagccgc     60

ctgggcgagc tggccgagaa cctgtggtgg tcgtggaacc cgcaggcgcg catgctgttt    120

aagatgctgg accgccaggc ctggaaggag agcggccaca acccggacgc catgctgaag    180

aagctgccac agcacctgct ccaggaagcc gcccaggacc gcaactacct ccgccactac    240

gacctggtga tgagccagtt cgaccaacag gccaaccatg acaacgtgga ggaccggtcg    300

cccgtcgcct acttctccgc cgaatacggc ctgcaccaca gcctgccgtt cttcgccggc    360

ggcctgggcc tgctggccgg cgaccactta aaagagtgca gcgacatgcg cctgccgctg    420

gtcgcggtgg gcttcatgta cccgagcggg tacctgaagc agaccatcaa caaggacggc    480

tggcaggaat cggtgaccca gaccgtcgac cgcgaaagcg ccagcatcaa ccagatcttc    540
```

```
gacacgtcgg gcgagcgcat catcatcgag atcccccatc tggagccgcg catccgcgcc    600

gcggtgtgga aggtcgccgt gggccgcgtc agcctgttcc tgattgacac cgagatcgaa    660

gagaacccgg agtggatcca gcacatcgca cgccagctgt acacctcgga ccaggagcac    720

cgcctcctgc aggaagcggt cctcggccta ggcggctaca ccctgctgcg ccgcctgggc    780

atcgacccgt acatgatcca cctgaacgaa ggccacccgg ccttcgccct gctggaggcc    840

atgcgcgatc tgatgcagca gggtcgctcg ttcgaccagg cgaagaagga gatccgcgaa    900

aagtcgctgt tcaccaccca caccccggtg cccgccggcc acgacgtctt cccggccgag    960

ctgatggaca agtacttccc gagctattgg caggcgctgg gcctggaccg tgagagcttc   1020

ctggaactgg gcaagcaccc ggagaagccg gagagcggct tcaacatgac cgtcctggcg   1080

atgcgcctga cgggccagtg caacgcggtg agccgtcggc acggcgaggt gacgcgccag   1140

atgtggcagg gcctctggcc ggacaagcag gcggaggaca tcccgatcga ccacgtcacc   1200

aacggggtgc acctcccgac ctggctcgac cccaagatcc gcctgctgta caatcagcac   1260

ttcgacgagg gctggatcat ggagcacgat aacccggcca tctgggagtt catcgaggag   1320

atcccggacg agaagctgtg gcagacccac tacctgctga aggtgaagct gctgaaccac   1380

atccgccagc tggcccgcga aaactggcgg caacgccaga ccccggacct gatccccgcc   1440

ctgggcacca tgctggagcc gagcatcctg acgatcggct tcggccgccg cttcgccacc   1500

tacaagcggg ccgacctgat cttgcaggat cccgagcgcc tgaagcagct ggtcaacgac   1560

tcctggcggc ccatccagat catcttcgcg ggcaaggccc acccggcgga ccacgagggc   1620

cagcgcctga tgcagcgggt gatccacttc gcgcaggacc cggaattcag cggtcggatc   1680

gccttcgtgg agaacttcaa cgagcagctg gcccagtaca tggtgcacgg cgtcgatgta   1740

tggctgaaca ccccccagcc cccgatggag gcgtccggca ccagcggcat gaaggcctcg   1800

atcaacggcg tgccgaacct gagcatcccg gacgggtggt ggctggaagg cgccagcccc   1860

ggcaacggct ggaccatccc gctgcaccag gacgcggagc cgggagagca ggactggctg   1920

gaagcccgcg aactgtatca cctgatcgag gagcgcctga tcccgaagta ctacagtagc   1980

tcggagaccg gcgtgcccca cgagtgggtg agaattatga aggaagccat caagaccgtg   2040

gccccgcact tcagcgcccg ccgcatggtg aaggagtacc agcagaagca ctaccagaag   2100

cagagccgcc atgag                                                    2115
```

<210> SEQ ID NO 80
<211> LENGTH: 2106
<212> TYPE: DNA
<213> ORGANISM: Artificial sequence
<220> FEATURE:
<223> OTHER INFORMATION: Codon-optimized sequence encoding GP-046.

<400> SEQUENCE: 80

```
gtggctagcc acgcccatct gcgcgacgac ctggaccggc tggcgcgcaa cgtgcgctgg     60

gcctggaccc cgccggcccg ccgcgtgctg gaggagctcg acccggccgc ctggcgtcgg    120

accggcggca accccgccgc catcttgagc gacctgaccg acgaacgcct ggaggccgcg    180

gcggcgcagc cggactacct gggccgcgtg cacgacgcct ccgaggagct ggcccgctat    240

ctggatgacg gcgacacctg gtacgcccgc agcggtggcg accccgaccg ccgtgtggtg    300

tacctgagcg ccgagtatgg cctgaccgac tgcctccgga tctactcggg cggcctgggc    360

gtgctggccg gcgaccacct gcgcagcgcc agcgacctgg gcctgccgct gaccgccatc    420

ggcctggcct atcgcaacgg gtacttccgc cagcacctgg acgggtcggg ctggcagatc    480
```

```
gccgaggtgg ccagtaacga cttcgagcgc agccccgcca cgctggtgct ggatgacgag    540
ggcgccccgc tggaagtcca tgtcgagatg ggcgacggtg aggtgacggt gcgcgcgtgg    600
caggtgcacg tcgggcgtgt cccgttgtac ctgctggaca ccgacgtcga aggcaacggc    660
gaccatcatc gcgccatcac cggtcagctg tacggcggcg actccgacac tcgcctgcgc    720
caggagctca tcctgggcgt cggcgggatg cgcctcctgg acgcgctggg cgtccacgcc    780
gacgtgatcc acctgaacga aggccacgcc gccttcgcca ccctggagct cctgcgcggt    840
cacctggacg gctcggcggg cctggacgac gccgtggcgg aagtgtcgga gcgcctggtg    900
ttcacgaccc acaccccggt gccggccggg cacgacgtct tcgacggcgg cctggcctcg    960
tggcacctgg gcccgctcgc ccagcggatc ggggtgccct tcgagcaact gtggcggctg   1020
gcctgcgccg aaggcgacaa catctggagc cagaccgtcc tcgcgctgac cttcgcccgc   1080
cgcaccaacg gcgtcgcgcg cctgcacggc gaggtgagcc gccgcatgtg ggcgcgcctg   1140
tggccggacc gggacgtcga cgacgtgccc attacgcata tcaccaacgg ggtccacccg   1200
gccatgtggg tcggcgagga cctggcccgc atcctggact ggagcctggg tccgggctgg   1260
cgcatggatg acgacgcgga gcgctgggag cgggtgcgcg aggtggcccc ggccgagctg   1320
tggcgtgtcc acgacgacgc ccggtaccgc ctgatccgcg aggtccgccg ccgcctccgc   1380
gcgcagtcgc gccggttcgg catcggccct gacggcgcgg gcttggaccc tgacgccctc   1440
accatcggct tcgcgcgccg cttcgccacc tacaagcgcg ccaccctgct ggcccatgac   1500
ctggaccgcc tggccgccat cctggggtca gacgaccgcc cggtccaggt ggtggtggcc   1560
ggcaaggcgc acccgcagga cgagggcggc aagcacctga tccagcaact cgtgggtctg   1620
tcgcgtgacc cccagctgcg cggccggctg gccttcgtcg agggctacga cctggagctc   1680
gcccacgccc tggtgaccgg cgtggacgtg tggctgaaca acccccctccg cccgatggag   1740
gccagcggca cgtccgggat gaaggcggcc atgaacggcg tgctgaacct gtccgtcctg   1800
gacgggtggt gggacgaggc ggtggccgac ctgaccccac tggcccgcga gggcttcggc   1860
tgggccatcg gcgaccgcac cgagggcgat gaccgcggcg cccgcgacgc cgcggacgcg   1920
gcgtcgttct acgacctgct ggaacagcgc gtggtgccca ccttctacga acgcggcgcc   1980
gacgacgtcc ctcagcgctg ggtgaccatg atgcaggacg cgatcgcgat cctggccccc   2040
cgcttcagca cccaccgcat ggtggccgac tacgccagca gcgtgtacgc ccacagcaag   2100
ggcgcc                                                               2106
```

<210> SEQ ID NO 81
<211> LENGTH: 2070
<212> TYPE: DNA
<213> ORGANISM: Artificial sequence
<220> FEATURE:
<223> OTHER INFORMATION: Codon-optimized sequence encoding GP-048.

<400> SEQUENCE: 81

```
gtgacctcgc gcgacaagct ggaagccatc gccgccaacc tgtggtggag ctggaacccg     60
gaggccctgg ccctgttcga gcagctgaac cccgaggcct tccgggccag ccaacacaac    120
ccgctggcgg ccctgcgcac cgcggacccg gccctgctga ccgaccgccc cttcatcaag    180
gccgtggaca aggtctacga agccttcacc gcctacctga acgccccgcc ccgcatcacc    240
gacgccccgc gcaccgcgta cttctgcatg gagtacggcc tgcacgagag tctgccgttc    300
tacgcgggcg gcctgggcgt cctggccggt gaccacatca aggccgccag cgacctgggc    360
```

-continued

```
ctgccgatga ccgcggtggg cctgttcctg cgcgagggct acttccgcca gcgcttcgaa    420

ccgaacggct ggcagatcgc ggagtacccg gcgatggacc cggccgatca cccgatgacc    480

ctggtgcacg ggccggatgg ctacccgctc gtgatcaccg tgcatctcgg ccgccagccc    540

ttctacttgc gggcgtggaa gttggacgtg ggccgcgtgc ccctgtacct gctggacggc    600

gccttcgacg cgaacccgga accgctgcgc agcctgaccc gccgcctgta ccagggcgac    660

cgccgcctgc gcctgcagca ggaaatcatc ctgggcatcg gggcgtccg cctgctgcgc    720

gccctcgacc tcgactttga aacctatcac ctgaacgaag gccactgcgc cttcgtggcg    780

ctcgaactgc tccgcgagcg cctggccgcg ggcgaggccc gtgaggccgc cgaggcctgg    840

gtgcgcgacc actgcgtctt caccacccac accccagtga tggccggcca tgaccgcttc    900

tcgcccgagc tgttcctgga gcagatggag accttccgcc accagctggg cctgagcgag    960

acggagctgc tggcctacgg ccgcgtcaac cccaacgact cgacggaggc gttcaccatg   1020

acggtgctgg ggttgaagct gagccgcaag accaacggcg tgagcgccat caattcggtc   1080

gtagcccgcc gccagtggca ccacctgtac ccggatcgcc cgctgaacga ggtgcccatc   1140

ggttacatta ctaacggcgt gcacctgccg acgtggaccg tggcgcatgc ccgcccgttc   1200

ctcgcccagc acctcggcga ctggctggag ggacgcttca acccggacct gtggcgcaag   1260

atcgactcga tcagcgacgc ggagctgtgg cagtaccgct gcatgctgcg ccgccgcctg   1320

gtagagttcg tgaacgagta cgtgaagcac cagtccctgc cgcaggaagc ccacctgtcc   1380

cccgaggtcc tgaccatcgg cttcgcgcgg cggttcgcca cctacaaacg cgcccgctg   1440

ctgttcgagg acatggagcg cgcgatccag ctgttctccc gccaggaccg cccgatccag   1500

ctgatctacg cgggcaaggc ccacccggcg gatgacggcg gcaaacgctt catccagcag   1560

atctacgaga tcacccagca tccggcgttc cggggcaagg tggtgttcgt cgaggactac   1620

gacatgcaca tcgcgcgcat gctcgtcagc gggtgcgacg tgtggctgaa caacccgcgc   1680

cgcccgctgg aggcgagcgg cacgagcggc cagaagaccg cgatccacgg cggcctgaac   1740

ctgagcgtgt tcgacggttg gtggccggag ggctacaatg gccagaacgg ctgggccttc   1800

ggccgcgagg ccaccggcct gtacgaagac ccgatcacgc aggacgtgga ggaccgcgag   1860

gcgctgtacc gggtgctgga gtacgaagtg atcccggcct tctacgatcg caatggtgaa   1920

ggcttgccac tgcgttggtt gacccgcatg cgtcaggcaa tgcgcaccat tccggcacag   1980

tttaatgctg tgcgtatggt gcgtgaatac gtcgaacaga tgtatagacc ggccgccatg   2040

ccggccaccg tgaccgccgc cgccgcccag                                    2070
```